United States Patent
Hollick et al.

(10) Patent No.: US 9,493,471 B2
(45) Date of Patent: Nov. 15, 2016

(54) PYRIMIDINE DERIVATIVES AS PROTEIN KINASE INHIBITORS

(71) Applicant: Cyclacel Limited, London (GB)

(72) Inventors: Jonathan James Hollick, Perth (GB);
Stuart Donald Jones, Cheshire (GB);
Claire June Flynn, Angus (GB);
Michael George Thomas, Braco (GB)

(73) Assignee: Cyclacel Limited, London (GB)

(*) Notice: Subject to any disclaimer, the term of this patent is extended or adjusted under 35 U.S.C. 154(b) by 0 days.

(21) Appl. No.: 14/820,711

(22) Filed: Aug. 7, 2015

(65) Prior Publication Data

US 2015/0344486 A1    Dec. 3, 2015

Related U.S. Application Data

(63) Continuation of application No. 13/910,349, filed on Jun. 5, 2013, now Pat. No. 9,133,199, which is a continuation of application No. 12/680,353, filed as application No. PCT/GB2008/003305 on Sep. 29, 2008, now Pat. No. 8,563,542.

(30) Foreign Application Priority Data

Sep. 28, 2007 (GB) .................................. 0719038.2
Apr. 15, 2008 (GB) .................................. 0806844.7

(51) Int. Cl.
| | |
|---|---|
| *A61K 31/551* | (2006.01) |
| *C07D 487/04* | (2006.01) |
| *C07D 519/00* | (2006.01) |
| *C07D 487/10* | (2006.01) |
| *C07D 453/02* | (2006.01) |

(52) U.S. Cl.
CPC ........... *C07D 487/04* (2013.01); *A61K 31/551* (2013.01); *C07D 453/02* (2013.01); *C07D 487/10* (2013.01); *C07D 519/00* (2013.01)

(58) Field of Classification Search
CPC . A61K 31/551; C07D 487/04; C07D 519/00
See application file for complete search history.

(56) References Cited

U.S. PATENT DOCUMENTS

| | | |
|---|---|---|
| 5,818,889 A | 10/1998 | Cook |
| 8,563,542 B2 | 10/2013 | Hollick et al. |
| 8,710,009 B2 | 4/2014 | Ficht et al. |
| 8,710,068 B2 | 4/2014 | Berezov et al. |
| 9,133,199 B2 | 9/2015 | Hollick et al. |
| 2014/0066436 A1 | 3/2014 | Hollick et al. |
| 2015/0320762 A1 | 11/2015 | Davis et al. |

FOREIGN PATENT DOCUMENTS

| | | |
|---|---|---|
| CA | 2517020 A1 | 9/2004 |
| EA | 008778 B1 | 8/2007 |
| WO | 2004/076454 A1 | 9/2004 |
| WO | 2007/095188 A2 | 8/2007 |
| WO | 2008/003958 A2 | 1/2008 |
| WO | 2008/113711 A1 | 9/2008 |
| WO | 2009/040556 A1 | 4/2009 |
| WO | 2009/067547 A1 | 5/2009 |
| WO | 2013144632 A1 | 10/2013 |

OTHER PUBLICATIONS

International Preliminary Report on Patentability for Application No. PCT/GB2008/003305, 7 pages, dated Mar. 30, 2010.
Lei, M. et al., "Plk1 depletion in nontransformed diploid cells activates the DNA-damage checkpoint," Oncogene, vol. 27:3935-3943 (2008).
Li, Donghui et al., "Overexpression of Oncogenic STK15/BTAK/Aurora A Kinase in Human Pancreatic Cancer," Clinical Cancer Research, vol. 9:991-997 (2003).
Liu, Xiaoqi et al., "Polo-like kinase (Plk)1 depletion induces apoptosis in cancer cells," PNAS, vol. 100(10):5789-5794 (2003).
Mao, H.W. et al., "Expression of plk-1 gene in acute leukemia patients and its significance," Zhongguo Shi Yan Xue Ye Xue Za Zhi, vol. 14(5):876-879 (2006)—Abstract only.
Murugan, Ravichandran N. et al., "Plk1-Targeted Small Molecule Inhibitors: Molecular Basis for Their Potency and Specificity," Mol. Cells, vol. 32:209-220 (2011).
Reagan-Shaw, Shannon et al., "Polo-like Kinase (Plk) 1 as a Target for Prostate Cancer Management," IUBMB Life, vol. 57(10):677-682 (2005).
Spankuch-Schmitt, Birgit et al., "Downregulation of human polo-like kinase activity by antisense oligonucleotides induces growth inhibition in cancer cells," Oncogene, vol. 21:3162-3171 (2002).
Strebhardt, Klaus et al., "Targeting polo-like kinase 1 for cancer therapy," Nature Reviews Cancer, vol. 6:321-330 (2006).
Girdler, F. et al., "Validating Aurora B as an anti-cancer drug target," Journal of Cell Science, vol. 119, pp. 3664-3675 (2006).
John Theurer Cancer Center, "Phase 2 study of MLN8237: Investigational aurora A kinase (aak) inhibitor in patients with acute myelogenous leukemia (AML) or myelodysplastic syndromes (MDS)," Science Daily, pp. 1-3, Dec. 7, 2010.

*Primary Examiner* — Bruck Kifle
(74) *Attorney, Agent, or Firm* — Nelson Mullins Riley & Scarborough LLP; Cynthia L. Kanik

(57) ABSTRACT

The present invention relates to pyrimidine derivatives capable of inhibiting one or more protein kinases. Further aspects relate to pharmaceutical compositions comprising the pyrimidine derivatives and the use thereof in the treatment of proliferative disorders.

8 Claims, 3 Drawing Sheets

PYRIMIDINE DERIVATIVES AS PROTEIN KINASE INHIBITORS

CROSS REFERENCE TO RELATED APPLICATIONS

This application is a continuation of U.S. patent application Ser. No. 13/910,349, filed on Jun. 5, 2013, which is a continuation of U.S. Pat. No. 8,563,542, filed Nov. 1, 2010, which is a national stage filing of International Application No. PCT/GB2008/003305, filed Sep. 29, 2008, which claims priority to Great Britain Application No. 0719038.2, filed Sep. 28, 2007, and Great Britain Application No. 0806844.7, filed Apr. 15, 2008. The contents of the aforementioned applications are hereby incorporated by reference in their entireties.

BACKGROUND TO THE INVENTION

The present invention relates to substituted pyrimidine derivatives and their use in therapy. More specifically, but not exclusively, the invention relates to compounds that are capable of inhibiting one or more protein kinases, particularly polo-like kinases.

The Polo-like kinase family consists of key cell cycle regulatory enzymes with integral roles in controlling entry into and progression through mitosis. Many tumour cells express high levels of PLK1 and are responsive to antisense oligonucleotides targeting this protein.

Initiation of mitosis requires activation of M-phase promoting factor (MPF), i.e. the complex between CDK1 and B-type cyclins [Nurse, P. (1990) Nature, 344, 503-508]. The latter accumulate during the S and G2 phases of the cell cycle and promote the inhibitory phosphorylation of the MPF complex by WEE1, MIK1, and MYT1 kinases. At the end of the G2 phase, corresponding dephosphorylation by the dual-specificity phosphatase CDC25C triggers the activation of MPF [Nigg, E. A. (2001) Nat. Rev. Mol. Cell Biol., 2, 21-32]. In interphase, cyclin B localizes to the cytoplasm and becomes phosphorylated during prophase, followed by nuclear translocation. The nuclear accumulation of active MPF during prophase is thought to be important for initiating M-phase events [Takizawa, C. G. and Morgan, D. O. (2000) Curr. Opin. Cell Biol., 12, 658-665]. However, nuclear MPF is kept inactive by WEE1 unless counteracted by CDC25C. The phosphatase CDC25C itself, localized to the cytoplasm during interphase, accumulates in the nucleus in prophase. The nuclear entry of both cyclin B and CDC25C are promoted through phosphorylation by PLK1 [Roshak, A. K., Capper, E. A., Imburgia, C., Fornwald, J., Scott, G. and Marshall, L. A. (2000) Cell. Signalling, 12, 405-411]. This kinase is thus an important regulator of M-phase initiation.

In humans, there exist three closely related polo-like kinases (PLKs) [Glover, D. M., Hagan, I. M. and Tavares, A. A. (1998) Genes Dev., 12, 3777-3787]. They contain a highly homologous N-terminal catalytic kinase domain and their C-termini contain two or three conserved regions, the polo boxes. The function of the polo boxes remains incompletely understood but polo box-dependent PLK1 activity is required for proper metaphase/anaphase transition and cytokinesis [Seong, Y.-S., Kamijo, K., Lee, J.-S., Fernandez, E., Kuriyama, R., Miki, T. and Lee, K. S. (2002) J. Biol. Chem., 277, 32282-32293]. Of the three PLKs, PLK1 is the best characterized; it regulates a number of cell division cycle effects, including the onset of mitosis, DNA-damage checkpoint activation, regulation of the anaphase promoting complex, phosphorylation of the proteasome, and centrosome duplication and maturation. Mammalian PLK2 (also known as SNK) and PLK3 (also known as PRK and FNK) were originally shown to be immediate early gene products. PLK3 kinase activity appears to peak during late S and G2 phase. It is also activated during DNA damage checkpoint activation and severe oxidative stress. PLK3 also plays an important role in the regulation of microtubule dynamics and centrosome function in the cell and deregulated PLK3 expression results in cell cycle arrest and apoptosis [Wang, Q., Xie, S., Chen, J., Fukusawa, K., Naik, U., Traganos, F., Darzynkiewicz, Z., Jhanwar-Uniyal, M. and Dai, W. (2002) Mol. Cell. Biol., 22, 3450-3459]. PLK2 is the least-well understood homologue of the three PLKs. Both PLK2 and PLK3 may have additional important post-mitotic functions [Kauselmann, G., Weiler, M., Wulff, P., Jessberger, S., Konietzko, U., Scafidi, J., Staubli, U., Bereiter-Hahn, J., Strebhardt, K. and Kuhl, D. (1999) EMBO J., 18, 5528-5539].

The fact that human PLKs regulate some fundamental aspects of mitosis was shown by anti-PLK1 antibody microinjection of human tumour cells [Lane, H. A. and Nigg, E. A. (1996) J. Cell. Biol., 135, 1701-1713]. This treatment had no effect on DNA replication but impaired cell division. Cells were arrested in mitosis and showed abnormal distribution of condensed chromatin and monoastral microtubules nucleated from duplicated but unseparated centrosomes. By contrast, non-immortalized human cells arrested as single, mononucleated cells in G2. Moreover, when PLK1 function was blocked through adenovirus-mediated delivery of a dominant-negative gene, tumour-selective apoptosis in many tumour cell lines was observed, whereas again normal epithelial cells, although arrested in mitosis, escaped the mitotic catastrophe seen in tumour cells [Cogswell, J. P., Brown, C. E., Bisi, J. E. and Neill, S. D. (2000) Cell Growth Differ., 11, 615-623]. PLK1 activity is thus necessary for the functional maturation of centrosomes in late G2/early prophase and subsequent establishment of a bipolar spindle. Furthermore, these results suggest the presence in normal cells of a centrosome-maturation checkpoint that is sensitive to PLK1 impairment. Depletion of cellular PLK1 through the small interfering RNA (siRNA) technique also confirmed that this protein is required for multiple mitotic processes and completion of cytokinesis [Liu, X. and Erikson, R. L. (2003) Proc. Natl. Acad. Sci. USA, 100, 5789-5794]. A potential therapeutic rationale for PLK inhibition is also suggested by work with PLK1-specific antisense oligonucleotides, which were shown to induce growth inhibition in cancer cells both in vitro and in vivo [Spankuch-Schmitt, B., Wolf, G., Solbach, C., Loibl, S., Knecht, R., Stegmuller, M., von Minckwitz, G., Kaufmann, M. and Strebhardt, K. (2002) Oncogene, 21, 3162-3171]. Constitutive expression of PLK1 in mammalian cells was shown to lead to malignant transformation [Smith, M. R., Wilson, M. L., Hamanaka, R., Chase, D., Kung, H., Longo, D. L. and Ferris, D. K. (1997) Biochem. Biophys. Res. Commun., 234, 397-405]. Furthermore, overexpression of PLK1 is frequently observed in human tumours and PLK1 expression is of prognostic value for patients suffering from various types of tumours [Takahashi, T., Sano, B., Nagata, T., Kato, H., Sugiyama, Y., Kunieda, K., Kimura, M., Okano, Y. and Saji, S. (2003) Cancer Science, 94, 148-152; Tokumitsu, Y., Mori, M., Tanaka, S., Akazawa, K., Nakano, S. and Niho, Y. (1999) Int. J. Oncol., 15, 687-692; Wolf, G., Elez, R., Doermer, A., Holtrich, U., Ackermann, H., Stutte, H. J., Altmannsberger, H.-M., Rübsamen-Waigmann, H. and Strebhardt, K. (1997) Oncogene, 14, 543-549].

Although the therapeutic potential of pharmacological PLK inhibition has been appreciated [Kraker, A. J. and Booher, R. N. (1999) In *Annual Reports in Medicinal Chemistry* (Vol. 34) (Doherty, A. M., ed.), pp. 247-256, Academic Press], very little has been reported to date concerning small molecule PLK inhibitors that may be useful as drugs. One of the few biochemical PLK1 inhibitors characterized to date is scytonemin, a symmetric indolic marine natural product [Stevenson, C. S., Capper, E. A., Roshak, A. K., Marquez, B., Eichman, C., Jackson, J. R., Mattern, M., Gerwick, W. H., Jacobs, R. S. and Marshall, L. A. (2002) *J. Pharmacol. Exp. Ther.*, 303, 858-866; Stevenson, C. S., Capper, E. A., Roshak, A. K., Marquez, B., Grace, K., Gerwick, W. H., Jacobs, R. S. and Marshall, L. A. (2002) *Inflammation Research*, 51, 112-114].

Scytonemin inhibits phosphorylation of CDC25C by recombinant PLK1 with an $IC_{50}$ value of about 2 µM (at an ATP concentration of 10 µM). Inhibition is apparently reversible and the mechanism with respect to ATP of mixed-competitive mode. Similar potency against other protein serine/threonine- and dual specificity cell-cycle kinases, including MYT1, CHK1, CDK1/cyclin B, and PKC, was observed. Scytonemin showed pronounced anti-proliferative effects on various human cell lines in vitro. Further small molecule PLK inhibitors and their use in the treatment of proliferative disorders are described in International patent application WO2004/067000 in the name of Cyclacel Limited.

The present invention seeks to elucidate new small molecule PLK inhibitors. More specifically, the invention seeks to provide small molecule PLK inhibitors that have therapeutic applications in the treatment of a range of proliferative disorders.

SUMMARY OF THE INVENTION

A first aspect of the invention relates to a compound of formula VIII, or a pharmaceutically acceptable salt or ester thereof,

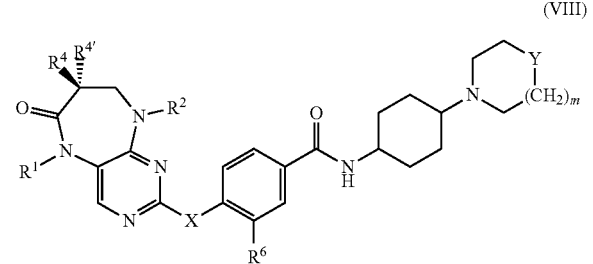

(VIII)

wherein:
X is $NR^7$;
Y is O or N—$(CH_2)_nR^{19}$;
n is 1, 2 or 3;
m is 1 or 2;
$R^1$ and $R^2$ are each independently H, alkyl or cycloalkyl;
$R^4$ and $R^{4'}$ are each independently H or alkyl; or
$R^4$ and $R^{4'}$ together form a Spiro cycloalkyl group;
$R^{19}$ is H, alkyl, aryl or a cycloalkyl group;
$R^6$ is $OR^8$ or halogen; and
$R^7$ and $R^8$ are each independently H or alkyl.

A second aspect of the invention relates to a compound of formula VI, or a pharmaceutically acceptable salt or ester thereof,

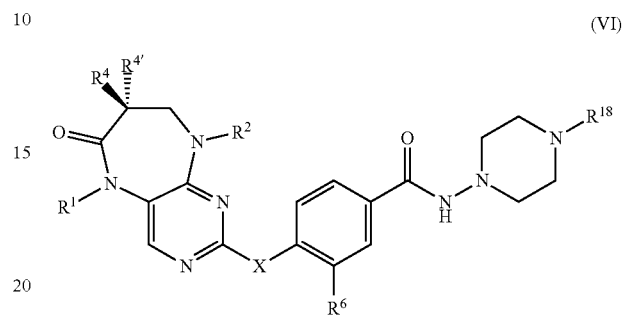

(VI)

wherein:
X is $NR^7$;
$R^1$ and $R^2$ are each independently H, alkyl or cycloalkyl;
$R^4$ and $R^{4'}$ are each independently H or alkyl; or
$R^4$ and $R^{4'}$ together form a spiro cycloalkyl group;
$R^{18}$ is H or alkyl, wherein said alkyl group is optionally substituted by $R^6$;
each $R^6$ is independently $OR^8$ or halogen; and
$R^7$ and $R^8$ are each independently H or alkyl.

A third aspect of the invention relates to a compound of formula VII, or a pharmaceutically acceptable salt or ester thereof,

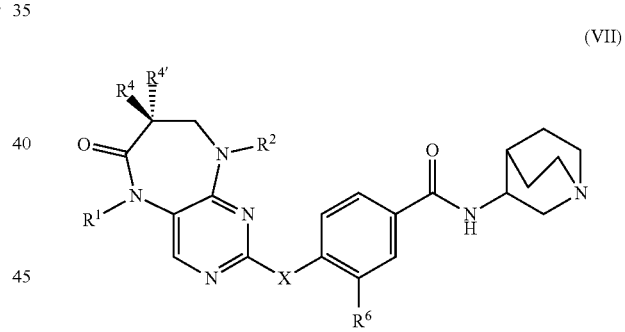

(VII)

wherein:
X is $NR^7$;
$R^1$ and $R^2$ are each independently H, alkyl or cycloalkyl;
$R^4$ and $R^{4'}$ are each independently H or alkyl; or
$R^4$ and $R^{4'}$ together form a Spiro cycloalkyl group;
$R^6$ is $OR^8$ or halogen; and
$R^7$ and $R^8$ are each independently H or alkyl.

A fourth aspect of the invention relates to a compound selected from the following:

| Compound No. | Name |
|---|---|
| 254 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(4-methylpiperazin-1-yl)benzamide |
| 218 | (±)-4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-3-methoxy-N-(quinuclidin-3-yl)benzamide |

-continued

| Compound No. | Name |
|---|---|
| 195 | 4-(9-Cyclopentyl-5,7,7-trimethyl-6-oxo-6,7,8,9-tetrahydro-5H-pyrimido[4,5-b][1,4]diazepin-2-ylamino)-3-methoxy-N-(4-methyl-piperazin-1-yl)-benzamide |
| 221 | 4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-3-methoxy-N-(4-methylpiperazin-1-yl)benzamide |
| 371 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((trans)-4-(4-(cyclopropylmethyl)piperazin-1-yl)cyclohexyl)-3-methoxybenzamide |
| 372 | 4-(9-cyclopentyl-5,7,7-trimethyl-6-oxo-6,7,8,9-tetrahydro-5H-pyrimido[4,5-b][1,4]diazepin-2-ylamino)-N-((trans)-4-(4-(cyclopropylmethyl)piperazin-1-yl)cyclohexyl)-3-methoxybenzamide |
| 345 | 4-(9-Cyclopentyl-5-methyl-6-oxo-6,7,8,9-tetrahydro-5H-pyrimido[4,5-b][1,4]diazepin-2-ylamino)-3-methoxy-N-[1-(tetrahydro-pyran-4-yl)-piperidin-4-yl]-benzamide |
| 373 | 4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-3-fluoro-N-(4-methylpiperazin-1-yl)benzamide |
| 374 | 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-fluoro-N-(4-methylpiperazin-1-yl)benzamide |
| 194 | (±)-4-(9-cyclopentyl-5,7,7-trimethyl-6-oxo-6,7,8,9-tetrahydro-5H-pyrimido[4,5-b][1,4]diazepin-2-ylamino)-3-methoxy-N-(quinuclidin-3-yl)benzamide |
| 186 | (±)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(quinuclidin-3-yl)benzamide |
| 375 | 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-N-(4-(2-hydroxyethyl)piperazin-1-yl)-3-methoxybenzamide |
| 376 | 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-morpholinobenzamide |
| 347 | (R)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(quinuclidin-3-yl)benzamide |
| 348 | (S)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(quinuclidin-3-yl)benzamide |
| 377 | 4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-N-((trans)-4-(4-(cyclopropylmethyl)piperazin-1-yl)cyclohexyl)-3-methoxybenzamide |
| 378 | 4-(9-cyclopentyl-5-methyl-6-oxo-6,7,8,9-tetrahydro-5H-pyrimido[4,5-b][1,4]diazepin-2-ylamino)-N-((trans)-4-(4-(cyclopropylmethyl)piperazin-1-yl)cyclohexyl)-3-methoxybenzamide |
| 379 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((trans)-4-(4-ethylpiperazin-1-yl)cyclohexyl)-3-methoxybenzamide |
| 380 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((cis)-4-(4-ethylpiperazin-1-yl)cyclohexyl)-3-methoxybenzamide |
| 381 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-(4-(4-(cyclopropylmethyl)-1,4-diazepan-1-yl)cyclohexyl)-3-methoxybenzamide |
| 382 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-(4-(4-ethyl-1,4-diazepan-1-yl)cyclohexyl)-3-methoxybenzamide |
| 383 | N-(4-(4-benzyl-1,4-diazepan-1-yl)cyclohexyl)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzamide |
| 384 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((trans)-4-(4-methylpiperazin-1-yl)cyclohexyl)-3-methoxybenzamide |
| 385 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((cis)-4-(4-methylpiperazin-1-yl)cyclohexyl)-3-methoxybenzamide |
| 386 | N-((trans)-4-(4-benzylpiperazin-1-yl)cyclohexyl)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzamide |
| 387 | N-((cis)-4-(4-benzylpiperazin-1-yl)cyclohexyl)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzamide |
| 388 | 4-(9-cyclopentyl-5,7,7-trimethyl-6-oxo-6,7,8,9-tetrahydro-5H-pyrimido[4,5-b][1,4]diazepin-2-ylamino)-3-methoxy-N-((trans)-4-morpholinocyclohexyl)benzamide |

-continued

| Compound No. | Name |
|---|---|
| 389 | 4-(9-cyclopentyl-5,7,7-trimethyl-6-oxo-6,7,8,9-tetrahydro-5H-pyrimido[4,5-b][1,4]diazepin-2-ylamino)-3-methoxy-N-((cis)-4-morpholinocyclohexyl)benzamide |
| 390 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-((trans)-4-morpholinocyclohexyl)benzamide |
| 391 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-((cis)-4-morpholinocyclohexyl)benzamide |

A fifth aspect of the invention relates to a pharmaceutical composition comprising a compound as described above admixed with a pharmaceutically acceptable diluent, excipient or carrier.

A sixth aspect of the invention relates to the use of a compound as described above in the preparation of a medicament for treating a proliferative disorder.

A seventh aspect of the invention relates to a method of treating a proliferative disorder, said method comprising administering to a subject a therapeutically effective amount of a compound as described above.

An eighth aspect of the invention relates to a method of treating a PLK-dependent disorder, said method comprising administering to a subject a therapeutically effective amount of a compound as described above.

A ninth aspect of the invention relates to a process for preparing compounds as defined above.

DETAILED DESCRIPTION

Figure 1:
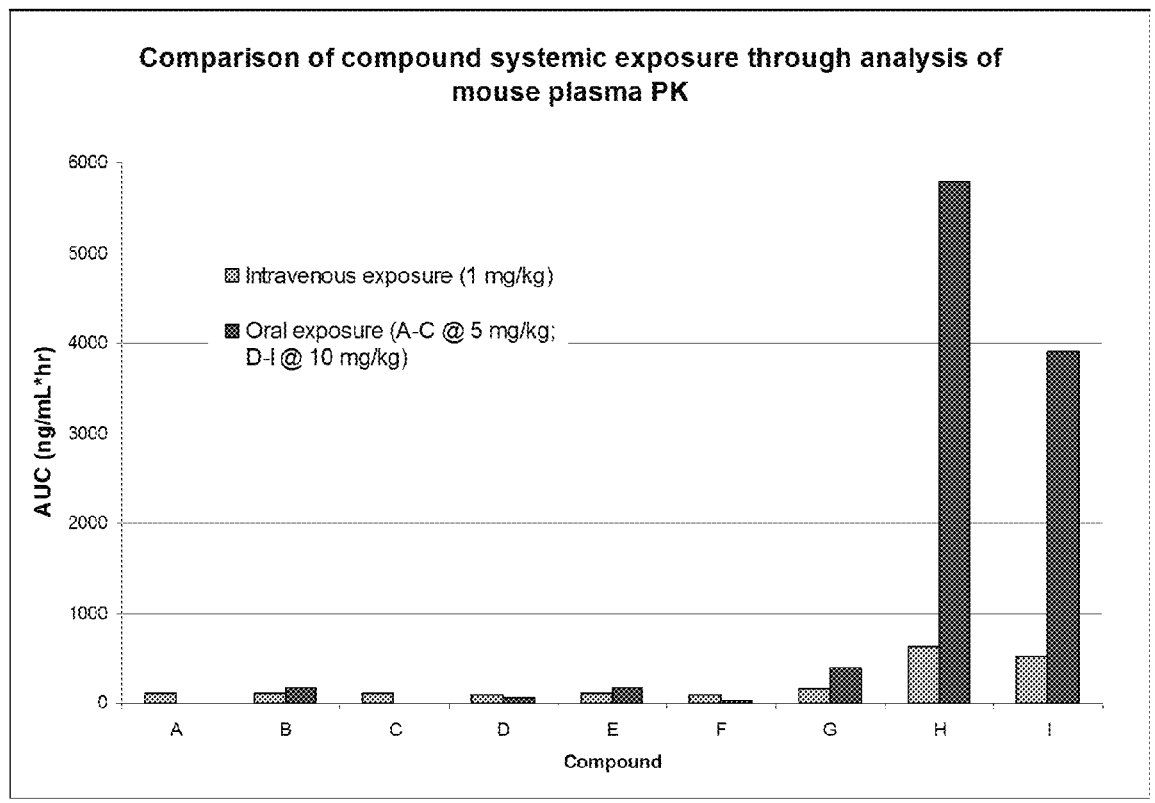
FIG. 1 shows the area under the curve (AUC) for the plasma concentration of compounds A-H versus time for each compound tested. The dosing vehicle across these experiments remained constant (intravenous=citrate buffer pH 3, 1 mL/kg; oral=DMA/PEG400/10 mM Tartrate buffer, pH 4 (1:3:6), 5 ml/kg)

As used herein, the term "alkyl" includes both saturated straight chain and branched alkyl groups which may be substituted (mono- or poly-) or unsubstituted. Preferably, the alkyl group is a $C_{1-20}$ alkyl group, more preferably a $C_{1-15}$, more preferably still a $C_{1-12}$ alkyl group, more preferably still, a $C_{1-6}$ alkyl group, more preferably a $C_{1-3}$ alkyl group. Particularly preferred alkyl groups include, for example, methyl, ethyl, propyl, isopropyl, butyl, isobutyl, tert-butyl, pentyl and hexyl. Suitable substituents include, for example, one or more $R^6$ groups. Preferably, the alkyl group is unsubstituted.

As used herein, the term "cycloalkyl" refers to a cyclic alkyl group which may be substituted (mono- or poly-) or unsubstituted. Preferably, the cycloalkyl group is a $C_{3-12}$ cycloalkyl group, more preferably a $C_{3-6}$ cycloalkyl group. Suitable substituents include, for example, one or more $R^6$ groups.

As used herein, the term "aryl" refers to a $C_{6-12}$ aromatic group which may be substituted (mono- or poly-) or unsubstituted. Typical examples include phenyl and naphthyl etc. Suitable substituents include, for example, one or more $R^6$ groups.

Compounds of Formula VIII

As mentioned above, one aspect of the invention relates to a compound of formula VIII, or a pharmaceutically acceptable salt or ester thereof.

In one particularly preferred embodiment, the invention relates to a compound of formula VIIIa, or a pharmaceutically acceptable salt or ester thereof,

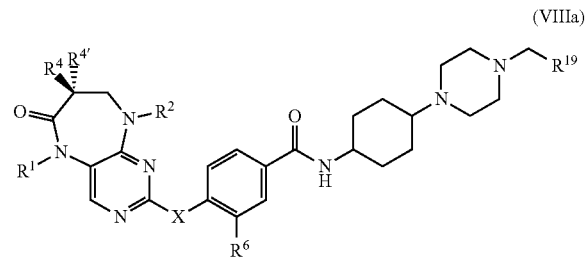

(VIIIa)

wherein:
X is $NR^7$;
$R^1$ and $R^2$ are each independently H, alkyl or cycloalkyl;
$R^4$ and $R^{4'}$ are each independently H or alkyl; or
$R^4$ and $R^{4'}$ together form a Spiro cycloalkyl group;
$R^{19}$ is H, alkyl, aryl or a cycloalkyl group;
$R^6$ is $OR^8$ or halogen; and
$R^7$ and $R^8$ are each independently H or alkyl.

In one preferred embodiment, $R^{19}$ is H, alkyl, or a cycloalkyl group.

Preferably, $R^1$ is H or alkyl, more preferably, alkyl. Even more preferably, $R^1$ is methyl or ethyl, more preferably still, Me.

Preferably, $R^2$ is a cycloalkyl group, more preferably a $C_{3-6}$ cycloalkyl group. Even more preferably, $R^2$ is a cyclopentyl or cyclohexyl group, more preferably still, cyclopentyl.

Preferably, $R^7$ is H or alkyl, more preferably, H or methyl, even more preferably, H. In one preferred embodiment, one of $R^4$ and $R^{4'}$ is alkyl, and the other is H or alkyl. In another preferred embodiment, $R^4$ and $R^{4'}$ are each independently alkyl. More preferably, $R^4$— and $R^{4'}$ are both methyl.

In another preferred embodiment, $R^4$ and $R^{4'}$ are both H.

In another preferred embodiment, $R^4$ and $R^{4'}$ together form a spiro cycloalkyl group, more preferably, a spiro $C_{3-6}$ cycloalkyl group. Even more preferably, $R^4$ and $R^{4'}$ together form a spiro $C_3$ or $C_4$ cycloalkyl group, more preferably still, a $C_3$ cycloalkyl group.

In one preferred embodiment, $R^6$ is $OR^8$, even more preferably, OMe.

Preferably, $R^{19}$ is cyclopropyl.

In another particularly preferred embodiment, the invention relates to a compound of formula VIIIb, or a pharmaceutically acceptable salt or ester thereof,

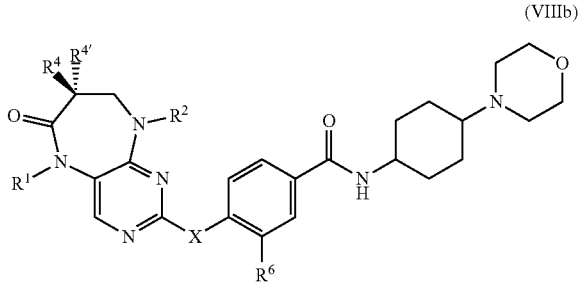

(VIIIb)

wherein $R^1$, $R^2$, $R^6$, $R^4$, $R^{4'}$ and X are as defined above.

In another particularly preferred embodiment, the invention relates to a compound of formula VIIIc, or a pharmaceutically acceptable salt or ester thereof,

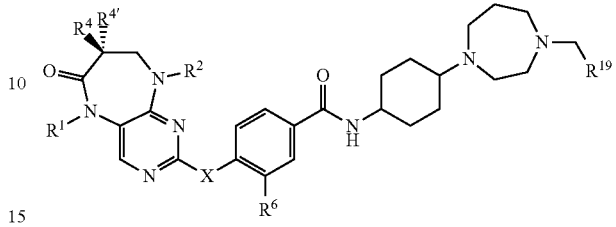

(VIIIc)

wherein X, $R^1$, $R^2$, $R^6$, $R^4$, $R^{4'}$ and $R^{19}$ are as defined above.

In one particularly preferred embodiment, said compound of formula VIII is selected from the following:

| Compound No. | Name |
|---|---|
| 371 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((trans)-4-(4-(cyclopropylmethyl)piperazin-1-yl)cyclohexyl)-3-methoxybenzamide |
| 372 | 4-(9-cyclopentyl-5,7,7-trimethyl-6-oxo-6,7,8,9-tetrahydro-5H-pyrimido[4,5-b][1,4]diazepin-2-ylamino)-N-((trans)-4-(4-(cyclopropylmethyl)piperazin-1-yl)cyclohexyl)-3-methoxybenzamide |
| 377 | 4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-N-((trans)-4-(4-(cyclopropylmethyl)piperazin-1-yl)cyclohexyl)-3-methoxybenzamide |
| 378 | 4-(9-cyclopentyl-5-methyl-6-oxo-6,7,8,9-tetrahydro-5H-pyrimido[4,5-b][1,4]diazepin-2-ylamino)-N-((trans)-4-(4-(cyclopropylmethyl)piperazin-1-yl)cyclohexyl)-3-methoxybenzamide |
| 379 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((trans)-4-(4-ethylpiperazin-1-yl)cyclohexyl)-3-methoxybenzamide |
| 380 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((cis)-4-(4-ethylpiperazin-1-yl)cyclohexyl)-3-methoxybenzamide |
| 381 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-(4-(4-(cyclopropylmethyl)-1,4-diazepan-1-yl)cyclohexyl)-3-methoxybenzamide |
| 382 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-(4-(4-ethyl-1,4-diazepan-1-yl)cyclohexyl)-3-methoxybenzamide |
| 383 | N-(4-(4-benzyl-1,4-diazepan-1-yl)cyclohexyl)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzamide |
| 384 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((trans)-4-(4-methylpiperazin-1-yl)cyclohexyl)-3-methoxybenzamide |
| 385 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((cis)-4-(4-methylpiperazin-1-yl)cyclohexyl)-3-methoxybenzamide |
| 386 | N-((trans)-4-(4-benzylpiperazin-1-yl)cyclohexyl)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzamide |
| 387 | N-((cis)-4-(4-benzylpiperazin-1-yl)cyclohexyl)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzamide |
| 388 | 4-(9-cyclopentyl-5,7,7-trimethyl-6-oxo-6,7,8,9-tetrahydro-5H-pyrimido[4,5-b][1,4]diazepin-2-ylamino)-3-methoxy-N-((trans)-4-morpholinocyclohexyl)benzamide |
| 389 | 4-(9-cyclopentyl-5,7,7-trimethyl-6-oxo-6,7,8,9-tetrahydro-5H-pyrimido[4,5-b][1,4]diazepin-2-ylamino)-3-methoxy-N-((cis)-4-morpholinocyclohexyl)benzamide |
| 390 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-((trans)-4-morpholinocyclohexyl)benzamide |
| 391 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-((cis)-4-morpholinocyclohexyl)benzamide | and pharmaceutically acceptable salts and esters thereof.

More preferably, the compound of formula VIII is selected from the following:

| Compound No. | Name |
|---|---|
| 371 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((trans)-4-(4-(cyclopropylmethyl)piperazin-1-yl)cyclohexyl)-3-methoxybenzamide |
| 372 | 4-(9-cyclopentyl-5,7,7-trimethyl-6-oxo-6,7,8,9-tetrahydro-5H-pyrimido[4,5-b][1,4]diazepin-2-ylamino)-N-((trans)-4-(4-(cyclopropylmethyl)piperazin-1-yl)cyclohexyl)-3-methoxybenzamide |
| 377 | 4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-N-((trans)-4-(4-(cyclopropylmethyl)piperazin-1-yl)cyclohexyl)-3-methoxybenzamide |
| 378 | 4-(9-cyclopentyl-5-methyl-6-oxo-6,7,8,9-tetrahydro-5H-pyrimido[4,5-b][1,4]diazepin-2-ylamino)-N-((trans)-4-(4-(cyclopropylmethyl)piperazin-1-yl)cyclohexyl)-3-methoxybenzamide | or a pharmaceutically acceptable salt or ester thereof.

Even more preferably, the compound of the invention is compound [371].

Compounds of Formula VII

One aspect of the invention relates to a compound of formula VII, or a pharmaceutically acceptable salt or ester thereof,

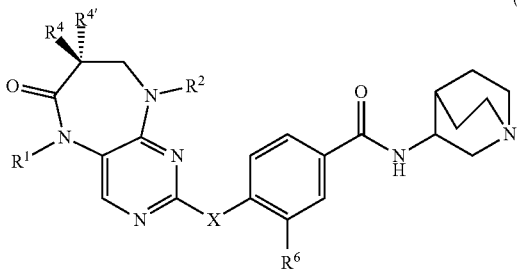

wherein:
X is $NR^7$;
$R^1$ and $R^2$ are each independently H, alkyl or cycloalkyl;
$R^4$ and $R^{4'}$ are each independently H or alkyl; or
$R^4$ and $R^{4'}$ together form a Spiro cycloalkyl group; and
$R^6$ is $OR^8$ or halogen; and
$R^7$ and $R^8$ are each independently H or alkyl.

Preferably, $R^1$ is alkyl, more preferably, methyl.

Preferably, $R^2$ is a cycloalkyl group, more preferably a $C_{3-6}$ cycloalkyl group. Even more preferably, $R^2$ is a cyclopentyl or cyclohexyl group, more preferably still, cyclopentyl.

Preferably, $R^7$ is H or alkyl, more preferably, H or methyl, even more preferably, H.

In one preferred embodiment, one of $R^4$ and $R^{4'}$ is alkyl, and the other is H or alkyl.

In another preferred embodiment, $R^4$ and $R^{4'}$ are each independently alkyl. More preferably, $R^4$— and $R^{4'}$ are both methyl.

In another preferred embodiment, $R^4$ and are both H.

In another preferred embodiment, $R^4$ and $R^{4'}$ together form a spiro cycloalkyl group, more preferably, a spiro $C_{3-6}$ cycloalkyl group. More preferably, $R^4$ and $R^{4'}$ together form a spiro $C_3$ or $C_4$ cycloalkyl group, even more preferably, a $C_3$ cycloalkyl group.

Preferably, $R^6$ is $OR^8$, even more preferably, OMe.

In one preferred embodiment, the compound of formula VII is selected from the following:

| Compound No. | Name |
|---|---|
| 218 | (±)-4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-3-methoxy-N-(quinuclidin-3-yl)benzamide |
| 194 | (±)-4-(9-cyclopentyl-5,7,7-trimethyl-6-oxo-6,7,8,9-tetrahydro-5H-pyrimido[4,5-b][1,4]diazepin-2-ylamino)-3-methoxy-N-(quinuclidin-3-yl)benzamide |
| 186 | (±)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(quinuclidin-3-yl)benzamide |
| 347 | (R)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(quinuclidin-3-yl)benzamide |
| 348 | (S)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(quinuclidin-3-yl)benzamide | and pharmaceutically acceptable salts and esters thereof.

Compounds of Formula VI

One aspect of the invention relates to a compound of formula VI, or a pharmaceutically acceptable salt or ester thereof,

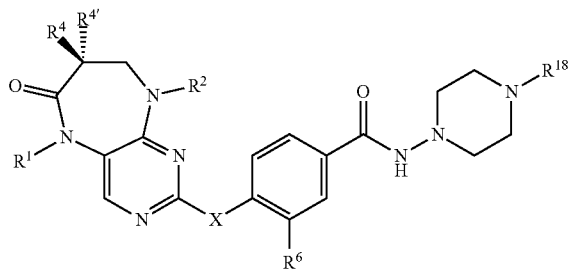

(VI)

wherein:
X is $NR^7$;
$R^1$ and $R^2$ are each independently H, alkyl or cycloalkyl;
one of $R^4$ and $R^{4'}$ is alkyl, and the other is H or alkyl; or $R^4$ and $R^{4'}$ together form a spiro cycloalkyl group;
$R^{18}$ is H or alkyl, wherein said alkyl group is optionally substituted by $R^6$;
each $R^6$ is independently $OR^8$ or halogen; and
$R^7$ and $R^8$ are each independently H or alkyl.

Preferably, $R^1$ is alkyl, more preferably methyl.

Preferably, $R^2$ is a cycloalkyl group, more preferably, a $C_{3-6}$ cycloalkyl group. Even more preferably, $R^2$ is cyclopentyl or cyclohexyl, more preferably still, cyclopentyl.

Preferably, $R^7$ is H or alkyl, more preferably, H or methyl, even more preferably, H.

In one preferred embodiment, one of $R^4$ and $R^{4'}$ is alkyl, and the other is H or alkyl.

In another preferred embodiment, $R^4$ and $R^{4'}$ are each independently alkyl. More preferably, $R^4$— and $R^{4'}$ are both methyl.

In another preferred embodiment, $R^4$ and $R^{4'}$ are both H.

In another preferred embodiment, $R^4$ and $R^{4'}$ together form a spiro cycloalkyl group, more preferably, a spiro $C_{3-6}$ cycloalkyl group. Even more preferably, $R^4$ and $R^{4'}$ together form a spiro $C_3$ or $C_4$ cycloalkyl group, even more preferably, a $C_3$ cycloalkyl group.

Preferably, $R^6$ is OMe or F.

Preferably, $R^{18}$ is methyl or $CH_2CH_2OH$.

In one preferred embodiment, the compound of formula VI is selected from the following:

| | |
|---|---|
| 254 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(4-methylpiperazin-1-yl)benzamide |
| 195 | 4-(9-Cyclopentyl-5,7,7-trimethyl-6-oxo-6,7,8,9-tetrahydro-5H-pyrimido[4,5-b][1,4]diazepin-2-ylamino)-3-methoxy-N-(4-methyl-piperazin-1-yl)-benzamide |
| 221 | 4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-3-methoxy-N-(4-methylpiperazin-1-yl)benzamide |
| 373 | 4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-3-fluoro-N-(4-methylpiperazin-1-yl)benzamide |
| 374 | 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-fluoro-N-(4-methylpiperazin-1-yl)benzamide |
| 375 | 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-N-(4-(2-hydroxyethyl)piperazin-1-yl)-3-methoxybenzamide | and pharmaceutically acceptable salts and esters thereof.

In one especially preferred embodiment, the compound is [254], or a pharmaceutically acceptable salt or ester thereof.

In one highly preferred embodiment, the compound is the HCl salt of compound [254], i.e. 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(4-methylpiperazin-1-yl)benzamide.HCl.

Another aspect of the invention relates to a compound which is selected from the following:

| Compound No. | Name |
|---|---|
| 254 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(4-methylpiperazin-1-yl)benzamide |
| 218 | (±)-4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-3-methoxy-N-(quinuclidin-3-yl)benzamide |
| 195 | 4-(9-Cyclopentyl-5,7,7-trimethyl-6-oxo-6,7,8,9-tetrahydro-5H-pyrimido[4,5-b][1,4]diazepin-2-ylamino)-3-methoxy-N-(4-methyl-piperazin-1-yl)-benzamide |
| 221 | 4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-3-methoxy-N-(4-methylpiperazin-1-yl)benzamide |

| Compound No. | Name |
|---|---|
| 371 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((trans)-4-(4-(cyclopropylmethyl)piperazin-1-yl)cyclohexyl)-3-methoxybenzamide |
| 372 | 4-(9-cyclopentyl-5,7,7-trimethyl-6-oxo-6,7,8,9-tetrahydro-5H-pyrimido[4,5-b][1,4]diazepin-2-ylamino)-N-((trans)-4-(4-(cyclopropylmethyl)piperazin-1-yl)cyclohexyl)-3-methoxybenzamide |
| 345 | 4-(9-Cyclopentyl-5-methyl-6-oxo-6,7,8,9-tetrahydro-5H-pyrimido[4,5-b][1,4]diazepin-2-ylamino)-3-methoxy-N-[1-(tetrahydro-pyran-4-yl)-piperidin-4-yl]-benzamide |
| 373 | 4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-3-fluoro-N-(4-methylpiperazin-1-yl)benzamide |
| 374 | 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-fluoro-N-(4-methylpiperazin-1-yl)benzamide |
| 194 | (±)-4-(9-cyclopentyl-5,7,7-trimethyl-6-oxo-6,7,8,9-tetrahydro-5H-pyrimido[4,5-b][1,4]diazepin-2-ylamino)-3-methoxy-N-(quinuclidin-3-yl)benzamide |
| 186 | (±)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(quinuclidin-3-yl)benzamide |
| 375 | 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-N-(4-(2-hydroxyethyl)piperazin-1-yl)-3-methoxybenzamide |
| 376 | 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-morpholinobenzamide |
| 347 | (R)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(quinuclidin-3-yl)benzamide |
| 348 | (S)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(quinuclidin-3-yl)benzamide |
| 377 | 4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-N-((trans)-4-(4-(cyclopropylmethyl)piperazin-1-yl)cyclohexyl)-3-methoxybenzamide |
| 378 | 4-(9-cyclopentyl-5-methyl-6-oxo-6,7,8,9-tetrahydro-5H-pyrimido[4,5-b][1,4]diazepin-2-ylamino)-N-((trans)-4-(4-(cyclopropylmethyl)piperazin-1-yl)cyclohexyl)-3-methoxybenzamide |
| 379 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((trans)-4-(4-ethylpiperazin-1-yl)cyclohexyl)-3-methoxybenzamide |
| 380 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((cis)-4-(4-ethylpiperazin-1-yl)cyclohexyl)-3-methoxybenzamide |
| 381 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-(4-(4-(cyclopropylmethyl)-1,4-diazepan-1-yl)cyclohexyl)-3-methoxybenzamide |
| 382 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-(4-(4-ethyl-1,4-diazepan-1-yl)cyclohexyl)-3-methoxybenzamide |
| 383 | N-(4-(4-benzyl-1,4-diazepan-1-yl)cyclohexyl)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzamide |
| 384 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((trans)-4-(4-methylpiperazin-1-yl)cyclohexyl)-3-methoxybenzamide |
| 385 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((cis)-4-(4-methylpiperazin-1-yl)cyclohexyl)-3-methoxybenzamide |
| 386 | N-((trans)-4-(4-benzylpiperazin-1-yl)cyclohexyl)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzamide |
| 387 | N-((cis)-4-(4-benzylpiperazin-1-yl)cyclohexyl)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzamide |
| 388 | 4-(9-cyclopentyl-5,7,7-trimethyl-6-oxo-6,7,8,9-tetrahydro-5H-pyrimido[4,5-b][1,4]diazepin-2-ylamino)-3-methoxy-N-((trans)-4-morpholinocyclohexyl)benzamide |
| 389 | 4-(9-cyclopentyl-5,7,7-trimethyl-6-oxo-6,7,8,9-tetrahydro-5H-pyrimido[4,5-b][1,4]diazepin-2-ylamino)-3-methoxy-N-((cis)-4-morpholinocyclohexyl)benzamide |
| 390 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-((trans)-4-morpholinocyclohexyl)benzamide |

-continued

| Compound No. | Name |
|---|---|
| 391 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-((cis)-4-morpholinocyclohexyl)benzamide | and pharmaceutically acceptable salts and esters thereof.

Preferably, the compound is selected from the following:

| Compound No. | Name |
|---|---|
| 254 | 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(4-methylpiperazin-1-yl)benzamide |
| 218 | (±)-4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-3-methoxy-N-(quinuclidin-3-yl)benzamide |
| 195 | 4-(9-Cyclopentyl-5,7,7-trimethyl-6-oxo-6,7,8,9-tetrahydro-5H-pyrimido[4,5-b][1,4]diazepin-2-ylamino)-3-methoxy-N-(4-methyl-piperazin-1-yl)-benzamide |
| 221 | 4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-3-methoxy-N-(4-methylpiperazin-1-yl)benzamide |
| 345 | 4-(9-Cyclopentyl-5-methyl-6-oxo-6,7,8,9-tetrahydro-5H-pyrimido[4,5-b][1,4]diazepin-2-ylamino)-3-methoxy-N-[1-(tetrahydro-pyran-4-yl)-piperidin-4-yl]-benzamide |
| 194 | (±)-4-(9-cyclopentyl-5,7,7-trimethyl-6-oxo-6,7,8,9-tetrahydro-5H-pyrimido[4,5-b][1,4]diazepin-2-ylamino)-3-methoxy-N-(quinuclidin-3-yl)benzamide |
| 186 | (±)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(quinuclidin-3-yl)benzamide |
| 347 | (R)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(quinuclidin-3-yl)benzamide |
| 348 | (S)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(quinuclidin-3-yl)benzamide | and pharmaceutically acceptable salts and esters thereof.

Advantageously, certain compounds of the invention exhibit improved selectivity for one or more kinases compared to structurally related compounds previously known in the art In one preferred embodiment, the compound of the invention exhibits selectivity for one or more kinases over one or more other kinases.

For example, in one preferred embodiment, the compound of the invention is capable of preferentially inhibiting PLK family kinases over one or more other protein kinases; thus the compound is capable of "selectively" inhibiting PLK family kinases over one or more other protein kinases. As used herein, the term "selectively" refers to the compounds that are selective for PLK over one or more other protein kinases. Preferably, the selectivity ratio for PLK family kinases over one or more other protein kinases is greater than about 2 to 1, more preferably greater than about 5 to 1 or about 10 to 1, even more preferably greater than about 20 to 1, or 50 to 1 or 100 to 1. Selectivity ratios may be determined by the skilled person in the art.

In one particularly preferred embodiment, the compound of the invention displays selectivity for PLK1. Thus, in one preferred embodiment, the compound of the invention is capable of preferentially inhibiting PLK1 over one or more other protein kinases. Preferably, the selectivity ratio for PLK1 over one or more other protein kinases is greater than about 2 to 1, more preferably greater than about 5 to 1 or about 10 to 1, even more preferably greater than about 20 to 1, or 50 to 1 or 100 to 1.

In an even more preferred embodiment, the compound of the invention displays selectivity for PLK1 over PLK2 and/or PLK3. Thus, in one preferred embodiment, the compound of the invention is capable of preferentially inhibiting PLK1 over PLK2 and/or PLK3. Preferably, the selectivity ratio for PLK1 over PLK2 and/or PLK3 is greater than about 2 to 1, more preferably greater than about 5 to 1 or about 10 to 1, even more preferably greater than about 20 to 1, or 50 to 1 or 100 to 1.

By way of illustration, compound [218] displays selectivity for PLK1 over PLK2 and PLK3 compared with selected compounds of the prior art. For example, compound [218] of the invention is twice as selective for PLK1 versus PLK2 compared to compound [1-64] of WO 07/095188, ca 6-fold more selective than compound [1-76] and 7-fold more selective than compound [I-4] of WO 07/095188. Similarly, compound [218] is 5-fold more selective for PLK1 versus PLK3 compared to compound [1-64] of WO 07/095188, ca 12-fold more selective than compound [1-76] and 5-fold more selective than compound [I-4] of WO 07/095188. Further details may be found in the accompanying Examples.

In another preferred embodiment, the compounds of the invention exhibit superior solubility and/or pharmacokinetic properties when compared to structurally related compounds already known in the art.

For Example, compound [254] displays superior solubility and/or pharmacokinetic properties to Examples [1-76] and [1-253] of WO 07/095188, thereby rendering the compound more suitable for the treatment of diseases. Again, further details of these comparative studies may be found in the accompanying Examples.

Similarly, compound [371] displays advantageous pharmacokinetic properties in terms of its systemic exposure and oral bioavailability, compared to structurally related compounds known in the art.

One preferred embodiment of the invention relates to a subset of compounds that are characterised by low cellular efflux by the ATP-binding cassette (ABC) transporters such as the drug-efflux pump P-glycoprotein (P-gp). It is known that P-gp efflux substrates commonly show poor oral absorption due to the action of P-gp which can transport absorbed drug back into the gut [Ambudkar S. V., et al. (2003) *Oncogene*, 22, 7468-7485]. P-gp can also reduce the systemic exposure of substrates through promoting excretion into bile and urine. In addition to being drug efflux pumps, ABC transporters can confer drug resistance to tumour cells through elevated expression. Expression of P-gp is widely known to be a mechanism by which cancer cells can acquire multi-drug resistance (MDR) [Gottesman M. M., et al. (2002) *Nat. Rev. Cancer*, 2, 48-58]. Certain tumours derived from cells that normally express P-gp can exhibit intrinsic drug resistance [Ambudkar S. V., et al. (2005) *Trends Pharmacol. Sci.*, 26, 385-387]. Drugs that are readily transported out of cells do not accumulate in high levels in transporter-expressing cells, limiting the success of the therapy due to reduced drug-target interaction.

Compounds exhibiting low cellular efflux therefore potentially have applications in the oral treatment of cancer, treatment of epithelial cell derived tumours and drug-resistant malignancies, as well has having a lower potential for inducing drug resistance through increased efflux pump expression. Particularly preferred compounds of the invention that exhibit low cellular efflux include compounds [371], [372] and [377]-[391]. Further details of cell viability assays and cellular efflux studies may be found in the Example 9 and FIG. 3.

In addition, compounds of the invention which exhibit low MDR/parental cell asymmetry in cell viability assays are also more effective at inhibiting PLK1 within MDR tumour cells than compounds of the prior art. Thus, these compounds have greater potential as therapeutic PLK inhibitors. Details of experiments measuring PLK1 inhibition in A2780-A2780/ADR cell line pairs are set forth in the accompanying examples.

Therapeutic Use

The compounds of the invention have been found to possess anti-proliferative activity and are therefore believed to be of use in the treatment of proliferative disorders such as cancers, leukaemias and other disorders associated with uncontrolled cellular proliferation such as psoriasis and restenosis.

Thus, one aspect of the invention relates to the use of a compound of the invention, or a pharmaceutically acceptable salt thereof, in the preparation of a medicament for treating a proliferative disorder.

As used herein the phrase "preparation of a medicament" includes the use of one or more of the above described compounds directly as the medicament in addition to its use in a screening programme for further antiproliferative agents or in any stage of the manufacture of such a medicament.

As defined herein, an anti-proliferative effect within the scope of the present invention may be demonstrated by the ability to inhibit cell proliferation in an in vitro whole cell assay, for example using any of the cell lines AGS, H1299 or SJSA-1. Using such assays it may be determined whether a compound is anti-proliferative in the context of the present invention.

One preferred embodiment relates to the use of one or more compounds of the invention in the treatment of proliferative disorders. Preferably, the proliferative disorder is a cancer or leukaemia. The term proliferative disorder is used herein in a broad sense to include any disorder that requires control of the cell cycle, for example cardiovascular disorders such as restenosis and cardiomyopathy, auto-immune disorders such as glomerulonephritis and rheumatoid arthritis, dermatological disorders such as psoriasis, anti-inflammatory, anti-fungal, antiparasitic disorders such as malaria, emphysema and alopecia. In these disorders, the compounds of the present invention may induce apoptosis or maintain stasis within the desired cells as required.

In one preferred embodiment of the invention, the proliferative disorder is cancer or leukaemia, more preferably cancer.

In one preferred embodiment, the proliferative disorder is a solid tumour.

In another preferred embodiment, the proliferative disorder is a hematological cancer. Preferably, the haematological cancer is leukaemia, more preferably, advanced leukemias or myelodysplastic syndromes (MDS). Other examples include acute myelogenous leukemia (AML), acute lymphocytic leukemia (ALL) or chronic lymphocytic leukemia (CLL).

In another preferred embodiment, the proliferative disorder is glomerulonephritis.

In yet another preferred embodiment, the proliferative disorder is rheumatoid arthritis.

In another preferred embodiment, the proliferative disorder is psoriasis.

In another preferred embodiment, the proliferative disorder is a chronic obstructive pulmonary disorder.

The compounds of the invention may inhibit any of the steps or stages in the cell cycle, for example, formation of the nuclear envelope, exit from the quiescent phase of the cell cycle (G0), G1 progression, chromosome decondensation, nuclear envelope breakdown, START, initiation of DNA replication, progression of DNA replication, termination of DNA replication, centrosome duplication, G2 progression, activation of mitotic or meiotic functions, chromosome condensation, centrosome separation, microtubule nucleation, spindle formation and function, interactions with microtubule motor proteins, chromatid separation and segregation, inactivation of mitotic functions, formation of contractile ring, and cytokinesis functions. In particular, the compounds of the invention may influence certain gene functions such as chromatin binding, formation of replication complexes, replication licensing, phosphorylation or other secondary modification activity, proteolytic degradation, microtubule binding, actin binding, septin binding, microtubule organising centre nucleation activity and binding to components of cell cycle signalling pathways.

In one embodiment of the invention, the compound of the invention is administered in an amount sufficient to inhibit at least one PLK enzyme.

A further aspect of the invention relates to a method of treating a PLK-dependent disorder, said method comprising administering to a subject in need thereof, a compound of the invention or a pharmaceutically acceptable salt thereof, as defined above in an amount sufficient to inhibit PLK.

The polo-like kinases (PLKs) constitute a family of serine/threonine protein kinases. Mitotic *Drosophila melanogaster* mutants at the polo locus display spindle abnormalities [Sunkel et al., *J. Cell Sci.*, 1988, 89, 25] and polo was found to encode a mitotic kinase [Llamazares et al., *Genes Dev.*, 1991, 5, 2153]. In humans, there exist three closely related PLKs [Glover et al., *Genes Dev.*, 1998, 12, 3777]. They contain a highly homologous amino-terminal catalytic kinase domain and their carboxyl termini contain two or three conserved regions, the polo boxes. The function of the polo boxes remains incompletely understood but they are implicated in the targeting of PLKs to subcellular compartments [Lee et al., *Proc. Natl. Acad. Sci. USA*, 1998, 95, 9301; Leung et al., *Nat. Struct. Biol.*, 2002, 9, 719], mediation of interactions with other proteins [Kauselmann et al., *EMBO J.*, 1999, 18, 5528], or may constitute part of an autoregulatory domain [Nigg, *Curr. Opin. Cell Biol.*, 1998, 10, 776]. Furthermore, the polo box-dependent PLK1 activity is required for proper metaphase/anaphase transition and cytokinesis [Yuan et al., *Cancer Res.*, 2002, 62, 4186; Seong et al., *J. Biol. Chem.*, 2002, 277, 32282].

Studies have shown that human PLKs regulate some fundamental aspects of mitosis [Lane et al., *J. Cell. Biol.*, 1996, 135, 1701; Cogswell et al., *Cell Growth Differ.*, 2000, 11, 615]. In particular, PLK1 activity is believed to be necessary for the functional maturation of centrosomes in late G2/early prophase and subsequent establishment of a bipolar spindle. Depletion of cellular PLK1 through the small interfering RNA (siRNA) technique has also confirmed that this protein is required for multiple mitotic processes and completion of cytokinesis [Liu et al., *Proc. Natl. Acad. Sci. USA*, 2002, 99, 8672].

In a more preferred embodiment of the invention, the compound of the invention is administered in an amount sufficient to inhibit PLK1.

Of the three human PLKs, PLK1 is the best characterized; it regulates a number of cell division cycle effects, including the onset of mitosis [Toyoshima-Morimoto et al., *Nature*, 2001, 410, 215; Roshak et al., *Cell. Signalling*, 2000, 12, 405], DNA-damage checkpoint activation [Smits et al., *Nat. Cell Biol.*, 2000, 2, 672; van Vugt et al., *J. Biol. Chem.*, 2001, 276, 41656], regulation of the anaphase promoting complex [Sumara et al., *Mol. Cell*, 2002, 9, 515; Golan et al., *J. Biol. Chem.*, 2002, 277, 15552; Kotani et al., *Mol. Cell*, 1998, 1, 371], phosphorylation of the proteasome [Feng et al., *Cell Growth Differ.*, 2001, 12, 29], and centrosome duplication and maturation [Dai et al., *Oncogene*, 2002, 21, 6195].

In one particularly preferred embodiment, the compounds of the invention are ATP-antagonistic inhibitors of PLK1.

In the present context ATP antagonism refers to the ability of an inhibitor compound to diminish or prevent PLK catalytic activity, i.e. phosphotransfer from ATP to a macromolecular PLK substrate, by virtue of reversibly or irreversibly binding at the enzyme's active site in such a manner as to impair or abolish ATP binding.

In another preferred embodiment, the compound of the invention is administered in an amount sufficient to inhibit PLK2 and/or PLK3.

A further aspect of the invention relates to a method of inhibiting PLK in a cell comprising contacting said cell with an amount of a compound of formula I, or a pharmaceutically acceptable salt thereof, such that PLK is inhibited in said cell.

Yet another aspect of the invention relates to a method of treating a proliferative disorder comprising inhibiting PLK by administering to a subject in need thereof, a therapeutically effective amount of a compound of formula I, or a pharmaceutically acceptable salt thereof, such that treatment of said proliferative disorder occurs.

In another preferred embodiment, the compound of the invention is administered in an amount sufficient to inhibit at least one aurora kinase. Preferably, the aurora kinase is aurora kinase A, aurora kinase B or aurora kinase C.

A further aspect of the invention relates to a method of treating an aurora kinase-dependent disorder, said method comprising administering to a subject in need thereof, a compound of the invention or a pharmaceutically acceptable salt thereof, as defined above in an amount sufficient to inhibit an aurora kinase.

Another aspect relates to the use of a compound of the invention for inhibiting a protein kinase.

A further aspect of the invention relates to a method of inhibiting a protein kinase, said method comprising contacting said protein kinase with a compound of the invention.

Preferably, the protein kinase is selected from an aurora kinase and a PLK. More preferably, the protein kinase is a PLK, more preferably PLK1.

Pharmaceutical Compositions

A further aspect of the invention relates to a pharmaceutical composition comprising a compound of the invention admixed with one or more pharmaceutically acceptable diluents, excipients or carriers. Even though the compounds of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and PJ Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Salts/Esters

The compounds of the invention can be present as salts or esters, in particular pharmaceutically acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Preferably, the salt is an HCl salt.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers and tautomers of the compounds of the invention. The person skilled in the art will recognise compounds that possess an optical properties (one or more chiral carbon atoms) or tautomeric characteristics. The corresponding enantiomers and/or tautomers may be isolated/prepared by methods known in the art.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes solvate forms of the compounds of the present invention. The terms used in the claims encompass these forms.

Polymorphs

The invention furthermore relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes the compounds of the present invention in prodrug form. Such prodrugs are generally compounds of the invention wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.01 to 30 mg/kg body weight, such as from 0.1 to 10 mg/kg, more preferably from 0.1 to 1 mg/kg body weight.

In an exemplary embodiment, one or more doses of 10 to 150 mg/day will be administered to the patient for the treatment of malignancy.

Combinations

In a particularly preferred embodiment, the one or more compounds of the invention are administered in combination with one or more other active agents, for example, existing anticancer drugs available on the market. In such cases, the compounds of the invention may be administered consecutively, simultaneously or sequentially with the one or more other active agents.

Anticancer drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance in early tumor cells which would have been otherwise responsive to initial chemotherapy with a single agent. An example of the use of biochemical interactions in selecting drug combinations is demonstrated by the administration of leucovorin to increase the binding of an active intracellular metabolite of 5-fluorouracil to its target, thymidylate synthase, thus increasing its cytotoxic effects.

Numerous combinations are used in current treatments of cancer and leukemia. A more extensive review of medical practices may be found in "Oncologic Therapies" edited by E. E. Vokes and H. M. Golomb, published by Springer.

Beneficial combinations may be suggested by studying the growth inhibitory activity of the test compounds with agents known or suspected of being valuable in the treatment of a particular cancer initially or cell lines derived from that cancer. This procedure can also be used to determine the order of administration of the agents, i.e. before, simultaneously, or after delivery. Such scheduling may be a feature of all the cycle acting agents identified herein.

Process

Another aspect relates to a process for preparing a compound of the invention, said process comprising the steps of:

(i) converting a compound of formula (II) to a compound of formula (IV) either directly or via isolation of a compound of formula (III); and (ii) converting said compound of formula (IV) to a compound of formula (I)

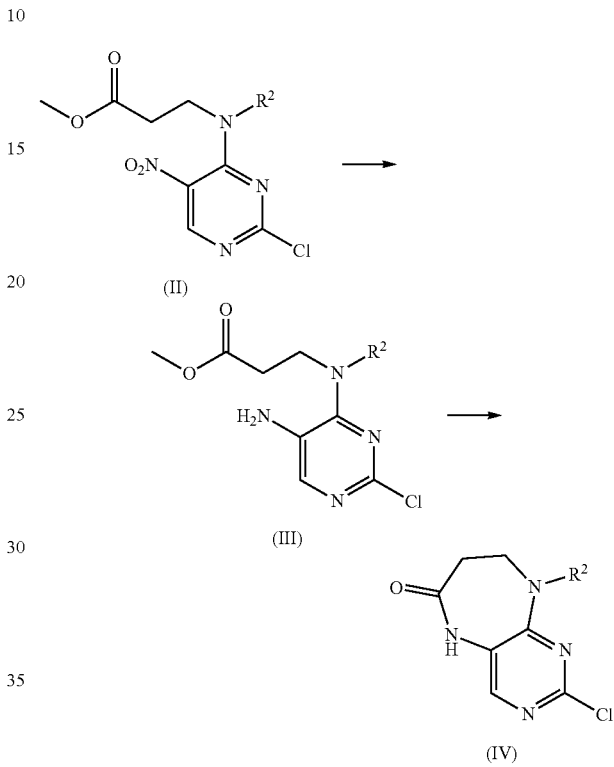

Preferably, step (i) comprises heating said compound of formula (II) with $NH_4Cl$ and Fe in is $EtOH/H_2O$.

The present invention is further illustrated by way of the following non-limiting examples.

EXAMPLES

General Experimental

Chemicals and solvents were purchased from commercial sources and were used as received unless otherwise stated. Anhydrous $MgSO_4$ was used as a standard drying agent for organic solutions unless otherwise stated. NMR spectra were recorded using a Varian INOVA-500 instrument. Chemical shifts are reported in parts per million relative to internal tetramethyl silane standard. Coupling constants (J) are quoted to the nearest 0.1 Hz. The following abbreviations are used: s, singlet; d, doublet; t, triplet; q, quartet; qu, quintuplet; m, multiplet and br, broad. Mass spectra were obtained using a Waters ZQ2000 single quadrupole mass spectrometer with electro spray ionisation (ESI). Analytical and preparative RP-HPLC was performed using either Vydac 218TP54 (250×4.6 mm) and Vydac 218TP1022 (250×22 mm) columns using a linear gradient elution of water/acetonitrile systems (containing 0.1% trifluoroacetic acid) at flow rates of 1 mL/min (analytical) and 9 mL/min (preparative). Analytical gradients used were as follows:

| Method | % Acetonitrile Time = 0 min | % Acetonitrile Time = 20 min | % Acetonitrile Time = 25 min |
| --- | --- | --- | --- |
| Vydac 1 | 0 | 60 | 100 |
| Vydac 2 | 10 | 70 | 100 |
| Vydac 3 | 20 | 80 | 100 |

Alternatively Xbridge (100×4.6 mm) and Xbridge (100× 19 mm) columns using a linear gradient of water/acetonitrile systems (containing 0.1% ammonium hydroxide) at flow rates of 1 mL/min (analytical) and 20 mL/min (preparative). Analytical gradients used were as follows:

| Method | % Acetonitrile Time = 0 min | % Acetonitrile Time = 5 min | % Acetonitrile Time = 10 min | % Acetonitrile Time = 12 min |
| --- | --- | --- | --- | --- |
| XBridge1 | 0 | | 50 | 100 |
| XBridge2 | 10 | | | 100 |
| XBridge3 | 20 | 70 | | 100 |

Silica gel (EM Kieselgel 60, 0.040-0.063 mm, Merck) or ISOLUTE pre-packed columns (Biotage) were used for flash chromatography.

Abbreviations:
DIPEA diisopropylethyl amine
DCM dichloromethane
DMF dimethylformamide
DMSO dimethyl sulfoxide
EtOAc ethyl acetate
EtOH ethanol
HCl hydrochloric acid
$K_2CO_3$ potassium carbonate
MeI methyl iodide
MeOH methanol
$MgSO_4$ magnesium sulfate
NaH sodium hydride
NaCl sodium chloride
$NH_4Cl$ ammonium chloride
RM reaction mixture
rt room temperature
TBTU O-(Benzotriazol-1-yl)-N,N,N',N'-tetramethyluronium tetrafluoroborate
TFA trifluoroacetic acid
TFE 2,2,2-trifluoroethanol
THF tetrahydrofuran

Example 1

Compound [2]: 4-(9-Cyclopentyl-5-methyl-6-oxo-6,7,8,9-tetrahydro-5H-pyrimido[4,5-b][1,4]diazepin-2-ylamino)-N-(1-methyl-piperidin-4-yl)-benzamide

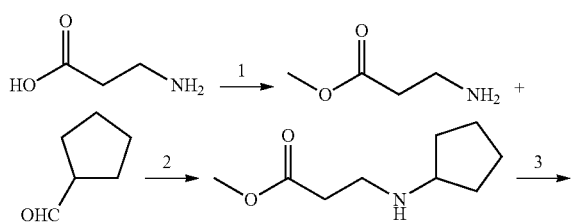

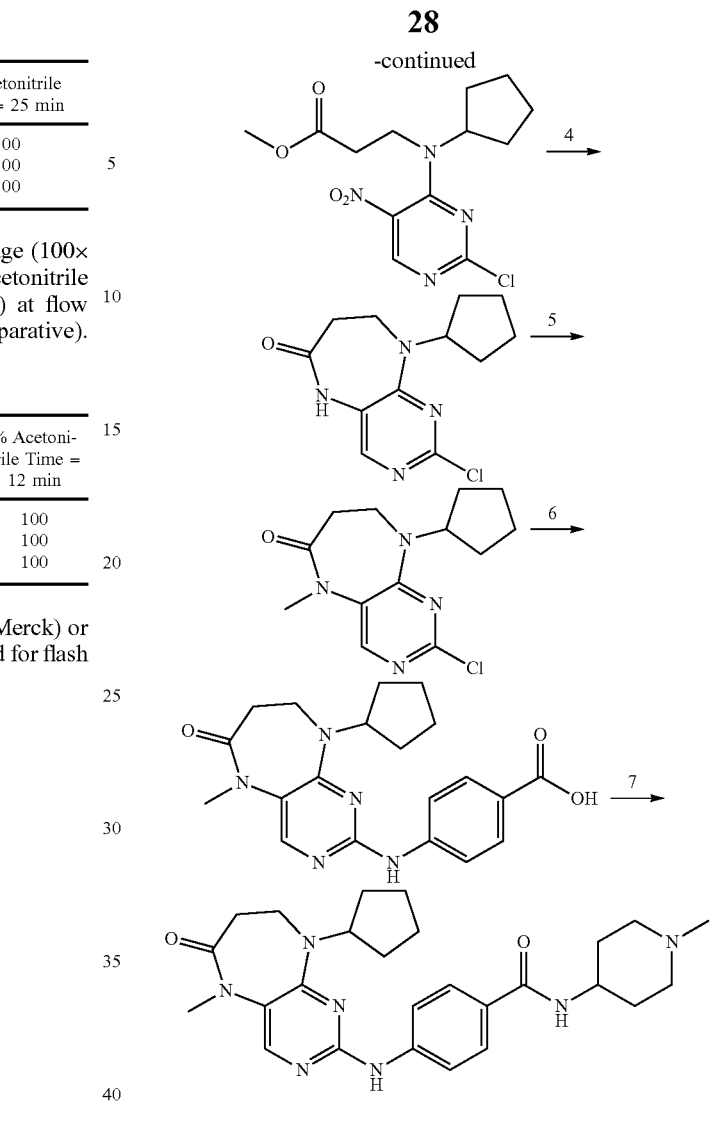

1. Thionyl chloride (2.1 eq), MeOH, 0° C. for addition, reflux 2 h; 2. cyclopentanone (0.77 eq), sodium acetate (0.77 eq), sodium triacetoxyborohydride (1.11 eq), DCM, rt 16 h; 3. 2,4-dichloro-5-nitropyrimidine (1.1 eq), $K_2CO_3$ (1 eq), acetone, 0° C.-rt 16 h; 4. $NH_4Cl$ (8.5 eq), Fe (8 eq), EtOH/H2O (4:1), reflux 2.5 h; —not isolated 5. MeI (1.18 eq), NaH (1.07 eq), DMF, −10° C.—rt, 3 h; 6. 4-amino-3-methoxybenzoic acid (1.5 eq), conc. HCl, $H_2O$/EtOH (4:1), reflux 48 h; 7. DIPEA (2 eq), TBTU (1.1 eq), 4-aminomethylpiperidine (1.2 eq), DCM, rt 16 h.

Step 1: Methyl 3-aminopropanoate

β-Alanine (9.37 g, 0.105 mol), was added to MeOH (50 ml) and the mixture cooled to 0° C. using an ice-bath before the dropwise addition of thionyl chloride [caution: exothermic addition]. Once the addition was complete the reaction was warmed to rt, then refluxed for 2 h. The solvent was next evaporated under reduced pressure and the resulting oil treated with t-butylmethyl ester and the resulting crystals filtered off and further dried in vacuo to give a white crystalline solid (11 g, quant.); $^1H$ (DMSO-$d_6$): δ 2.73 (dd, J=7 Hz, 2H, $CH_2$), 2.98 (dd, J=7 Hz, 2H, $CH_2$), 3.61 (s, 3H, $CH_3$), 8.28 (bs, 2H, $NH_2$); MS+ve: 104.1.

Step 2: Methyl 3-(cyclopentylamino)propanoate

Methyl 3-aminopropanoate (9.37 g, 0.09 mol) was solubilised in DCM (200 ml) and cyclopentanone (6.43 ml, 0.07 mol), sodium acetate (5.96 g, 0.07 mol) and sodium triacetoxyborohydride (22 g, 0.10 mol) were added. The reaction was stirred at rt for 16 h. 20% sodium bicarbonate (100 ml) and 2M sodium hydroxide (50 ml) were then added and the product extracted using DCM/$H_2O$. The organic extracts were combined, washed with sat NaCl, dried using $MgSO_4$, filtered and the filtrate evaporated under reduced pressure and further dried in vacuo to give the product as a pale yellow oil (8.90 g, 55%); MS+ve: 172.4.

Step 3: Methyl 3-[cyclopentyl(2-chloro-5-nitropyrimidin-4-yl)amino]propanoate Methyl 3-(cyclopentylamino)propanoate (838 mg, 0.005 mol) and $K_2CO_3$ (676 mg, 0.005 mol) were added to acetone (5 ml) and the resulting mixture cooled to 0° C. using an ice-bath before the addition of 2,4-dichloro-5-nitropyrimidine (1.044 g, 1.1 eq). The reaction mixture (RM) was then warmed to rt and stirring continued for an additional 16 h before the addition of a further 0.12 eq of the pyrimidine. Stirring was then continued for a further 3 h. The RM was then evaporated under reduced pressure and the product extracted using EtOAc/$H_2O$. The organic extracts were combined, washed with sat NaCl, dried using $MgSO_4$, filtered and the filtrate evaporated under reduced pressure and further dried in vacuo to give the product as a brown oily residue (1.04 g, 65%); $R_t$=16 min (Vydac 1); ME+ve: 329.1.

Step 4: 2-Chloro-9-cyclopentyl-5,7,8,9-tetrahydro-6H-pyrimido[4,5-b][1,4]diazepin-6-one Methyl 3-[cyclopentyl(2-chloro-5-nitropyrimidin-4-yl)amino]propanoate (1.00 g, 0.003 mol) and $NH_4Cl$ (1.38 g, 0.025 mol, 8.5 eq) were added to EtOH/$H_2O$ (4:1 ml, 10 ml) and the mixture heated to reflux before the portion-wise addition of iron powder (1.36 g, 0.024 mol, 8 eq). The RM was then refluxed for an additional 2 h. Progress of the reaction was monitored by HPLC and when no SM remained the RM was filtered hot through celite. The celite was washed with EtOAc (10 ml) and EtOH (10 ml) [both hot] and the filtrate evaporated under reduced pressure and further dried in vacuo to give the product as a brown solid (350 mg, 43%); $R_t$=12 min (Vydac 1); MS+ve: 267.2.

Step 5: 2-Chloro-9-cyclopentyl-5-methyl-5,7,8,9-tetrahydro-6H-pyrimido[4,5-b][1,4]diazepin-6-one 2-Chloro-9-cyclopentyl-5,7,8,9-tetrahydro-6H-pyrimido[4,5-b][1,4]diazepin-6-one (318 mg, 0.0012 mol) and MeI (88 µl, 0.0014 mol, 1.18 eq) were added to DMF (5 ml) and the solution cooled to −10° C. using acetone/dry ice before the addition of NaH (30 mg, 0.0013 mol, 1.07 eq). The RM was then stirred at 0° C. for 30 min and rt for 30 min. The RM was concentrated and the product extracted using EtOAc/$H_2O$. The organic extracts were combined, washed with sat NaCl, dried using $MgSO_4$, filtered and the filtrate evaporated under reduced pressure and further dried in vacuo to give the product as a purple oily residue (252 mg, 75%); $R_t$=13 min (Vydac 1); MS+ve: 281.2.

Step 6: (Compound [1]) 4-(9-Cyclopentyl-5-methyl-6-oxo-6,7,8,9-tetrahydro-5H-pyrimido[4,5-b][1,4]diazepin-2-ylamino)-benzoic acid Coupling Method A
2-Chloro-9-cyclopentyl-5-methyl-5,7,8,9-tetrahydro-6H-pyrimido[4,5-b][1,4]diazepin-6-one (248 mg, 0.0009 mol) and 4-amino-3-methoxybenzoic acid (221 mg, 0.0013 mol, 1.5 eq), conc. HCl (152 µl) and $H_2O$/EtOH (8:2 ml) were added to a RBF and the resulting RM heated to reflux for 4 h. Progress of the reaction was monitored by HPLC and when no starting material remained (4 h reaction time), the RM was concentrated under reduced pressure and the product extracted using DCM/$H_2O$. The organic extracts were combined, washed with sat NaCl, dried using $MgSO_4$, filtered and the filtrate evaporated under reduced pressure and further dried in vacuo to give a brown oily residue. A few drops of MeOH were added to the residue and the solid ppt formed was collected by suction filtration, washed with MeOH and further dried in vacuo to give the product as a purple solid (51 mg, 14%); $R_t$=11.2 min (0_60_20 min, purity 100%); $^1$H NMR (DMSO-$d_6$): δ 1.61 (bs, 4H, cyclopent-H), 1.72 (bs, 2H, cyclopent-H), 1.94 (bs, 2H, cyclopent-H), 2.59 (dd, J=4.5 Hz, 2H, $CH_2$), 3.18 (s, 3H, $CH_3$), 3.63 (dd, J=4.5 Hz, 2H, $CH_2$), 3.95 (s, 3H, $CH_3$), 7.51 (s, 1H), 7.56 (d, J=8 Hz, 1H, phe-H), 7.82 (s, 1H, 8.10 (s, 1H, 8.47 (d, J=8.5 Hz, 1H, phe-H), 12.64 (bs, 1H, NH); MS+ve: 412.2.

Step 7: (Compound [2]): 4-(9-Cyclopentyl-5-methyl-6-oxo-6,7,8,9-tetrahydro-5H-pyrimido[4,5-b][1,4]diazepin-2-ylamino)-N-(1-methyl-piperidin-4-yl)-benzamide 4-(9-Cyclopentyl-5-methyl-6-oxo-6,7,8,9-tetrahydro-5H-pyrimido[4,5-b][1,4]diazepin-2-ylamino)-benzoic acid (35 mg, 0.085 mmol), DIPEA (28 µl, 0.17 mmol, 2 eq) and TBTU (30 mg, 0.093 mmol, 1.1 eq) were added to 3 ml DCM and the resulting solution stirred at rt for 30 min before the addition of 4-aminomethylpiperidine (13 µl, 0.10 mmol, 1.2 eq). The RM was then stirred at rt for 16 h. The RM was concentrated and the product extracted using DCM/$H_2O$. The organic extracts were combined, washed with sat NaCl, dried using $MgSO_4$, filtered and the filtrate evaporated under reduced pressure and further dried in vacuo to give a yellow oily residue (21 mg, 49%); $R_t$=9.86 min (0_60_20 min, purity 100%); $^1$H NMR ($CD_3OD$): δ 1.69-1.75 (m, 6H), 1.82 (bs, 2H), 1.96-1.99 (m, 2H), 2.03-2.05 (bs, 2H), 2.18-2.23 (m, 2H), 2.34 (s, 3H, $CH_3$), 2.68 (dd, J=4.5 Hz, 2H, $CH_2$), 2.95-2.97 (m, 2H), 3.28 (s, 3H, $CH_3$), 3.73 (dd, J=4.5 Hz, 2H, $CH_2$), 3.89-3.94 (m, 1H, CH), 4.01 (s, 3H, $CH_3$), 4.91-4.96 (m, 1H, CH), 7.49-7.51 (m, 2H), 8.02 (bs, 1H), 8.50 (d, J=8.5 Hz, 1H, phe-H); MS+ve: 508.2.

Aminoester Intermediates
The following intermediates were prepared by the method described in Example 1, step 2: 3-Cyclopentylamino-butyric acid methyl ester

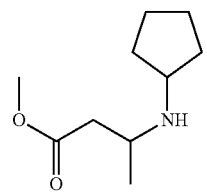

MS+ve: 186.3

3-Cyclohexylamino-butyric acid methyl ester

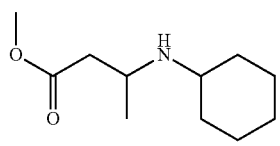

MS+ve: 200.3

3-Cyclopentylamino-2-methyl-propionic acid methyl ester

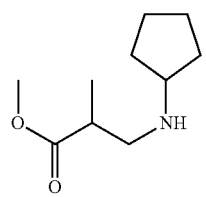

$^1$H NMR (CDCl$_3$): 1.18 (3H, d, J 7 Hz, CH3), 1.33 (2H, m, CH2), 1.53 (2H, m, CH2), 1.67 (2H, m, CH2), 1.82 (2H, m, CH2), 2.63 (2H, m, CH2), 2.87 (1H, m, CH), 3.06 (1H, m, CH), 3.69 (3H, s, OCH3)

3-Cyclohexylamino-propionic acid methyl ester

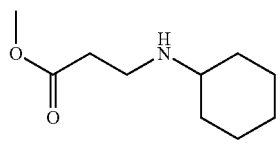

MS+ve: 186.4.

3-Cyclopentylamino-4-methyl-pentanoic acid methyl ester

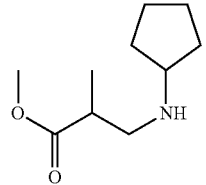

$^1$H NMR (CDCl$_3$): 1.18 (3H, d, J 7 Hz, CH3), 1.33 (2H, m, CH2), 1.53 (2H, m, CH2), 1.67 (2H, m, CH2), 1.82 (2H, m, CH2), 2.63 (2H, m, CH2), 2.87 (1H, m, CH), 3.06 (1H, m, CH), 3.69 (3H, s, OCH3)

3-(1-Ethyl-propylamino)-propionic acid methyl ester

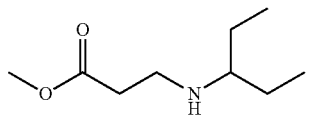

$^1$H NMR (CDCl$_3$): 0.89 (6H, t, J 8 Hz, CH3), 1.44 (4H, m, CH2CH3), 1.77 (1H, bs, NH), 2.39 (1H, m, CH), 2.53 (2H, m, CH2), 2.89 (2H, m, CH2), 3.69 (3H, s, OCH3)

3-(Tetrahydro-pyran-4-ylamino)-propionic acid methyl ester

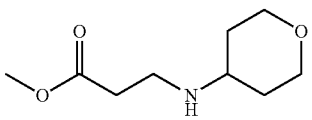

$^1$H NMR (CDCl$_3$): 1.41 (2H, m, CH2), 1.86 (2H, m, CH2), 2.54 (2H, m, CH2), 2.71 (1H, m, CH), 2.95 (2H, m, CH2), 3.44 (2H, t, J 11.5 Hz, CH2), 3.71 (3H, s, OCH3), 3.99 (2H, d, J 11 Hz, CH2) 1-Cyclopentylaminomethyl-cyclopropanecarboxylic acid methyl ester

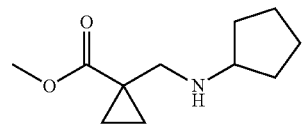

$^1$H NMR (CDCl$_3$): 0.84 (3H, t, J 7 Hz, CH3), 1.25 (4H, m, CH2), 1.37 (2H, m, CH), 1.54 (2H, m, CH), 1.70 (2H, m, CH), 1.83 (2H, m, CH), 2.71 (2H, s, CH2), 3.10 (1H, m, CH), 4.16 (2H, q, J 7 Hz, CH2CH3)

3-Cyclopentylamino-2,2-dimethyl-propionic acid ethyl ester

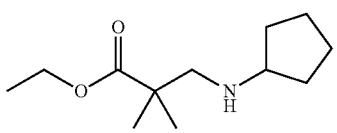

$^1$H NMR (CDCl3): 1.19 (6H, s, CH3), 1.25 (3H, t, J 7 Hz, CH3), 1.28 (2H, m, CH), 1.49 (2H, m, CH), 1.65 (2H, m, CH), 2.64 (1H, s, CH2), 3.01 (1H, m, CH), 4.10 (2H, q, J 7.5 Hz, CH2)

Alternative Method Step 2a: Methyl 3-aminopropanoate

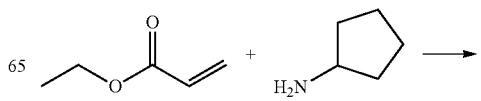

-continued

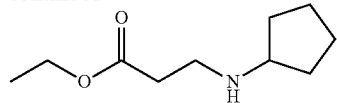

Methyl acrylate (4.50 ml, 4.302 g, 49.97 mmole, 0.99 eq) was added dropwise to a solution of cyclopentylamine (5.00 ml, 4.315 g, 50.68 mmole) in methanol (120 ml) at −60° C. (dry ice, acetone). The reaction mixture was allowed to warm to room temperature and stirred overnight. The solvent was removed (reduced pressure, vacuo) to afford the product as an oil (8.236 g, 96% crude yield). Proton NMR indicated that the product contained ~25% of a dialkylated byproduct.

The following compounds were prepared by a similar method. 3-Phenylamino-propionic acid ethyl ester

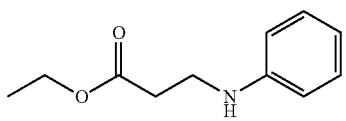

$^1$H NMR (CDCl3): 1.29 (3H, t, J 7.5 Hz, CH3), 2.64 (2H, t, J 6.5 Hz, CH2), 3.48 (2H, t, J 6.5 Hz, CH2), 4.18 (2H, q, J 7 Hz, CH2), 6.65-6.74 (5H, m, Ar—H)

Nitropyrimidine Intermediates

The following intermediates were also prepared by the method described in Example 1 step 3: 3-[(2-Chloro-5-nitro-pyrimidin-4-yl)-cyclopentyl-amino]-butyric acid methyl ester

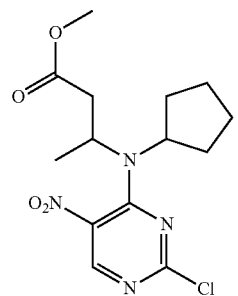 [SMILES: COC(=O)CC(C)N(c1nc(Cl)ncc1[N+](=O)[O-])C1CCCC1]

$R_t$=18.0 min (0_60_20 min); MS+ve: 343.20.

3-[(2-Chloro-5-nitro-pyrimidin-4-yl)-cyclohexyl-amino]-butyric acid methyl ester

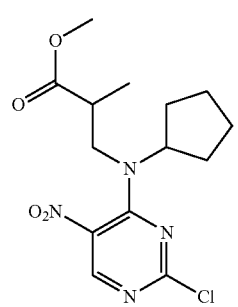 [SMILES: COC(=O)C(C)CN(c1nc(Cl)ncc1[N+](=O)[O-])C1CCCC1]

MS+ve: 357.2.

3-[(2-Chloro-5-nitro-pyrimidin-4-yl)-cyclopentyl-amino]-2-methyl-propionic acid methyl ester

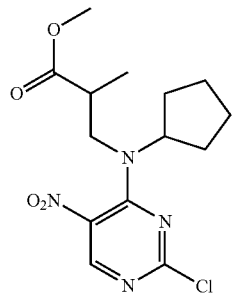

$^1$H NMR (CDCl3): 1.22 (3H, d, J 12 Hz, CH3), 1.57 (2H, m, CH2), 1.76 (2H, m, CH2), 1.93 (2H, m, CH2), 1.98 (2H, m, CH2), 3.18 (1H, s, CH), 3.61 (3H, m, CH+CH2), 3.68 (3H, s, OCH3), 8.74 (1H, s, Pyr-H)

3-[(2-Chloro-5-nitro-pyrimidin-4-yl)-cyclohexyl-amino]-propionic acid methyl ester

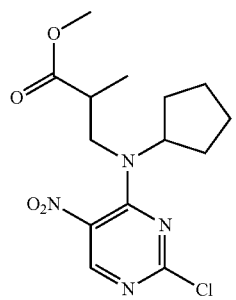

Rt=17.6 min (Vydac 1); MS+ve: 343.1.

3-[(2-Chloro-5-nitro-pyrimidin-4-yl)-cyclopentyl-amino]-4-methyl-pentanoic acid methyl ester

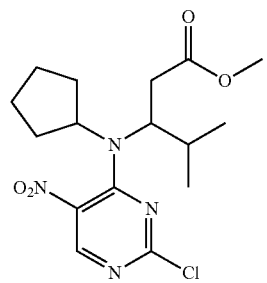 [SMILES: COC(=O)CC(C(C)C)N(c1nc(Cl)ncc1[N+](=O)[O-])C1CCCC1]

$^1$H NMR (CDCl3): 0.94 (6H, t, J 7 Hz), 1.45-1.82 (7H, m, 3×CH2+CH), 2.17 (1H, m, CH), 2.69 (2H, m, 2×CH), 3.35 (2H, m, CH2), 2.58 (1H, m, CH), 3.73 (3H, s, OCH3), 8.64 (1H, s, Pyr-H)

3-[(2-Chloro-5-nitro-pyrimidin-4-yl)-(1-ethyl-propyl)-amino]-propionic acid methyl ester

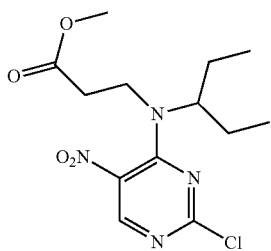 [SMILES: CCC(CC)N(CCC(=O)OC)c1nc(Cl)ncc1[N+](=O)[O-]]

MS (+ve) 331.1, 333.1

3-[(2-Chloro-5-nitro-pyrimidin-4-yl)-(tetrahydro-pyran-4-yl)-amino]-propionic acid methyl ester

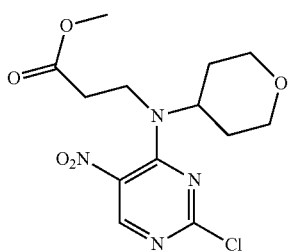 [SMILES: COC(=O)CCN(c1nc(Cl)ncc1[N+](=O)[O-])C1CCOCC1]

MS (+ve) 345.1, 347.0; tR=12.62 min (Vydac 1).

3-[Benzyl-(2-chloro-5-nitro-pyrimidin-4-yl)-amino]-propionic acid ethyl ester

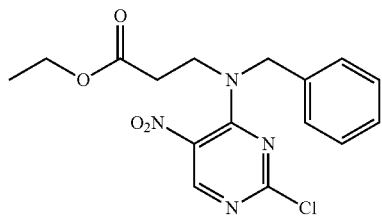 [SMILES: CCOC(=O)CCN(Cc1ccccc1)c1nc(Cl)ncc1[N+](=O)[O-]]

$^1$H NMR (CDCl3): 1.26 (3H, t, J 7 Hz, CH3), 2.73 (2H, t, J 7 Hz, CH2), 3.85 (2H, m, CH2), 4.16 (2H, q, J 7 Hz, CH2), 4.71 (2H, s, CH2), 7.20 (2H, m, Ar—H), 7.37 (3H, m, Ar—H), 8.69 (1H, s, Pyr-H).

3-[(2-Chloro-5-nitro-pyrimidin-4-yl)-phenyl-amino]-propionic acid ethyl ester

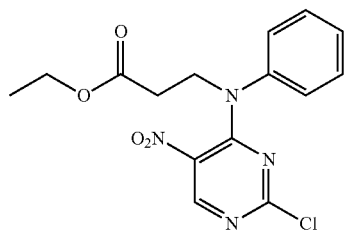 [SMILES: CCOC(=O)CCN(c1ccccc1)c1nc(Cl)ncc1[N+](=O)[O-]]

$^1$H NMR (CDCl3): 1.22 (3H, t, J 7.5 Hz, CH3), 2.73 (2H, t, J 7 Hz, CH2), 4.09 (2H, q, J 7 Hz, CH2), 4.43 (2H, t, J 7 Hz, CH2), 7.14-7.48 (5H, m, Ar—H), 8.57 (1H, s, Pyr-H).

1-{[(2-Chloro-5-nitro-pyrimidin-4-yl)-cyclopentyl-amino]-methyl}cyclopropanecarboxylic acid ethyl ester

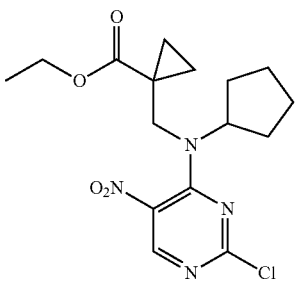 [SMILES: CCOC(=O)C1(CN(c2nc(Cl)ncc2[N+](=O)[O-])C2CCCC2)CC1]

MS (+ve) 381.1, 383.3; tR=4.80 min (XBridge 1).

3-[(2-Chloro-5-nitro-pyrimidin-4-yl)-cyclopentyl-amino]-2,2-dimethyl-propionic acid ethyl ester

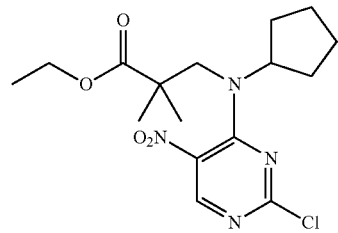 [SMILES: CCOC(=O)C(C)(C)CN(c1nc(Cl)ncc1[N+](=O)[O-])C1CCCC1]

MS (+ve) 371.1, 373.1; tR=4.67 min (XBridge 1).

Aminopyrimidine-Esters Leading to Chloropyrimidine-Diazepines

The following compounds were isolated from the reduction reaction as shown in Example 1, Step 4 as uncyclised intermediates.

3-[(5-Amino-2-chloro-pyrimidin-4-yl)-benzyl-amino]-propionic acid ethyl ester

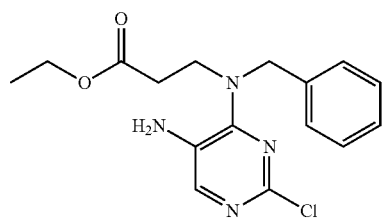 [SMILES: CCOC(=O)CCN(Cc1ccccc1)c1nc(Cl)ncc1N]

$^1$H NMR (CDCl3): 1.26 (3H, t, J 7.5 Hz, CH3), 2.73 (2H, t, J 7 Hz, CH2), 3.86 (2H, t, J 7 Hz, CH2), 4.14 (2H, q, J 7 Hz, CH2), 4.86 (2H, s, CH2), 7.26-7.39 (5H, m, Ar—H), 7.94 (1H, s, Pyr-H)

3-[(5-Amino-2-chloro-pyrimidin-4-yl)-phenyl-amino]-propionic acid ethyl ester

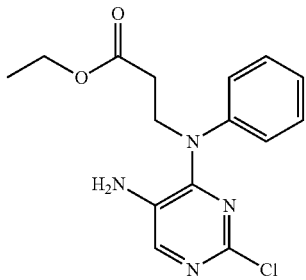 [SMILES: CCOC(=O)CCN(c1ccccc1)c1nc(Cl)ncc1N]

MS (+ve) 321.2, 323.2; tR=3.54 min (XBridge 1).

1-{[(5-Amino-2-chloro-pyrimidin-4-yl)-cyclopentyl-amino]-methyl}-cyclopropanecarboxylic acid ethyl ester

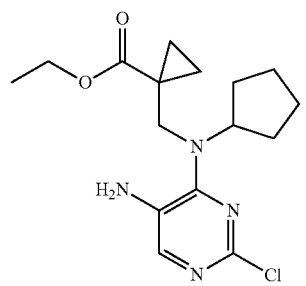

MS (+ve) 339.2, 341.2; tR=4.15 min (XBridge 1).

3-[(5-Amino-2-chloro-pyrimidin-4-yl)-cyclopentyl-amino]-2,2-dimethyl-propionic acid ethyl ester

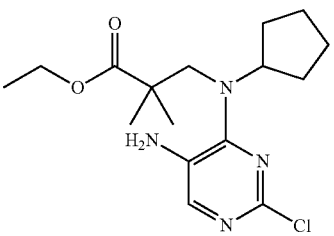 [SMILES: CCOC(=O)C(C)(C)CN(c1nc(Cl)ncc1N)C1CCCC1]

MS (+ve) 341.2, 343.2; tR=4.25 min (XBridge 1).

The above compounds were then cyclised using the following method.

The relevant compound (5 mmol) in DMF (10 ml) was heated to 140° C. for 2 hours. Solvent was evaporated in vacuo, ethyl acetate (10 ml) added, and the resulting solid filtered and dried under vacuum to give the compounds listed below.

Note: This reaction may also be carried out with DMSO/NaH

9-Benzyl-2-chloro-5,7,8,9-tetrahydro-pyrimido[4,5-b][1,4]diazepin-6-one

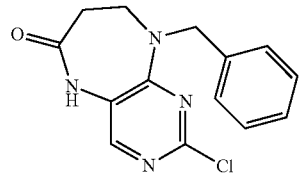

¹H NMR (DMSO): 2.72 (2H, m, CH2), 3.67 (2H, m, CH2), 4.86 (2H, s, CH2), 7.26-7.37 (5H, m, Ar—H), 7.88 (1H, s, Pyr-H), 9.77 (1H, s, NH)

2-Chloro-9-phenyl-5,7,8,9-tetrahydro-pyrimido[4,5-b][1,4]diazepin-6-one

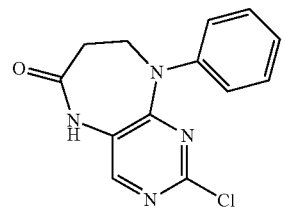 [SMILES: O=C1CCN(c2ccccc2)c2nc(Cl)ncc2N1]

MS (+ve) 275.2, 277.2; tR=2.80 min (XBridge 1).

2-Chloro-9-cyclopentyl-5,7,8,9-tetrahydro-pyrimido[4,5-b][1,4]diazepin-7,1'-cyclopropan]-6-one

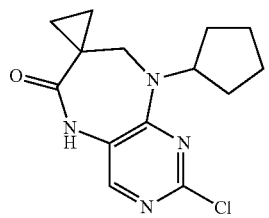 [SMILES: O=C1Nc2cnc(Cl)nc2N(C2CCCC2)CC12CC2]

MS (+ve) 293.2, 295.2; tR=3.48 min (XBridge 1).

2-Chloro-9-cyclopentyl-7,7-dimethyl-5,7,8,9-tetrahydro-pyrimido[4,5-b][1,4]diazepin-6-one

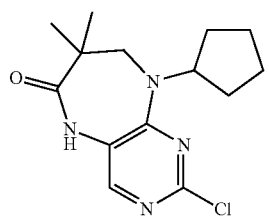 [SMILES: CC1(C)CN(C2CCCC2)c2nc(Cl)ncc2NC1=O]

MS (+ve) 295.1, 297.2; tR=3.58 min (XBridge 1).
Alkylated Diazepinones

The following intermediates were also prepared by the method described in Example 1, step 5:

2-Chloro-9-cyclopentyl-5,8-dimethyl-5,7,8,9-tetra-hydro-pyrimido[4,5-b][1,4]diazepin-6-one

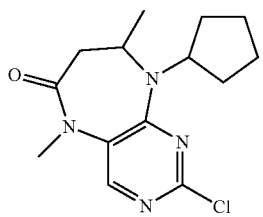 [SMILES: CC1CC(=O)N(C)c2cnc(Cl)nc2N1C1CCCC1]

R$_t$=14.6 min (Vydac 1); MS+ve: 295.2.

2-Chloro-9-cyclopentyl-5,7-dimethyl-5,7,8,9-tetra-hydro-pyrimido[4,5-b][1,4]diazepin-6-one

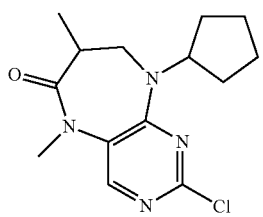 [SMILES: CC1CN(C2CCCC2)c2nc(Cl)ncc2N(C)C1=O]

MS (+ve) 295.1, 297.2; tR=9.11 min (XBridge 2).

2-Chloro-9-cyclopentyl-8-isopropyl-5-methyl-5,7,8,9-tetrahydro-pyrimido[4,5-b][1,4]diazepin-6-one

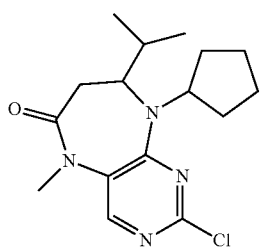 [SMILES: CC(C)C1CC(=O)N(C)c2cnc(Cl)nc2N1C1CCCC1]

MS (+ve) 323.1, 325.1; tR=10.17 min (XBridge 2).

2-Chloro-9-cyclopentyl-5-ethyl-7-methyl-5,7,8,9-tetrahydro-pyrimido[4,5-b][1,4]diazepin-6-one

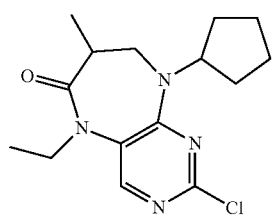 [SMILES: CCN1C(=O)C(C)CN(C2CCCC2)c2nc(Cl)ncc21]

$^1$H NMR (CDCl3): 1.08 (6H, m, 2×CH3), 1.38 (1H, m, CH), 1.55-1.70 (5H, m, CH+CH2), 1.70 (1H, m, CH), 2.10 (1H, m, CH), 2.73 (1H, m, CH), 3.48 (2H, m, CH2), 4.03 (1H, m, CH), 4.72 (1H, m, CH), 7.98 (1H, s, Pyr-H)

2-Chloro-9-(1-ethyl-propyl)-5-methyl-5,7,8,9-tetra-hydro-pyrimido[4,5-b][1,4]diazepin-6-one MS (+ve) 283.2, 285.1; tR=8.44 min (XBridge 2).

2-Chloro-9-(1-ethyl-propyl)-5-ethyl-5,7,8,9-tetra-hydro-pyrimido[4,5-b][1,4]diazepin-6-one MS (+ve) 297.12, 299.14; tR=3.67 min (XBridge 2).

2-Chloro-5-methyl-9-(tetrahydro-pyran-4-yl)-5,7,8,9-tetrahydro-pyrimido[4,5-b][1,4]diazepin-6-one MS (+ve) 297.1, 299.2; tR=5.74 min (XBridge 2).

9-Benzyl-2-chloro-5-methyl-5,7,8,9-tetrahydro-pyrimido[4,5-b][1,4]diazepin-6-one MS (+ve) 303.1, 305.2; tR=13.57 min (Vydac 1).

2-Chloro-5-methyl-9-phenyl-5,7,8,9-tetrahydro-pyrimido[4,5-b][1,4]diazepin-6-one

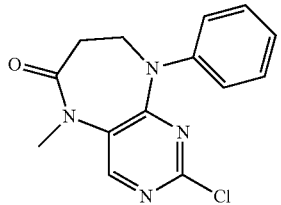 [SMILES: CN1C(=O)CCN(c2ccccc2)c2nc(Cl)ncc21]

MS (+ve) 289.1, 291.1; tR=2.93 min (XBridge 2).

2-Chloro-9-cyclopentyl-5-methyl-5,7,8,9-tetrahydro-pyrimido[4,5-b][1,4]diazepin-7,1'-cyclopropan]-6-one

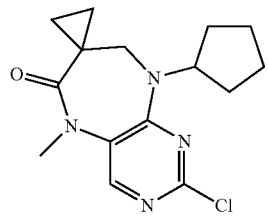 [SMILES: CN1C(=O)C2(CC2)CN(C2CCCC2)c2nc(Cl)ncc21]

MS (+ve) 307.1, 309.2; tR=3.67 min (XBridge 2).

2-Chloro-9-cyclopentyl-5,7,7-trimethyl-5,7,8,9-tetrahydro-pyrimido[4,5-b][1,4]diazepin-6-one

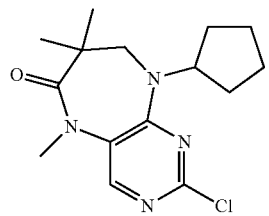 [SMILES: CN1C(=O)C(C)(C)CN(C2CCCC2)c2nc(Cl)ncc21]

MS (+ve) 309.1, 311.2; tR=3.90 min (XBridge 2).

Coupled Pyrimidinediazepinones

The following were also prepared by the method described in Example 1, step 6, Coupling Method A:

Compound [3]: 4-(9-Cyclopentyl-8-methyl-6-oxo-6,7,8,9-tetrahydro-5H-pyrimido[4,5-b][1,4]diazepin-2-ylamino)-3-methoxy-benzoic acid

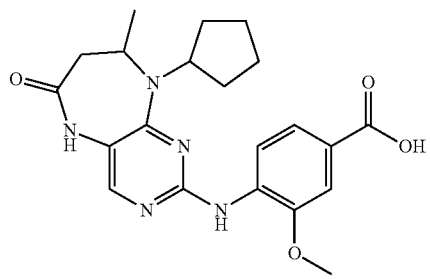 [SMILES: COc1cc(C(=O)O)ccc1Nc1ncc2c(n1)N(C1CCCC1)C(C)CC(=O)N2]

Purple solid (29%) $^1$H NMR (DMSO-d$_6$): δ 1.33 (d, J=Hz, 3H, CH$_3$), 1.52-1.58 (m, 3H, cyclopent-H), 1.70-1.78 (m, 3H, cyclopent-H), 1.87-1.93 (m, 2H, cyclopent-H), 2.97-3.00 (m, 2H, CH$_2$), 3.94 (s, 3H, CH$_3$), 4.15-4.17 (m, 1H, CH), 4.93-4.97 (m, 1H, CH), 7.59-7.60 (m, 2H), 7.82 (1, 1H), 8.01 (d, J=9 Hz, 1H, phe-H), 9.55 (bs, 1H, OH), 9.96 (s, 1H); MS+ve: 426.2. R$_t$=11.08 min (purity 100%, (Vydac 1))

Compound [4]: 4-(9-Cyclopentyl-5,8-dimethyl-6-oxo-6,7,8,9-tetrahydro-5H-pyrimido[4,5-b][1,4]diazepin-2-ylamino)-3-methoxy-benzoic acid

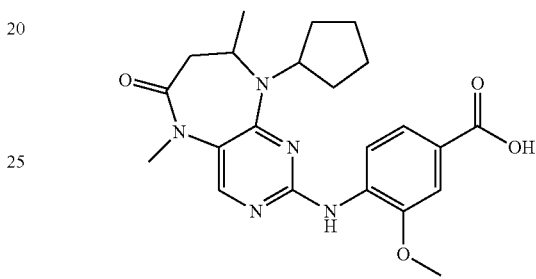

Purple solid (67%). 1H NMR (DMSO-d6): δ 1.26 (d, J=Hz, 3H, CH3), 1.43-1.93 (m, 8H, cyclopent-H), 2.52 (s, 3H, CH3), 2.99-3.02 (m, 2H, CH2), 3.96 (s, 3H, CH3), 4.13-4.16 (m, 1H, CH), 4.65-4.69 (m, 1H, CH), 7.60-7.61 (m, 2H), 8.06 (d, J=9 Hz, 1H, phe-H), 8.17 (s, 1H), 9.35 (bs, 1H); MS+ve: 426.2. Rt=11.59 min (purity 96%, (Vydac 1))

Compound [5]: 4-(9-Cyclohexyl-8-methyl-6-oxo-6,7,8,9-tetrahydro-5H-pyrimido[4,5-b][1,4]diazepin-2-ylamino)-3-methoxy-benzoic acid

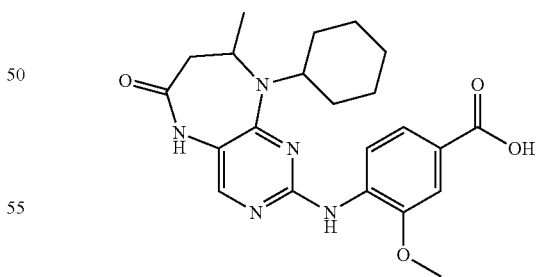

Brown solid (12%); $^1$H NMR (DMSO-d$_6$): δ 1.27 (d, J=6.5 Hz, 3H, CH$_3$), 1.58-1.87 (m, 10H, cyclohex-H), 2.85-2.88 (m, 2H, CH$_2$), 3.94 (s, 3H, CH$_3$), 4.21-4.23 (m, 1H, CH), 4.77 (bs, 1H, CH), 7.03 (s, 1H), 7.13 (s, 1H), 7.23 (s, 1H), 7.57-7.58 (m, 2H), 7.086 (s, 1H), 8.07-8.08 (m, 1H), 9.89 (bs, 1H, NH); ME+ve: 426.2. R$_t$=11.58 min (purity 90%, (Vydac 1))

Compound [6]: 4-(9-Cyclopentyl-6-oxo-6,7,8,9-tetrahydro-5H-pyrimido[4,5-b][1,4]diazepin-2-ylamino)-3-methoxy-benzoic acid

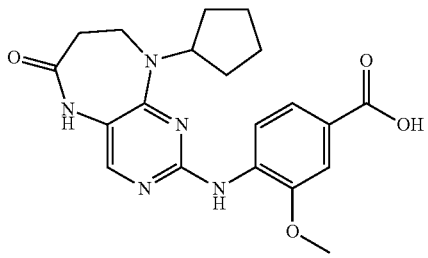

Purple solid (13%); $^1$H NMR (DMSO-$d_6$): δ 1.55-1.86 (m, 8H, cyclopent-H), 2.70-2.73 (m, 2H, CH$_2$), 3.70-3.72 (m, 2H, CH$_2$), 5.02-5.09 (m, 1H, CH), 7.57-7.59 (m, 2H), 7.77 (s, 1H, pyrimid-H), 8.06 (d, J=8.5 Hz, 1H, phe-H), 9.54 (bs, 1H, OH), 9.75 (s, 1H, NH); MS+ve: 398.2. R$_t$=10.55 min (purity 96%, (Vydac 1))

Compound [7]: 4-(9-Cyclopentyl-8-methyl-6-oxo-6,7,8,9-tetrahydro-5H-pyrimido[4,5-b][1,4]diazepin-2-ylamino)-benzoic acid

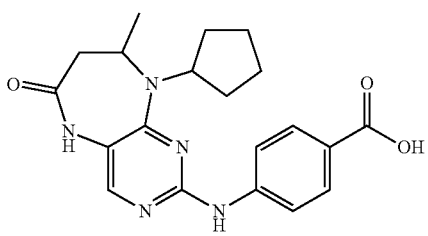 [SMILES: CC1CC(=O)Nc2cnc(Nc3ccc(C(=O)O)cc3)nc2N1C1CCCC1]

Off-white solid (10%); $^1$H NMR (DMSO-$d_6$): δ 1.27 (d, J=6.5 Hz, 3H, CH$_3$), 1.46-1.90 (m, 8H, cyclopent-H), 2.83-2.86 (m, 2H, CH$_2$), 4.07-4.09 (m, 1H, CH), 5.04-5.09 (m, 1H, CH), 7.20 (dd, J=3.5 and 8.5 Hz, 2H, phe-H), 7.79 (d, J=2.0 Hz, 1H, pyrimid-H), 7.86 (d, J=8.5 Hz, 2H, phe-H), 9.78 (bs, 1H, NH); MS+ve: 382.2. R$_t$=10.46 min (purity 90%, (Vydac 1))

Compound [8]: 4-(9-Cyclopentyl-5,8-dimethyl-6-oxo-6,7,8,9-tetrahydro-5H-pyrimido[4,5-b][1,4]diazepin-2-ylamino)-benzoic acid

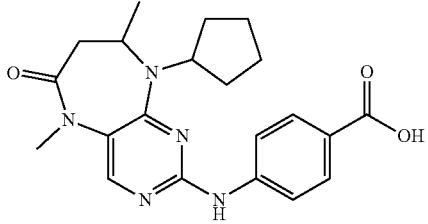 [SMILES: CC1CC(=O)N(C)c2cnc(Nc3ccc(C(=O)O)cc3)nc2N1C1CCCC1]

Off-white solid (25%); $^1$H NMR (DMSO-$d_6$): δ 1.19 (d, J=6.0 Hz, 3H, CH$_3$), 1.32-2.10 (m, 8H, cyclopent-H), 2.73-2.76 (m, 2H, CH$_2$), 3.22 (s, 3H, CH$_3$), 4.04 (m, 1H, CH, 4.70-4.75 (m, 1H, CH, 7.78-7.85 (m, 4H, phe-H), 8.12 (s, 1H, pyrimid-H), 9.68 (bs, 1H, NH); MS+ve: 394.0. R$_t$=11.05 min (purity 96%, (Vydac 1))

Compound [9]: 4-(9-Cyclohexyl-6-oxo-6,7,8,9-tetrahydro-5H-pyrimido[4,5-b][1,4]diazepin-2-ylamino)-3-methoxy-benzoic acid

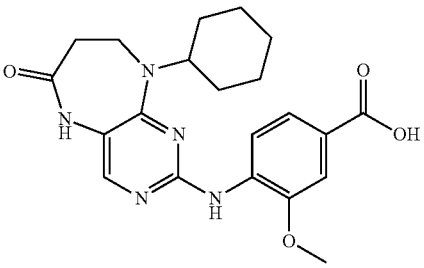 [SMILES: COc1cc(C(=O)O)ccc1Nc1ncc2c(n1)N(C1CCCCC1)CCC(=O)N2]

Brown solid (15%); $^1$H NMR (DMSO-$d_6$): δ 1.15-1.86 (m, 10H, cyclohex-H), 2.72 (dd, J=4.5 Hz, 2H, CH$_2$), 3.75 (dd, J=4.5 Hz, 2H, CH$_2$), 3.96 (s, 3H, CH$_3$), 4.58-4.63 (m, 1H, CH), 7.58-7.60 (m, 2H), 7.79 (s, 1H, pyrimid-H), 8.16 (d, J=8.5 Hz, 1H, phe-H), 9.74 (bs, 1H, NH); MS+ve: 412.2. R$_t$=11.19 min (purity 100%, (Vydac 1))

Compound [10]: 9-Cyclohexyl-2-(4-hydroxy-phenylamino)-5,7,8,9-tetrahydro-pyrimido[4,5-b][1,4]diazepin-6-one

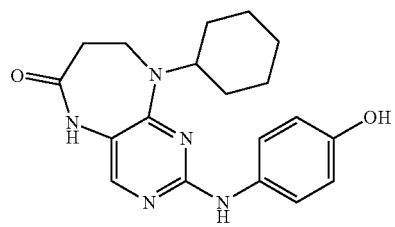 [SMILES: O=C1CCN(C2CCCCC2)c2nc(Nc3ccc(O)cc3)ncc2N1]

Purple solid (7%); $^1$H NMR (DMSO-$d_6$): δ 1.17-1.87 (m, 10H, cyclohex-H), 2.72 (bs, 2H, CH$_2$), 3.72 (bs, 2H, CH$_2$), 4.62-4.66 (m, 1H, CH), 6.82 (d, J=8.5 Hz, 2H, phe-H), 7.13 (s, 1H), 7.23 (s, 1H), 7.34-7.37 (m, 3H, 2×phe-H and NH); MS+ve: 354.2. R$_t$=10.63 min (purity 100%, (Vydac 1))

Compound [11]: 9-Cyclopentyl-2-(4-hydroxy-phenylamino)-7-methyl-5,7,8,9-tetrahydro-pyrimido[4,5-b][1,4]diazepin-6-one

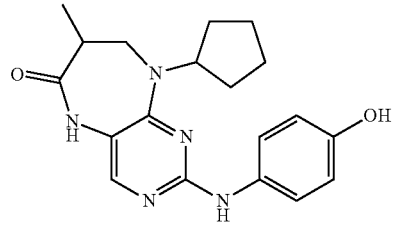 [SMILES: CC1CN(C2CCCC2)c2nc(Nc3ccc(O)cc3)ncc2NC1=O]

$^1$H NMR (CD3OD): 1.18 (3H, d, J 7 Hz, CH3), 1.52 (1H, m, CH), 1.61-1.84 (6H, m, CH), 1.99 (1H, m, CH), 2.85 (1H, m, CH), 3.53 (2H, m, CH), 5.14 (1H, m, CH), 6.74 (2H, m, Ar—H), 7.34 (2H, m, Ar—H), 7.64 (1H, s, Pyr-H); MS(+ve): 354.2; tR=10.85 min (Vydac 1).

Compound [12]: 9-Cyclopentyl-2-(4-hydroxy-phenylamino)-8-isopropyl-5-methyl-5,7,8,9-tetrahydro-pyrimido[4,5-b][1,4]diazepin-6-one

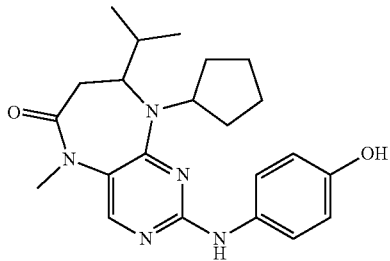 [SMILES: CC(C)C1CC(=O)N(C)c2cnc(Nc3ccc(O)cc3)nc2N1C1CCCC1]

$^1$H NMR (DMSO): 0.72 (3H, d, J 7 Hz, CHCH3), 0.85 (2H, d, J7 Hz, CHCH3), 1.29 (1H, m, CH), 1.51 (4H, m, CH), 1.60 (2H, m, CH), 1.93 (1H, m, CH), 2.08 (1H, m, CH), 2.29 (2H, m, 2×CH), 3.13 (3H, s, N—CH3), 3.82 (1H, m, CH), 4.15 (1H, m, CH), 6.65 (2H, d, J 6 Hz, Ar—H), 7.47 (2H, d, J 6 Hz, Ar—H), 8.14 (1H, s, Pyr-H), 8.99 (1H, s, NH); MS(+ve): 396.1; tR=12.54 min (Vydac 1).

Compound [13]: 9-Cyclopentyl-2-(4-hydroxy-phenylamino)-5,8-dimethyl-5,7,8,9-tetrahydro-pyrimido[4,5-b][1,4]diazepin-6-one

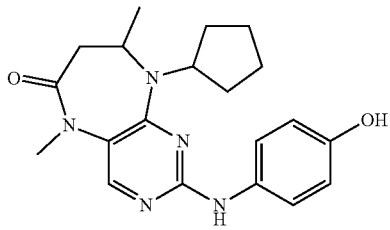 [SMILES: CC1CC(=O)N(C)c2cnc(Nc3ccc(O)cc3)nc2N1C1CCCC1]

White solid (27%); $^1$H NMR (DMSO-$d_6$): δ 1.22 (d, J=6.5 Hz, 3H, CH$_3$), 1.38-1.85 (m, 8H, cyclopent-H), 2.49-2.53 (m, 2H, CH$_2$), 3.18 (s, 3H, CH$_3$), 4.05-4.10 (m, 1H, CH), 4.51-4.60 (m, 1H, CH), 6.80 (d, J=9.0 Hz, 2H, phe-H), 7.22 (d, J=9.0 Hz, 2H, phe-H), 7.98 (s, 1H, pyrimid-H), 9.53 (bs, 1H, OH), 10.05 (bs, 1H, NH); MS+ve: 368.3. R$_t$=10.81 min (purity 93%, (Vydac 1))

Compound [14]: 4-(9-Benzyl-5-methyl-6-oxo-6,7,8,9-tetrahydro-5H-pyrimido[4,5-b][1,4]diazepin-2-ylamino)-3-methoxy-benzoic acid

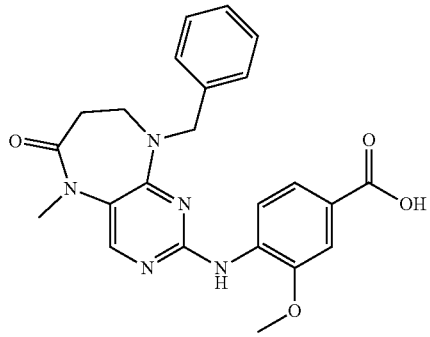 [SMILES: COc1cc(C(=O)O)ccc1Nc1ncc2c(n1)N(Cc1ccccc1)CCC(=O)N2C]

$^1$H NMR (DMSO): 2.72 (2H, m, CH2), 3.68 (2H, m, CH2), 3.90 (3H, s, OCH3), 4.88 (2H, s, CH2), 7.22-7.44 (6H, m, Ar—H), 7.44 (1H, s, Ar—H), 7.77 (1H, s, Pyr-H), 8.10 (1H, d, J 7 Hz), 8.18 (1H, s, NH); MS(+ve): 434.2; tR=10.97 min (Vydac 1).

Compound [15]: 4-(5-Methyl-6-oxo-9-phenyl-6,7,8,9-tetrahydro-5H-pyrimido[4,5-b][1,4]diazepin-2-ylamino)-benzoic acid

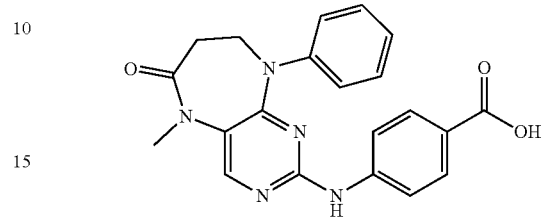

$^1$H NMR (DMSO): 2.84 (2H, m, CH2), 3.28 (3H, s, CH3), 4.08 (2H, m, CH2), 7.24 (2H, d, J 8.5 Hz, Ar—H), 7.35-7.37 (3H, m, Ar—H), 7.47-7.52 (4H, m, Ar—H), 8.29 (1H, s, Pyr-H), 9.77 (1H, s, NH); MS(+ve): 390.2; tR=1.93 min (XBridge 2).

Compound [16]: 4-(9-Cyclopentyl-5,7,7-trimethyl-6-oxo-6,7,8,9-tetrahydro-5H-pyrimido[4,5-b][1,4]diazepin-2-ylamino)-benzoic acid

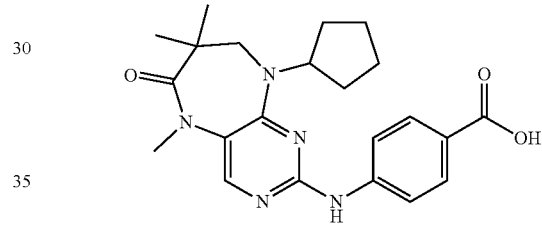

$^1$H NMR (DMSO): 1.09 6H, s, CH3), 1.60 (4H, m, CH), 1.74 (2H, m, CH), 1.88 (2H, m, CH), 3.19 (3H, s, N—CH3), 3.37 (2H, s, CH2), 5.23 (1H, s, CH), 7.82 (4H, m, Ar—H), 7.99 (1H, s, Pyr-H), 9.57 (1H, s, NH); MS(+ve): 410.25; tR=2.25 min (XBridge 2).

Preparation and Reaction of Amino-Benzamides

4-Amino-3-methoxy-N-(1-methyl-piperidin-4-yl)-benzamide

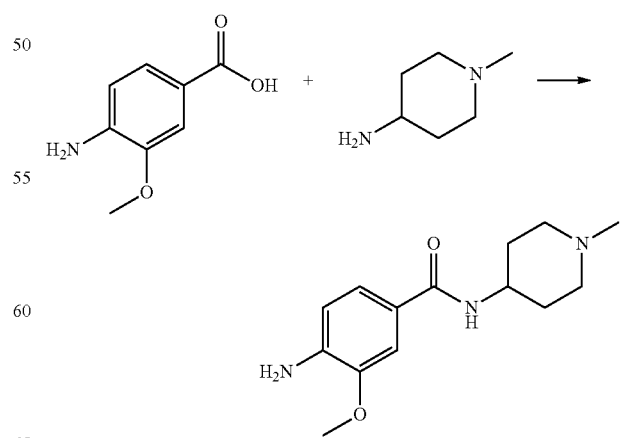

To 4-amino-3-methoxybenzoic acid (1.064 g mg, 6.37 mmol) in dichloromethane (50 ml) was added DIPEA (2.22 ul, 12.74 mmol) and TBTU (2.25 g, 7.0 mmol) and the mixture stirred for 10 minutes. 4-amino-1-methylpiperidine (0.872 g, 7.65 mmol) was added and stirring continued for 16 hours. The resulting solid was filtered and dried under vacuum (1.04 g, 3.95 mmol, 62%).

$^1$H NMR (DMSO): 1.54 (2H, m, CH), 1.68 (2H, m, CH), 1.90 (2H, m, CH), 2.15 (3H, s, N—CH3), 2.76 (2H, d, J 11.5 Hz, CH), 3.66 (1H, m, CH), 3.77 (3H, s, OCH3), 6.56 (1H, m, Ar—H), 7.26 (1H, m, Ar—H), 7.75 (1H, d, J 7.5 Hz); MS (+ve) 264.4; tR=7.45 min (Vydac 2).

The following amino-benzamides were prepared by a similar method:

4-Amino-N-(1-methyl-pip eridin-4-yl)-benzamide via [4-(1-Methyl-piperidin-4-ylcarbamoyl)-phenyl]-carbamic acid tert-butyl ester

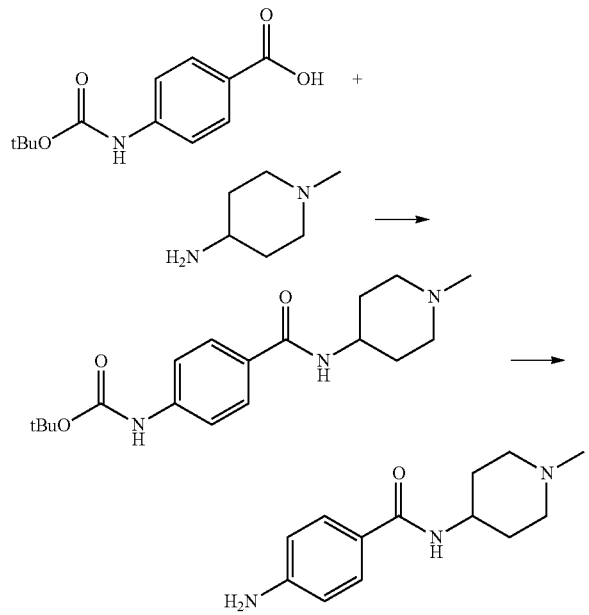

[4-(1-Methyl-piperidin-4-ylcarbamoyl)-phenyl]-carbamic acid tert-butyl ester $^1$H NMR (DMSO): 1.44 (9H, s, C(CH3)3), 1.52 (2H, m, CH), 1.71 (2H, m, CH), 1.92 (2H, m, CH), 1.92 (3H, s, N—CH3), 2.74 (2H, m, CH), 3.68 (1H, m, N—CH), 7.47 (2H, d, J 8.5 Hz, Ar—H), 7.72 (2H, d, J 8.5 Hz, Ar—H), 8.00 (1H, d, J 7.5 Hz, NH), 9.54 (1H, s, NH)

This compound was used without prior deprotection when using Coupling Method B (below)

Coupling Method B

Compound [17]: 4-(9-Cyclopentyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide

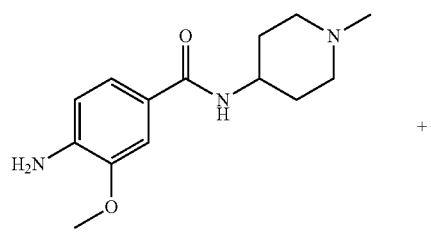

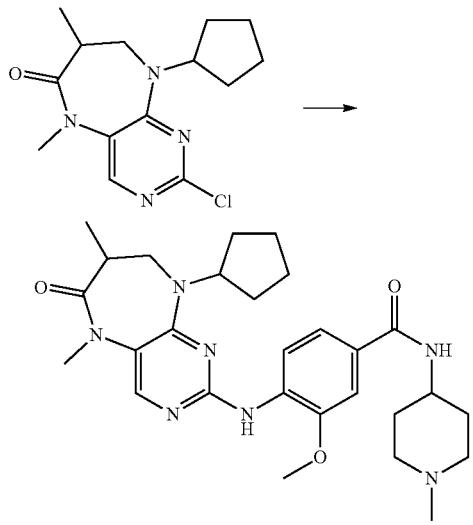

The aniline (149 mg, 0.57 mmol), pyrimidine (53 mg, 0.19 mmol) and TFA □1, 0.95 mmol) in 2,2,2-trifluoroethanol (5 ml) were heated to reflux for 18 hours. Solvent was evaporated, Ethyl acetate (10 ml) added, washed with sat. NaHCO3, brine and the solvent evaporated. Ethyl acetate (10 ml) was added and the resulting solid filtered and dried under vacuum (30 mg, 0.06 mmol, 30%).

$^1$H NMR (DMSO): 1.06 (3H, d, J 7 Hz, CHCH3), 1.52-1.78 (10H, m, alkyl CH+CH2), 2.01 (2H, m, CH), 2.36 (3H, s, N—CH3), 2.73 (1H, m, CH), 2.85 (2H, m, CH), 3.45 (1H, m, CH), 3.71 (1H, m, CH), 3.94 (3H, s, OCH3), 5.06 (1H, m, CH), 7.46 (2H, m, Ar-h), 7.61 (1H, s, Ar—H), 7.77 (1H, s, NH), 8.10 (1H, d, J 8 Hz, Ar—H), 8.36 (1H, d, J 8 Hz), Ar—H), 9.44 (1H, s, NH); MS(+ve): 508.2; tR=7.30 min (XBridge 2).

The following compounds were prepared in a similar manner to the above example:

Compound [18]: 4-(9-Cyclopentyl-7-methyl-6-oxo-6,7,8,9-tetrahydro-5H-pyrimido[4,5-b][1,4]diazepin-2-ylamino)-N-(1-methyl-piperidin-4-yl)-benzamide

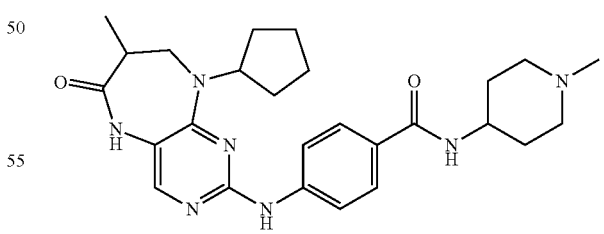

$^1$H NMR (DMSO): 1.08 (3H, d, J 7 Hz, CHCH3), 1.53-1.80 (10H, m, alkyl CH+CH2), 2.01 (2H, m, CH), 2.12 (2H, m, CH), 2.29 (3H, s, N—CH3), 2.75 (1H, m, CH), 2.90 (2H, m, CH), 3.48 (1H, m, CH), 3.77 (1H, m, CH), 5.11 (1H, m, CH), 7.78 (4H, m, Ar—H), 8.04 (1H, d, J 7.5 Hz, NH), 9.35 (1H, s, CONH), 9.43 (1H, s, CONH); MS(+ve): 478.2; tR=6.74 min (XBridge 2).

Compound [19]: 4-(9-Cyclopentyl-8-isopropyl-6-oxo-6,7,8,9-tetrahydro-5H-pyrimido[4,5-b][1,4]diazepin-2-ylamino)-3-methoxy-N-(1-methyl-piperidin-4-yl)-benzamide

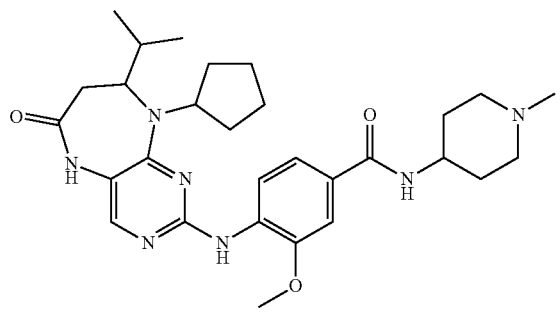 [SMILES: COc1cc(C(=O)NC2CCN(C)CC2)ccc1Nc1ncc2c(n1)N(C1CCCC1)C(C(C)C)CC(=O)N2]

¹H NMR (CD3OD): 0.92 (3H, d, J 6.5 Hz, CHCH3), 1.04 (3H, d, J 6 Hz, CHCH3), 1.65-1.97 (14H, m, alkyl CH+CH2), 2.25 (2H, dd, J 11.5 Hz, 11.5 Hz, CH), 2.36 (3H, s, N—CH3), 2.67 (1H, m, CH), 3.03 (3H, m, CH+CH2), 3.51 (1H, m, CH), 3.95 (1H, m, CH), 4.02 (3H, s, OCH3), 5.09 (1H, m, CH), 7.59 (2H, m, Ar—H), 7.87 (1H, s, pyr-H—H), 8.46 (1H, d, J 7 Hz, Ar—H); MS(+ve): 536.3; tR=7.68 min (XBridge 2).

Compound [20]: 4-(9-Cyclopentyl-5,7-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide

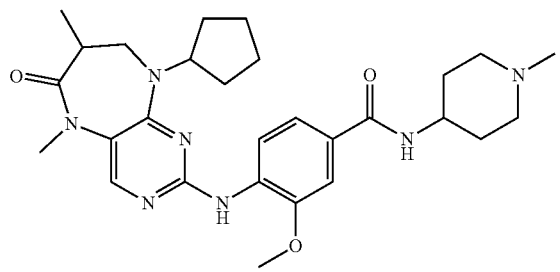 [SMILES: COc1cc(C(=O)NC2CCN(C)CC2)ccc1Nc1ncc2c(n1)N(C1CCCC1)CC(C)C(=O)N2C]

¹H NMR (DMSO): 1.02 (3H, d, J 6.5 Hz, CHCH3), 1.54-1.80 (12H, m, alkyl CH+CH2), 2.10 (3H, m, (CH+CH2), 2.27 (3H, s, N—CH3), 2.84 (3H, m, CH3), 3.15 (3H, s, CH3), 3.46 (1H, m, CH), 3.80 (1H, m, N—CH), 3.95 (3H, s, OCH3), 4.76 (1H, m, CH), 7.50 (2H, m, Ar—H), 7.75 (1H, s, Ar—H), 8.10 (1H, s, NH), 8.14 (1H, d, J 7.5 Hz, Ar—H), 8.40 (1H, d, J 8 Hz, Ar—H); MS(+ve): 522.3; tR=7.76 min (XBridge 2).

Compound [21]: 4-[9-(1-Ethyl-propyl)-6-oxo-6,7,8,9-tetrahydro-5H-pyrimido[4,5-b][1,4]diazepin-2-ylamino]-3-methoxy-N-(1-methyl-piperidin-4-yl)-benzamide

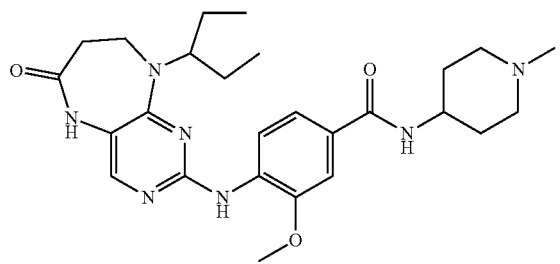 [SMILES: CCC(CC)N1CCC(=O)Nc2cnc(Nc3ccc(C(=O)NC4CCN(C)CC4)cc3OC)nc21]

¹H NMR (DMSO): 0.85 (6H, d, J 7 Hz, CH2CH3), 1.59 (4H, m, CH2CH3), 1.66 (2H, m, CH), 1.83 (2H, m, CH), 2.37 (3H, s, N—CH3), 2.65 (2H, m, CH2), 2.98 (2H, m, CH), 3.50 (2H, m, CH2), 3.83 (1H, m, N—CH), 3.94 (3H, s, OCH3), 4.93 (1H, s, CH), 4;49 (2H, m, Ar—H+NH), 7.57 (1H, s, NH), 7.79 (1H, s, Ar—H), 8.15 (1H, d, J 6.5 Hz, Ar—H), 8.37 (1H, d, J 8.5 Hz, Ar—H), 9.41 (1H, s, NH); MS(+ve): 496.2; tR=6.73 min (XBridge 2).

Compound [22]: 4-[9-(1-Ethyl-propyl)-6-oxo-6,7,8,9-tetrahydro-5H-pyrimido[4,5-b][1,4]diazepin-2-ylamino]-N-(1-methyl-piperidin-4-yl)-benzamide

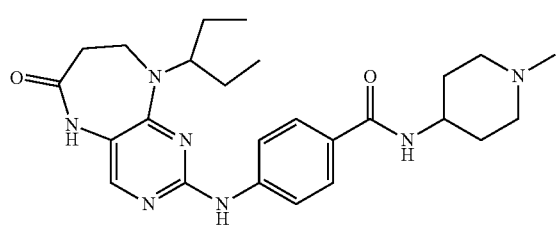 [SMILES: CCC(CC)N1CCC(=O)Nc2cnc(Nc3ccc(C(=O)NC4CCN(C)CC4)cc3)nc21]

¹H NMR (DMSO): 0.86 (6H, d, J 7 Hz, CH2CH3), 1.56 (4H, m, CH2CH3), 1.62 (2H, m, CH), 1.76 (2H, m, CH), 2.52 (3H, s, N—CH3), 2.63 (2H, m, CH2), 3.22 (2H, m, CH), 3.49 (2H, m, CH2), 3.92 (1H, m, CH), 4.97 (1H, m, CH), 7.78 (4H, m, Ar—H), 8.15 (1H, s, Pyr-H), 9.31 (1H, s, NH), 9.39 (1H, s, NH); MS(+ve): 466.3; tR=6.26 min (XBridge 2).

Compound [23]: 4-(9-Cyclopentyl-8-isopropyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide

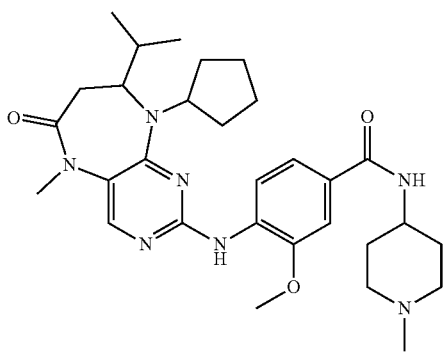 [SMILES: COc1cc(C(=O)NC2CCN(C)CC2)ccc1Nc1ncc2c(n1)N(C1CCCC1)C(C(C)C)CC(=O)N2C]

¹H NMR (CD3OD): 0.83 (3H, d, J 7 Hz, CHCH3), 0.93 (3H, d, J 7 Hz, CHCH3), 1.41 (2H, m, CH), 1.65 (4H, m, CH), 1.79 (2H, M, CH), 1.91 (2H, m, CH), 2.17 (2H, m, CH), 2.41 (2H, m, 2×CH), 2.71 (4H, m, CH3+CH), 2.91 (2H, m, CH), 3.35 (3H, s, CH3), 3.90 (1H, m, CH), 3.94 (3H, s, OCH3), 4.21 (1H, m, CH), 4.27 (1H, m, CH), 7.18 (2H, m, Ar—H), 8.23 (1H, s, Pyr-H), 8.56 (1H, d, J 8.5 Hz, Ar—H); MS(+ve): 550.3; tR=8.40 min (XBridge 2).

Compound [24]: 4-[9-(1-Ethyl-propyl)-5-methyl-6-oxo-6,7,8,9-tetrahydro-5H-pyrimido[4,5-b][1,4]diazepin-2-ylamino]-3-methoxy-N-(1-methyl-piperidin-4-yl)-benzamide

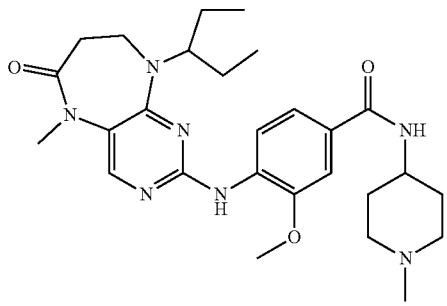 [SMILES: CCC(CC)N1CCC(=O)N(C)c2cnc(Nc3ccc(C(=O)NC4CCN(C)CC4)cc3OC)nc21]

$^1$H NMR (DMSO): 0.85 (6H, t, J 7.5, CH2CH3), 1.62 (8H, m, CH+CH2), 1.76 (2H, d, J 7 Hz, CH), 1.94 (2H, dd, J 10 Hz, 10 Hz, CH), 2.17 (3H, s, N—CH3), 2.64 (2H, m, CH2), 2.80 (2H, d, J 11 Hz, CH), 3.18 (3H, s, N—CH3), 3.49 (2H, m, CH2), 3.75 (1H, m, CH), 3.95 (3H, s, OCH3), 4.65 (1H, m, CH), 7.49 (2H, m, Ar—H), 7.69 (1H, s, Pyr-H), 8.07 (1H, s, NH), 8.10 (1H, d, J 9 Hz, Ar—H), 8.37 (1H, d, J 9 Hz, Ar—H); MS(+ve): 510.3; tR=8.35 min (XBridge 2).

Compound [25]: 3-Methoxy-N-(1-methyl-piperidin-4-yl)-4-[6-oxo-9-(tetrahydro-pyran-4-yl)-6,7,8,9-tetrahydro-5H-pyrimido[4,5-b][1,4]diazepin-2-ylamino]-benzamide

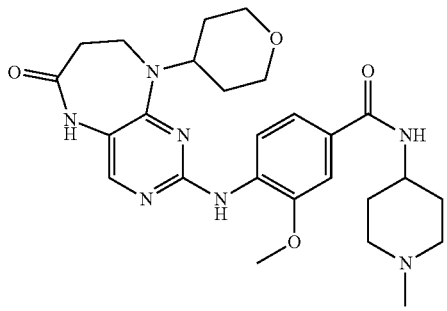 [SMILES: COc1cc(C(=O)NC2CCN(C)CC2)ccc1Nc1ncc2c(n1)N(C1CCOCC1)CCC(=O)N2]

$^1$H NMR (CD3OD): 1.60 (2H, m, CH), 1.69 (2H, d, J 11 Hz, CH), 1.93 (2H, d, J 12 Hz, CH), 1.97 (2H, dd, J 12 Hz, 12 Hz, CH), 2.18 (3H, s, N—CH3), 2.61 (2H, m, CH2), 2.80 (2H, d, J 10.5 Hz, CH), 3.48 (2H, dd, J 11 Hz, CH), 3.62 (2H, m, CH2), 3.75 (1H, m, CH), 3.95 (3H, s, OCH3), 4.04 (2H, d, J 8 Hz, CH), 4.85 (1H, s, CH), 7.49 (2H, m, Ar—H), 7.66 (1H, s, NH), 7.81 (1H, s, Pyr-H), 8.11 (1H, d, J 7.5 Hz, Ar—H), 8.33 (1H, d, J 8 Hz, Ar—H), 9.45 (1H, s, NH); MS(+ve): 510.1; tR=5.34 min (XBridge 2).

Compound [26]: 3-Methoxy-4-[5-methyl-6-oxo-9-(tetrahydro-pyran-4-yl)-6,7,8,9-tetrahydro-5H-pyrimido[4,5-b][1,4]diazepin-2-ylamino]-N-(1-methyl-piperidin-4-yl)-benzamide

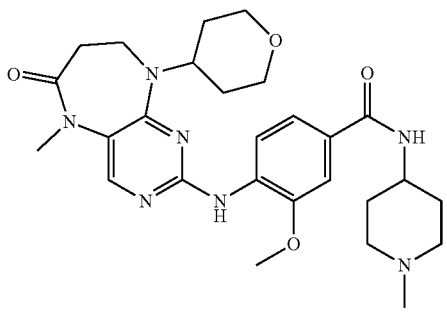 [SMILES: COc1cc(C(=O)NC2CCN(C)CC2)ccc1Nc1ncc2c(n1)N(C1CCOCC1)CCC(=O)N2C]

$^1$H NMR (CD3OD): 1.73 (2H, ddd, J 3 Hz, 12 Hz, 18 Hz, CH), 1.84 (2H, d, J 11 Hz, CH), 1.98 (4H, m, alkyl CH), 2.19 (2H, dd, J 10.5 Hz, 10.5 Hz, CH), 2.33 (3H, s, N—CH3), 2.71 (2H, m, CH2), 2.97 (2H, d, J 12 Hz, CH), 3.65 (2H, dd, J 11 Hz, CH), 3.75 (2H, m, CH2), 3.92 (1H, m, CH), 4.02 (3H, s, OCH3), 4.12 (1H, dd, J 4 Hz, 11 Hz, CH), 4.78 (1H, m, CH), 7.53 (2H, m, Ar—H), 8.04 (1H, s, Pyr-H), 8.45 (1H, d, J 9 Hz, Ar—H); MS(+ve): 524.3; tR=5.71 min (XBridge 2).

Compound [27]: 4-[5-Ethyl-9-(1-ethyl-propyl)-6-oxo-6,7,8,9-tetrahydro-5H-pyrimido[4,5-b][1,4]diazepin-2-ylamino]-3-methoxy-N-(1-methyl-piperidin-4-yl)-benzamide

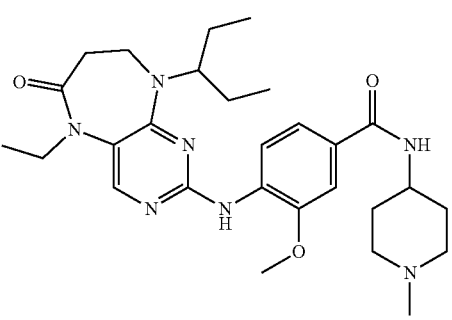 [SMILES: CCC(CC)N1CCC(=O)N(CC)c2cnc(Nc3ccc(C(=O)NC4CCN(C)CC4)cc3OC)nc21]

$^1$H NMR (DMSO): 0.86 (6H, t, J 7.5 Hz, CH3), 0.94 (3H, d, J 7 Hz, CH3), 1.63 (6H, m, alkyl CH+CH2), 1.78 (2H, d, J 11 Hz, CH), 1.94 (2H, dd, J 11.5 Hz, CH), 2.18 (3H, s, N—CH3), 2.57 (2H, m, CH2), 2.80 (2H, m, CH2), 3.47 (2H, m, CH2), 3.77 (3H, m, CH+CH2), 3.96 (3H, s, OCH3), 4.59 (1H, m, CH), 7.50 (2H, m, Ar—H), 7.24 (1H, s, NH), 8.01 (2H, m, Ar—H+Pyr-H), 8.39 (1H, d, J 9 Hz, Ar—H); MS(+ve): 524.3; tR=7.56 min (XBridge 2).

Compound [29]: 4-(9-Benzyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide

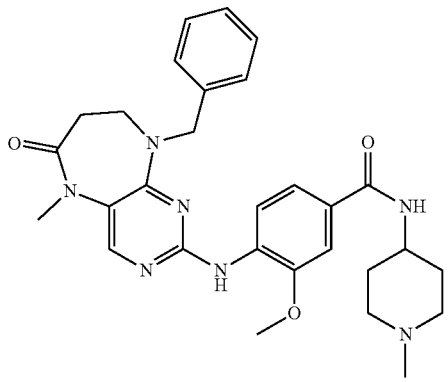 [SMILES: COc1cc(C(=O)NC2CCN(C)CC2)ccc1Nc1ncc2c(n1)N(Cc1ccccc1)CCC(=O)N2C]

$^1$H NMR (DMSO): 1.58 (2H, ddd, J 4 Hz, 12.5 Hz, 24.5 Hz, CH), 1.73 (2H, d, J11.5 Hz, CH), 1.93 (2H, dd, J 15 Hz, CH), 2.17 (3H, s, N—CH3), 2.69 (2H, m, CH2), 2.78 (2H, d, J 11.5 Hz, CH), 3.22 (3H, s, N—CH3), 3.63 (2H, m, CH2), 3.72 (1H, m, CH), 3.91 (3H, s, OCH3), 4.87 (2H, s, CH2), 7.23-7.32 (4H, m, Ar—H), 7.35-7.43 (2H, m, Ar—H), 7.44 (1H, d, J 2 Hz, Ar—H), 7.72 (1H, s, Pyr-H), 8.04 (1H, d, J 7.5 Hz, Ar—H), 8.12 (1H, d, J 8.5 Hz), 8.16 (1H, s, NH); MS(+ve): 530.4; tR=4.55 min (XBridge 2).

Compound [30]: 3-Methoxy-4-(5-methyl-6-oxo-9-phenyl-6,7,8,9-tetrahydro-5H-pyrimido[4,5-b][1,4]diazepin-2-ylamino)-N-(1-methyl-piperidin-4-yl)-benzamide

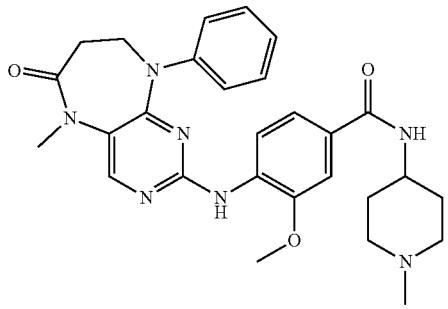 [SMILES: COc1cc(C(=O)NC2CCN(C)CC2)ccc1Nc1ncc2c(n1)N(c1ccccc1)CCC(=O)N2C]

$^1$H NMR (DMSO): 1.56 (2H, dd, J 11.5 Hz, 20.5 Hz, CH), 1.75 (2H, d, J 10 Hz, CH), 1.95 (2H, m, CH), 2.18 (3H, s, N—CH3), 2.83 (3H, m, CH+CH2), 3.16 (1H, s, CH), 3.27 (3H, s, N—CH3), 3.71 (1H, m, N—CH), 3.88 (3H, s, OCH3), 4.06 (2H, m, CH2); MS(+ve): 516.3; tR=2.72 min (XBridge 2).

Compound [31]: 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-N-(1-methyl-piperidin-4-yl)-benzamide

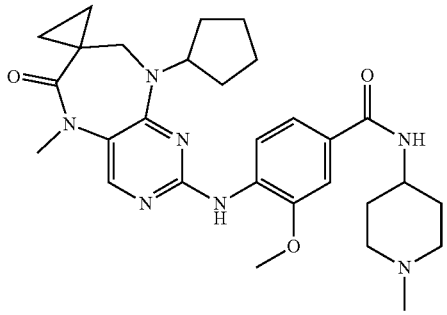 [SMILES: COc1cc(C(=O)NC2CCN(C)CC2)ccc1Nc1ncc2c(n1)N(C1CCCC1)CC1(CC1)C(=O)N2C]

$^1$H NMR (DMSO): 0.66 (2H, d, J 6 Hz, cyclopropyl-CH), 0.91 (2H, d, J 6 Hz, cyclopropyl-CH), 1.50 (2H, m, CH), 1.58 (4H, m, CH), 1.69 (2H, m, CH), 1.77 (2H, m, CH), 1.95 (4H, m, CH), 2.16 (3H, s, N—CH3), 2.73 (1H, s, CH), 2.79 (2H, d, J 11 Hz, CH), 2.89 (1H, s, CH), 3.16 (3H, s, N—CH3), 3.47 (2H, s, CH2), 3.72 (1H, m, CH), 3.94 (3H, s, OCH3), 4.86 (1H, m, CH), 7.46 (2H, m, Ar—H), 7.67 (1H, s, NH), 7.95 (1H, s, Pyr-H), 8.07 (1H, d, J 8 Hz, Ar—H), 8.38 (1H, d, J 8 Hz, Ar—H); MS(+ve): 534.3; tR=3.05 min (XBridge 2).

Compound [32]: 4-(9-Cyclopentyl-5,7,7-trimethyl-6-oxo-6,7,8,9-tetrahydro-5H-pyrimido[4,5-b][1,4]diazepin-2-ylamino)-3-methoxy-N-(1-methyl-piperidin-4-yl)-benzamide

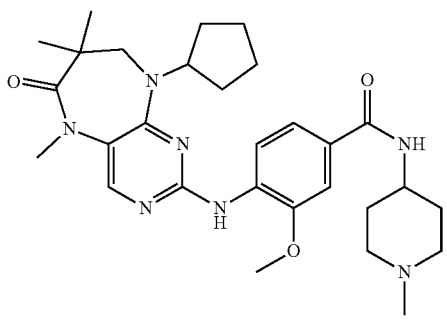 [SMILES: COc1cc(C(=O)NC2CCN(C)CC2)ccc1Nc1ncc2c(n1)N(C1CCCC1)CC(C)(C)C(=O)N2C]

$^1$H NMR (DMSO): 1.09 6H, s, CH3), 1.58 (6H, m, CH2), 1.74 (4H, m, CJ), 1.95 (4H, m, CH), 2.16 (3H, s, NCH3), 2.73 (2H, d, J 11.5 Hz, CH), 3.18 (3H, s, NCH3), 3.37 (2H, s, CH2), 3.74 (1H, m, CH), 3.94 (3H, s, OCH3), 5.19 (1H, m, CH), 7.46 (2H, m, Ar—H), 7.67 (1H, s, NH), 7.98 (1H, s, Pyr-H), 8.07~(1H, d, J 8 Hz, Ar—H), 8.36 (1H, d, J 8 Hz); MS(+ve): 536.40; tR=3.32 min (XBridge 2).

Amide Couplings

The following were also prepared by the method described in Example 1, step 7:

Compound [33]: 4-(9-Cyclopentyl-5,8-dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide

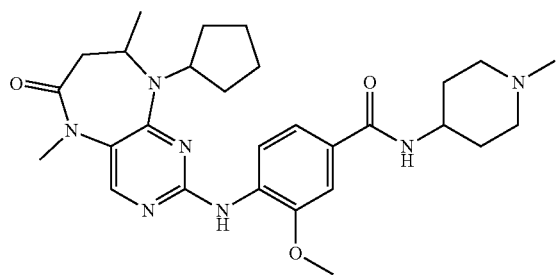 [SMILES: COc1cc(C(=O)NC2CCN(C)CC2)ccc1Nc1ncc2c(n1)N(C1CCCC1)C(C)CC(=O)N2C]

Yellow solid (31%). $^1$H NMR (CD$_3$OD): δ 1.24 (d, J=6.5 Hz, 3H, CH$_3$), 1.36-2.17 (m, 16H, 8×cyclopent-H and 4×piperid-H), 2.51 (s, 3H, CH$_3$), 3.14-3.16 (m, 2H, CH$_2$), 3.28 (s, 3H, CH$_3$), 4.00 (s, 3H, CH$_3$), 4.04-4.06 (m, 1H, CH), 4.71-4.74 (m, 1H, CH), 7.49-7.52 (m, 2H), 7.99 (s, 1H), 8.41 (d, J=8.5 Hz, 1H, phe-H); MS+ve: 522.4. R$_t$=10.03 min (purity 97%, Vydac 1)

Compound [34]: 4-(9-Cyclopentyl-8-methyl-6-oxo-6,7,8,9-tetrahydro-5H-pyrimido[4,5-b][1,4]diazepin-2-ylamino)-3-methoxy-N-(1-methyl-piperidin-4-yl)-benzamide

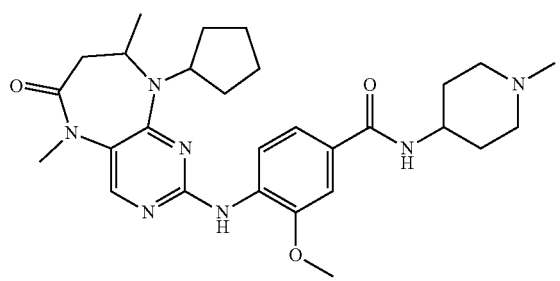 [SMILES: COc1cc(C(=O)NC2CCN(C)CC2)ccc1Nc1ncc2c(n1)N(C1CCCC1)C(C)CC(=O)N2C]

Yellow solid (38%); MS+ve: 508.3. R$_t$=9.53 min (purity 97%, Vydac 1)

Compound [35]: 4-(9-Cyclohexyl-8-methyl-6-oxo-6,7,8,9-tetrahydro-5H-pyrimido[4,5-b][1,4]diazepin-2-ylamino)-3-methoxy-N-(1-methyl-piperidin-4-yl)-benzamide

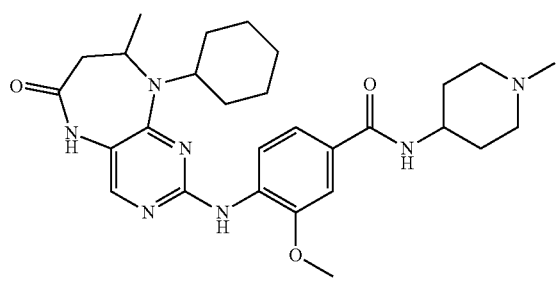 [SMILES: COc1cc(C(=O)NC2CCN(C)CC2)ccc1Nc1ncc2c(n1)N(C1CCCCC1)C(C)CC(=O)N2]

Off-white solid (33%); $^1$H NMR (CD$_3$OD): δ 1.34-1.41 (m, 2H), 1.44 (d, J=6.5 Hz, 3H, CH$_3$), 1.60-1.99 (m, 8H), 2.22-2.26 (m, 2H), 2.73-2.77 (m, 1H), 2.91 (s, 3H, CH$_3$), 2.96-3.25 (m, 5H), 3.61-3.63 (m, 2H, CH$_2$), 4.01 (s, 3H, CH$_3$), 4.17-4.21 (m, 1H, CH), 4.33-4.36 (m, 1H, CH), 7.59 (dd, J=2.0 and 8.5 Hz, 1H, phe-H), 7.63 (d, J=2.0 Hz, 1H, phe-H), 7.69 (s, 1H, pyrimid-H), 8.00 (d, J=8.5 Hz, 1H, phe-H); MS+ve: 522.2. R$_t$=10.17 min (purity 100%, Vydac 1)

Compound [36]: 4-(9-Cyclopentyl-6-oxo-6,7,8,9-tetrahydro-5H-pyrimido[4,5-b][1,4]diazepin-2-ylamino)-3-methoxy-N-(1-methyl-piperidin-4-yl)-benzamide

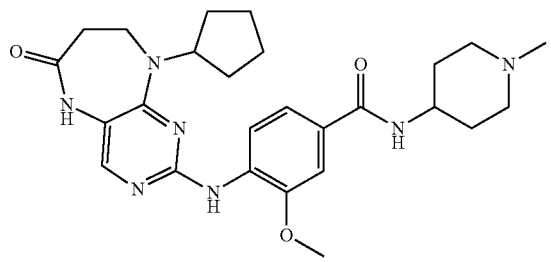 [SMILES: COc1cc(C(=O)NC2CCN(C)CC2)ccc1Nc1ncc2c(n1)N(C1CCCC1)CCC(=O)N2]

Purple solid (40%); $^1$H NMR (CD$_3$OD): δ 1.65-2.25 (m, 8H, cyclopent-H), 2.34 (s, 3H, CH$_3$), 2.73-2.75 (m, 2H, CH$_2$), 3.69-3.71 (m, 2H, CH$_2$), 3.90-3.94 (m, 1H, CH), 4.01 (s, 3H, CH$_3$), 5.22-5.25 (m, 1H, CH), 7.48-7.51 (m, 2H, 2×phe-H), 7.76 (s, 1H, pyrimid-H), 8.47 (s, 1H, NH); MS+ve: 493.4. R$_t$=9.21 min (purity 92%, Vydac 1)

Compound [37]: 4-(9-Cyclopentyl-5,8-dimethyl-6-oxo-6,7,8,9-tetrahydro-5H-pyrimido[4,5-b][1,4]diazepin-2-ylamino)-N-(1-methyl-piperidin-4-yl)-benzamide

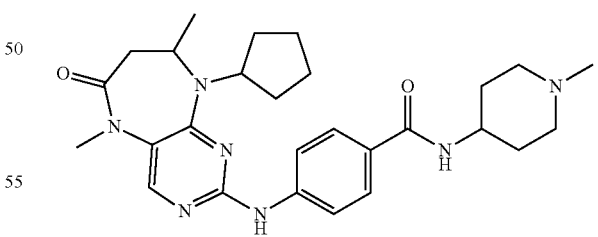

Off-white solid (45%); $^1$H NMR (DMSO-d$_6$): δ 1.17 (d, J=6.0 Hz, 3H, CH$_3$), 1.29-2.10 (m, 16H, 8×cyclopent-H and 8×piperid-H), 2.21 (bs, 3H, CH$_3$), 2.81-2.83 (m, 2H, CH$_2$), 3.21 (s, 3H, CH$_3$), 3.73-3.76 (m, 1H, CH), 4.03-4.05 (m, 1H, CH, 4.68-4.72 (m, 1H, CH), 7.74-7.79 (m, 4H, phe-H), 8.11 (s, 1H, pyrimid-H), 9.47 (bs, 1H, NH); MS+ve: 492.3. R$_t$=9.70 min (purity 92%, Vydac 1)

Compound [38]: 4-(9-Cyclopentyl-8-methyl-6-oxo-6,7,8,9-tetrahydro-5H-pyrimido[4,5-b][1,4]diazepin-2-ylamino)-N-(1-methyl-piperidin-4-yl)-benzamide

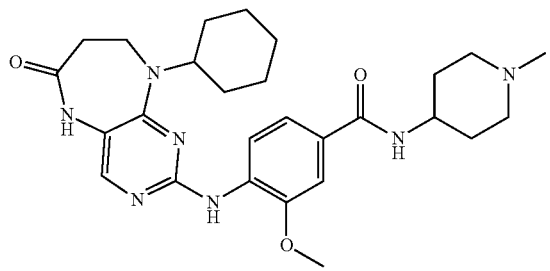 [SMILES: COc1cc(C(=O)NC2CCN(C)CC2)ccc1Nc1ncc2c(n1)N(C1CCCCC1)CCC(=O)N2]

Off-white solid (15%); ¹H NMR (DMSO-d$_6$): δ 1.25 (d, J=7.0 Hz, 3H, CH$_3$), 1.51-2.04 (m, 10H), 2.09 (s, 3H, CH$_3$), 2.55-2.66 (m, 6H), 2.78-2.79 (m, 2H, CH$_2$), 3.05-3.15 (m, 1H, CH), 3.95-4.04 (m, 1H, CH), 5.13-5.15 (m, 1H, CH), 7.75 (dd, J=8.5 Hz, 4H, phe-H), 7.81 (s, 1H, pyrimid-H), 8.24 (d, J=7 Hz, 1H, NH), 9.48 (s, 1H, NH), 9.66 (bs, 1H, NH); MS+ve: 478.3. R$_t$=9.28 min (purity 100%, Vydac 1)

Compound [39]: 4-(9-Cyclohexyl-6-oxo-6,7,8,9-tetrahydro-5H-pyrimido[4,5-b][1,4]diazepin-2-ylamino)-3-methoxy-N-(1-methyl-piperidin-4-yl)-benzamide

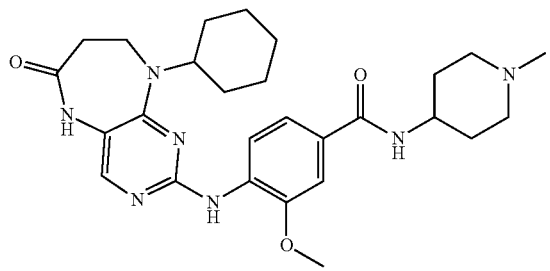 [SMILES: COc1cc(C(=O)NC2CCN(C)CC2)ccc1Nc1ncc2c(n1)N(C1CCCCC1)CCC(=O)N2]

Off-white solid (19%); ¹H NMR (DMSO-d$_6$): δ 1.16-1.98 (m, 18H, 10×cyclohex-H and 8×piperid-H), 2.18 (s, 3H, CH$_3$), 2.60 (dd, J=5 Hz, 2H, CH$_2$), 3.60 (dd, J=5 Hz, 2H, CH$_2$), 3.73-3.76 (m, 1H, CH), 3.95 (s, 3H, CH$_3$), 4.58-4.63 (m, 1H, CH), 7.46 (dd, J=2.0 and 8.0 Hz, 1H, phe-H), 7.49 (d, J=2 Hz, 1H, phe-H), 7.60 (s, 1H), 7.78 (s, 1H), 8.10 (d, J=8.0 Hz, 1H, NH), 8.37 (d, J=8.0 Hz, 1H, phe-H), 9.41 (bs, 1H, NH); MS+ve: 508.4. R$_t$=9.70 min (purity 95%, Vydac 1)

Example 2

General Experimental

Analytical and preparative RP-HPLC-MS was performed using Waters XBridge (50×4.6 mm C18 3.5 μm or 100×4.6 mm C18 3.5 μm) and XBridge (100×19 mm C18 5 μm) columns using a linear gradient of solvent A (water containing 0.1% ammonium hydroxide and 5% acetonitrile)/solvent B (acetonitrile) systems. Preparative RP-HPLC was performed using Apex Prepsil ODS 10μ column (22×250 mm) using a linear gradient of solvent A (water containing 0.1% TFA)/solvent B (acetonitrile). Mass spectra were obtained using a Waters ZQ2000 single quadrupole mass spectrometer with electro spray ionisation (ESI).

Gradients used were as follows:

| Mode | Method | Column | Flow rate mL/min | % solvent B | | | | | | | |
|------|--------|--------|------------------|-------------|---|---|---|---|---|---|---|
| | | | | 0 min | 0.5 min | 4 min | 6 min | 8.5 min | 10 min | 12 min | 40 min |
| Analytical | Analytical_1 | 4.6 × 50 | 1.6 | 10 | | 100 | 100 | | | | |
| Analytical | Analytical_2 | 4.6 × 100 | 1 | 10 | | | | | 50 | 100 | |
| Analytical | Analytical_3 | 4.6 × 100 | 1 | | | | | | | | |
| Preparative | Preparative_1 | 19 × 100 | 20 | 10 | 10 | | | 100 | | 100 | |
| Preparative | Preparative_2 | 19 × 100 | 20 | 30 | 30 | | | 80 | | 100 | |
| Preparative | Preparative_3 | 19 × 100 | 20 | 10 | 10 | | | 55 | | 100 | |
| Preparative | Preparative_4 | 22 × 250 | 9 | 0 | | | | | | | 60 |
| Preparative | Preparative_5 | 19 × 100 | 20 | 55 | 55 | | | 100 | | 100 | |

Intermediate 1: 2-chloro-9-cyclopentyl-5-methyl-8,9-dihydro-5H-pyrimido[4,5-b][1,4]diazepin-6(7H)-one

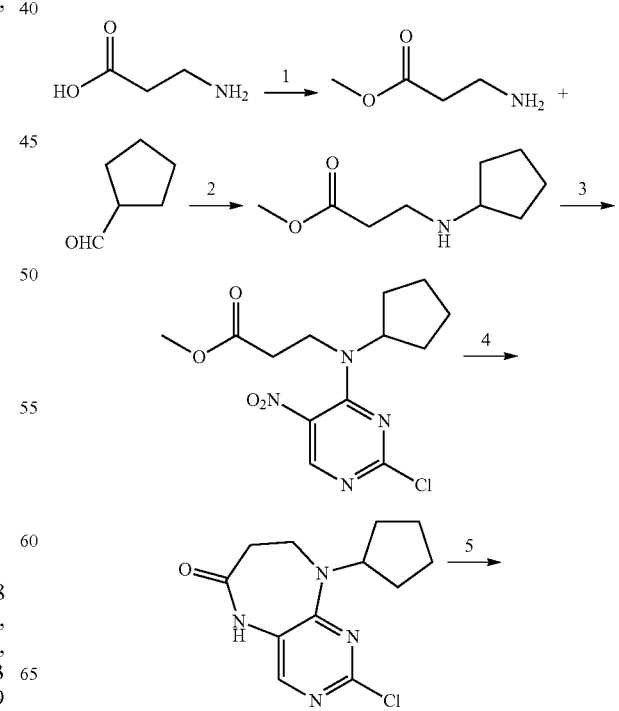

-continued

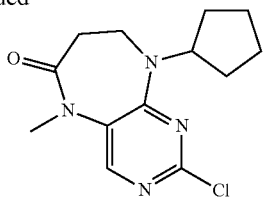

1. Thionyl chloride (2.1 eq), MeOH, 0° C. for addition, reflux 2 h; 2. Cyclopentanone (0.77 eq), sodium acetate (0.77 eq), sodium triacetoxyborohydride (1.11 eq), DCM, rt 16 h; 3. 2,4-Dichloro-5-nitropyrimidine (1.1 eq), $K_2CO_3$ (1 eq), acetone, 0° C.-rt 16 h; 4. $NH_4Cl$ (8.5 eq), Fe (8 eq), EtOH/$H_2O$ (4:1), reflux 2.5 h; 5. MeI (1.18 eq), NaH (1.07 eq), DMF, −10° C.-rt, 3 h.

Step 1: Methyl 3-aminopropanoate

β-Alanine (9.37 g, 0.105 mol, 1.0 eq), was added to MeOH (50 mL) and the mixture cooled to 0° C. before the dropwise addition of thionyl chloride (16 mL, 0.221 mol, 2.1 eq) [caution: exothermic addition]. The reaction was allowed to warm to rt then heated at reflux for 2 h. The solution was concentrated in vacuo, treated with t-butylmethyl ester and the resulting crystals removed by filtration. The product was a white crystalline solid (11 g, 100%); $^1$H (DMSO-$d_6$): δ 2.73 (2H, dd, J=7 Hz, $CH_2$), 2.98 (2H, dd, J=7 Hz, $CH_2$), 3.61 (3H, s, $CH_3$), 8.28 (2H, bs, $NH_2$); MS+ve: 104.1.

Step 2: Methyl 3-(cyclopentylamino)propanoate

Methyl 3-aminopropanoate (9.37 g, 0.09 mol) was dissolved in DCM (200 mL). Cyclopentanone (6.43 mL, 0.07 mol, 0.77 eq), sodium acetate (5.96 g, 0.07 mol, 0.77 eq) and sodium triacetoxyborohydride (22 g, 0.10 mol, 1.11 eq) were added then the reaction was stirred at rt for 16 h. 20% Sodium bicarbonate (100 mL) and 2 M sodium hydroxide (50 mL) were added and the product extracted using DCM/$H_2O$. The organic extracts were combined, washed with sat. NaCl, dried ($MgSO_4$) and evaporated under reduced pressure to give the product as a pale yellow oil (8.90 g, 55%); MS+ve: 172.4.

Step 3: Methyl 3-[cyclopentyl(2-chloro-5-nitropyrimidin-4-yl)amino]propanoate

Methyl 3-(cyclopentylamino)propanoate (0.838 g, 0.005 mol, 1 eq) and $K_2CO_3$ (0.676 g, 0.005 mol, 1 eq) were added to acetone (5 mL) and the resulting mixture cooled to 0° C. before the dropwise addition of 2,4-dichloro-5-nitropyrimidine (1.04 g, 0.0055 mol, 1.1 eq). The reaction mixture (RM) was warmed to rt and stirring continued for an additional 16 h before the addition of a further 0.12 eq of the pyrimidine. Stirring continued for a further 3 h. The RM was evaporated under reduced pressure and the product extracted using EtOAc/$H_2O$. The organic extracts were washed with sat NaCl, dried ($MgSO_4$) and evaporated under reduced pressure to give the product as a brown oily residue (1.04 g, 65%); MS+ve: 329.2; $R_t$=3.78 min (Analytical_1).

Step 4: 2-Chloro-9-cyclopentyl-5,7,8,9-tetrahydro-6H-pyrimido[4,5-b][1,4]diazepin-6-one Methyl 3-[cyclopentyl(2-chloro-5-nitropyrimidin-4-yl)amino]propanoate (1.0 g, 0.003 mol, 1 eq) and $NH_4Cl$ (1.38 g, 0.025 mol, 8.5 eq) were added to EtOH/$H_2O$ (4:1, 10 mL) and the mixture heated to reflux. Iron powder (1.36 g, 0.024 mol, 8 eq) was added portionwise and after 2 h the RM was hot filtered through celite washing through with EtOAc (10 mL) and EtOH (10 mL) [both hot]. The solvent was evaporated under reduced pressure to give the product as a brown solid (0.35 g, 43%); $^1$H (DMSO-$d_6$): δ 1.55 (4H, m, $2CH_2$), 1.7 (2H, m, $CH_2$), 1.83 (2H, m, $CH_2$), 2.66 (2H, t, J=5 Hz, $CH_2$), 3.57 (2H, t, J=5 Hz, $CH_2$), 5.01 (1H, m, CH), 7.83 (1H, s, CH), 9.71 (1H, s, NH); MS+ve: 267.2; $R_t$=2.87 min (Analytical_1).

Step 5: 2-chloro-9-cyclopentyl-5-methyl-8,9-dihydro-5H-pyrimido[4,5-b][1,4]diazepin-6(7H)-one 2-Chloro-9-cyclopentyl-5,7,8,9-tetrahydro-6H-pyrimido[4,5-b][1,4]diazepin-6-one (0.318 g, 0.0012 mol) and MeI (0.088 mL, 0.0014 mol, 1.18 eq) were added to DMF (5 mL) and the solution cooled to −10° C. NaH (0.03 g, 0.0013 mol, 1.07 eq) was added and the RM was stirred at 0° C. for 30 min and rt for 30 min. The solvent was evaporated under reduced pressure and the product extracted using EtOAc/$H_2O$. The organic extracts were combined, washed with sat NaCl, dried ($MgSO_4$) and evaporated under reduced pressure to give the product as a purple oily residue (0.25 g, 75%); $^1$H (DMSO-$d_6$): δ 1.55 (4H, m, $2CH_2$), 1.7 (2H, m, $CH_2$), 1.9 (2H, m, $CH_2$), 2.63 (2H, t, J=5 Hz, $CH_2$), 3.17 (3H, s, $CH_3$), 3.65 (2H, t, J=5 Hz, $CH_2$), 4.74 (1H, m, CH), 8.14 (1H, s, CH); MS+ve: 281.2; $R_t$=3.11 min (Analytical_1).

Using similar methods to those described above for Intermediate 1, the following intermediates 2-4 were prepared:

Intermediate 2: 2'-Chloro-9'-cyclopentyl-5'-methyl-8',9'-dihydrospiro[cyclopropane-1,7'-pyrimido[4,5-b][1,4]diazepin]-6'(5'H)-one Reaction of 1-aminomethyl-cyclopropanecarboxylic acid ethyl ester with cyclopentanone, sodium acetate and sodium triacetoxyborohydride in DCM gave 1-cyclopentylaminomethyl-cyclopropanecarboxylic acid ethyl ester

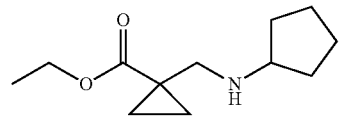

$^1$H NMR (CDCl$_3$): 0.84 (3H, t, J 7 Hz, CH3), 1.25 (4H, m, CH2), 1.37 (2H, m, CH), 1.54 (2H, m, CH), 1.70 (2H, m, CH), 1.83 (2H, m, CH), 2.71 (2H, s, CH2), 3.10 (1H, m, CH), 4.16 (2H, q, J 7 Hz, $\overline{CH2}$CH3)

Reaction of 1-cyclopentylaminomethyl-cyclopropanecarboxylic acid methyl ester with 2,4-dichloro-5-nitropyrimidine and $K_2CO_3$ in acetone gave 1-{[(2-Chloro-5-nitro-pyrimidin-4-yl)-cyclopentyl-amino]-methyl}cyclopropanecarboxylic acid ethyl ester. Treatment with $NH_4Cl$ and iron powder in ethanol gave 1-{[(5-Amino-2-chloro-pyrimidin-4-yl)-cyclopentyl-amino]-methyl}-cyclopropanecarboxylic acid ethyl ester

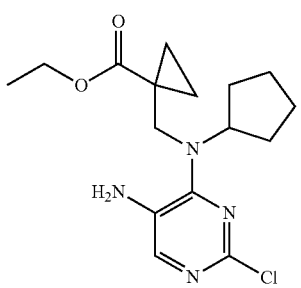 [SMILES: CCOC(=O)C1(CN(c2nc(Cl)ncc2N)C2CCCC2)CC1]

MS (+ve): 339.2, 341.2; Rt=4.15 min (Analytical_2).

The above compound in DMF was heated to 140° C. for 2 hours. Solvent was evaporated in vacuo, ethyl acetate added, and the resulting solid filtered and dried under vacuum to give 2'-chloro-9'-cyclopentyl-8',9'-dihydrospiro[cyclopropane-1,7'-pyrimido[4,5-b][1,4]diazepin]-6'(5'H)-one

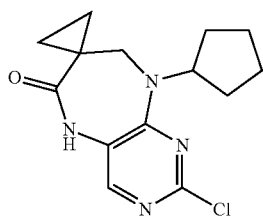 [SMILES: O=C1Nc2cnc(Cl)nc2N(C2CCCC2)CC12CC2]

MS (+ve): 293.2, 295.2; Rt=3.48 min (Analytical_2).

Reaction of 2-chloro-9-cyclopentyl-5,7,8,9-tetrahydro-pyrimido[4,5-b][1,4]diazepin-7,1'-cyclopropan]-6-one with MeI and NaH in DMF gave 2'-chloro-9'-cyclopentyl-5'-methyl-8',9'-dihydrospiro[cyclopropane-1,7'-pyrimido[4,5-b][1,4]diazepin]-6'(5'H)-one

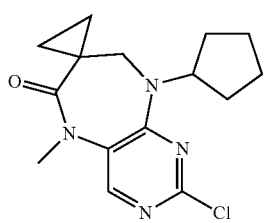 [SMILES: CN1C(=O)C2(CC2)CN(C2CCCC2)c2nc(Cl)ncc21]

MS (+ve): 307.1, 309.2; Rt=3.67 min (Analytical_3).

Intermediate 3: 2-chloro-9-cyclopentyl-5,7,7-trimethyl-8,9-dihydro-5H-pyrimido[4,5-b][1,4]diazepin-6(7H)-one Reaction of 3-amino-2,2-dimethyl-propionic acid ethyl ester with cyclopentanone, sodium acetate and sodium triacetoxyborohydride in DCM gave 3-Cyclopentylamino-2,2-dimethyl-propionic acid ethyl ester

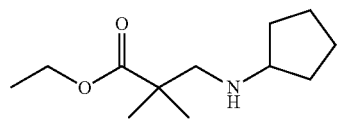

¹H NMR (CDCl3): 1.19 (6H, s, CH3), 1.25 (3H, t, J 7 Hz, CH3), 1.28 (2H, m, CH), 1.49 (2H, m, CH), 1.65 (2H, m, CH), 2.64 (1H, s, CH2), 3.01 (1H, m, CH), 4.10 (2H, q, J 7.5 Hz, CH2)

Reaction of 3-cyclopentylamino-2,2-dimethyl-propionic acid ethyl ester with 2,4-dichloro-5-nitropyrimidine and K₂CO₃ in acetone gave 3-[(2-Chloro-5-nitro-pyrimidin-4-yl)-cyclopentyl-amino]-2,2-dimethyl-propionic acid ethyl ester

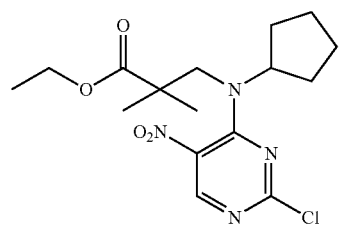 [SMILES: CCOC(=O)C(C)(C)CN(c1nc(Cl)ncc1N)C1CCCC1]

MS (+ve): 371.1, 373.1; Rt=4.67 min (Analytical_2).

Reaction of 3-[(2-chloro-5-nitro-pyrimidin-4-yl)-cyclopentyl-amino]-2,2-dimethyl-propionic acid ethyl ester with NH₄Cl and iron powder in ethanol gave 3-[(5-Amino-2-chloro-pyrimidin-4-yl)-cyclopentyl-amino]-2,2-dimethyl-propionic acid ethyl ester

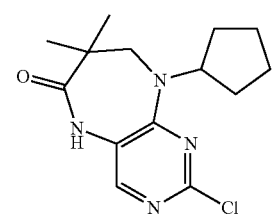 [SMILES: CC1(C)CN(C2CCCC2)c2nc(Cl)ncc2NC1=O]

MS (+ve): 341.2, 343.2; Rt=4.25 min (Analytical_2).

3-[(5-Amino-2-chloro-pyrimidin-4-yl)-cyclopentyl-amino]-2,2-dimethyl-propionic acid ethyl ester in DMF was heated to 140° C. for 2 hours. Solvent was evaporated in vacuo, ethyl acetate added, and the resulting solid filtered and dried under vacuum to give 2-Chloro-9-cyclopentyl-7,7-dimethyl-5,7,8,9-tetrahydro-pyrimido[4,5-b][1,4]diazepin-6-one

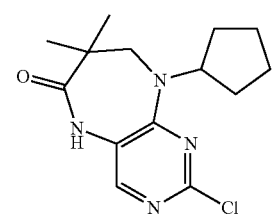 [SMILES: CC1(C)CN(C2CCCC2)c2nc(Cl)ncc2NC1=O]

MS (+ve): 295.1, 297.2; Rt=3.58 min (Analytical_2).

Reaction of 2-chloro-9-cyclopentyl-7,7-dimethyl-5,7,8,9-tetrahydro-pyrimido[4,5-b][1,4]diazepin-6-one with MeI and NaH in DMF gave 2-chloro-9-cyclopentyl-5,7,7-trimethyl-8,9-dihydro-5H-pyrimido[4,5-b][1,4]diazepin-6(7H)-one

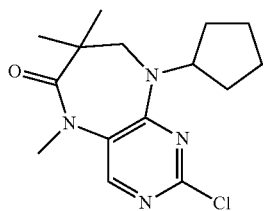 [SMILES: CN1C(=O)C(C)(C)CN(C2CCCC2)c2nc(Cl)ncc21]

MS (+ve): 309.1, 311.2; Rt=3.90 min (Analytical_3).

Intermediate 4: 2'-chloro-9'-cyclopentyl-5'-methyl-8',9'-dihydrospiro[cyclobutane-1,7'-pyrimido[4,5-b][1,4]diazepin]-6'(5'H)-one Reaction of 1-aminomethyl-cyclobutanecarboxylic acid methyl ester with cyclopentanone, sodium acetate and sodium triacetoxyborohydride in DCM gave 1-cyclopentylaminomethyl-cyclobutanecarboxylic acid methyl ester

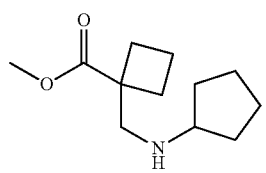

¹H NMR (CDCl3): 1.36 (2H, m, CH2), 1.51 (2H, m, CH2), 1.66 (2H, m, CH2), 1.95 (4H, m, 2×CH2), 2.15 (2H, m, CH2), 2.43 (4H, m, 2×CH2), 2.93 (2H, s, CH2), 3.21 (1H, m, CH), 3.76 (3H, s, CH3)

Reaction of 1-cyclopentylaminomethyl-cyclobutanecarboxylic acid methyl ester with 2,4-dichloro-5-nitropyrimidine and K₂CO₃ in acetone gave 4-{[(2-chloro-5-nitro-pyrimidin-4-yl)-cyclopentyl-amino]-methyl}-cyclobutanecarboxylic acid methyl ester

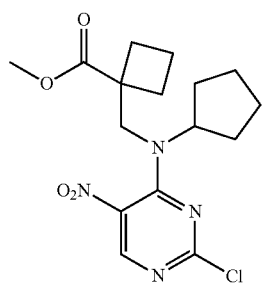 [SMILES: COC(=O)C1(CN(c2nc(Cl)ncc2[N+](=O)[O-])C2CCCC2)CCC1]

MS(+ve): 369.2, 371.2; Rt=3.48 min (Analytical_1).
Reaction of 1-{[(2-chloro-5-nitro-pyrimidin-4-yl)-cyclopentyl-amino]-methyl}-cyclobutanecarboxylic acid methyl ester with NH₄Cl and iron powder in ethanol gave 2'-chloro-9'-cyclopentyl-8',9'-dihydrospiro[cyclobutane-1,7'-pyrimido[4,5-b][1, 4]diazepin]-6'(5'H)-one, isolated directly.

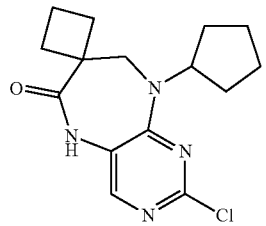 [SMILES: O=C1Nc2cnc(Cl)nc2N(C2CCCC2)CC12CCC2]

MS(+ve): 307.2, 309.2; Rt=3.48 min (Analytical_1).
Reaction of 2-chloro-9-cyclopentyl-5,7,8,9-tetrahydropyrimido[4,5-b][1,4]diazepin-7,1'-cyclobutan]-6-one with MeI and NaH in DMF gave 2'-chloro-9'-cyclopentyl-5'-methyl-8',9'-dihydrospiro[cyclobutane-1,7'-pyrimido[4,5-b][1,4]diazepin]-6'(5'H)-one

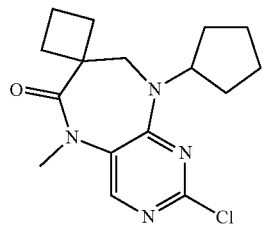 [SMILES: CN1C(=O)C2(CCC2)CN(C2CCCC2)c2nc(Cl)ncc21]

MS(+ve); 321.2, 323.3; Rt=3.77 min (Analytical_1).

Intermediate 5: 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzoic acid 2'-Chloro-9'-cyclopentyl-5'-methyl-8',9'-dihydrospiro[cyclopropane-1,7'-pyrimido[4,5-b][1,4]diazepin]-6'(5'H)-one (Intermediate 2) (0.70 g, 2.5 mmol, 1 eq), 4-amino-3-methoxybenzoic acid (1.25 g, 7.5 mmol, 3 eq) and TFA (1.43 g, 12.5 mmol, 5 eq) were heated to reflux in TFE (25 mL) for 18 hours. Solvent was evaporated in vacuo and the resulting residue was triturated with MeOH to give 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzoic acid (0.81 g, 74%).

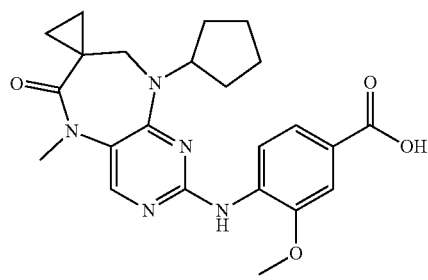 [SMILES: COc1cc(C(=O)O)ccc1Nc1ncc2c(n1)N(C1CCCC1)CC1(CC1)C(=O)N2C]

Rt=1.88 min (Analytical_1) MS(+ve): 438.4, MS (–ve): 436.5.

Intermediate 6: 4-(9-cyclopentyl-5,7,7-trimethyl-6-oxo-6,7,8,9-tetrahydro-5H-pyrimido[4,5-b][1,4]diazepin-2-ylamino)-3-methoxybenzoic acid 2-Chloro-9-cyclopentyl-5,7,7-trimethyl-8,9-dihydro-5H-pyrimido[4,5-b][1,4]diazepin-6(7H)-one (Intermediate 3)

(0.35 g, 1.14 mmol, 1 eq), 4-amino-3-methoxybenzoic acid (0.57 g, 3.42 mmol, 3 eq) and TFA (0.42 mL, 5.7 mmol, 5 eq) were heated to reflux in TFE (10 mL) for 36 hours. Solvent was evaporated in vacuo and the resulting residue was triturated with EtOAc to give 4-(9-cyclopentyl-5,7,7-trimethyl-6-oxo-6,7,8,9-tetrahydro-5H-pyrimido[4,5-b][1,4]diazepin-2-ylamino)-3-methoxybenzoic acid (0.38 g, 76%).

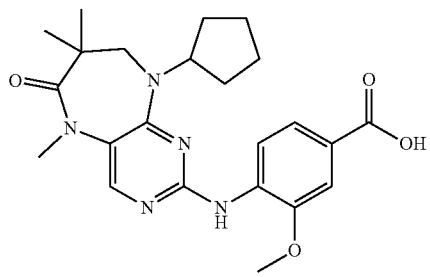 [SMILES: COc1cc(C(=O)O)ccc1Nc1ncc2c(n1)N(C1CCCC1)CC(C)(C)C(=O)N2C]

MS(+ve): 440.3, MS(−ve): 438.5.

Intermediate 7: 4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-3-methoxybenzoic acid 2'-Chloro-9'-cyclopentyl-5'-methyl-8',9'-dihydrospiro[cyclobutane-1,7'-pyrimido[4,5-b][1,4]diazepin]-6'(5'H)-one (Intermediate 4) (1.02 g, 3.18 mmol, 1 eq), 4-amino-3-methoxybenzoic acid (1.6 g, 9.5 mmol, 3 eq) and TFA (1.2 mL, 15.9 mmol, 5 eq) were heated to reflux in TFE (40 mL) for 24 hours. Solvent was evaporated in vacuo and the resulting residue was triturated with EtOAc to give 4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-3-methoxybenzoic acid (1.08 g, 75%).

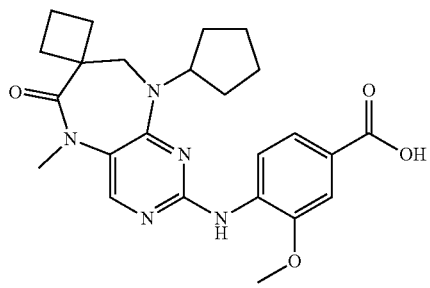 [SMILES: COc1cc(C(=O)O)ccc1Nc1ncc2c(n1)N(C1CCCC1)CC1(CCC1)C(=O)N2C]

Rt=2.10 min (Analytical_1); MS(+ve): 452.3, MS (−ve): 450.4.

Intermediate 8: 4-(9-Cyclopentyl-5-methyl-6-oxo-6,7,8,9-tetrahydro-5H-pyrimido[4,5-b][1,4]diazepin-2-ylamino)-3-methoxybenzoic acid 2-Chloro-9-cyclopentyl-5-methyl-8,9-dihydro-5H-pyrimido[4,5-b][1,4]diazepin-6(7H)-one (Intermediate 1) (0.70 g, 2.5 mmol, 1 eq), 4-amino-3-methoxybenzoic acid (1.25 g, 7.5 mmol, 3 eq) and TFA (0.93 mL, 12.5 mmol, 5 eq) were heated to reflux in TFE (25 mL) for 20 hours. Solvent was evaporated in vacuo and the resulting residue was triturated with MeOH to give 4-(9-cyclopentyl-5-methyl-6-oxo-6,7,8,9-tetrahydro-5H-pyrimido[4,5-b][1,4]diazepin-2-ylamino)-3-methoxybenzoic acid (0.66 g, 64%).

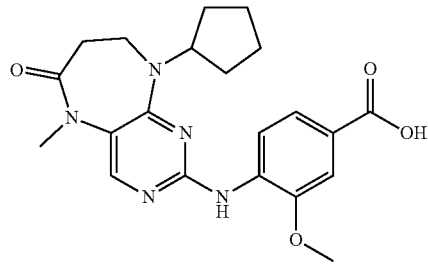 [SMILES: COc1cc(C(=O)O)ccc1Nc1ncc2c(n1)N(C1CCCC1)CCC(=O)N2C]

Rt=1.88 min (Analytical_1); MS(+ve): 412.4, MS (−ve): 410.5.

Intermediate 9: 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-fluorobenzoic acid 2'-Chloro-9'-cyclopentyl-5'-methyl-8',9'-dihydrospiro[cyclopropane-1,7'-pyrimido[4,5-b][1,4]diazepin]-6'(5'H)-one (Intermediate 2) (0.42 g, 1.36 mmol, 1 eq), 4-amino-3-fluorobenzoic acid (0.63 g, 4.1 mmol, 3 eq) and TFA (0.51 mL, 6.8 mmol, 5 eq) were heated to reflux in TFE (10 mL) for 36 hours. Further 4-amino-3-fluorobenzoic acid (0.63 g, 4.1 mmol, 3 eq) and TFA (0.51 mL, 6.8 mmol, 5 eq) were added and the reaction was heated to reflux again for 4 days. Solvent was evaporated in vacuo and the resulting residue was triturated with EtOAc to give 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-fluorobenzoic acid (0.41 g, 71%).

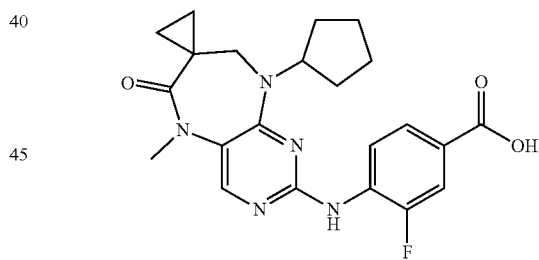

Rt=1.93 min (Analytical_1); MS(+ve): 426.3

Intermediate 10: 4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-3-fluorobenzoic acid 2'-Chloro-9'-cyclopentyl-5'-methyl-8',9'-dihydrospiro[cyclobutane-1,7'-pyrimido[4,5-b][1,4]diazepin]-6'(5'H)-one (Intermediate 4) (0.20 g, 0.63 mmol, 1 eq), 4-amino-3-fluorobenzoic acid (0.30 g, 1.9 mmol, 3 eq) and TFA (0.24 mL, 3.2 mmol, 5 eq) were heated to reflux in TFE for 18 hours. Further 4-amino-3-fluorobenzoic acid (0.20 g) and TFA (0.1 mL) were added and the reaction was heated to reflux again for 2 days. Further TFA (0.24 mL) was added and the reaction was heated to reflux again for 3 days. Solvent was evaporated in vacuo and the resulting residue was triturated with EtOAc to give 4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-3-fluorobenzoic acid (0.15 g, 55%).

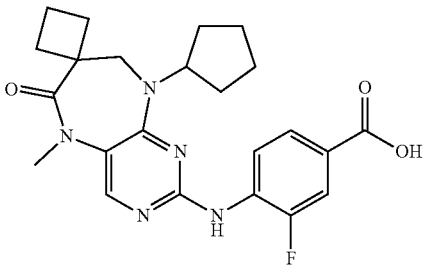 [SMILES: CN1C(=O)C2(CCC2)CN(C2CCCC2)c2nc(Nc3ccc(C(=O)O)cc3F)ncc21]

Rt=2.02 min (Analytical_1); MS(+ve): 440.3; MS(−ve): 438.4

Intermediate 11: 4-Amino-N-(trans-4-(4-(cyclopropylmethyl)piperazin-1-yl)cyclohexyl)-3-methoxybenzamide

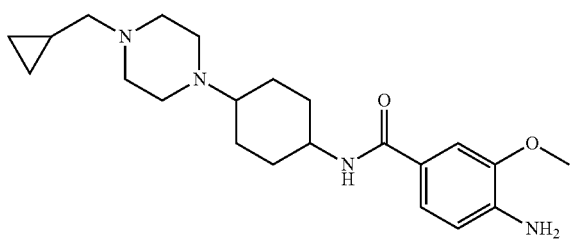 [SMILES: COc1cc(C(=O)NC2CCC(N3CCN(CC4CC4)CC3)CC2)ccc1N]

4-Amino-N-(trans-4-(4-(cyclopropylmethyl)piperazin-1-yl)cyclohexyl)-3-methoxybenzamide is a compound known in the art and was prepared by the methods described in WO 2007/090844 A1.

Intermediate 12: 4-(9-Cyclopentyl-5-methyl-6-oxo-6,7,8,9-tetrahydro-5H-pyrimido[4,5-b][1,4]diazepin-2-ylamino)-3-methoxy-N-(piperidin-4-yl)benzamide 4-(9-Cyclopentyl-5-methyl-6-oxo-6,7,8,9-tetrahydro-5H-pyrimido[4,5-b][1,4]diazepin-2-ylamino)-3-methoxybenzoic acid (Intermediate 8) (0.49 g, 1.2 mmol, 1 eq), TBTU (0.42 g, 1.3 mmol, 1.1 eq) and DIPEA (0.40 mL, 2.4 mmol, 2 eq) were stirred together in DCM (25 mL) for 30 min before addition of 4-amino-1-BOC-piperidine (0.29 g, 1.4 mmol, 1.2 eq). The RM was stirred at rt for 20 hours before diluting with DCM (30 mL) and washing sequentially with water (2×15 mL), 50% saturated aqueous sodium hydrogen carbonate (1×20 mL), saturated aqueous potassium carbonate (1×20 mL) and saturated brine (1×20 mL). Concentrated in vacuo to isolate 4-(9-cyclopentyl-5-methyl-6-oxo-6,7,8,9-tetrahydro-5H-pyrimido[4,5-b][1,4]diazepin-2-ylamino)-3-methoxy-N-(1-BOC-piperidin-4-yl)benzamide that was used without further purification (0.71 g). Rt=3.58 min (Analytical_1).

Methanolic hydrochloric acid was added and the solution was stirred for 4 hours at rt. Concentration in vacuo provided the hydrochloride salt of 4-(9-cyclopentyl-5-methyl-6-oxo-6,7,8,9-tetrahydro-5H-pyrimido[4,5-b][1,4]diazepin-2-ylamino)-3-methoxy-N-(piperidin-4-yl)benzamide. This salt was partitioned between DCM and aqueous potassium carbonate solution at pH 8. The DCM layer was separated and the aqueous layer extracted with DCM and EtOAc.

The combined organic layers were dried (MgSO4) and concentrated in vacuo to provide 4-(9-cyclopentyl-5-methyl-6-oxo-6,7,8,9-tetrahydro-5H-pyrimido[4,5-b][1,4]diazepin-2-ylamino)-3-methoxy-N-(piperidin-4-yl)benzamide as free base (0.51 g).

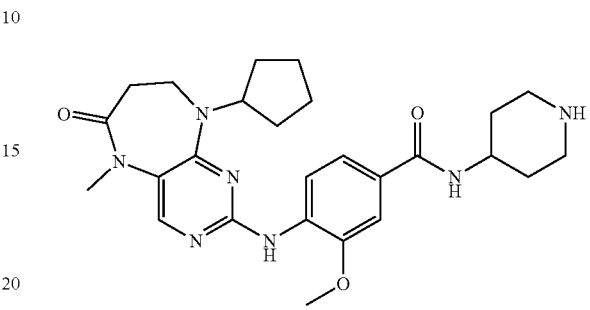

Rt=2.78 min (Analytical_1); MS(+ve): 494; MS(−ve): 492.

Compound [254]: 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(4-methylpiperazin-1-yl)benzamide 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzoic acid (Intermediate 5) (22 mg, 0.05 mmol, 1 eq), DIPEA (17 μl, 0.10 mmol, 2 eq) and TBTU (18 mg, 0.055 mmol, 1.1 eq) were added to 0.5 mL DMF and the resulting solution stirred at rt for 30 min before the addition of 1-amino-4-methylpiperazine (12 μl, 0.1 mmol, 2 eq). The RM was then stirred at rt for 4 hours before purifying by preparative RP-HPLC-MS (Preparative_1) to provide 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(4-methylpiperazin-1-yl)benzamide (white solid, 8 mg, 30%).

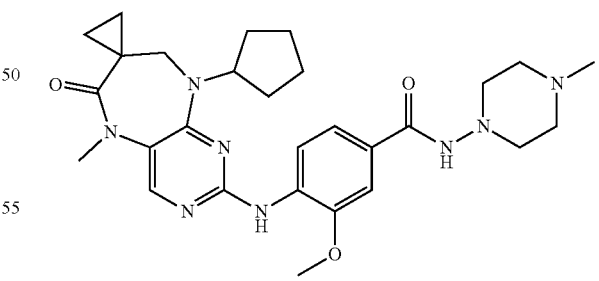

Rt=2.63 min (Analytical_1) MS(+ve): 535.5; MS(−ve): 533.6; 1H NMR (DMSO-d6) δ ppm: 0.63-0.70 (2H, m), 0.87-0.94 (2H, m), 1.43-1.54 (2H, m), 1.55-1.63 (2H, m), 1.64-1.73 (2H, m), 1.83-1.94 (2H, m), 2.18 (3H, s), 2.31-2.48 (4H, m), 2.92 (4H, m), 3.16 (3H, s), 3.47 (2H, s), 3.94 (3H, s), 4.78-4.91 (1H, m), 7.35-7.48 (2H, m), 7.68 (1H, s), 7.98 (1H, s), 8.39 (1H, d, J=8.3 Hz), 9.31 (1H, s).

Compound [218]: (±)-4-(9'-Cyclopentyl-5'-methyl-6'-oxo-5',6',8',9'-tetrahydrospiro[cyclobutane-1,7'-pyrimido[4,5-b][1,4]diazepine]-2'-ylamino)-3-methoxy-N-(quinuclidin-3-yl)benzamide 4-(9'-Cyclopentyl-5'-methyl-6'-oxo-5',6',8',9'-tetrahydrospiro[cyclobutane-1,7'-pyrimido[4,5-b][1,4]diazepine]-2'-ylamino)-3-methoxybenzoic acid (Intermediate 7) (15 mg, 0.033 mmol), DIPEA (12 μl, 0.066 mmol, 2 eq) and TBTU (12 mg, 0.036 mmol, 1.1 eq) were added to 0.5 mL DMF and the resulting solution stirred at rt for 5 min before the addition of 3-aminoquinuclidine dihydrochloride (8 mg, 0.04 mmol, 1.2 eq) and DIPEA (13 μL). The RM was then stirred at rt for 3 hours before purifying by preparative RP-HPLC-MS (Preparative_2) to provide (±)-4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-3-methoxy-N-(quinuclidin-3-yl)benzamide.

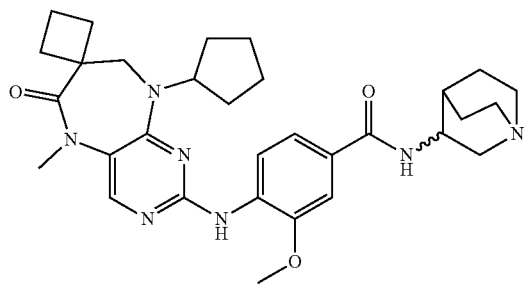 [SMILES: COc1cc(C(=O)NC2CN3CCC2CC3)ccc1Nc1ncc2c(n1)N(C1CCCC1)CC1(CCC1)C(=O)N2C]

Rt=3.26 min (Analytical_1); MS(+ve): 560.4; 1H NMR (DMSO-d6) δ ppm: 8.37 (d, J=8.3 Hz, 1H), 8.08 (d, J=6.8 Hz, 1H), 8.05 (s, 1H), 7.73 (s, 1H), 7.45-7.53 (m, 2H), 4.82 (quin, J=8.3 Hz, 1H), 3.84-4.01 (m, 4H), 3.64 (s, 2H), 3.18 (s, 3H), 3.04-3.14 (m, 1H), 2.88 (t, J=9.8 Hz, 1H), 2.58-2.75 (m, 4H), 2.21-2.33 (m, 2H), 2.07 (s, 2H), 1.97 (br. s., 2H), 1.87 (br. s., 2H), 1.76 (d, J=4.9 Hz, 2H), 1.56-1.70 (m, 8H), 1.30 (br. s., 1H)

Compound [195]: 4-(9-Cyclopentyl-5,7,7-trimethyl-6-oxo-6,7,8,9-tetrahydro-5H-pyrimido[4,5-b][1,4]diazepin-2-ylamino)-3-methoxy-N-(4-methyl-piperazin-1-yl)-benzamide 4-(9-Cyclopentyl-5,7,7-trimethyl-6-oxo-6,7,8,9-tetrahydro-5H-pyrimido[4,5-b][1,4]diazepin-2-ylamino)-3-methoxybenzoic acid (Intermediate 6) (20 mg, 0.046 mmol, 1 eq), DIPEA (16 μl, 0.091 mmol, 2 eq) and TBTU (16 mg, 0.05 mmol, 1.1 eq) were added to 0.5 mL DMF and the resulting solution stirred at rt for 5 min before the addition of 1-amino-4-methylpiperazine (7 mg). The RM was then stirred at rt for 16 hours before purifying by preparative RP-HPLC-MS (Preparative_1) to provide 4-(9-cyclopentyl-5,7,7-trimethyl-6-oxo-6,7,8,9-tetrahydro-5H-pyrimido[4,5-b][1,4]diazepin-2-ylamino)-3-methoxy-N-(4-methyl-piperazin-1-yl)-benzamide.

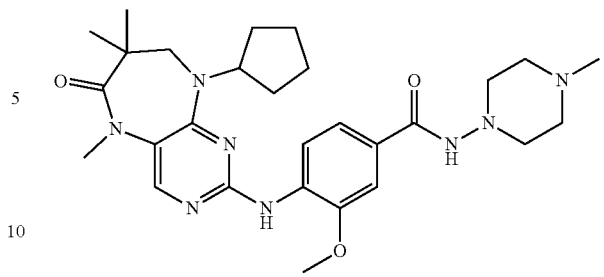

Rt=2.81 min (Analytical_1); MS(+ve): 537.5; 1H NMR (DMSO-d6) δ ppm: 1.09 (6H, s), 1.61 (4H, m), 1.73 (2H, m), 1.87 (2H, m), 2.19 (3H, s), 2.42 (2H, m), 2.92 (4H, m), 3.29 (3H, s), 3.37 (3H, m), 3.93 (3H, s), 3.17 (1H, m), 7.40 (2H, m), 7.68 (1H, s), 7.98 (1H, s), 8.37 (1H, d, J 7 Hz), 9.30 (1H, s).

Compound [221]: 4-(9'-Cyclopentyl-5'-methyl-6'-oxo-5',6',8',9'-tetrahydrospiro[cyclobutane-1,7'-pyrimido[4,5-b][1,4]diazepine]-2'-ylamino)-3-methoxy-N-(4-methylpiperazin-1-yl)benzamide 4-(9'-Cyclopentyl-5'-methyl-6'-oxo-5',6',8',9'-tetrahydrospiro[cyclobutane-1,7'-pyrimido[4,5-b][1,4]diazepine]-2'-ylamino)-3-methoxybenzoic acid (Intermediate 7) (15 mg, 0.033 mmol, 1 eq), DIPEA (12 μl, 0.066 mmol, 2 eq) and TBTU (12 mg, 0.036 mmol, 1.1 eq) were added to 0.5 mL DMF and the resulting solution stirred at rt for 5 min before the addition of 1-amino-4-methylpiperazine (5 mg) and DIPEA (13 μL). The RM was then stirred at rt for 3 hours before purifying by preparative RP-HPLC-MS (Preparative_2) to provide 4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-3-methoxy-N-(4-methylpiperazin-1-yl)benzamide.

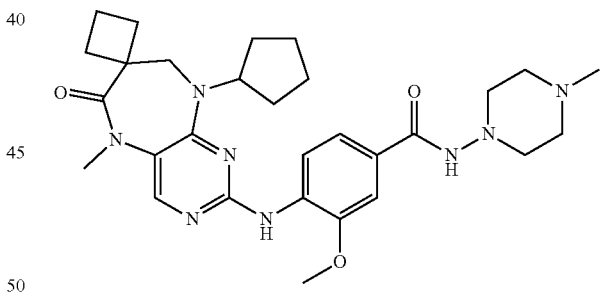

Rt=2.79 min (Analytical_1); MS(+ve): 549.5; 1H NMR (DMSO-d6) δ ppm: 9.31 (s, 1H), 8.37 (d, J=8.3 Hz, 1H), 8.05 (s, 1H), 7.72 (s, 1H), 7.37-7.47 (m, 2H), 4.73-4.86 (m, 1H), 3.93 (s, 3H), 3.64 (s, 2H), 3.18 (s, 3H), 2.92 (br. s., 4H), 2.36 (br. s., 4H), 2.27 (d, J=9.3 Hz, 2H), 2.18 (s, 3H), 1.97 (br. s., 2H), 1.79-1.91 (m, 1H), 1.76 (br. s., 2H), 1.54-1.72 (m, 7H).

Compound [371]: -(9'-Cyclopentyl-5'-methyl-6'-oxo-5',6',8',9'-tetrahydrospiro[cyclopropane-1,7'-pyrimido[4,5-b][1,4]diazepine]-2'-ylamino)-N-((trans)-4-(4-(cyclopropylmethyl)piperazin-1-yl)cyclohexyl)-3-methoxybenzamide 2'-Chloro-9'-cyclopentyl-5'-methyl-8',9'-dihydrospiro[cyclopropane-1,7'-pyrimido[4,5-b][1,4]diazepin]-6'(5'H)-one (Intermediate 2) (0.14 g, 0.45 mmol, 1 eq), 4-amino-N-(trans-4-(4-(cyclopropylmethyl)piperazin-1-yl)cyclohexyl)-3-methoxybenzamide (Intermediate 11) (0.26 g, 0.67 mmol, 1.5 eq) and TFA (0.17 mL, 2.2 mmol, 5 eq) in TFE (3 mL) were heated together at 80° C. for 18 hours. Further quantity of Intermediate 2 (0.14 g) was added and the reaction further heated for 48 hours. RM was concentrated in vacuo and the residue was purified by flash column chromatography on silica eluting with 020% ammonia/MeOH in DCM gradient followed by preparative HPLC (Preparative_4) then finally preparative RP-HPLC-MS (Preparative_1) to give 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((trans)-4-(4-(cyclopropylmethyl)piperazin-1-yl)cyclohexyl)-3-methoxybenzamide (0.11 g, 25%).

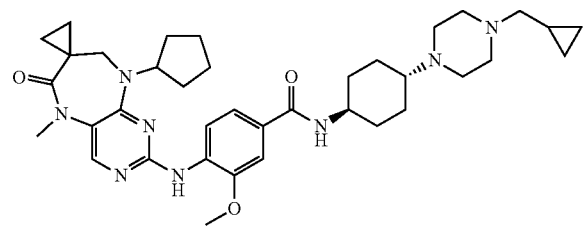 [SMILES: COc1cc(C(=O)N[C@H]2CC[C@H](N3CCN(CC4CC4)CC3)CC2)ccc1Nc1ncc2c(n1)N(C1CCCC1)CC1(CC1)C(=O)N2C]

Rt=3.18 min (Analytical_1); ES(+ve): 657.6; ES(−ve): 655.7; 1H NMR (DMSO-d6) δ ppm: 0.05 (d, J=4.20 Hz, 3H), 0.44 (d, J=7.74 Hz, 2H), 0.67 (d, J=1.61 Hz, 2H), 0.74-0.85 (m, 1H), 0.90 (s, 2H), 1.23-1.44 (m, 3H), 1.44-1.55 (m, 2H), 1.54-1.64 (m, 2H), 1.64-1.74 (m, 2H), 1.88 (br. s., 5H), 2.08 (s, 3H), 2.13 (d, J=6.45 Hz, 2H), 2.17-2.28 (m, 1H), 2.29-2.47 (m, 3H), 2.60-2.67 (m, 1H), 3.06-3.23 (m, 5H), 3.47 (s, 2H), 3.65-3.79 (m, 1H), 3.94 (s, 2H), 4.05-4.13 (m, 1H), 4.78-4.91 (m, 1H), 7.48 (s, 2H), 7.67 (s, 1H), 7.98 (s, 1H), 8.00-8.07 (m, 1H), 8.31-8.45 (m, 1H).

Compound [372]: 4-(9-Cyclopentyl-5,7,7-trimethyl-6-oxo-6,7,8,9-tetrahydro-5H-pyrimido[4,5-b][1,4]diazepin-2-ylamino)-N-((trans)-4-(4-(cyclopropylmethyl)piperazin-1-yl)cyclohexyl)-3-methoxybenzamide 2-Chloro-9-cyclopentyl-5,7,7-trimethyl-8,9-dihydro-5H-pyrimido[4,5-b][1,4]diazepine-6(7H)-one (Intermediate 3) (0.13 g, 0.43 mmol, 1 eq), 4-amino-N-(trans-4-(4-(cyclopropylmethyl)piperazin-1-yl)cyclohexyl)-3-methoxybenzamide (Intermediate 11) (0.26 g, 0.67 mmol, 1.5 eq) and TFA (0.17 mL, 2.2 mmol, 5 eq) in TFE (3 mL) were heated together at 80° C. for 18 hours. Further quantity of Intermediate 6 (0.13 g) was added and the reaction further heated for 48 hours. RM was concentrated in vacuo and the residue was purified by flash column chromatography on silica eluting with 020% ammonia/MeOH in DCM gradient followed by preparative HPLC (Preparative_4) then finally preparative RP-HPLC-MS (Preparative_1) to give 4-(9-cyclopentyl-5,7,7-trimethyl-6-oxo-6,7,8,9-tetrahydro-5H-pyrimido[4,5-b][1,4]diazepin-2-ylamino)-N-((trans)-4-(4-(cyclopropylmethyl)piperazin-1-yl)cyclohexyl)-3-methoxybenzamide (0.03 g, 7%).

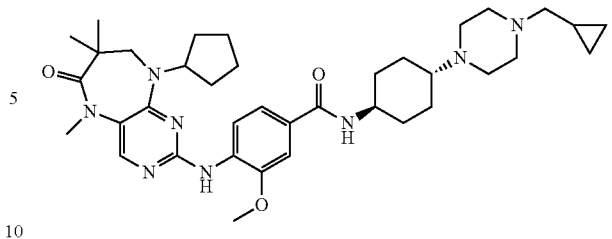

Rt=3.38 min (Analytical_1); ES(+ve): 659.6; ES(−ve): 657.7; 1H NMR (DMSO-d6) δ ppm: 0.05 (d, J=3.86 Hz, 3H), 0.40-0.48 (m, 3H), 0.73-0.84 (m, 2H), 1.03-1.13 (m, 10H), 1.18 (s, 1H), 1.24-1.43 (m, 6H), 1.61 (br. s., 3H), 1.74 (d, J=9.65 Hz, 2H), 1.88 (br. s., 5H), 2.08 (s, 5H), 2.13 (d, J=6.75 Hz, 2H), 2.17-2.25 (m, 1H), 2.36 (br. s., 3H), 2.60-2.67 (m, 1H), 3.14-3.22 (m, 2H), 3.37 (s, 1H), 3.51 (s, 1H), 3.94 (s, 2H), 5.18 (t, J=8.52 Hz, 1H), 7.43-7.50 (m, 1H), 7.67 (s, 1H), 7.98 (s, 1H), 8.03 (d, J=7.72 Hz, 1H), 8.35 (d, J=8.36 Hz, 1H).

Alternatively, the skilled person would appreciate that Examples 5, 6 could be synthesised by reaction of Intermediates 5 or 6 with the known compound trans-4-(4-cyclopropylmethyl-piperazin-1-yl)-cyclohexylamine (described in U.S. Pat. No. 6,861,422 B2) using standard amide bond formation conditions such as those described in Example 1.

Compound [345]: 4-(9-Cyclopentyl-5-methyl-6-oxo-6,7,8,9-tetrahydro-5H-pyrimido[4,5-b][1,4]diazepin-2-ylamino)-3-methoxy-N-[1-(tetrahydro-pyran-4-yl)-piperidin-4-yl]-benzamide 4-(9-Cyclopentyl-5-methyl-6-oxo-6,7,8,9-tetrahydro-5H-pyrimido[4,5-b][1,4]diazepin-2-ylamino)-3-methoxy-N-(piperidin-4-yl)benzamide (Intermediate 12) (35 mg, 0.07 mmol, 1 eq) and sodium triacetoxyborohydride (18 mg, 0.084 mmol, 1.2 eq) in DCM (0.5 mL) were reacted with tetrahydropyran-4-one (6.5 μL, 0.07 mmol, 1 eq) at rt for 2 days. Further and sodium triacetoxyborohydride (18 mg, 1.2 eq), tetrahydropyran-4-one (6.5 μL, 1 eq) were added and acetic acid (4 μL, 1 eq). After two days the RM was diluted with DCM, washed with water and the organic layer concentrated in vacuo. The resulting residue was purified by preparative RP-HPLC-MS (Preparative_1) to provide 4-(9-cyclopentyl-5-methyl-6-oxo-6,7,8,9-tetrahydro-5H-pyrimido[4,5-b][1,4]diazepin-2-ylamino)-3-methoxy-N-[1-(tetrahydro-pyran-4-yl)-piperidin-4-yl]-benzamide (10 mg, 25%).

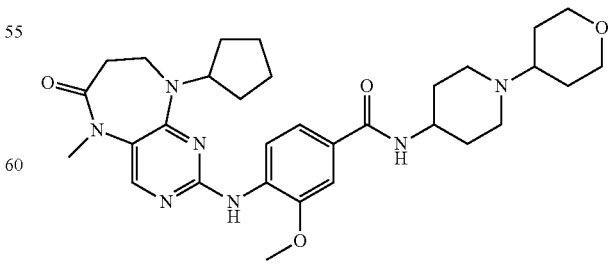

Rt=2.74 min (Analytical_1); ES(+ve): 578.5; ES(−ve): 576.7.

Compound [373]: 4-(9'-Cyclopentyl-5'-methyl-6'-oxo-5',6',8',9'-tetrahydrospiro[cyclobutane-1,7'-pyrimido[4,5-b][1,4]diazepine]-2'-ylamino)-3-fluoro-N-(4-methylpiperazin-1-yl)benzamide 4-(9'-Cyclopentyl-5'-methyl-6'-oxo-5',6',8',9'-tetrahydrospiro[cyclobutane-1,7'-pyrimido[4,5-b][1,4]diazepine]-2'-ylamino)-3-fluorobenzoic acid (Intermediate 10) (100 mg, 0.23 mmol, 1 eq), DIPEA (80 µl, 0.46 mmol, 2 eq) and TBTU (80 mg, 0.25 mmol, 1.1 eq) were added to 1 mL DMF and the resulting solution stirred at rt for 10 min before the addition of 1-amino-4-methylpiperazine (33 µL, 0.27 mmol, 1.2 eq). The RM was then stirred at rt for 1 hour before splitting into two equal batches and purifying by preparative RP-HPLC-MS (Preparative_3) to provide 4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-3-fluoro-N-(4-methylpiperazin-1-yl)benzamide (0.05 g, 41%).

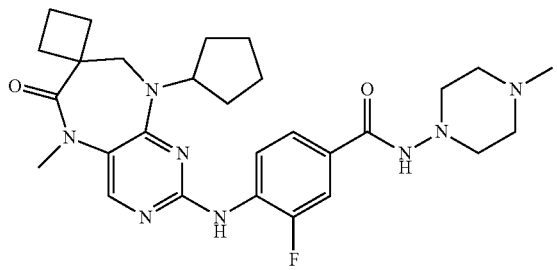 [SMILES: CN1CCN(NC(=O)c2ccc(Nc3ncc4c(n3)N(C3CCCC3)CC3(CCC3)C(=O)N4C)c(F)c2)CC1]

Rt=2.74 min (Analytical_1); MS(+ve): 537.5; 1H NMR (DMSO-d6) δ ppm: 1.55-1.65 (8H, m), 1.71 (2H, m), 1.88 (2H, m), 2.18 (3H, s), 2.28 (2H, q, J 10.5 Hz), 2.41-2.52 (4H, m), 2.89 (4H, m), 3.18 (3H, s), 3.61 (2H, s), 4.76 (1H, quintet, 8.5 Hz), 7.61 (2H, m), 8.03 (1H, s), 8.12 (1H, dd, J 8 Hz, 8.5 Hz), 8.76 (1H, s), 9.36 (1H, s).

Compound [374]: 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-fluoro-N-(4-methylpiperazin-1-yl)benzamide 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-fluorobenzoic acid (Intermediate 9) (0.27 g, 0.63 mmol, 1 eq), DIPEA (0.21 mL, 1.26 mmol, 2 eq) and TBTU (0.22 g, 0.69 mmol, 1.1 eq) were added to 5 mL DCM and the resulting solution stirred at rt for 30 min before the addition of 1-amino-4-methylpiperazine (91 µl, 0.75 mmol, 1.2 eq). The RM was then stirred at rt for 4 hours before washing with water, concentrating in vacuo and purifying the residue by preparative RP-HPLC-MS (Preparative_1) to provide 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-fluoro-N-(4-methylpiperazin-1-yl)benzamide (0.14 g, 44%).

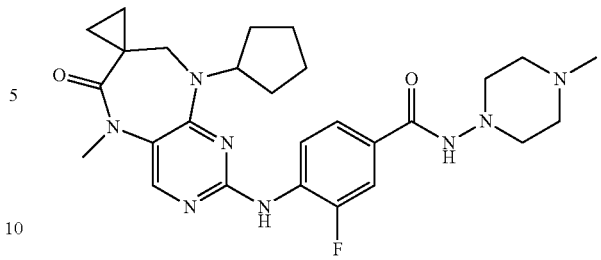

Rt=2.58 min (Analytical_1); MS(+ve): 523.4; 1H NMR (DMSO-d6) δ ppm: 0.65-0.67 (2H, s, CH2), 0.85-0.95 (2H, m, CH2), 1.23-1.82 (8H, m, alkyl-H), 2.18 (3H, s, CH3), 2.36-2.41 (4H, m, alkyl-H), 2.88 (4H, s, alkyl-H), 3.16 (3H, s, CH3), 3.44 (2H, s, alkyl-H), 4.77-4.80 (1H, m, CH), 7.6 (2H, m, aryl-H), 7.96 (1H, s, aryl-H), 8.16 (1H, t, J=8 Hz, aryl-H), 8.70 (1H, s, NH), 9.35 (1H, s, NH).

Compound [194]: (±)-4-(9-Cyclopentyl-5,7,7-trimethyl-6-oxo-6,7,8,9-tetrahydro-5H-pyrimido[4,5-b][1,4]diazepin-2-ylamino)-3-methoxy-N-(quinuclidin-3-yl)benzamide 4-(9-Cyclopentyl-5,7,7-trimethyl-6-oxo-6,7,8,9-tetrahydro-5H-pyrimido[4,5-b][1,4]diazepin-2-ylamino)-3-methoxybenzoic acid (Intermediate 6) (20 mg, 0.046 mmol, 1 eq), DIPEA (16 µl, 0.091 mmol, 2 eq) and TBTU (16 mg, 0.05 mmol, 1.1 eq) were added to 0.5 mL DMF and the resulting solution stirred at rt for 5 min before the addition of 3-aminoquinuclidine dihydrochloride (11 mg, 0.055 mmol, 1.1 eq). The RM was then stirred at rt for 16 hours before purifying by preparative RP-HPLC-MS (Preparative_1) to provide (±)-4-(9-cyclopentyl-5,7,7-trimethyl-6-oxo-6,7,8,9-tetrahydro-5H-pyrimido[4,5-b][1,4]diazepin-2-ylamino)-3-methoxy-N-(quinuclidin-3-yl)benzamide (8 mg, 32%).

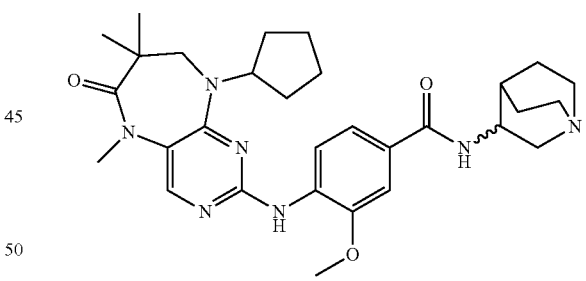

Rt=3.28 min (Analytical_1); MS(+ve): 548.5; 1H NMR (DMSO-d6) δ ppm: 8.37 (1H, d, J 8 Hz), 8.07 (1H, d, J 6.5 Hz), 7.98 (1H, s), 7.69 (1H, s), 7.47-7.50 (2H, m), 5.19 (1H, quint, J 8 Hz), 3.95 (4H, m), 3.37 (2H, s), 3.18 (3H, s), 3.11 (1H, m), 2.89 (1H, m), 2.65-2.72 (4H, m), 1.88 (2H, m), 1.73-1.87 (4H, m), 1.57-1.61 (6H, m), 1.31 (1H, m), 1.09 (6H, s).

Compound [186]: (±)-4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(quinuclidin-3-yl)benzamide 4-(9'-Cyclopentyl-5'-methyl-6'-oxo-5',6',8',9'-tetrahydrospiro[cyclopropane-1,7'-pyrimido[4,5-b][1,4]diazepine]-

2'-ylamino)-3-methoxybenzoic acid (Intermediate 5) (25 mg, 0.057 mmol, 1 eq), DIPEA (20 µL, 0.11 mmol, 2 eq) and TBTU (20 mg, 0.063 mmol, 1.1 eq) were added to 0.5 mL DMF and the resulting solution stirred at rt for 15 min before the addition of 3-aminoquinuclidine dihydrochloride (11 mg, 0.055 mmol, 1.1 eq) and DIPEA (40 µL). The RM was then stirred at rt for 16 hours before purifying by preparative RP-HPLC-MS (Preparative_1) to provide (±)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(quinuclidin-3-yl)benzamide.

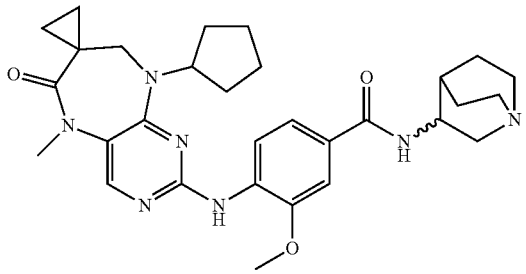

Rt=3.02 min (Analytical_1); MS(+ve): 546.4; 1H NMR (DMSO-d6) δ ppm: 8.40 (1H, d, J 8 Hz), 8.08 (1H, d, J 7 Hz), 7.98 (1H, s), 7.69 (1H, s), 7.47-7.50 (2H, m), 4.87 (1H, quint, J 9 Hz), 4.10 (1H, q, J 5.5 Hz), 3.95 (4H, m), 3.47 (2H, s), 3.27 (3H, s), 3.07 (1H, m), 2.08 (1H, m), 2.63-2.86 (4H, m), 1.88 (3H, m), 1.78 (1H, m), 1.68 (2H, m), 1.50-1.62 (5H, m), 1.32 (1H, m), 0.90 (2H, m), 0.66 (2H, m).

Compound [375]: 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-N-(4-(2-hydroxyethyl)piperazin-1-yl)-3-methoxybenzamide 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzoic acid (Intermediate 5) (48 mg, 0.11 mmol, 1 eq), DIPEA (36 µL, 0.22 mmol, 2 eq) and TBTU (39 mg, 0.12 mmol, 1.1 eq) were added to 5 mL DCM and the resulting solution stirred at rt for 15 min before the addition of 2-(4-aminopiperazin-1-yl)ethanol (19 mg, 0.13 mmol, 1.2 eq). The RM was then stirred at rt for 16 hours before concentrating in vacuo and purifying by preparative RP-HPLC-MS (Preparative_1) to provide 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-(4-(2-hydroxyethyl)piperazin-1-yl)-3-methoxybenzamide (24 mg, 39%).

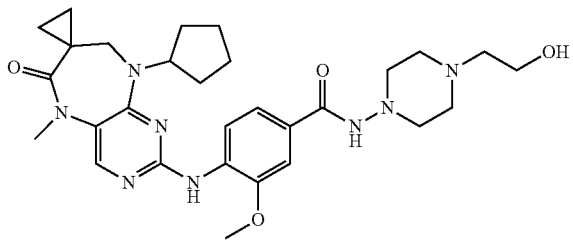 [SMILES: COc1cc(C(=O)NN2CCN(CCO)CC2)ccc1Nc1ncc2c(n1)N(C1CCCC1)CC1(CC1)C(=O)N2C]

Rt=2.48 min (Analytical_1); MS(+ve): 565.4; 1H NMR (DMSO) δ ppm: 0.66-0.67 (2H, m, CH2), 0.88-0.90 (2H, m, CH2), 1.23-1.90 (8H, m, alkyl-H), 2.34-2.41 (4H, m, alkyl-H), 2.91 (4H, t, J=4 Hz, alkyl-H), 3.16 (3H, s, CH3), 3.46-3.51 (4H, m), 3.93 (3H, s, CH3), 4.38-4.45 (1H, m), 4.81-4.87 (1H, m, CH), 7.40 (2H, d, J=10.5 Hz, aryl-H), 7.67 (1H, s), 7.98 (1H, s), 8.39 (1H, d, J=8 Hz, aryl-H), 9.30 (1H, s, NH).

Compound [376]: 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-morpholinobenzamide 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzoic acid (Intermediate 5) (50 mg, 0.11 mmol, 1 eq), DIPEA (38 µL, 0.23 mmol, 2 eq) and TBTU (40 mg, 0.12 mmol, 1.1 eq) were added to 5 mL DCM and the resulting solution stirred at rt for 15 min before the addition of 4-aminomorpholine (12 mg, 0.14 mmol, 1.2 eq). The RM was then stirred at rt for 16 hours before concentrating in vacuo and purifying by preparative RP-HPLC-MS (Preparative_1) to provide 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-morpholinobenzamide (26 mg, 44%).

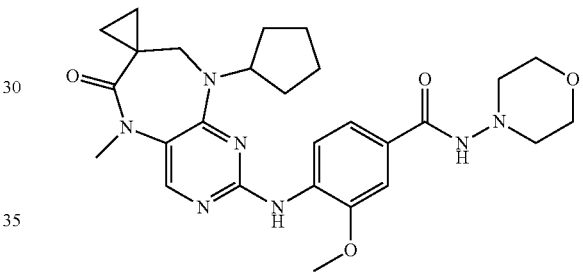

Rt=2.72 min (Analytical_1); MS(+ve): 522.4; 1H NMR (DMSO) δ ppm: 0.65-0.71 (2H, m, CH2), 0.85-0.91 (2H, m, CH2), 1.23-1.88 (8H, m, alkyl-H), 2.92 (4H, t, J=4 Hz, alkyl-H), 3.16 (3H, s, CH3), 3.47 (2H, s, alkyl-H), 3.66 (4H, t, J=4.5 Hz), 3.94 (3H, s, CH3), 4.81-4.87 (1H, m, CH), 7.41 (2H, d, J=9.5 Hz), 7.69 (1H, s), 7.98 (1H, s), 8.40 (1H, d, J=8 Hz), 9.41 (1H, s, NH).

Compound [347]: (R)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(quinuclidin-3-yl)benzamide 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzoic acid (Intermediate 5) (0.11 g, 0.25 mmol, 1 eq), DIPEA (0.17 mL) and TBTU (88 mg, 0.28 mmol, 1.1 eq) were added to 5 mL DCM and the resulting solution stirred at rt for 30 min before the addition of (R)-(+)-3-aminoquinuclidine dihydrochloride (60 mg, 0.30 mmol, 1.2 eq). The RM was then stirred at rt for 16 hours before diluting with DCM and washing sequentially with water (×2), 50% saturated aqueous sodium hydrogen carbonate, saturated aqueous sodium hydrogen carbonate and saturated brine. The organic layer was dried (MgSO4) and concentrated in vacuo. The residue was dissolved in the minimum quantity of EtOAc before addition of n-heptane to precipitate (R)-4-(9'-cyclopentyl-5'-methyl-6'-oxo-5',6',8',9'-tetrahydrospiro[cyclopropane-1,7'-pyrimido[4,5-b][1,4]

diazepine]-2'-ylamino)-3-methoxy-N-(quinuclidin-3-yl)
benzamide (white solid, 0.13 g, 96%).

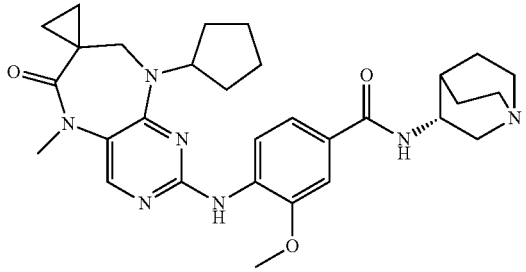 [SMILES: COc1cc(C(=O)N[C@H]2CN3CCC2CC3)ccc1Nc1ncc2c(n1)N(C1CCCC1)CC1(CC1)C(=O)N2C]

Rt=3.07 min (Analytical_1); MS(+ve): 546.5; MS(−ve): 544.6; 1H NMR (DMSO-d6) δ ppm 0.62-0.72 (2H, m), 0.87-0.94 (2H, m), 1.20-1.38 (1H, m), 1.44-1.54 (2H, m), 1.54-1.64 (4H, m), 1.64-1.74 (2H, m), 1.75-1.85 (1H, m), 1.85-1.95 (3H, m), 2.65-2.79 (4H, m), 2.83-3.01 (1H, m), 3.11-3.21 (4H, m), 3.47 (2H, s), 3.95 (4H, s), 4.77-4.93 (1H, m), 7.42-7.54 (2H, m), 7.69 (1H, s), 7.98 (1H, s), 8.10 (1H, d, J=6.3 Hz), 8.39 (1H, d, J=8.3 Hz).

Compound [348]: (S)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(quinuclidin-3-yl)benzamide 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzoic acid (Intermediate 5) (0.11 g, 0.25 mmol, 1 eq), DIPEA (0.17 mL) and TBTU (88 mg, 0.28 mmol, 1.1 eq) were added to 5 mL DCM and the resulting solution stirred at rt for 30 min before the addition of (S)-(−)-3-aminoquinuclidine dihydrochloride (60 mg, 0.30 mmol, 1.2 eq). The RM was then stirred at rt for 16 hours before diluting with DCM and washing sequentially with water (×2), 50% saturated aqueous sodium hydrogen carbonate, saturated aqueous sodium hydrogen carbonate and saturated brine. The organic layer was dried (MgSO4) and concentrated in vacuo. The residue was dissolved in the minimum quantity of EtOAc before addition of n-heptane to precipitate (S)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(quinuclidin-3-yl)benzamide (white solid, 0.075 g, 55%).

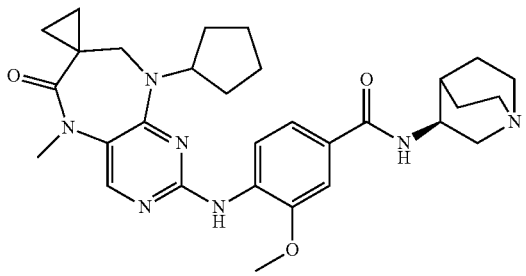 [SMILES: COc1cc(C(=O)N[C@@H]2CN3CCC2CC3)ccc1Nc1ncc2c(n1)N(C1CCCC1)CC1(CC1)C(=O)N2C]

Rt=3.04 min (Analytical_1); MS(+ve): 546.5; MS(−ve): 544.6; 1H NMR (DMSO-d6) δ ppm: 0.59-0.74 (2H, m), 0.86-0.97 (2H, m), 1.20-1.43 (1H, m), 1.45-1.75 (7H, m), 1.76-1.98 (4H, m), 2.66-2.86 (3H, m), 2.89-3.07 (1H, m), 3.17 (3H, s), 3.47 (3H, s), 3.89-4.02 (4H, m), 4.76-4.96 (1H, m), 7.42-7.59 (2H, m), 7.70 (1H, s), 7.98 (1H, s), 8.14 (1H, d, J=6.3 Hz), 8.40 (1H, d, J=7.8 Hz).

Compound [377]: 4-(9'-Cyclopentyl-5'-methyl-6'-oxo-5',6',8',9'-tetrahydrospiro[cyclobutane-1,7'-pyrimido[4,5-b][1,4]diazepine]-2'-ylamino)-N-((trans)-4-(4-(cyclopropylmethyl)piperazin-1-yl)cyclohexyl)-3-methoxybenzamide 2'-Chloro-9'-cyclopentyl-5'-methyl-8',9'-dihydrospiro[cyclobutane-1,7'-pyrimido[4,5-b][1,4]diazepin]-6'(5'H)-one (Intermediate 4) (0.065 g, 0.2 mmol, 1 eq), 4-amino-N-(trans-4-(4-(cyclopropylmethyl)piperazin-1-yl)cyclohexyl)-3-methoxybenzamide (Intermediate 11) (0.24 g, 0.6 mmol, 3 eq) and TFA (75 µL, 1 mmol, 5 eq) in TFE (6 mL) were heated to reflux together 40 hours. RM was concentrated in vacuo and the residue was partitioned between EtOAc and saturated sodium hydrogen carbonate. The organic layer was separated, washed with saturated brine and concentrated in vacuo to a residue that was purified by preparative RP-HPLC-MS (Preparative_1) to give 4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-N-((trans)-4-(4-(cyclopropylmethyl)piperazin-1-yl)cyclohexyl)-3-methoxybenzamide.

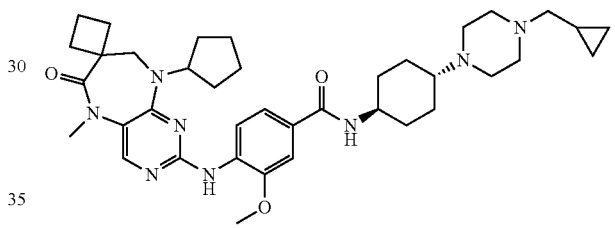

Rt=3.41 min (Analytical_1); ES(+ve): 671.6; ES(−ve): 669.7; 1H NMR (DMSO-d6) δ ppm: 0.03 (2H, dd, J 9.5 Hz, 5 Hz), 0.41 (2H, dd, J 10 Hz, 5 Hz), 0.79 (1H, m), 1.20-1.37 (4H, m), 1.55-1.94 (18H, m), 2.04 (2H, d, J 6.5 Hz), 2.16-2.46 (8H, m), 3.15 (3H, s), 3.32 (2H, s), 3.69 (1H, m), 3.90 (3H, s), 4.79 (1H, m), 7.44 (2H, m), 7.68 (1H, s), 8.01 (2H, m), 8.34 (1H, d, J 8.5 Hz).

Compound [378]: 4-(9-cyclopentyl-5-methyl-6-oxo-6,7,8,9-tetrahydro-5H-pyrimido[4,5-b][1,4]diazepin-2-ylamino)-N-((trans)-4-(4-(cyclopropylmethyl)piperazin-1-yl)cyclohexyl)-3-methoxybenzamide 2-Chloro-9-cyclopentyl-5-methyl-8,9-dihydro-5H-pyrimido[4,5-b][1,4]diazepin-6(7H)-one (Intermediate 1) (0.13 g, 0.43 mmol, 1 eq), 4-amino-N-(trans-4-(4-(cyclopropylmethyl)piperazin-1-yl)cyclohexyl)-3-methoxybenzamide (Intermediate 11) (0.26 g, 0.67 mmol, 1.5 eq) and TFA (0.17 mL, 2.2 mmol, 5 eq) in TFE (3 mL) were heated together at 80° C. for 18 hours. Further quantity of Intermediate 1 (0.10 g) was added and the reaction further heated for 48 hours. RM was concentrated in vacuo and the residue was purified by flash column chromatography on silica eluting with 020% ammonia/MeOH in DCM gradient followed by preparative HPLC (Preparative_4) then finally preparative RP-HPLC-MS (Preparative_1) to give 4-(9-cyclopentyl-5-methyl-6-oxo-6,7,8,9-tetrahydro-5H-pyrimido[4,5-b][1,4]diazepin-2-ylamino)-N-((trans)-4-(4-(cyclopropylmethyl)piperazin-1-yl)cyclohexyl)-3-methoxybenzamide (0.11 g, 26%).

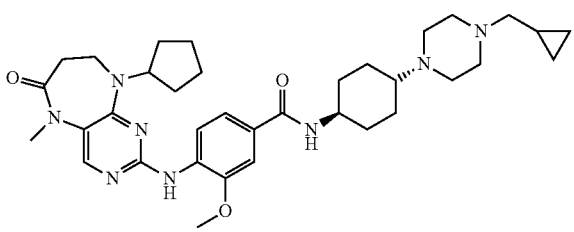

Rt=2.88 min (Analytical_1); ES(+ve): 631.5; ES(−ve): 629.6; 1H NMR (DMSO-d6) δ ppm: −0.15-0.11 (m, 2H), 0.40 (d, J=8.06 Hz, 2H), 0.63-0.85 (m, 1H), 1.11-1.41 (m, 3H), 1.57 (br. s., 2H), 1.69 (d, J=17.73 Hz, 2H), 1.74-1.95 (m, 6H), 2.04 (s, 2H), 2.09 (d, J=6.45 Hz, 2H), 2.16 (d, J=9.67 Hz, 1H), 2.32 (br. s., 2H), 2.49 (br. s., 1H), 2.51-2.59 (m, 2H), 2.59 (br. s., 1H), 3.07-3.17 (m, 3H), 3.27 (s, 5H), 3.53-3.62 (m, 2H), 3.67 (dd, J=7.41, 3.55 Hz, 1H), 3.89 (s, 2H), 4.04 (q, J=5.37 Hz, 1H), 4.76 (quin, J=8.22 Hz, 1H), 7.38-7.48 (m, 2H), 7.68 (s, 1H), 7.99 (d, J=7.74 Hz, 1H), 8.03 (s, 1H), 8.33 (d, J=8.06 Hz, 1H).

Intermediates 13-19:
4-(amine-substituted)cyclohexanamines

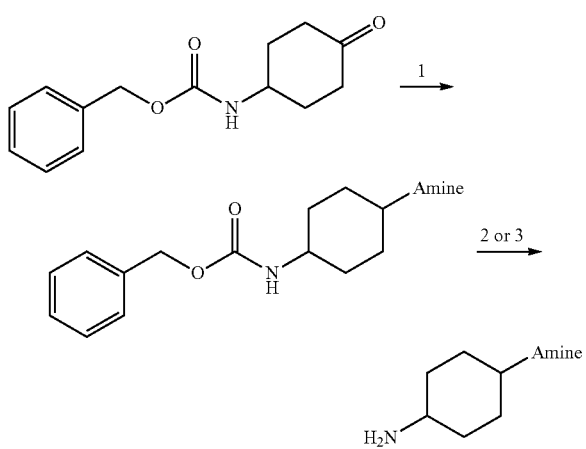

1. [Analogous to Method III in Abdel-Magid A. F. et al. (1996) *J. Org. Chem.*, 61, 3849-3862] sodium triacetoxyborohydride (1.5 eq), acetic acid (1 eq), amine (1.1 eq), THF, rt 20 h; 2. $H_2$, 10% Pd/C, 60° C., methanol, flow hydrogenation; 3. sodium iodide (4 eq), chlorotrimethylsilane (4 eq), acetonitrile, 0° C.-rt, 18 h.

Step 1:

N-benzyloxycarbonyl-4-aminocyclohexanone, a compound known in the art [WO2007/002181 A2] (typically 1 mmol scale), was added to a reaction tube containing THF (5 mL), the appropriate substituted-piperazine, -homopiperazine, or morpholine, along with acetic acid and sodium triacetoxyborohydride. The reaction was stirred at ambient temperature for 20 hours. The reaction was quenched with $NaHCO_3$ solution (2 mL) before acidifying to pH2 with 1N HCl solution. The mixture was washed with EtOAc before separating the aqueous layer and basifying to pH10 with 2N NaOH solution. The product was extracted into EtOAc, which was washed with sat. NaCl, dried ($MgSO_4$) and evaporated under reduced pressure to provide the required benzyl 4-(amine-substituted)cyclohexylcarbamate.

Step 2:

Each benzyl 4-(amine-substituted)cyclohexylcarbamate were dissolved in methanol to a concentration of 0.05 M. Hydrogenation was conducted using an H-Cube™ (ThalesNano Inc.) flow reactor at 1 mL/mim flow rate over 10% Pd/C catalyst heated to 60° C. under full hydrogen mode. Concentration under reduced pressure provided the desired 4-(amine-substituted)cyclohexanamine product as oils. Solid hydrochloride salts could be obtained by stirring with ethereal HCl.

Where it was required to selectively deprotect the benzylcarbamates in the presence of an N-benzyl group (intermediates 16 & 18), step 3 was employed instead of step 2.

Step 3:

Sodium iodide (1.5 mmol, 4 eq) was dissolved in anhydrous acetonitrile (5 mL) and was stirred whilst chlorotrimethylsilane (1.5 mmol, 4 eq) was added. After 5 minutes this mixture was added slowly to a solution of the 4-(amine-substituted)cyclohexanamine dissolved in anhydrous acetonitrile (2 mL) cooled in an ice-water bath. After 1 hour the cooling bath was removed and the RM was stirred at ambient temperature for 18 hours. RM was concentrated under reduced pressure and redissolved in 1% water in methanol solution. The mixture was absorbed onto an SCX II column, washed with methanol and eluted with ammonia in methanol. Concentrated in vacuo to provide the desired 4-(amine-substituted)cyclohexanamine.

| Intermediate | Structure | ES(+ve) [M + H]+ | Analytical_1 Rt (min) |
|---|---|---|---|
| 13 | 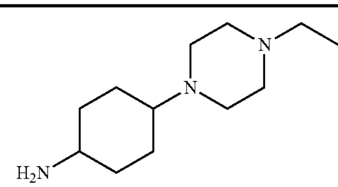 | 212.3 | 2.05 |
| 14 | 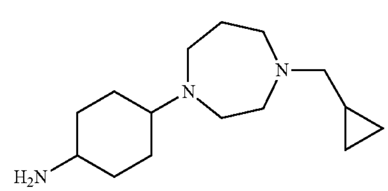 [SMILES: NC1CCC(N2CCCN(CC3CC3)CC2)CC1] | 252.3 | 2.42 |

-continued

| Intermediate | Structure | ES(+ve) [M + H]+ | Analytical_1 Rt (min) |
|---|---|---|---|
| 15 | 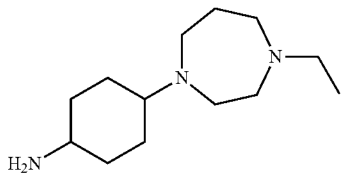 [SMILES: CCN1CCCN(C2CCC(N)CC2)CC1] | nd | — |
| 16 | 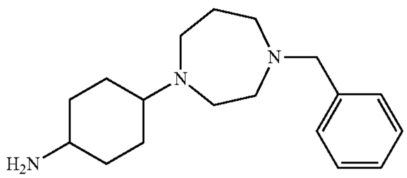 [SMILES: NC1CCC(N2CCCN(Cc3ccccc3)CC2)CC1] | nd | — |
| 17 | 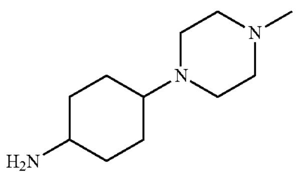 | nd | — |
| 18 | 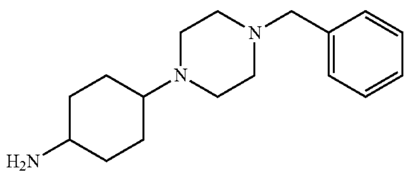 [SMILES: NC1CCC(N2CCN(Cc3ccccc3)CC2)CC1] | 274.3 | 3.27 |
| 19 | | 185.2 | 1.47 | nd = no data (ionization not detected under standard conditions)

Compound [379]: 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((trans)-4-(4-ethylpiperazin-1-yl)cyclohexyl)-3-methoxybenzamide 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzoic acid (Intermediate 5) (66 mg, 0.15 mmol, 1 eq), DIPEA (52 µl, 0.3 mmol, 2 eq) and TBTU (54 mg, 0.17 mmol, 1.1 eq) were added to 1.5 mL DMF and the resulting solution was stirred at rt for 20 min before the addition of 4-(4-ethylpiperazin-1-yl)cyclohexanamine (Intermediate 13) as the trihydrochloride salt (58 mg, 0.18 mmol, 1.2 eq) and DIPEA (78 µL, 0.45 mmol, 3 eq). The RM was then stirred at rt for 2 hours before purifying by preparative RP-HPLC-MS (Preparative_2) to provide 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((trans)-4-(4-ethylpiperazin-1-yl)cyclohexyl)-3-methoxybenzamide (colourless glass, 26 mg, 28%).

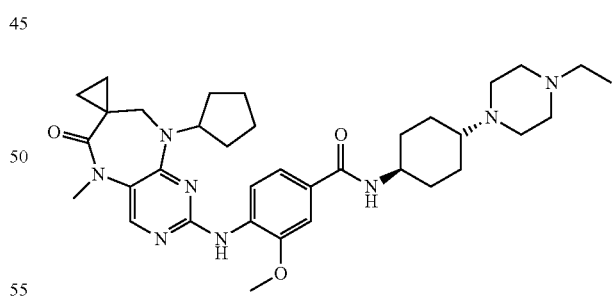

Rt=3.00 min (Analytical_1) MS(+ve) 631.6; MS(−ve) 629.7; Rt=3.00 min (Analytical_1) MS(+ve) 631.6; MS(−ve) 629.7; 1H NMR (DMSO-d6) δ ppm: 0.59-0.72 (2H, m), 0.81-0.92 (2H, m), 0.97 (3H, t, J=7.1 Hz), 1.20-1.42 (4H, m), 1.42-1.55 (2H, m), 1.54-1.64 (2H, m), 1.64-1.73 (2H, m), 1.83 (2H, d, J=11.7 Hz), 1.89 (4H, d, J=7.8 Hz), 2.14-2.42 (7H, m), 3.16 (3H, s), 3.47 (2H, s), 3.64-3.79 (1H, m), 3.94 (3H, s), 4.84 (1H, quin, J=8.7 Hz), 7.40-7.54 (2H, m), 7.67 (1H, s), 7.98 (1H, s), 8.03 (1H, d, J=7.8 Hz), 8.38 (1H, d, J=8.3 Hz).

Compound [380]: 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((cis)-4-(4-ethylpiperazin-1-yl)cyclohexyl)-3-methoxybenzamide From the synthesis and purification of Compound [379] was isolated as a separate compound 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((cis)-4-(4-ethylpiperazin-1-yl)cyclohexyl)-3-methoxybenzamide (colourless glass, 27 mg, 29%).

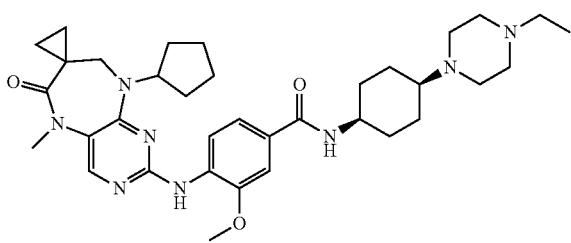 [SMILES: CCN1CCN([C@H]2CC[C@@H](NC(=O)c3ccc(Nc4ncc5c(n4)N(C4CCCC4)CC4(CC4)C(=O)N5C)c(OC)c3)CC2)CC1]

Rt=3.13 min (Analytical_1) MS(+ve) 631.6; MS(−ve) 629.7; $^1$H NMR (DMSO-$d_6$) δ ppm: 0.60-0.72 (2H, m), 0.83-0.93 (2H, m), 0.98 (3H, t, J=7.1 Hz), 1.38-1.55 (6H, m), 1.55-1.63 (2H, m), 1.63-1.80 (4H, m), 1.80-1.96 (4H, m), 2.02-2.17 (1H, m), 2.16-2.44 (7H, m), 3.16 (3H, s), 3.47 (2H, s), 3.79-3.92 (1H, m), 3.94 (3H, s), 4.84 (1H, quin, J=8.5 Hz), 7.44-7.58 (2H, m), 7.67 (1H, s), 7.98 (1H, s), 8.03 (1H, d, J=7.3 Hz), 8.37 (2H, d, J=8.8 Hz).

Compound [381]: 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-(4-(4-(cyclopropylmethyl)-1,4-diazepan-1-yl)cyclohexyl)-3-methoxybenzamide 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzoic acid (Intermediate 5) (88 mg, 0.2 mmol, 1 eq), DIPEA (70 μl, 0.4 mmol, 2 eq) and TBTU (72 mg, 0.24 mmol, 1.2 eq) were added to 2 mL DMF and the resulting solution was stirred at rt for 20 min before the addition of 4-(4-(cyclopropylmethyl)-1,4-diazepan-1-yl)cyclohexanamine (Intermediate 14) (60 mg, 0.24 mmol, 1.2 eq). The RM was then stirred at rt for 2 hours before purifying by preparative RP-HPLC-MS (Preparative_2) to provide 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-(4-(4-(cyclopropylmethyl)-1,4-diazepan-1-yl)cyclohexyl)-3-methoxybenzamide as a mixture cis and trans isomers (off-white solid, 67 mg, 50%).

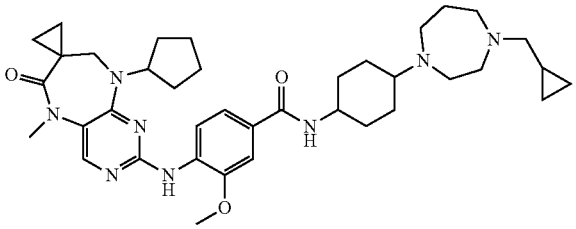 [SMILES: COc1cc(C(=O)NC2CCC(N3CCCN(CC4CC4)CC3)CC2)ccc1Nc1ncc2c(n1)N(C1CCCC1)CC1(CC1)C(=O)N2C]

Rt=4.12 min (broad peak) (Analytical_1) MS(+ve) 671.6; MS(−ve) 669.7; $^1$H NMR (DMSO-$d_6$) δ ppm: 0.01 (2H, d, J=4.4 Hz), 0.40 (2H, d, J=7.3 Hz), 0.63 (2H, br. s.), 0.71-0.83 (1H, m), 0.87 (2H, br. s.), 1.02 (1H, t, J=7.1 Hz), 1.25-1.38 (2.5H, m), 1.39-1.52 (3.5H, m), 1.52-1.61 (2H, m), 1.65 (4H, d, J=5.9 Hz), 1.70-1.80 (3H, m), 1.85 (3H, d, J=4.4 Hz), 2.21-2.31 (1H, m), 2.55-2.83 (8H, m), 3.13 (3.5H, s), 3.35-3.55 (3H, m), 3.69 (0.5H, br. s.), 3.91 (3.5H, s), 4.31 (0.5H, t, J=5.1 Hz), 4.81 (1H, t, J=8.5 Hz), 7.25-7.54 (2H, m), 7.64 (1H, s), 7.84-8.16 (2H, m), 8.35 (1H, d, J=8.3 Hz).

Compound [382]: 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-(4-(4-ethyl-1,4-diazepan-1-yl)cyclohexyl)-3-methoxybenzamide 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzoic acid (Intermediate 5) (44 mg, 0.1 mmol, 1 eq), DIPEA (35 μl, 0.2 mmol, 2 eq) and TBTU (36 mg, 0.12 mmol, 1.2 eq) were added to 1 mL DMF and the resulting solution was stirred at rt for 20 min before the addition of 4-(4-ethyl-1,4-diazepan-1-yl)cyclohexanamine (Intermediate 15) as the trihydrochloride salt (32 mg, 0.1 mmol, 1 eq) and DIPEA (53 μL, 0.3 mmol, 3 eq). The RM was then stirred at rt for 2 hours before purifying by preparative RP-HPLC-MS (Preparative_2) to provide 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-(4-(4-ethyl-1,4-diazepan-1-yl)cyclohexyl)-3-methoxybenzamide as a mixture cis and trans isomers (white solid, 10 mg, 16%).

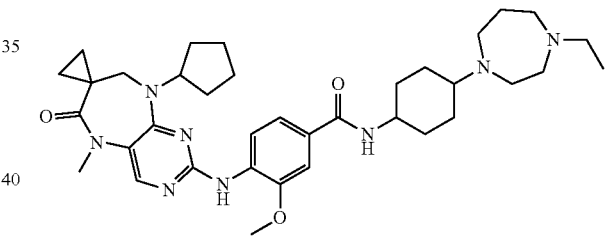

Rt=3.98 min, 4.18 min (broad peaks) (Analytical_1) MS(+ve) 645.6; MS(−ve) 643.7; $^1$H NMR (DMSO-$d_6$) δ ppm: 0.57-0.74 (2H, m), 0.82-0.93 (2H, m), 0.95-1.09 (3H, m), 1.30-1.42 (2H, m), 1.42-1.54 (3.5H, m), 1.58 (2H, d, J=4.4 Hz), 1.63-1.75 (3.5H, m), 1.75-1.83 (1.5H, m), 1.88 (3.5H, br. s.), 1.98-2.16 (1.5H, m), 2.59-2.86 (4H, m), 3.17 (4H, s), 3.41-3.53 (3.5H, m), 3.78 (2.5H, m), 3.88-4.02 (3.5H, m), 4.06-4.38 (1H, m), 4.76-4.91 (1H, m), 7.39-7.57 (2H, m), 7.59-7.78 (1H, m), 7.98 (2H, s), 8.31-8.45 (1H, m)

Compound [383]: N-(4-(4-benzyl-1,4-diazepan-1-yl)cyclohexyl)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzamide 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzoic acid (Intermediate 5) (66 mg, 0.15 mmol, 1 eq), DIPEA (52 μl, 0.3 mmol, 2 eq) and TBTU (54 mg, 0.17 mmol, 1.1 eq) were added to 1 mL DMF and the resulting solution was stirred at rt for 20 min before the addition of 4-(4-benzyl-1,4-diazepan-1-yl)cyclohexanamine (Intermediate 16) (54 mg, 0.19 mmol, 1.27 eq) dissolved in DMF (0.5 mL). The RM was then stirred at rt for 2 hours before purifying by preparative RP-HPLC-MS (Preparative_5) to provide N-(4-(4-benzyl-1,4-diazepan-1-yl)cyclohexyl)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzamide as a mixture cis and trans isomers (off-white solid, 33 mg, 31%).

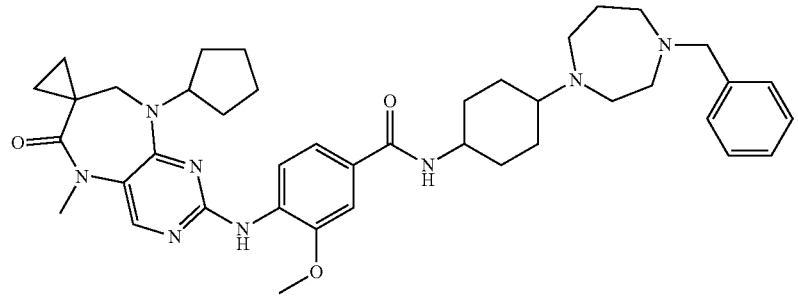 [SMILES: COc1cc(C(=O)NC2CCC(N3CCCN(Cc4ccccc4)CC3)CC2)ccc1Nc1ncc2c(n1)N(C1CCCC1)CC1(CC1)C(=O)N2C]

Rt=4.40 min (Analytical_1) MS(+ve) 707.6; MS(−ve) 705.7; ¹H NMR (DMSO-d₆) δ ppm: 0.73 (2H, br. s.), 0.96 (2H, br. s.), 1.22-2.22 (19H, m), 2.64-2.91 (4H, m), 3.23 (5H, s), 3.53 (8H, s), 3.89-4.24 (4H, m), 4.91 (1H, t, J=8.5 Hz), 5.82 (0H, s), 7.23-8.54 (10H, m).

Compound [384]: 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((trans)-4-(4-methylpiperazin-1-yl)cyclohexyl)-3-methoxybenzamide 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzoic acid (Intermediate 5) (66 mg, 0.15 mmol, 1 eq), DIPEA (52 μl, 0.3 mmol, 2 eq) and TBTU (54 mg, 0.17 mmol, 1.1 eq) were added to 1 mL DMF and the resulting solution was stirred at rt for 20 min before the addition of 4-(4-methylpiperazin-1-yl)cyclohexanamine (Intermediate 17) (35 mg, 0.18 mmol, 1.2 eq) dissolved in DMF (0.5 mL). The RM was then stirred at rt for 2 hours before purifying by preparative RP-HPLC-MS (Preparative_2 and Preparative_3) to provide 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((trans)-4-(4-methylpiperazin-1-yl)cyclohexyl)-3-methoxybenzamide (white solid, 17 mg, 18%).

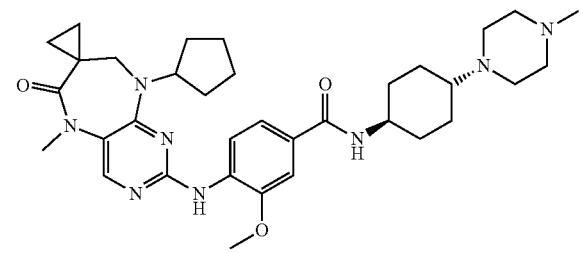

Rt=2.85 min (Analytical_1) MS(+ve) 617.5; MS(−ve) 615.6; ¹H NMR (DMSO-d₆) δ ppm: 0.61-0.76 (2H, m), 0.89 (1H, t, J=6.8 Hz), 0.92-0.98 (2H, m), 1.22-1.47 (5H, m), 1.47-1.79 (6H, m), 1.81-2.02 (5H, m), 2.07-2.20 (3H, m), 2.20-2.42 (4H, m), 3.20 (4H, s), 3.34 (3H, s), 3.51 (2H, s), 3.67-3.82 (1H, m), 3.98 (3H, s), 4.88 (1H, quin, J=8.5 Hz), 7.42-7.59 (2H, m), 7.71 (1H, s), 8.02 (1H, s), 8.08 (1H, d, J=7.8 Hz), 8.42 (1H, d, J=8.3 Hz).

Compound [385]: 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((cis)-4-(4-methylpiperazin-1-yl)cyclohexyl)-3-methoxybenzamide From the synthesis and purification of Compound [384] was isolated as a separate compound 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N-((cis)-4-(4-methylpiperazin-1-yl)cyclohexyl)-3-methoxybenzamide (white solid, 34 mg, 37%).

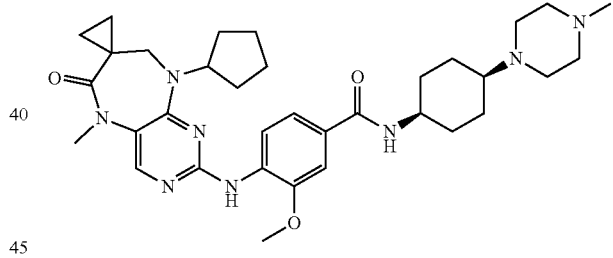

Rt=2.93 min (Analytical_1) MS(+ve) 617.5; MS(−ve) 615.6; ¹H NMR (DMSO-d₆) δ ppm: 0.62-0.80 (2H, m), 0.84-1.02 (4H, m), 1.18-1.36 (4H, m), 1.43-1.84 (12H, m), 1.84-2.03 (4H, m), 2.09-2.22 (4H, m), 2.41 (4H, br. s.), 3.21 (3H, s), 3.52 (2H, s), 3.89-3.97 (1H, m), 3.99 (3H, s), 4.89 (1H, quin, J=8.5 Hz), 7.47-7.61 (2H, m), 7.72 (1H, s), 8.03 (1H, s), 8.08 (1H, d, J=7.3 Hz), 8.43 (1H, d, J=9.3 Hz)

Compound [386]: N-((trans)-4-(4-benzylpiperazin-1-yl)cyclohexyl)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzamide 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzoic acid (Intermediate 5) (66 mg, 0.15 mmol, 1 eq), DIPEA (52 μl, 0.3 mmol, 2 eq) and TBTU (54 mg, 0.17 mmol, 1.1 eq) were added to 1 mL DMF and the resulting solution was stirred at rt for 20 min before the addition of 4-(4-benzylpiperazin-1-yl)cyclohexanamine (Intermediate 18) (35 mg, 0.18 mmol, 1.2 eq) dissolved in DMF (0.5 mL). The RM was then stirred at rt for 2 hours before purifying by preparative RP-HPLC-MS (Preparative_2) to provide N-((trans)-4-(4-benzylpiperazin-1-yl)cyclohexyl)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzamide (white solid, 13 mg, 13%).

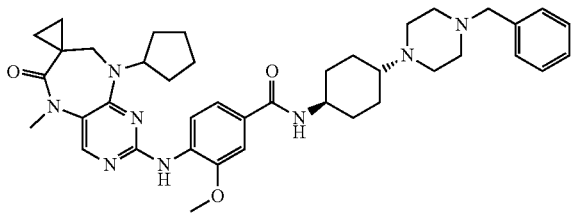

Rt=3.64 min (Analytical_1) MS(+ve) 693.6; MS(−ve) 691.7; $^1$H NMR (DMSO-d$_6$) δ ppm: 0.62-0.79 (2H, m), 0.85-1.02 (2H, m), 1.20-1.46 (4H, m), 1.46-1.58 (2H, m), 1.59-1.67 (2H, m), 1.67-1.78 (2H, m), 1.80-2.02 (6H, m), 2.12 (1H, s), 2.18-2.46 (6H, m), 3.20 (3H, s), 3.43-3.56 (5H, m), 3.67-3.84 (1H, m), 3.97 (3H, s), 4.88 (1H, quin, J=8.4 Hz), 7.22-7.42 (6H, m), 7.44-7.59 (2H, m), 7.71 (1H, s), 8.02 (1H, s), 8.08 (1H, d, J=7.8 Hz), 8.42 (1H, d, J=7.8 Hz)

Compound [387]: N-((cis)-4-(4-benzylpiperazin-1-yl)cyclohexyl)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzamide From the synthesis and purification of Compound [386] was isolated as a separate compound N-((cis)-4-(4-benzylpiperazin-1-yl)cyclohexyl)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzamide (white solid, 20 mg, 19%).

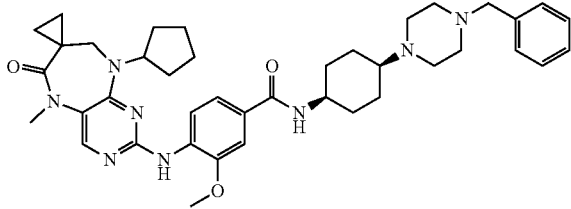 [SMILES: COc1cc(C(=O)N[C@H]2CC[C@@H](N3CCN(Cc4ccccc4)CC3)CC2)ccc1Nc1ncc2c(n1)N(C1CCCC1)CC1(CC1)C(=O)N2C]

Rt=3.85 min (Analytical_1) MS(+ve) 693.6; MS(−ve) 691.7; $^1$H NMR (DMSO-d$_6$) δ ppm: 0.62-0.79 (2H, m), 0.87-1.01 (2H, m), 1.43-1.59 (5H, m), 1.59-1.67 (2H, m), 1.66-1.74 (2H, m), 1.75-1.84 (2H, m), 1.92 (4H, br. s.), 2.07-2.29 (2H, m), 2.41 (4H, br. s.), 3.20 (3H, s), 3.51 (4H, s), 3.87-4.05 (4H, m), 4.74-4.99 (1H, m), 7.24-7.39 (5H, m), 7.50-7.56 (2H, m), 7.71 (1H, s), 8.02 (1H, s), 8.07 (1H, d, J=6.8 Hz), 8.42 (1H, d, J=8.8 Hz)

Compound [388]: 4-(9-cyclopentyl-5,7,7-trimethyl-6-oxo-6,7,8,9-tetrahydro-5H-pyrimido[4,5-b][1,4]diazepin-2-ylamino)-3-methoxy-N-((trans)-4-morpholinocyclohexyl)benzamide 4-(9-Cyclopentyl-5,7,7-trimethyl-6-oxo-6,7,8,9-tetrahydro-5H-pyrimido[4,5-b][1,4]diazepin-2-ylamino)-3-methoxybenzoic acid (Intermediate 6) (66 mg, 0.15 mmol, 1 eq), DIPEA (52 μl, 0.3 mmol, 2 eq) and TBTU (54 mg, 0.17 mmol, 1.1 eq) were added to 1.5 mL DMF and the resulting solution was stirred at rt for 20 min before the addition of 4-morpholinocyclohexanamine (Intermediate 16) (33 mg, 0.18 mmol, 1.2 eq). The RM was then stirred at rt for 2 hours before purifying by preparative RP-HPLC-MS (Preparative_2) to provide 4-(9-cyclopentyl-5,7,7-trimethyl-6-oxo-6,7,8,9-tetrahydro-5H-pyrimido[4,5-b][1,4]diazepin-2-ylamino)-3-methoxy-N-((trans)-4-morpholinocyclohexyl)benzamide (off-white solid, 10 mg, 11%).

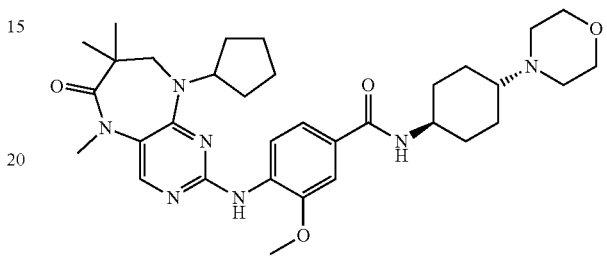

Rt=3.16 min (Analytical_1) MS(+ve) 606.4; MS(−ve) 604.5; $^1$H NMR (DMSO-d$_6$) δ ppm: 1.07-1.18 (7H, m), 1.24-1.49 (4H, m), 1.58-1.71 (4H, m), 1.71-1.84 (2H, m), 1.83-2.03 (6H, m), 2.23 (1H, t, J=10.5 Hz), 2.43-2.51 (3H, m), 3.17-3.28 (4H, m), 3.42 (3H, br. s.), 3.60 (4H, br. s.), 3.64 (1H, br. s.), 3.71-3.83 (1H, m), 3.98 (3H, s), 5.23 (1H, t, J=8.3 Hz), 7.44-7.60 (2H, m), 7.72 (1H, s), 8.02 (1H, s), 8.09 (1H, d, J=7.8 Hz), 8.40 (1H, d, J=8.3 Hz)

Compound [389]: 4-(9-cyclopentyl-5,7,7-trimethyl-6-oxo-6,7,8,9-tetrahydro-5H-pyrimido[4,5-b][1,4]diazepin-2-ylamino)-3-methoxy-N-((cis)-4-morpholinocyclohexyl)benzamide From the synthesis and purification of Compound [388] was isolated as a separate compound 4-(9-cyclopentyl-5,7,7-trimethyl-6-oxo-6,7,8,9-tetrahydro-5H-pyrimido[4,5-b][1,4]diazepin-2-ylamino)-3-methoxy-N-((cis)-4-morpholinocyclohexyl)benzamide (white solid, 22 mg, 24%).

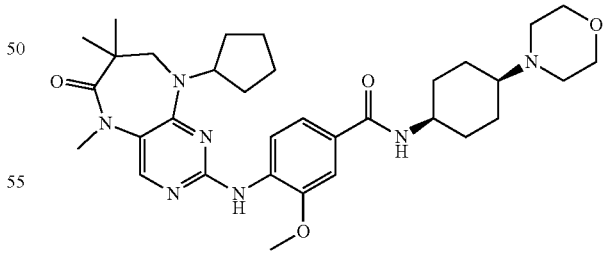

Rt=3.31 min (Analytical_1) MS(+ve) 606.4; MS(−ve) 604.5; $^1$H NMR (DMSO-d$_6$) δ ppm: 1.13 (6H, s), 1.39-1.60 (4H, m), 1.60-1.71 (4H, m), 1.71-1.85 (4H, m), 1.85-2.01 (4H, m), 2.07-2.22 (2H, m), 2.42-2.48 (4H, m), 3.22 (4H, s), 3.64 (4H, br. s.), 3.87-4.05 (4H, m), 5.14-5.31 (1H, m), 7.45-7.62 (2H, m), 7.71 (1H, s), 8.02 (1H, s), 8.09 (1H, d, J=7.3 Hz), 8.39 (1H, d, J=8.3 Hz)

Compound [390]: 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-((trans)-4-morpholinocyclohexyl)benzamide 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzoic acid (Intermediate 5) (66 mg, 0.15 mmol, 1 eq), DIPEA (52 μl, 0.3 mmol, 2 eq) and TBTU (54 mg, 0.17 mmol, 1.1 eq) were added to 1.5 mL DMF and the resulting solution was stirred at rt for 20 min before the addition of 4-morpholinocyclohexanamine (Intermediate 16) (33 mg, 0.18 mmol, 1.2 eq). The RM was then stirred at rt for 2 hours before purifying by preparative RP-HPLC-MS (Preparative_2) to provide 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-((trans)-4-morpholinocyclohexyl)benzamide (off-white solid, 13 mg, 14%).

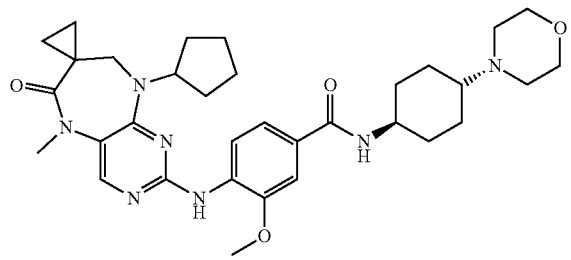

Rt=2.96 min (Analytical_1) MS(+ve) 604.4; MS(−ve) 602.5; $^1$H NMR (DMSO-d$_6$) δ ppm: 0.72 (2H, s), 0.95 (2H, s), 1.24-1.49 (4H, m), 1.49-1.60 (2H, m), 1.60-1.69 (2H, m), 1.69-1.82 (2H, m), 1.82-2.03 (6H, m), 2.14 (1H, s), 2.17-2.32 (1H, m), 3.22 (4H, s), 3.53 (2H, s), 3.61 (4H, br. s.), 3.71-3.84 (1H, m), 4.00 (3H, s), 4.90 (1H, quin, J=8.5 Hz), 7.43-7.61 (2H, m), 7.73 (1H, s), 8.04 (1H, s), 8.10 (1H, d, J=7.8 Hz), 8.44 (1H, d, J=8.3 Hz)

Compound [391]: 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-((cis)-4-morpholinocyclohexyl)benzamide From the synthesis and purification of Compound [390] was isolated as a separate compound 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-((cis)-4-morpholinocyclohexyl)benzamide (white solid, 27 mg, 30%).

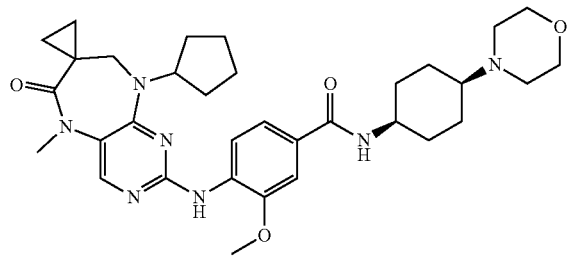 [SMILES: COc1cc(C(=O)N[C@H]2CC[C@@H](N3CCOCC3)CC2)ccc1Nc1ncc2c(n1)N(C1CCCC1)CC1(CC1)C(=O)N2C]

Rt=3.10 min (Analytical_1) MS(+ve) 604.4; MS(−ve) 602.5; $^1$H NMR (DMSO-d$_6$) δ ppm: 0.66-0.81 (2H, m), 0.88-1.03 (2H, m), 1.45-1.86 (12H, m), 1.87-2.02 (4H, m), 2.10-2.21 (1H, m), 2.47 (4H, br. s.), 3.22 (3H, s), 3.52 (2H, s), 3.65 (4H, br. s.), 3.89-4.05 (4H, m), 4.90 (1H, quin, J=8.5 Hz), 7.50-7.63 (2H, m), 7.73 (1H, s), 8.03 (1H, s), 8.10 (1H, d, J=7.3 Hz), 8.43 (1H, Example 3

A full-length human CDC25C clone was isolated by PCR from HeLa mRNA and was inserted on a BamHI-HindIII fragment into pRsetA. The amino terminal fragment of CDC25C (encoding residues 1-300) was excised from this vector and inserted into pET28a (between the NcoI and BamHI sites). Expression was under the control of the T7 promoter, and the encoded protein contained a His$_6$ tag at the carboxyl terminus. The vector was transformed into E. coli strain BRL(DE3) pLysS for expression experiments. CDC25C was expressed in BL21(DE3) RIL bacteria cells, grown in LB media at 37° C. until OD$_{600nm}$ of 0.6 was reached. The expression was induced with 1 mM IPTG and the bacterial culture was grown further for 3 h. The bacteria were harvested by centrifugation and the cell pellet was re-suspended in 50 mM Tris pH 7.5 and 10% sucrose, flash frozen, and stored at −70° C. until used. CDC25C protein was purified from E. coli inclusion bodies. The inclusion bodies were isolated in a buffer (50 mM Tris pH 8.0, 2 mM EDTA, 100 mM NaCl, 0.5% triton X-100). After denaturation in the presence of 6 M urea, the protein was refolded via slow dialysis of the urea. The protein was stored in 25 mM Tris pH 8.0, 100 mM NaCl, 1 mM DTT, 1 mM EDTA and 10% glycerol at −70° C. until used.

A full-length human PLK1 (XM_047240) (amino acids 1-603) clone was amplified from a foetal lung cDNA library using primers incorporating restriction enzyme sites. The 5' primer (gccgctagcgacgatgacgataagatgagtgctgcagtgactgcagggaagc) had an Nhe1 site prior to the ATG start codon. The 3' primer (ggaattcttaggaggccttgagacgg) incorporated a stop codon prior to the EcoR1 site. The PCR product was cloned into the Nhe1/EcoR1 sites of a baculovirus expression vector, pSSP1. Cloning into this vector resulted in a His$_6$ tag fusion at the amino terminus of the PLK1 construct. Sf9 cells of a passage number less than 20 were split back to give a 300 mL culture volume, at a cell density of 1.5×10$^6$ cells/mL. Cells were only used for expression in logarithmic growth phase. PLK1 baculovirus (from P2 amplification) was added to give a multiplicity of infection of 3, this is equivalent to 3 virus particles for each insect cell. The flasks were incubated at 27° C., with shaking at 100 r.p.m. for 48 h. On harvest, cell density and viability was determined, the cultures spun down at 2500 r.p.m. for 5 min and washed with ice-cold phosphate-buffered saline. The wash was re-spun at the same speed and the pellet was snap frozen. PLK1 protein was purified on a metal affinity column. The insect cell pellet was lysed in a buffer (10 mM Tris-HCl pH 8.0, 150 mM NaCl, 5 mM β-mercaptoethanol, 1 mM PMSF, 1 mM benzamidine, 20 mM imidazole and protease inhibitor cocktail (Sigma) and the pre-cleared supernatant was loaded onto NiNTA-agarose (Qiagen). The affinity column was washed with the lysis buffer and the bound protein was eluted with 250 mM imidazole in the same buffer. After overnight dialysis against 25 mM Tris HCl, pH 7.5, 100 mM NaCl, 1 mM DTT, 1 mM PMSF, 1 mM benzamidine, protease inhibitors cocktail (Sigma) and 10% glycerol, the purified protein was stored at −70° C. until used.

Example 4

PLK1 protein kinase assays were carried out using a 96-well plate format by incubating CDC25C (2 μg/well) with PLK1 (1 μg/well) in 20 mM Tris/HCl buffer pH 7.5, supplemented with 25 mM β-glycerophosphate, 5 mM EGTA, 1 mM DTT and 1 mM NaVO$_3$. Serial dilutions of test compound in assay buffer were added. Reaction was initiated by the addition of 100 μM ATP and 0.5 μCi of [γ-$^{32}$P]-ATP. The reaction mixture was incubated at 30° C. for 1 h, then stopped with 75 mM aq orthophosphoric acid, transferred onto a 96-well P81 filter plate (Whatman), dried, and the extent of CDC25C phosphorylation was assessed by scintillation counting using a Packard TopCount plate reader. The raw assay data was analysed by non-linear regression analysis parameters and IC$_{50}$ values were determined using the equation: y=A+((B−A)/(1+((C/x)^D))), where y is % inhibition, A is minimum inhibition, B is maximum inhibition, C is EC$_{50}$, and D is the slope factor.

Cellular proliferation assays using human tumour cell lines (obtained from the American Type Culture Collection, 10801 University Boulevard, Manessas, Va. 20110-2209, USA) were carried out. Standard 72-h MTT (thiazolyl blue; 3-[4,5-dimethylthiazol-2-yl]-2,5-diphenyltetrazolium bromide) assays were performed (Loveland et al, Biochem. Int., 1992, 27, 501; Haselsberger et al, Anti Cancer Drugs, 1996, 7, 331). In short: cells were seeded into 96-well plates according to doubling time and incubated overnight at 37° C. Test compounds were made up in DMSO and a ⅓ dilution series prepared in 100 μL cell media, added to cells (in triplicates) and incubated for 72 h at 37° C. MTT was made up as a stock of 5 mg/mL in cell media and filter-sterilised. Media was removed from cells followed by a wash with 200 μL PBS. MTT solution was then added at 20 μL per well and incubated in the dark at 37° C. for 4 h. MTT solution was removed and cells again washed with 200 μL PBS. MTT dye was solubilised with 200 μL per well of DMSO with agitation. Absorbance was read at 540 nm and data analysed using curve-fitting software (GraphPad Prism version 3.00 for Windows, GraphPad Software, San Diego Calif. USA) to determine IC$_{50}$ values (concentration of test compound which inhibits cell growth by 50%).

Example 5

PLK Selectivity

Table 4 shows the selectivity of compound [218] for PLK1 over PLK2 and PLK3 compared with selected compounds of the prior art. By way of illustration, compound [218] of the invention is twice as selective for PLK1 versus PLK 2 compared to compound [I-64] of WO 07/095188, ca 6-fold more selective than compound [I-76] and 7-fold more selective than compound [I-4] of WO 07/095188. Similarly, compound [218] is 5-fold more selective for PLK1 versus PLK3 compared to compound [I-64] of WO 07/095188, ca 12-fold more selective than compound [I-76] and 5-fold more selective than compound [I-4] of WO 07/095188.

Example 6

Solubility Studies

Table 5 shows that compound [254] (boxed structure below) has superior solubility and/or pharmacokinetic properties when compared to structurally related compounds already known in the art.

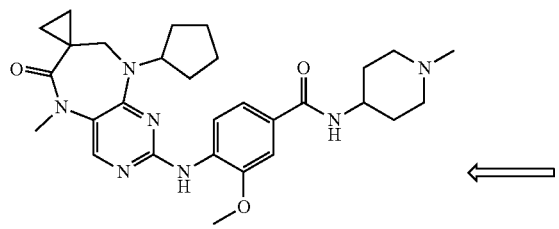

Example I-76 in WO 07/095188

Example 246 in WO 08/002958

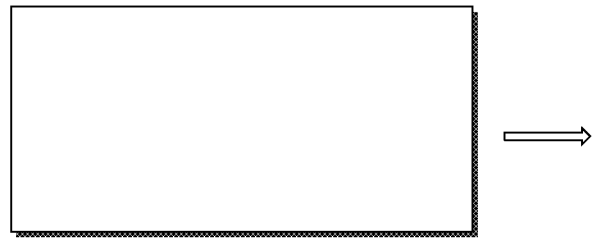

Compound [254]

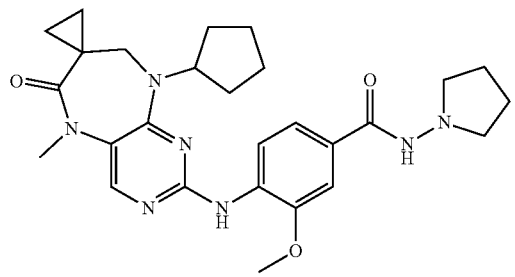

Example I-253 in WO 07/095188

Nephelometry Studies

If a DMSO solution of a water soluble compound is introduced into aqueous buffer, the mixture remains clear unless the aqueous solubility limit is reached. Above the solubility limit, precipitation occurs and light travelling through the turbid suspension is scattered. The measurement of the intensity of the scattered light is the basis of nephelometric solubility determination.

Selected compounds were screened using a nephelometer to identify the concentration at which turbidity occurs, thereby giving an indication of kinetic solubility. By nephelometry (2% DMSO: 98% phosphate buffered saline pH 7.5) compound [254] was freely soluble at 200 µM (>0.11 mg/mL) which is the highest concentration tested in this assay. In contrast, in the same nephelometry assay, the maximum soluble concentration of prior art Example [I-253] of WO 07/095188 was determined to be 75 µM (Table 6). This shows that compound [254] is more soluble in aqueous buffer in the concentration range used to study compound activity in vitro.

Pharmacokinetic Studies

In order to study compounds in vivo, higher concentrations are often required. To achieve these higher concentrations, salt forms of compounds are normally utilised.

Compound [254] and Example [I-76] of WO 07/095188 were studied as the free base and hydrochloride salts in various pharmaceutically relevant solvent mixtures that can be used for administration of compounds to living organisms. Having solubilized the compound by heating in the solvent, the solutions were cooled to 25° C. and observed. Rather than forming a precipitate, supersaturated mixtures tend to form a gelatinous mesophase after cooling that is not suitable or convenient for dosing. It is clear from the data presented in Table 5 that compound [254] and its HCl salt have consistently better solution profiles than Example [I-76] and its corresponding HCl salt.

The HCl salt of Example [I-76] was administered to mice as a solution in 3% DMA 97% water by intravenous injection. The maximum tolerated dose appears to be dictated by reaching the maximum concentration of compound in stable solution. At the maximum tolerated dose no xenograft antitumour efficacy was observed (qd×7 dosing) as insufficient compound concentration could be administered. In contrast, compound [254] and its salt, having significantly higher water solubility is able to be injected at concentrations more likely to produce efficacy in the treatment of diseases.

Example 8

Pharmacokinetic Properties of Compound [371]

(a) Methodology

Preliminary investigations of the pharmacokinetics of selected compounds were carried out in fasted conscious CD-1 mice (25-30 g). Compounds were dosed as 1 mg/kg by intravenous administration or 5-10 mg/kg by oral route. Twenty one male mice per administration route (n=3 mice per time point) received dose solution by single bolus injection in the tail vein or by oral gavage. Blood samples were collected by cardiac puncture at 5, 15, 30, 60, 120, 240 and 360 min following iv administration and at 30, 60, 120, 240, 360, 480 and 1440 min following oral administration. Blood samples were collected into tubes containing the anti-coagulant lithium heparin, mixed and placed promptly on crushed ice. Plasma was derived from whole blood by centrifugation, frozen and stored at −80° C. prior to analysis. Plasma concentrations were determined by liquid chromatography-tandem mass spectrometry in electrospray positive mode (ESI LC/MS/MS) using calibration curves prepared in the appropriate matrix. The lower level of quantification (LLOQ) in all cases was ca. 5 ng/mL. Plasma concentration-time data was processed using the computer program Win-NonLin version 5.2 from which areas under the plasma concentration-time curve ($AUC_{all}$) were calculated by non-compartmental analysis using Model 201 (IV-bolus Input) or Model 200 (Extravascular Input).

(b) Comparison of Compounds [371] and [378] with Selected Prior Art Compounds

Further pharmacokinetic studies were carried to compare compounds [371] and [378] with a series of related analogues (see Table 7; compound [371] corresponds to compound H; compound [378] corresponds to compound I).

Figure 2:
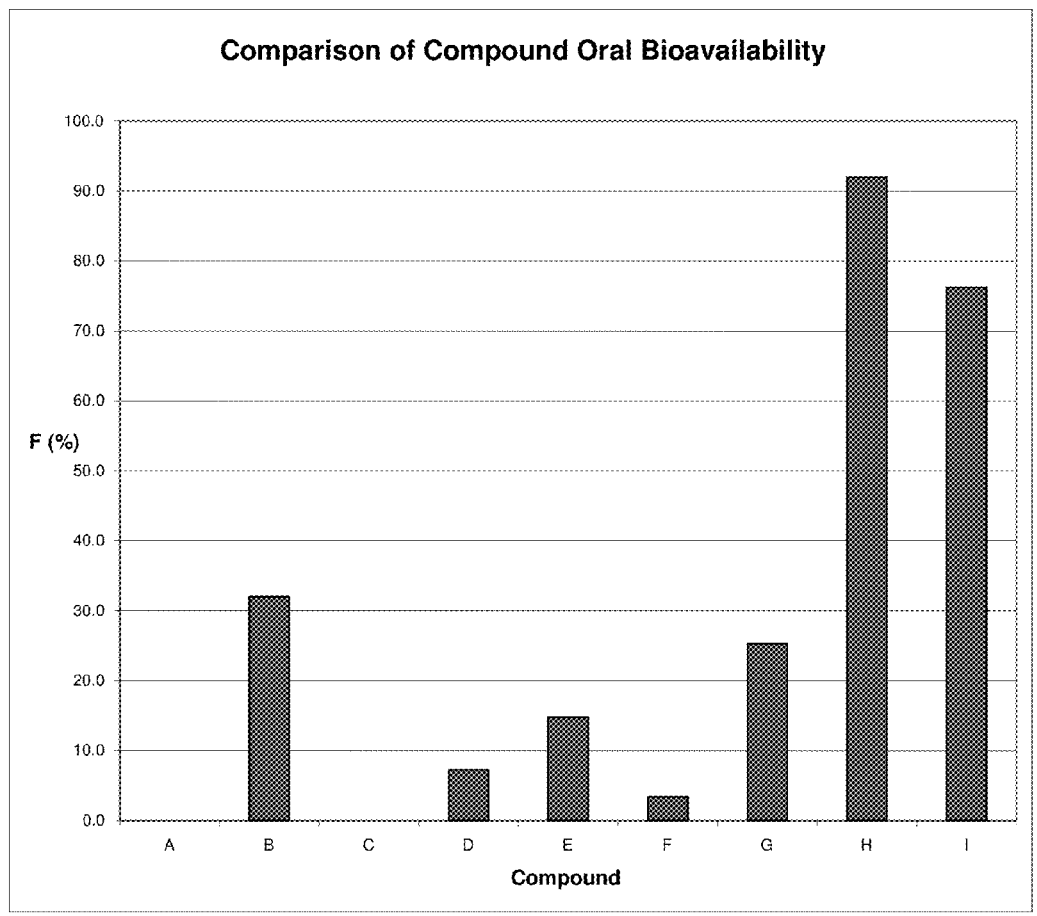
FIG. 2 represents the same data as FIG. 1, but in the form of oral bioavailability (% F) for each compound.

FIG. 1 plots the area under the curve (AUC) for plasma concentration vs time for each compound tested. The dosing vehicle across these experiments remained constant (intravenous=citrate buffer pH 3, 1 mL/kg; oral=DMA/PEG400/10 mM Tartrate buffer, pH 4 (1:3:6), 5 ml/kg). FIG. 2 represents the same data in the form of oral bioavailability (% F) for each compound.

The results indicate that compounds H and I exhibit markedly superior systemic exposure and oral bioavailability compared to compounds A-G.

Example 9

(a) Cellular Efflux Data

In vitro cell viability assays have been used to measure the effect of drug accumulation in paired parental and drug resistant tumour cell lines. The pairs used are the human ovarian carcinoma A2780 line with its MDR counterpart A2780/ADR and the human uterine sarcoma MES-SA line with its MDR counterpart MES-SA/Dx5 [Wesolowska O., et al. (2005) *Anticancer Res.*, 25, 383-389].

Method:

Cultivated human tumour cells of the ovarian cell line A2780 and its doxorubicin-resistant pair, A2780/ADR and the uterine cell line MES-SA and its doxorubicin-resistant pair, MES-SA/DX5 were seeded at 3000 cells per well in Nunc 96-well tissue culture plates, 100 µl per well in DMEM media containing 10% foetal calf serum and penicillin/streptomycin. The wells of the first column in each plate were filled with 100 µl DMEM media instead of cells to provide a blank control for the Alamar Blue. The cells were incubated overnight at 37° C. and 5% $CO_2$. The compounds of interest, dissolved in DMSO, were added on to the cells at various concentrations. Dilutions of the compounds were first prepared in DMEM at twice the final desired concentration and 100 µl of the dilutions added on to the cells. Each set of compounds were tested in triplicate in each cell line. After 72 hours incubation, 20 µl Alamar Blue reagent (AbD Serotec) were added to each well and incubated for 3 hours. The plates were then read at 544/595 nm.

The amount of Alamar Blue reagent reacted represents the metabolic activity of the cells. The relative cell activity was calculated as a percentage of the control (cells without compound) and the active compound concentration which inhibited the cell activity by 50% ($IC_{50}$) was derived. The values were calculated from the average of three individual measurements with blank correction (medium-only control).

Figure 3:
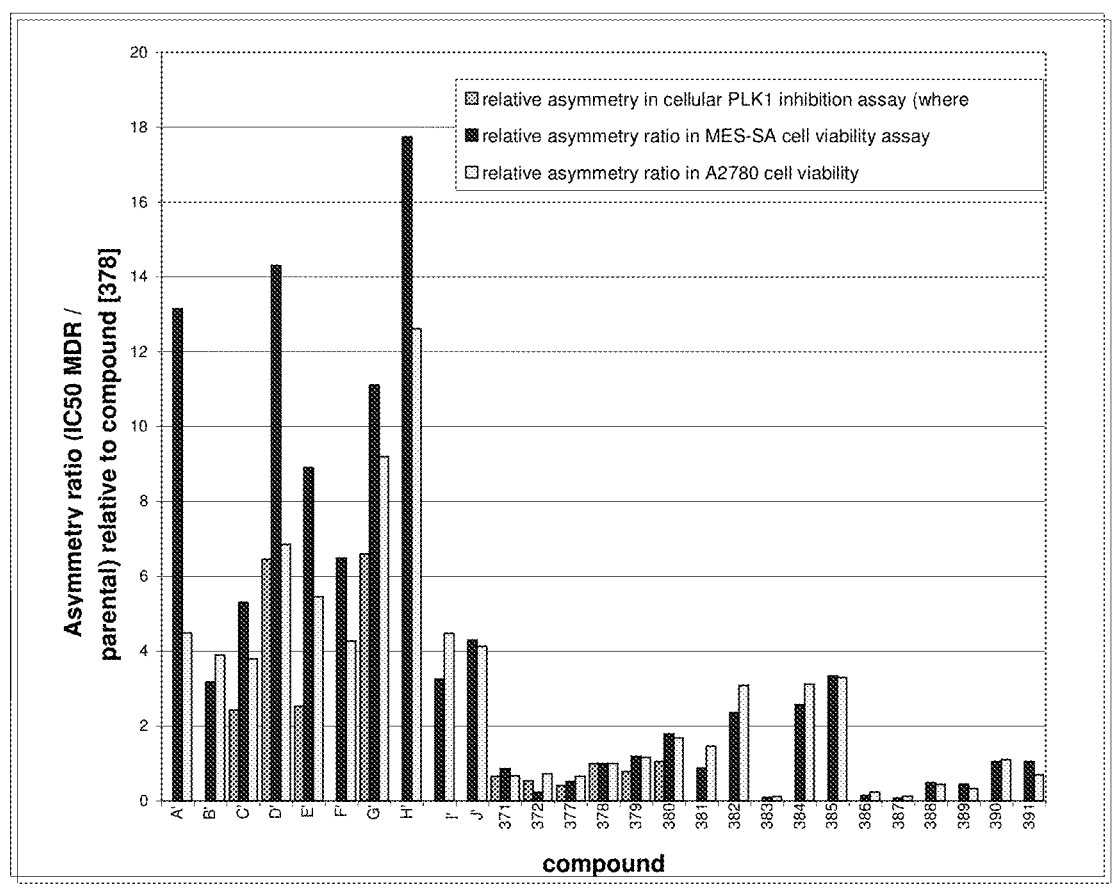
FIG. 3 shows a comparison of selected compounds versus prior art compounds A'-J' (defined in table 8) in parental and MDR tumor cells. Asymmetry ratios are presented relative to compound [378].

The assay was performed on the Biomek FxP, automation platform from Beckman Coulter. The plates were read on the Paradigm plate reader supplied by Beckman Coulter. Asymmetry ratios were calculated as the $IC_{50}$ value of the compound in the drug resistant cells divided by the $IC_{50}$ value in the parental cells. FIG. 3 shows a comparison of selected compounds versus prior art compounds A'-J' (defined in Table 8) in parental and MDR tumor cells. Asymmetry ratios are presented relative to compound [378].

(b) Inhibition of PLK1

In addition, compounds of this invention which exhibit low MDR/parental cell asymmetry in cell viability assays are also more effective at inhibiting PLK1 within MDR tumour cells than compounds of the prior art. Thus, they have greater potential as therapeutic PLK inhibitors. The intermediate filament protein vimentin is a cellular target of PLK1 phosphorylation. Inhibition of PLK1 is associated with a decrease in phospho-vimentin. This has been measured in the A2780-A2780/ADR cell line pair.

Method:

A2780 cells and A2780/ADR cells were plated in separate 96-well plates (Perkin Elmer) at a density of 20 000 cells/well and incubated overnight at 37° C. and 5% $CO_2$. Test compounds were added to cells at a range of concentrations, with triplicate wells for each concentration (top concentration of DMSO on cells was 0.1%). After 7 hrs incubation, the cells were fixed in ice-cold 3.7% formaldehyde for 10 mins. The cells were washed in PBS, then permeabilised in cold methanol for 10 mins. The cells were washed again in PBS then incubated with PBS containing 0.1% Triton X-100 for 5 mins. Cells were washed once with PBS containing 1% bovine serum albumin (Sigma) then incubated for 3 hrs with antibodies to phospho-histone H3-Ser10 (1:4000; Millipore) and phospho-vimentin-Ser82 (1:1000; MBL), in 1% bovine serum albumin. Antibodies were detected with goat anti-mouse IgG conjugated to Alexafluor 488 (Invitrogen) and goat anti-rabbit IgG conjugated to Alexafluor 546 (Invitrogen), in 1% bovine serum albumin with 300 nM DAPI (Cambridge Biosciences). Plates were scanned on a Cellomics Arrayscan II HCS Reader (Cellomics) using a 10× objective. The Cell Health Profiling V2 Bioapplication (Cellomics) was used to acquire and analyse the images. Phospho-vimentin staining, at intensities above a user-defined threshold, was measured in mitotic cells only (defined by the presence of phospho-histone H3) and the average staining intensity per mitotic cell for each well was reported. $IC_{50}$ values were derived using average values from three replicate wells. Asymmetry ratios were calculated as the $IC_{50}$ value of the compound in the drug resistant A2780/ADR cells divided by the $IC_{50}$ value in the parental A2780 cells. FIG. 3 shows a comparison of selected compounds versus prior art compounds A'-J' (defined in Table 8) in parental and MDR tumor cells. As before, asymmetry ratios are presented relative to compound [378].

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

TABLE 1

PLK $IC_{50}$ values (μM) for selected compounds of the invention; * denotes <0.1 μM $IC_{50}$;  denotes <1.0 μM $IC_{50}$; * denotes <10.0 μM $IC_{50}$

| | | AA | PLK1 | |
|---|---|---|---|---|
| 1 | 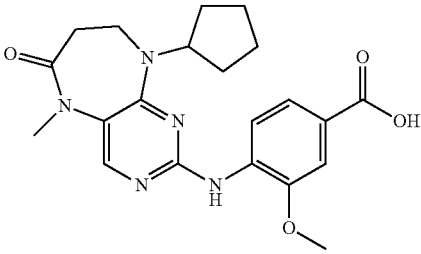 [SMILES: COc1cc(C(=O)O)ccc1Nc1ncc2c(n1)N(C1CCCC1)CCC(=O)N2C] | * | ** | 4-(9-Cyclopentyl-5-methyl-6-oxo-tetrahydro-5H-pyrimido[4,5-b][1,4]diazepin-2-ylamino)-3-methoxy-benzoic |
| 2 | 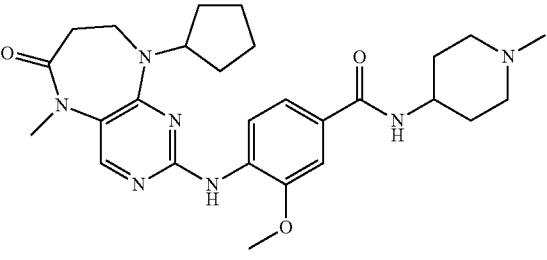 [SMILES: COc1cc(C(=O)NC2CCN(C)CC2)ccc1Nc1ncc2c(n1)N(C1CCCC1)CCC(=O)N2C] | | *** | 4-(9-Cyclopentyl-5-methyl-6-oxo-tetrahydro-5H-pyrimido[4,5-b][1,4]diazepin-2-ylamino)-3-methoxy-N-(1-methyl-piperidin-4-benzamide |
| 3 | 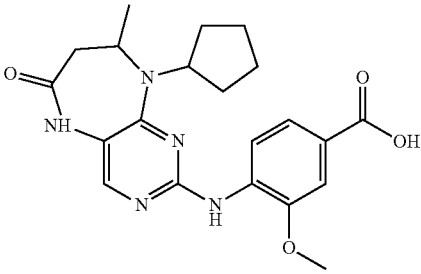 [SMILES: COc1cc(C(=O)O)ccc1Nc1ncc2c(n1)N(C1CCCC1)C(C)CC(=O)N2] | | * | 4-(9-Cyclopentyl-8-methyl-6-oxo-tetrahydro-5H-pyrimido[4,5-b][1,4]diazepin-2-ylamino)-3-methoxy-benzoic |

TABLE 1-continued

PLK IC$_{50}$ values (μM) for selected compounds of the invention; * denotes <0.1 μM IC$_{50}$;  denotes <1.0 μM IC$_{50}$; * denotes <10.0 μM IC$_{50}$

| | | AA | PLK1 | |
|---|---|---|---|---|
| 4 | | | * | 4-(9-Cyclopentyl-5,8-dimethyl-6-oxo-tetrahydro-5H-pyrimido[4,5-b][1,4]diazepin-2-ylamino)-3-methoxy-benzoic |
| 5 | | | * | 4-(9-Cyclohexyl-8-methyl-6-oxo-tetrahydro-5H-pyrimido[4,5-b][1,4]diazepin-2-ylamino)-3-methoxy-benzoic |
| 6 | | | | 4-(9-Cyclopentyl-6-oxo-6,7,8,9-tetrahydro-pyrimido[4,5-b][1,4]diazepin-2-ylamino)-methoxy-benzoic acid |
| 7 | | * | ** | 4-(9-Cyclopentyl-8-methyl-6-oxo-tetrahydro-5H-pyrimido[4,5-b][1,4]diazepin-2-ylamino)-benzoic acid |
| 8 | | *** | ** | 4-(9-Cyclopentyl-5,8-dimethyl-6-oxo-tetrahydro-5H-pyrimido[4,5-b][1,4]diazepin-2-ylamino)-benzoic acid |

TABLE 1-continued

PLK IC$_{50}$ values (μM) for selected compounds of the invention; * denotes <0.1 μM IC$_{50}$;  denotes <1.0 μM IC$_{50}$; * denotes <10.0 μM IC$_{50}$

| | | AA | PLK1 | |
|---|---|---|---|---|
| 9 | | | * | 4-(9-Cyclohexyl-6-oxo-6,7,8,9-tetrahydro-pyrimido[4,5-b][1,4]diazepin-2-ylamino)-methoxy-benzoic acid |
| 10 | | | * | 9-Cyclohexyl-2-(4-hydroxy-phenylamino)-tetrahydro-pyrimido[4,5-b][1,4]diazepin-6-one |
| 11 | | | * | 9-Cyclopentyl-2-(4-hydroxy-phenylamino)-methyl-5,7,8,9-tetrahydro-b][1,4]diazepin-6- |
| 12 | | | | 9-Cyclopentyl-2-(4-hydroxy-phenylamino)-isopropyl-5-methyl-5,7,8,9-pyrimido[4,5-b][1,4]diazepin-6-one |
| 13 | | | * | 9-Cyclopentyl-2-(4-hydroxy-phenylamino)-dimethyl-5,7,8,9-tetrahydro-b][1,4]diazepin-6- |

TABLE 1-continued

PLK IC$_{50}$ values (μM) for selected compounds of the invention; * denotes <0.1 μM IC$_{50}$;  denotes <1.0 μM IC$_{50}$; * denotes <10.0 μM IC$_{50}$

| | AA | PLK1 | |
|---|---|---|---|
| 14 | — | | 4-(9-Benzyl-5-methyl-6-oxo-6,7,8,9-5H-pyrimido[4,5-b][1,4]diazepin-2-ylamino)-methoxy-benzoic acid |
| 15 | ** | * | 4-(5-Methyl-6-oxo-9-phenyl-6,7,8,9-5H-pyrimido[4,5-b][1,4]diazepin-2-benzoic acid |
| 16 | | | 4-(9-Cyclopentyl-5,7,7-trimethyl-6-oxo-tetrahydro-5H-pyrimido[4,5-b][1,4]diazepin-2-ylamino)-benzoic acid |
| 17 | * | | 4-(9-Cyclopentyl-7-methyl-6-oxo-tetrahydro-5H-pyrimido[4,5-b][1,4]diazepin-2-ylamino)-3-methoxy-N-(1-methyl-piperidin-4-benzamide |
| 18 | * | * | 4-(9-Cyclopentyl-7-methyl-6-oxo-tetrahydro-5H-pyrimido[4,5-b][1,4]diazepin-2-ylamino)-N-(1-methyl-piperidin-4-yl)- |

TABLE 1-continued

PLK IC$_{50}$ values (μM) for selected compounds of the invention; * denotes <0.1 μM IC$_{50}$;  denotes <1.0 μM IC$_{50}$; * denotes <10.0 μM IC$_{50}$

| | | AA | PLK1 | |
|---|---|---|---|---|
| 19 | | | * | 4-(9-Cyclopentyl-8-isopropyl-6-oxo-tetrahydro-5H-pyrimido[4,5-b][1,4]diazepin-2-ylamino)-3-methoxy-N-(1-methyl-piperidin-4-benzamide |
| 20 | | | *** | 4-(9-Cyclopentyl-5,7-dimethyl-6-oxo-tetrahydro-5H-pyrimido[4,5-b][1,4]diazepin-2-ylamino)-3-methoxy-N-(1-methyl-piperidin-4-benzamide |
| 21 | | | | 4-[9-(1-Ethyl-propyl)-6-oxo-6,7,8,9-5H-pyrimido[4,5-b][1,4]diazepin-2-ylamino]-methoxy-N-(1-methyl-piperidin-4-yl)- |
| 22 | | | | 4-[9-(1-Ethyl-propyl)-6-oxo-6,7,8,9-5H-pyrimido[4,5-b][1,4]diazepin-2-ylamino]-N-methyl-piperidin-4-yl)-benzamide |
| 23 | | | * | 4-(9-Cyclopentyl-8-isopropyl-5-methyl-6-6,7,8,9-tetrahydro-5H-b][1,4]diazepin-2-ylamino)-3-methoxy-N-methyl-piperidin-4-yl)-benzamide |

TABLE 1-continued

PLK IC$_{50}$ values (μM) for selected compounds of the invention; * denotes <0.1 μM IC$_{50}$;  denotes <1.0 μM IC$_{50}$; * denotes <10.0 μM IC$_{50}$

| | AA | PLK1 | |
|---|---|---|---|
| 24 | | * | 4-[9-(1-Ethyl-propyl)-5-methyl-6-oxo-tetrahydro-5H-pyrimido[4,5-b][1,4]diazepin-2-ylamino]-3-methoxy-N-(1-methyl-piperidin-4-yl)-benzamide |
| 25 | | | 3-Methoxy-N-(1-methyl-piperidin-4-yl)-4-[6-oxo-9-(tetrahydro-pyran-4-yl)-6,7,8,9-tetrahydro-pyrimido[4,5-b][1,4]diazepin-2-benzamide |
| 26 | | ** | 3-Methoxy-4-[5-methyl-6-oxo-9-pyran-4-yl)-6,7,8,9-tetrahydro-5H-b][1,4]diazepin-2-ylamino]-N-(1-methyl-4-yl)-benzamide |
| 27 | | | 4-[5-Ethyl-9-(1-ethyl-propyl)-6-oxo-tetrahydro-5H-pyrimido[4,5-b][1,4]diazepin-2-ylamino]-3-methoxy-N-(1-methyl-piperidin-4-yl)-benzamide |
| 28 | | ** | 4-(9-Cyclopentyl-5-ethyl-7-methyl-6-oxo-tetrahydro-5H-pyrimido[4,5-b][1,4]diazepin-2-ylamino)-3-methoxy-N-(1-methyl-piperidin-4-benzamide |

TABLE 1-continued

PLK IC$_{50}$ values (μM) for selected compounds of the invention; * denotes <0.1 μM IC$_{50}$;  denotes <1.0 μM IC$_{50}$; * denotes <10.0 μM IC$_{50}$

| | | AA | PLK1 | |
|---|---|---|---|---|
| 29 | | — | * | 4-(9-Benzyl-5-methyl-6-oxo-6,7,8,9-5H-pyrimido[4,5-b][1,4]diazepin-2-ylamino)-methoxy-N-(1-methyl-piperidin-4-yl)- |
| 30 | | | ** | 3-Methoxy-4-(5-methyl-6-oxo-9-phenyl-tetrahydro-5H-pyrimido[4,5-b][1,4]diazepin-2-ylamino)-N-(1-methyl-piperidin-4-yl)- |
| 31 | | | *** | 4-(9-Cyclopentyl-5-methyl-6-oxo-tetrahydro-5H-spiro[pyrimido[4,5-b][1,4]diazepin-3,1'-cyclopropane]-2-ylamino)-N-(1-piperidin-4-yl)-benzamide |
| 32 | | | | 4-(9-Cyclopentyl-5,7,7-trimethyl-6-oxo-tetrahydro-5H-pyrimido[4,5-b][1,4]diazepin-2-ylamino)-3-methoxy-N-(1-methyl-piperidin-4-benzamide |
| 33 | | | ** | 4-(9-Cyclopentyl-5,8-dimethyl-6-oxo-tetrahydro-5H-pyrimido[4,5-b][1,4]diazepin-2-ylamino)-3-methoxy-N-(1-methyl-piperidin-4-benzamide |

TABLE 1-continued

PLK IC$_{50}$ values (μM) for selected compounds of the invention; * denotes <0.1 μM IC$_{50}$;  denotes <1.0 μM IC$_{50}$; * denotes <10.0 μM IC$_{50}$

| | AA | PLK1 | |
|---|---|---|---|
| 34 | | ** | 4-(9-Cyclopentyl-8-methyl-6-oxo-tetrahydro-5H-pyrimido[4,5-b][1,4]diazepin-2-ylamino)-3-methoxy-N-(1-methyl-piperidin-4-benzamide |
| 35 | | ** | 4-(9-Cyclohexyl-8-methyl-6-oxo-tetrahydro-5H-pyrimido[4,5-b][1,4]diazepin-2-ylamino)-3-methoxy-N-(1-methyl-piperidin-4-benzamide |
| 36 | | * | 4-(9-Cyclopentyl-6-oxo-6,7,8,9-tetrahydro-pyrimido[4,5-b][1,4]diazepin-2-ylamino)-methoxy-N-(1-methyl-piperidin-4-yl)- |
| 37 | | ** | 4-(9-Cyclopentyl-5,8-dimethyl-6-oxo-tetrahydro-5H-pyrimido[4,5-b][1,4]diazepin-2-ylamino)-N-(1-methyl-piperidin-4-yl)- |
| 38 | | ** | 4-(9-Cyclopentyl-8-methyl-6-oxo-tetrahydro-5H-pyrimido[4,5-b][1,4]diazepin-2-ylamino)-N-(1-methyl-piperidin-4-yl)- |

TABLE 1-continued
PLK IC$_{50}$ values (μM) for selected compounds of the invention; * denotes <0.1 μM IC$_{50}$;  denotes <1.0 μM IC$_{50}$; * denotes <10.0 μM IC$_{50}$
| | | AA | PLK1 | |
|---|---|---|---|---|
| 39 | 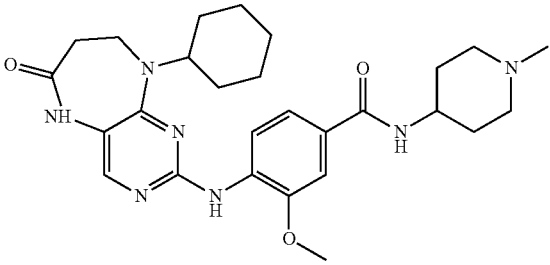 [SMILES: COc1cc(C(=O)NC2CCN(C)CC2)ccc1Nc1ncc2c(n1)N(C1CCCCC1)CCC(=O)N2] | | * | 4-(9-Cyclohexyl-6-oxo-6,7,8,9-tetrahydro-pyrimido[4,5-b][1,4]diazepin-2-ylamino)-methoxy-N-(1-methyl-piperidin-4-yl)- |

TABLE 2

| Cpd | Structure | AurA IC50 | PLK1 IC50 | Name | Data |
|---|---|---|---|---|---|
| 40 | 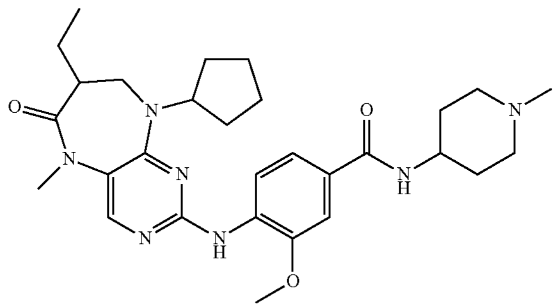 [SMILES: CCC1CN(C2CCCC2)c2nc(Nc3ccc(C(=O)NC4CCN(C)CC4)cc3OC)ncc2N(C)C1=O] | *** | | 4-(9-Cyclopentyl-7-ethyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide | MS(+ve): 536.3; tR = 3.33 min (xbridge 4). |
| 41 | 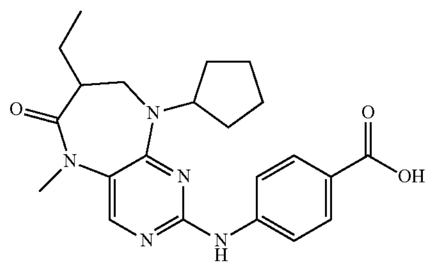 [SMILES: CCC1CN(C2CCCC2)c2nc(Nc3ccc(C(=O)O)cc3)ncc2N(C)C1=O] | * |  | 4-(9-Cyclopentyl-7-ethyl-5-methyl-6-oxo-6,7,8,9-tetrahydro-5H-pyrimido[4,5-b][1,4]diazepin-2-ylamino)-benzoic acid | MS(+ve): 410.2; tR = 2.28 min (xbridge 4). |
| 42 | 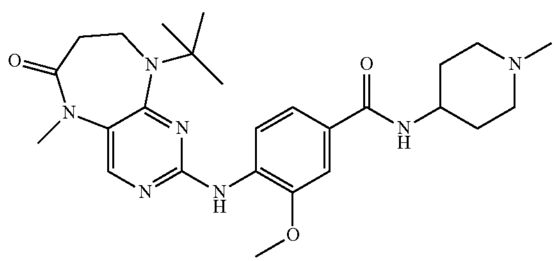 [SMILES: COc1cc(C(=O)NC2CCN(C)CC2)ccc1Nc1ncc2c(n1)N(C(C)(C)C)CCC(=O)N2C] | ** | * | 4-(9-tert-Butyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide | MS(+ve): 496.3; tR = 2.88 min (xbridge 4). |

TABLE 2-continued

| Cpd | Structure | AurA IC50 | PLK1 IC50 | Name | Data |
|---|---|---|---|---|---|
| 43 | 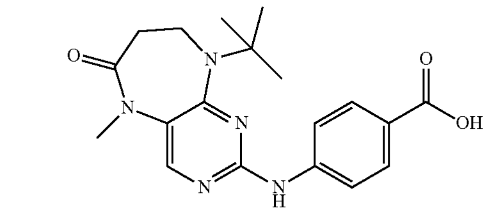 [SMILES: CN1C(=O)CCN(C(C)(C)C)c2nc(Nc3ccc(C(=O)O)cc3)ncc21] | ** | | 4-(9-tert-Butyl-5-methyl-6-oxo-6,7,8,9-tetrahydro-5H-pyrimido[4,5-b][1,4]diazepin-2-ylamino)-benzoic acid | MS(+ve): 370.1; tR = 2.08 min (xbridge 4). |
| 44 | 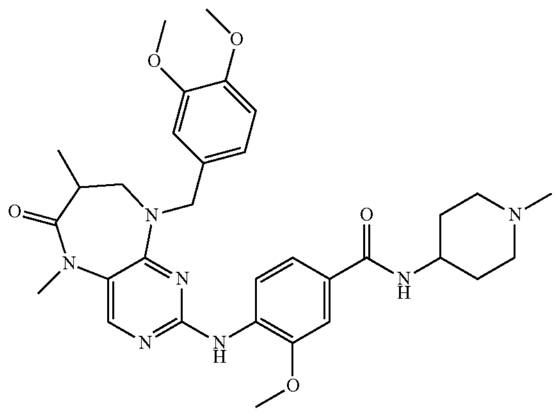 [SMILES: COc1cc(C(=O)NC2CCN(C)CC2)ccc1Nc1ncc2c(n1)N(Cc1ccc(OC)c(OC)c1)CC(C)C(=O)N2C] | * | | 4-[9-(3,4-Dimethoxy-benzyl)-5,7-dimethyl-6-oxo-6,7,8,9-tetrahydro-5H-pyrimido[4,5-b][1,4]diazepin-2-ylamino]-3-methoxy-N-(1-methyl-piperidin-4-yl)-benzamide | MS(+ve): 604.4; tR = 2.87 min (xbridge 4). |
| 45 | 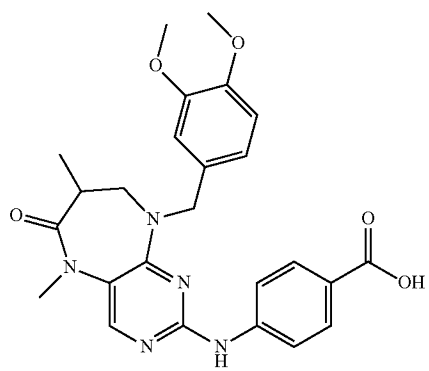 [SMILES: COc1ccc(CN2CC(C)C(=O)N(C)c3cnc(Nc4ccc(C(=O)O)cc4)nc32)cc1OC] | * | | 4-[9-(3,4-Dimethoxy-benzyl)-5,7-dimethyl-6-oxo-6,7,8,9-tetrahydro-5H-pyrimido[4,5-b][1,4]diazepin-2-ylamino]-benzoic acid | MS(+ve): 478.2; tR = 2.12 min (xbridge 4). |

TABLE 2-continued

| Cpd | Structure | AurA IC50 | PLK1 IC50 | Name | Data |
|---|---|---|---|---|---|
| 46 | 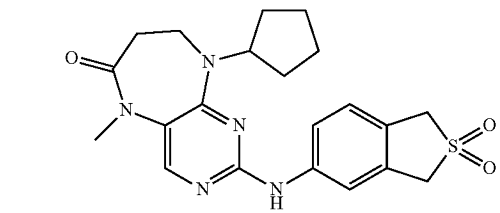 [SMILES: CN1C(=O)CCN(C2CCCC2)c2nc(Nc3ccc4c(c3)CS(=O)(=O)C4)ncc21] | | *** | 9-Cyclopentyl-2-(2,2-dioxo-2,3-dihydro-1H-2lambda*6*-benzo[c]thiophen-5-ylamino)-5-methyl-5,7,8,9-tetrahydro-pyrimido[4,5-b][1,4]diazepin-6-one | 1H NMR (DMSO): 1.56 (4H, m, CH2), 1.70 (2H, m, CH2), 1.89 (2H, m, CH2), 2.65 (2H, m, CH2), 3.16 (3H, s, NCH3), 3.67 (2H, m, CH2), 4.45 (4H, d, J 10 Hz, CH2), 4.84 (1H, m, CH), 7.33 (1H, d, J 8 Hz, Ar—H), 7.57 (1H, d, J 8 Hz, Ar—H), 7.71 (1H, s, Ar—H), 8.05 (1 H, s, Ar—H), 9.96 (1H, s, NH); MS (+ve): 428.3; tR = 6.54 min (XBridge 2). |
| 47 | 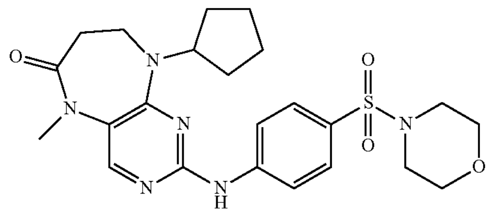 [SMILES: CN1C(=O)CCN(C2CCCC2)c2nc(Nc3ccc(S(=O)(=O)N4CCOCC4)cc3)ncc21] | | *** | 9-Cyclopentyl-5-methyl-2-[4-(morpholine-4-sulfonyl)-phenylamino]-5,7,8,9-tetrahydro-pyrimido[4,5-b][1,4]diazepin-6-one | 1H NMR (DMSO): 1.60-1.99 (8H, m, alkyl-H), 2.50 (4H, bs, morph-H), 2.58-2.60 (2H, m, CH2), 2.83 (4H, bs, morph-H), 3.18 (3H, s, CH3), 3.31 (2H, J 4.5 Hz, CH2), 4.79-4.84 (1H, m, CH), 7.60 (2H, d, J 8 Hz, Ar—H), 7.98 (2H, d, J 8 Hz, Ar—H), 8.11 (1H, s, Ar—H), 9.77 (1H, bs, NH); MS(+ve): 487.31; tR = 3.07 min (Xbridge 4). |
| 48 | 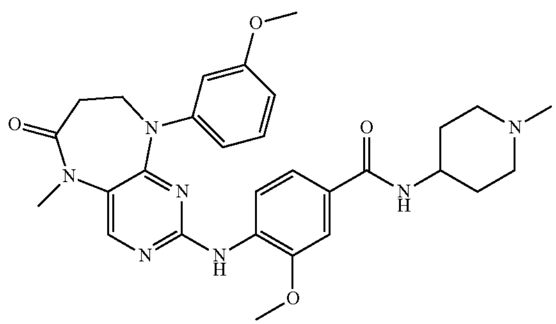 [SMILES: COc1cccc(N2CCC(=O)N(C)c3cnc(Nc4ccc(C(=O)NC5CCN(C)CC5)cc4OC)nc32)c1] | | * | 3-Methoxy-4-[9-(3-methoxy-phenyl)-5-methyl-6-oxo-6,7,8,9-tetrahydro-5H-pyrimido[4,5-b][1,4]diazepin-2-ylamino]-N-(1-methyl-piperidin-4-yl)-benzamide | 1H NMR (DMSO): 1.58 (2H, dd, J 12.5 Hz, 22 Hz, CH), 1.74 (2H, d, J 12 Hz, CH), 1.90 (2H, dd, J 11.5, 11.5 Hz, CH), 2.16 (3H, s, N—CH3), 2.79 (4H, m, CH + CH2), 3.29 (3H, s, N—CH3), 3.69 (1H, m, CH), 3.70 (3H, s, OCH3), 3.88 (3H, s, OCH3), 4.04 (2H, m, CH2), 6.88 (2H, m, Ar—H), 6.99 (1 H, d, J 8 Hz, Ar—H), 7.37 (2H, m, Ar—H), 7.54 (1H, d, J 8 Hz, Ar—H), 7.56 (1H, s, NH), 8.00 (1H, d, J 7.5 Hz, Ar—H), 8.29 (1H, s, Pyr—H); MS(+ve): 546.4; tR = 2.58 min (xbridge 4). |
| 49 | 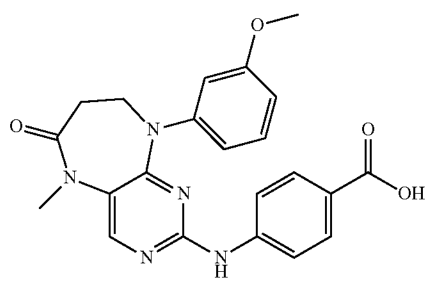 [SMILES: COc1cccc(N2CCC(=O)N(C)c3cnc(Nc4ccc(C(=O)O)cc4)nc32)c1] | | * | 4-[9-(3-Methoxy-phenyl)-5-methyl-6-oxo-6,7,8,9-tetrahydro-5H-pyrimido[4,5-b][1,4]diazepin-2-ylamino]-benzoic acid | MS(+ve): 420.22; tR = 1.44 min (xbridge 4). |

TABLE 2-continued

| Cpd | Structure | AurA IC50 | PLK1 IC50 | Name | Data |
|---|---|---|---|---|---|
| 50 | 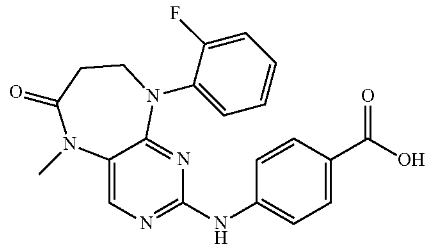 [SMILES: CN1C(=O)CCN(c2ccccc2F)c2nc(Nc3ccc(C(=O)O)cc3)ncc21] | | *** | 4-[9-(2-Fluoro-phenyl)-5-methyl-6-oxo-6,7,8,9-tetrahydro-5H-pyrimido[4,5-b][1,4]diazepin-2-ylamino]-benzoic acid | MS(+ve); 408.2; tR = 2.59 min (xbridge 4). |
| 51 | 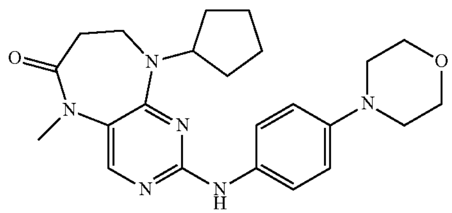 [SMILES: CN1C(=O)CCN(C2CCCC2)c2nc(Nc3ccc(N4CCOCC4)cc3)ncc21] | | ** | 9-Cyclopentyl-5-methyl-2-(4-morpholin-4-yl-phenylamino)-5,7,8,9-tetrahydro-pyrimido[4,5-b][1,4]diazepin-6-one | 1H NMR (DMSO): 1.56 (4H, m, CH2), 1.68 (2H, m, CH2), 1.91 (2H, m, CH2), 2.55 (2H, m, CH2), 3.01 (4H, m, CH2), 3.14 (3H, s, NCH3), 3.57 (2H, m, CH2), 3.73 (4H, m, CH2), 4.77 (1H, m, CH), 6.85 (1H, d, J 9 Hz, Ar—H), 7.55 (1H, d, J 9 Hz, Ar—H), 7.99 (1H, s, Ar—H), 8.92 (1H, s, NH); MS (+ve): 423.3; tR = 7.09 min (XBridge 2) (Vydac 1). |
| 52 | 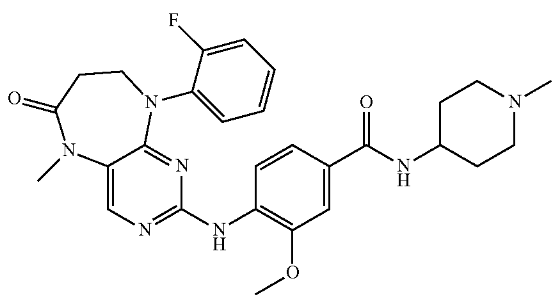 [SMILES: COc1cc(C(=O)NC2CCN(C)CC2)ccc1Nc1ncc2c(n1)N(c1ccccc1F)CCC(=O)N2C] | | ** | 4-[9-(2-Fluoro-phenyl)-5-methyl-6-oxo-6,7,8,9-tetrahydro-5H-pyrimido[4,5-b][1,4]diazepin-2-ylamino]-3-methoxy-N-(1-methyl-piperidin-4-yl)-benzamide | 1H NMR (DMSO): 1.58 (2H, dd, J 9.5 Hz, 21 Hz, CH), 1.74 (2H, d, J 11.5 Hz, CH), 1.92 (2H, dd, J 11 Hz, 11 Hz, CH), 2.16 (3H, s, N-CH3), 2.76 (2H, d, J 11 Hz, CH), 2.86 (2H, m, CH2), 3.70 (1H, m, CH), 3.82 (3H, s, OCH3), 4.02 (2H, m, CH2), 6.92 (2H, d, J 8.5 Hz, Ar—H), 7.32 (1H, d, J 8.5 Hz, Ar—H), 7.37 (2H, m, Ar—H), 7.46 (1H, m, Ar—H), 7.56 (1H, m, Ar—H), 7.66 (1H, s, NH), 7.99 (1H, d, J 7.5 Hz, Ar—H), 8.28 (1H, s, Ar—H); MS(+ve); 534.3; tR = 2.59 min (xbridge 4). |
| 53 | 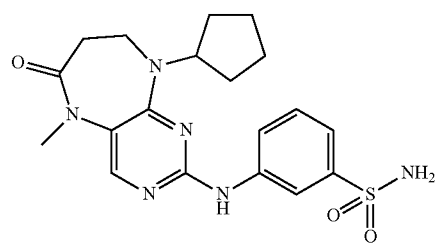 [SMILES: CN1C(=O)CCN(C2CCCC2)c2nc(Nc3cccc(S(N)(=O)=O)c3)ncc21] | | ** | 3-(9-Cyclopentyl-5-methyl-6-oxo-6,7,8,9-tetrahydro-5H-pyrimido[4,5-b][1,4]diazepin-2-ylamino)-benzenesulfonamide | 1H NMR (DMSO): 1.41-1.75 (8H, alkyl-H), 2.45 (2H, bs, CH2), 2.99 (3H, s, CH3), 3.47 (2H, bs, CH2), 4.74-4.75 (1H, m, CH), 7.13 (2H, bs, NH2), 7.29 (2H, bs, Ar—H), 7.59 (1H, bs, Ar—H), 7.89 (1H, bs, Ar—H), 8.06 (1H, bs, Ar—H), 9.72 (1H, bs, NH); MS(+ve): 417.22; tR = 2.62 (Xbridge 4). |

TABLE 2-continued

| Cpd | Structure | AurA IC50 | PLK1 IC50 | Name | Data |
|---|---|---|---|---|---|
| 54 | 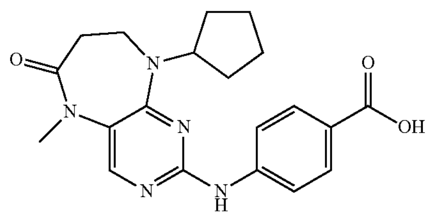 [SMILES: CN1C(=O)CCN(C2CCCC2)c2nc(Nc3ccc(C(=O)O)cc3)ncc21] | *** | | 4-(9-Cyclopentyl-5-methyl-6-oxo-6,7,8,9-tetrahydro-5H-pyrimido[4,5-b][1,4]diazepin-2-ylamino)-benzoic acid | 1H NMR (DMSO): 1.58-1.72 (6H, m, alkyl-H), 1.93-1.95 (2H, m, alkyl-H), 2.64 (2H, dd, J 4.5 Hz, CH2), 3.17 (3H, s, CH3), 3.67 (2H, dd, J 4.5 Hz, CH2), 4.83-4.89 (1H, m, CH), 7.78 (2H, dd, J 1.5 and 8 Hz, Ar—H), 7.87 (2H, d, J 8.5 Hz, Ar—H), 8.09 (1H, d, J 1.5 Hz, Ar—H), 10.02 (1H, s, NH); MS(+ve): 382.22; tR = 1.60 (Xbridge 4). |
| 55 | 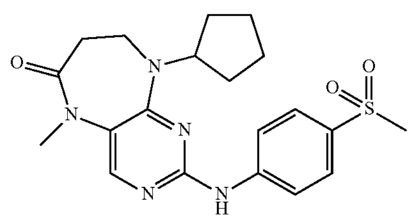 [SMILES: CN1C(=O)CCN(C2CCCC2)c2nc(Nc3ccc(S(C)(=O)=O)cc3)ncc21] | *** | * | 9-Cyclopentyl-2-(4-methanesulfonyl-phenylamino)-5-methyl-5,7,8,9-tetrahydro-pyrimido[4,5-b][1,4]diazepin-6-one | 1H NMR (DMSO): 1.61-1.99 (8H, m, alkyl-H), 2.59 (2H, dd, J 5 Hz, CH2), 3.14 (3H, s, CH3), 3.17 (3H, s, CH3), 3.63 (2H, dd, J 5 Hz, CH2), 4.82-4.86 (1H, m, CH), 7.76 (2H, d, J 9 Hz, Ar—H), 7.98 (2H, d, J 9 Hz, Ar—H), 8.11 (1H, s, Ar—H), 9.77 (1H, bs, NH); MS(+ve): 416.26; tR = 2.83 (Xbridge 4). |
| 56 | 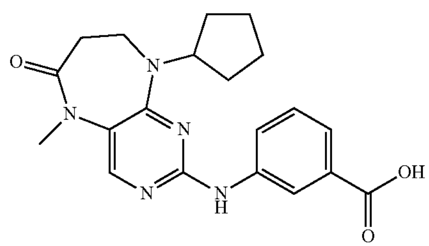 [SMILES: CN1C(=O)CCN(C2CCCC2)c2nc(Nc3cccc(C(=O)O)c3)ncc21] |  |  | 3-(9-Cyclopentyl-5-methyl-6-oxo-6,7,8,9-tetrahydro-5H-pyrimido[4,5-b][1,4]diazepin-2-ylamino)-benzoic acid | 1H NMR (DMSO): 1.39-1.73 (8H, m, alkyl-H), 2.48 (2H, bs, CH2), 2.99 (3H, s, CH3), 3.49 (2H, bs, CH2), 4.77 (1H, bs, CH) 7.26 (1H, bs, Ar—H), 7.44 (1H, bs, Ar—H), 7.52 (1H, bs, Ar—H), 7.89 (1H, bs, Ar—H), 8.23 (1H, bs, Ar—H), 9.83 (1H, bs, NH); MS(+ve): 382.28; tR = 1.93 (Xbridge 4). |
| 57 | 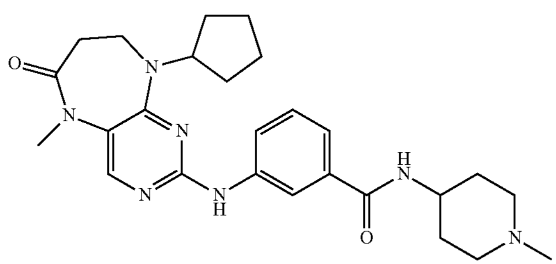 [SMILES: CN1CCC(NC(=O)c2cccc(Nc3ncc4c(n3)N(C3CCCC3)CCC(=O)N4C)c2)CC1] | ** | * | 3-(9-Cyclopentyl-5-methyl-6-oxo-6,7,8,9-tetrahydro-5H-pyrimido[4,5-b][1,4]diazepin-2-ylamino)-N-(1-methyl-piperidin-4-yl)-benzamide | 1H NMR (DMSO): 1.54-1.64 (8H, m, alkyl-H), 1.74-1.76 (2H, m, alkyl-H), 1.90-2.01 (4H, m, alkyl-H), 2.18 (3H, s, CH3), 2.56 (2H, dd, J 5 Hz, CH2), 2.77-2.80 (2H, m, alkyl-H), 3.16 (3H, s, CH3), 3.59 (2H, dd, J 5 Hz, CH2), 3.69-3.73 (1H, m, CH), 4.79-4.84 (1H, m, CH), 7.27-7.33 (2H, m, Ar—H), 7.74 (1H, d, J 8 Hz, Ar—H), 8.04 (1H, 1H, J 1 Hz, Ar—H), 8.11 (1H, d, J 8 Hz, Ar—H), 8.17 (1H, s, Ar—H), 9.28 (1H, s, NH); MS(+ve): 478.33; tR = 2.60 (Xbridge 4). |

TABLE 2-continued

| Cpd | Structure | AurA IC50 | PLK1 IC50 | Name | Data |
|---|---|---|---|---|---|
| 58 | 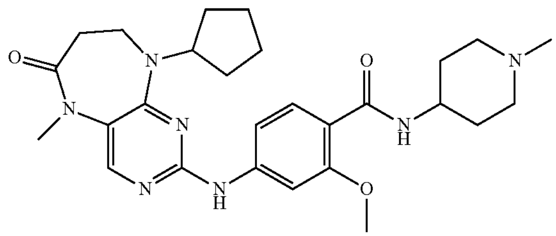 [SMILES: COc1cc(Nc2ncc3c(n2)N(C2CCCC2)CCC(=O)N3C)ccc1C(=O)NC1CCN(C)CC1] | * |  | 4-(9-Cyclopentyl-5-methyl-6-oxo-6,7,8,9-tetrahydro-5H-pyrimido[4,5-b][1,4]diazepin-2-ylamino)-2-methoxy-N-(1-methyl-piperidin-4-yl)-benzamide | ¹H NMR (DMSO): 1.50 (6H, m, CH), 1.70 (2H, m, CH), 1.81 (2H, m, CH), 1.98 (2H, m, CH), 2.07 (2H, m, CH), 2.16 (3H, s, NCH3), 2.57 (2H, m, CH2), 2.63 (2H, m, CH), 3.17 (3H, s, NCH3), 3.61 (2H, m, CH2), 3.75 (1H, m, CH), 3.89 (3H, s, OCH3), 4.86 (1H, m, CH), 7.48 (1H, s, ArH), 7.54 (1H, dd, J 2 Hz, 8.5 Hz, NH), 7.73 (1H, d, J 8.5 Hz, ArH), 7.83 (1H, d, J 7.5 Hz, ArH), 8.09 (1H, s, pyrH), 9.44 (1H, s, NH); MS(+ve): 508.4; tR = 2.68 min (xbridge 4). |
| 59 | 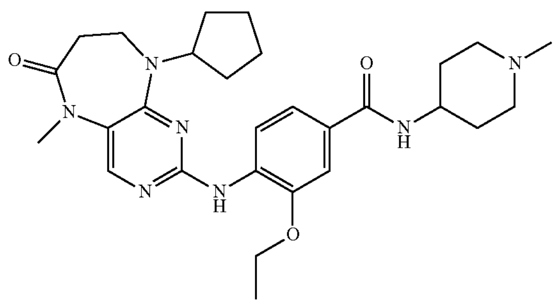 [SMILES: CCOc1cc(C(=O)NC2CCN(C)CC2)ccc1Nc1ncc2c(n1)N(C1CCCC1)CCC(=O)N2C] | | ** | 4-(9-Cyclopentyl-5-methyl-6-oxo-6,7,8,9-tetrahydro-5H-pyrimido[4,5-b][1,4]diazepin-2-ylamino)-3-ethoxy-N-(1-methyl-piperidin-4-yl)-benzamide | ¹H NMR (DMSO): 1.44 (3H, t, J 6.5 Hz), 1.59 (4H, m, CH), 1.76 (2H, m, CH), 1.93 (2H, m, CH), 2.16 (3H, s, N—CH3), 2.59 (2H, m, CH2), 2.78 (2H, d, J 11.5 Hz, CH2), 3.17 (3H, s, CH3), 3.63 (2H, m, CH2), 3.73 (1H, m, CH), 4.20 (2H, q, J 7 Hz, CH2CH3) 4.79 (1H, m, CH), 7.48 (2H, m, Ar—H), 7.70 (1H, s, NH), 8.06 (2H, m, Ar—H), 8.38 (1 H, d, J 8.5 Hz, NH); MS(+ve); 522.4; tR = 2.88 min (xbridge 4) |
| 60 | 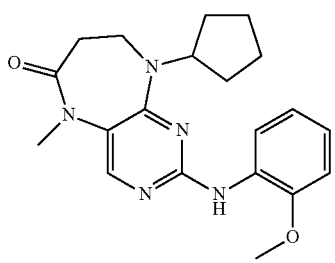 [SMILES: COc1ccccc1Nc1ncc2c(n1)N(C1CCCC1)CCC(=O)N2C] | | ** | 9-Cyclopentyl-2-(2-methoxy-phenylamino)-5-methyl-5,7,8,9-tetrahydro-pyrimido[4,5-b][1,4]diazepin-6-one | ¹H NMR (DMSO): 1.57 (4H, m, CH), 1.68 (2H, m, CH), 1.90 (2H, m, CH), 2.57 (2H, m, CH2), 3.16 (3H, s, N—CH3), 3.62 (2H, m, CH2), 3.86 (3H, s, OCH3), 4.75 (1H, m, CH), 6.90 (1H, dd, J 8 Hz, 8 Hz, Ar—H), 6.95 (1H, dd, J 8 Hz, 8 Hz, Ar—H), 7.02 (1H, d, J 8 Hz Ar—H), 7.60 (1H, s, NH), 8.03 (1H, s, pyr—H), 8.20 (1H, d, J 8 Hz, Ar—H): MS(+ve); 368.3; tR = 3.74 min (xbridge 4). |
| 61 | 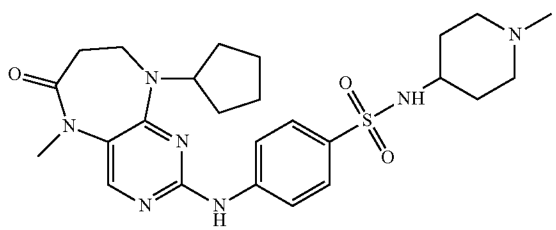 [SMILES: CN1CCC(NS(=O)(=O)c2ccc(Nc3ncc4c(n3)N(C3CCCC3)CCC(=O)N4C)cc2)CC1] | | * | 4-(9-Cyclopentyl-5-methyl-6-oxo-6,7,8,9-tetrahydro-5H-pyrimido[4,5-b][1,4]diazepin-2-ylamino)-N-(1-methyl-piperidin-4-yl)-benzenesulfonamide | ¹H NMR (DMSO): 1.57 (4H, m, CH2), 1.71 (2H, m, CH2), 1.93 (2H, m, CH2), 2.55 (2H, m, CH2), 2.70 (4H, m, CH2), 2.91 (4H, m, CH2), 3.17 (3H, s, NCH3), 3.63 (2H, m, CH2), 4.81 (1H, m, CH), 7.50 (1H, d, J 7 Hz, NH), 7.66 (2H, d, J 9 Hz, Ar—H), 7.89 (2H, d, J 9 Hz, Ar—H), 8.09 (1H, s, Ar—H), 9.67 (1H, s, NH); MS (+ve) 514.4; tR = 6.29 min (XBridge 2 |

TABLE 2-continued

| Cpd | Structure | AurA IC50 | PLK1 IC50 | Name | Data |
|---|---|---|---|---|---|
| 62 | 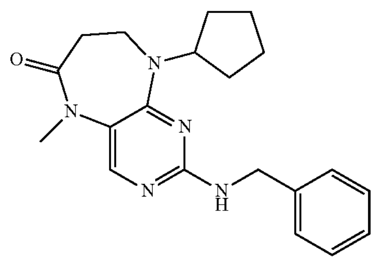 [SMILES: CN1C(=O)CCN(C2CCCC2)c2nc(NCc3ccccc3)ncc21] | | ** | 2-Benzylamino-9-cyclopentyl-5-methyl-5,7,8,9-tetrahydro-pyrimido[4,5-b][1,4]diazepin-6-one | |
| 63 | 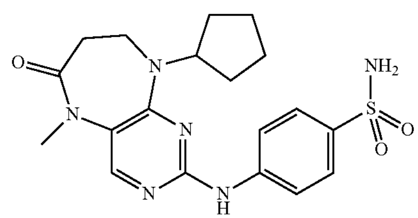 | | *** | 4-(9-Cyclopentyl-5-methyl-6-oxo-6,7,8,9-tetrahydro-5H-pyrimido[4,5-b][1,4]diazepin-2-ylamino)-benzenesulfonamide | 1H NMR (DMSO): 1.61-2.20 (16H, alkyl-H), 2.58 (2H, dd, J 5 Hz, CH2), 2.69 (3H, s, CH3), 3.31 (3H, s, CH3), 3.62 (2H, dd, J 5 Hz, CH2), 4.81-4.84 (1H, m, CH), 7.74-7.80 (2H, m, Ar—H), 8.08 (1H, s, Ar—H), 9.46 (1H, s, NH); MS(+ve): 478.40; tR = 2.56 (Xbridge 4). |
| 64 | 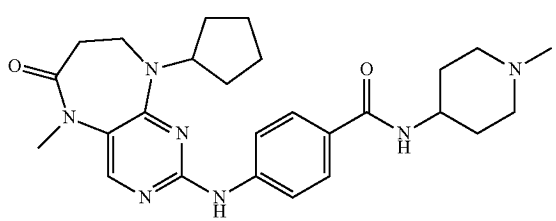 [SMILES: CN1CCC(NC(=O)c2ccc(Nc3ncc4c(n3)N(C3CCCC3)CCC(=O)N4C)cc2)CC1] | | *** | 4-(9-Cyclopentyl-5-methyl-6-oxo-6,7,8,9-tetrahydro-5H-pyrimido[4,5-b][1,4]diazepin-2-ylamino)-N-(1-methyl-piperidin-4-yl)-benzamide | |
| 65 | 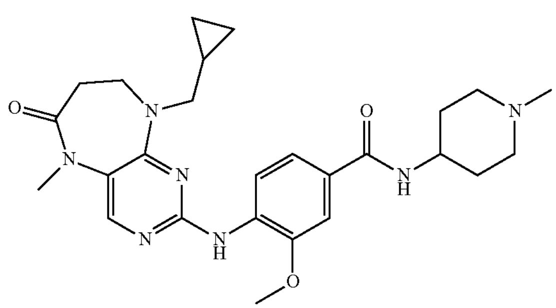 [SMILES: COc1cc(C(=O)NC2CCN(C)CC2)ccc1Nc1ncc2c(n1)N(CC1CC1)CCC(=O)N2C] | | *** | 4-(9-Cyclopropylmethyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide | 1H NMR (DMSO): 0.29 (2H, d, J 4 Hz, cyclopropyl CH), 0.52 (2H, d, J 4 Hz, cyclopropyl CH), 1.16 (1H, m, CH), 1.58 (2H, dd, J 11.5, 20.5, CH), 1.75 (2H, m, CH), 1.95 (2H, dd, J 10 Hz, 10 Hz, CH), 2.16 (3H, s, NCH3), 2.64 (2H, m, CH2), 2.79 (2H, d, J 11.5 Hz, CH), 3.18 (3H, s, NCH3), 3.50 (2H, d, J 6.5 Hz, CH2), 3.73 (1H, m, CH), 3.79 (2H, m, CH2), 3.94 (3H, s, OCH3), 7.48 (2H, m, ArH), 7.71 (1H, s, ArH), 8.07 (2H, m, ArH), 8.40 (1H, d, J 9 Hz, ArH) ; MS(+ve); 494.38; tR = 2.60 min (xbridge 4). |

TABLE 2-continued

| Cpd | Structure | AurA IC50 | PLK1 IC50 | Name | Data |
|---|---|---|---|---|---|
| 66 | 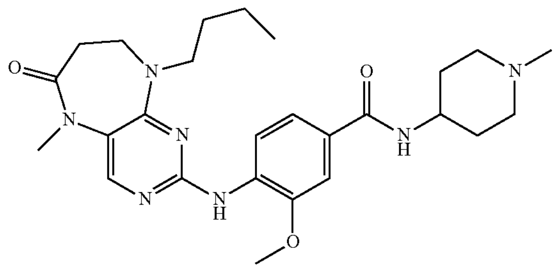 [SMILES: CCCCN1CCC(=O)N(C)c2cnc(Nc3ccc(C(=O)NC4CCN(C)CC4)cc3OC)nc21] | ** | | 4-(9-Butyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide | 1H NMR (DMSO): 0.91 (3H, t, J 7 Hz, CH3), 1.34 (2H, m, CH2), 1.62 (4H, m, CH2), 1.75 (2H, m, CH2), 1.93 (2H, d, J 11 Hz, CH2), 2.16 (3H, s, NCH3), 2.61 (2H, m, CH2), 2.77 (2H, d, J 11.5 Hz CH2), 3.16 (3H, s, NCH3), 3.56 (2H, m, CH2), 3.70 (3H, m, CH2 + CH), 3.94 (3H, s, OCH3), 7.48 (2H, m, ArH), 7.70 (1H, s, ArH), 8.06 (1H, s, ArH), 8.08 (1H, d, J 8 Hz, ArH), 8.34 (1H, d, J 8.5 Hz, ArH); MS(+ve); 496.4; tR = 2.69 min (xbridge 4). |
| 67 | 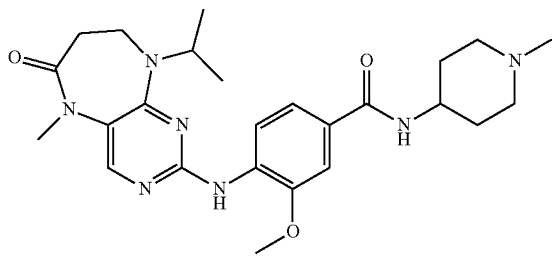 [SMILES: COc1cc(C(=O)NC2CCN(C)CC2)ccc1Nc1ncc2c(n1)N(C(C)C)CCC(=O)N2C] | *** | | 4-(9-Isopropyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide | 1H NMR (DMSO): 1.24 (6H, d, J 7 Hz, CH3), 1.61 (2H, ddd, J 3.5 Hz, 12 Hz, 18 Hz, CH), 1.76 (2H, d, J 9.5 Hz, CH), 1.93 (dd, J 9.5 Hz, 12 Hz, CH), 2.16 (3H, s, CH2), 2.59 (2H, m, CH2), 2.78 (2H, d, J 12 Hz, CH), 3.16 (3H, s, NCH3), 3.60 (2H, m, CH2), 3.73 (1H, m, CH), 3.94 (3H, s, OCH3), 4.80 (1H, m, CH), 7.48 (1 H, d, J 11.5 Hz, ArH), 7.51 (1H, d, J 8.5 Hz, ArH), 7.68 (1H, s, ArH), 8.06 (2H, m, ArH), 8.1 (1H, d, J 8.5 Hz, ArH) ; MS(+ve); 482.3; tR = 2.55 min (xbridge 4). |
| 68 | 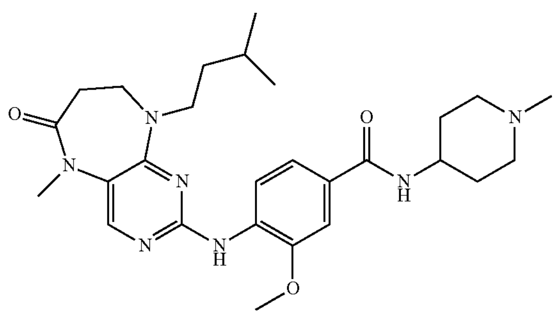 | ** | | 3-Methoxy-4-[5-methyl-9-(3-methyl-butyl)-6-oxo-6,7,8,9-tetrahydro-5H-pyrimido[4,5-b][1,4]diazepin-2-ylamino]-N-(1-methyl-piperidin-4-yl)-benzamide | 1H NMR (DMSO): 0.92 (6H, d, J 7 Hz, CH3), 1.54 (4H, m, CH2), 1.62 (2H, d, J 9.5 Hz, CH), 1.93 (2H, dd, J 9.5 Hz, 12 Hz, CH), 2.16 (3H, s, NCH3), 2.60 (2H, m, CH2), 2.78 (2H, d, J 11.5 Hz, CH), 3.16 (3H, s, NCH3), 3.67 (2H, m, CH2), 3.71 (2H, m, CH2), 3.73 (1H, m, CH), 3.94 (3H, s, OCH3); MS(+ve); 510.4; tR = 2.85 min (xbridge 4). |

Chemistry 29

TABLE 2-continued

| Cpd | Structure | AurA IC50 | PLK1 IC50 | Name | Data |
|---|---|---|---|---|---|
| 69 | 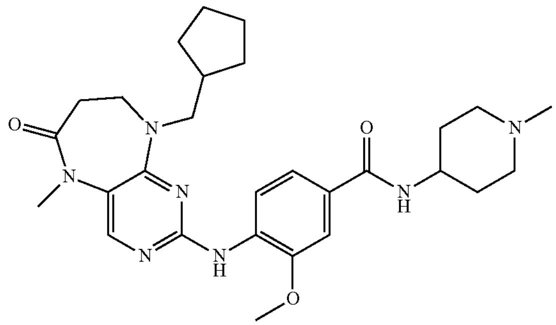 [SMILES: COc1cc(C(=O)NC2CCN(C)CC2)ccc1Nc1ncc2c(n1)N(CC1CCCC1)CCC(=O)N2C] | | ** | 4-(9-Cyclopentylmethyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide | 1H NMR (DMSO): 1.23 (2H, m, CH2), 1.49 (2H, m, CH2), 1.59 (4H, m, 2 × CH2), 1.69 (2H, m, CH2), 1.75 (2H, m, CH2), 1.93 (2H, dd, J 10 Hz, 12 Hz, CH2), 2.16 (3H, s, NCH3), 2.36 (1H, m, CH), 2.62 (2H, m, CH2), 2.79 (2H, d, J 12 Hz, CH2), 3.29 (3H, s, NCH3), 3.60 (2H, d, J 7.5 Hz, CH2), 3.73 (2H, m, CH2), 3.94 (3H, s, OCH3), 7.49 (2h, M, ArH), 7.70 (1H, S, ArH), 8.08 (2H, M, ArH), 8.32 (1H, d, J 8.5 Hz, ArH); MS(+ve); 522.4; tR = 2.89 min (xbridge 4). |
| 70 | 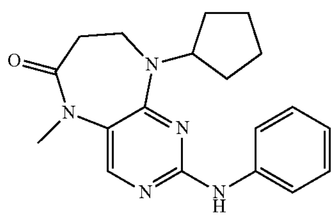 [SMILES: CN1C(=O)CCN(C2CCCC2)c2nc(Nc3ccccc3)ncc21] | ** | * | 9-Cyclopentyl-5-methyl-2-phenylamino-5,7,8,9-tetrahydro-pyrimido[4,5-b][1,4]diazepin-6-one | 1H NMR (DMSO): 1.62-2.00 (8H, m, alkyl-H), 2.76 (2H, dd, J 5 Hz, CH2), 3.27 (3H, s, CH3), 3.76 (2H, dd, J 5 Hz, CH2), 4.96-4.99 (1H, m, CH), 7.01-7.04 (1H, m, Ar—H), 7.16 (1H, t, J 7.5 Hz, Ar—H), 7.29 (1H, t, J 7.5 H, Ar—H), 7.37 (1H, t, J 7.5 Hz, Ar—H), 7.54-7.55 (2H, m, Ar—H), 7.89 (1H, bs, NH); MS(+ve): 338.26; tR = 3.52 (Xbridge 4). |
| 71 | 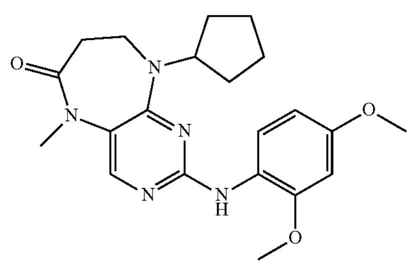 [SMILES: COc1ccc(Nc2ncc3c(n2)N(C2CCCC2)CCC(=O)N3C)c(OC)c1] | *** | | 9-Cyclopentyl-2-(2,4-dimethoxy-phenylamino)-5-methyl-5,7,8,9-tetrahydro-pyrimido[4,5-b][1,4]diazepin-6-one | 1H NMR (DMSO): 1.53 (4H, m, CH), 1.65 (2H, m, CH), 1.83 (2H, m, CH), 2.54 (2H, m, CH2), 3.14 (3H, s, NCH3), 3.55 (2H, m, CH2), 3.73 (3H, s, OCH3), 3.81 (3H, s, OCH3), 4.64 91H, m, CH), 6.47 (1H, dd, J 3 Hz, 9 Hz, ArH), 6.61 (1 H, d, J 3 Hz, ArH), 7.51 (1H, s, NH), 7.86 (1H, d, J 9 Hz, ArH), 7.97 (1H, s, PyrH); MS(+ve); 398.3; tR = 3.51 min (xbridge 4). |
| 72 | 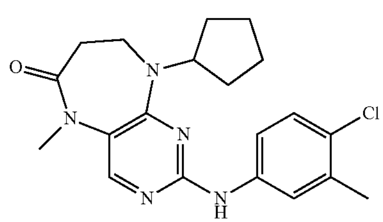 [SMILES: Cc1cc(Nc2ncc3c(n2)N(C2CCCC2)CCC(=O)N3C)ccc1Cl] | ** | | 2-(4-Chloro-3-methyl-phenylamino)-9-cyclopentyl-5-methyl-5,7,8,9-tetrahydro-pyrimido[4,5-b][1,4]diazepin-6-one | 1H NMR (CD3OD): 1.62-1.99 (8H, m, alkyl-H), 2.39 (3H, s, CH3), 2.76 (2H, dd, J 5.5 Hz, CH2), 3.23 (3H, s, CH3), 3.77 (2H, dd, J 5.5 Hz, CH2), 4.96-5.00 (1H, m, CH), 7.33-7.34 (2H, m, Ar—H), 7.56 (1 H, s, Ar—H), 7.90 (1H, s, Ar—H); MS(+ve): 386.23; tR = 4.13 (Xbridge 4). |

TABLE 2-continued

| Cpd | Structure | AurA IC50 | PLK1 IC50 | Name | Data |
|---|---|---|---|---|---|
| 73 | 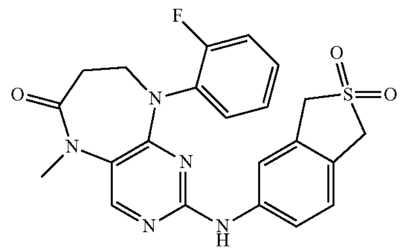 [SMILES: CN1C(=O)CCN(c2ccccc2F)c2nc(Nc3ccc4c(c3)CS(=O)(=O)C4)ncc21] | *** | | 2-(2,2-Dioxo-2,3-dihydro-1H-2lambda*6*-benzo[c]thiophen-5-ylamino)-9-(2-fluorophenyl)-5-methyl-5,7,8,9-tetrahydropyrimido[4,5-b][1,4]diazepin-6-one | 1H NMR (DMSO): 2.82 (2H, m, CH2), 3.27 (3H, s, CH3), 4.0 (2H, m, CH2), 4.12 (2H, s, CH2), 4.30 (2H, s, CH2), 6.91 (1 H, d, J 8.5 Hz, CH), 7.16 (2H, m, 2CH), 7.36 (2H, m, 2CH), 7.43 (1H, m, CH), 7.56 (1H, m, CH), 8.28 (1H, s, CH), 9.50 (1H, s, NH); MS(+ve): 454.3; tR = 2.67 min (XBridge 4). |
| 74 | 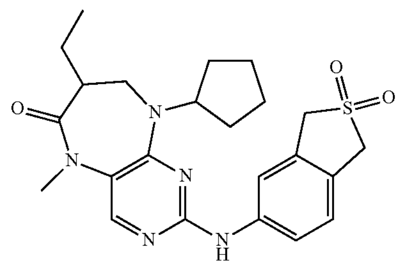 [SMILES: CCC1CN(C2CCCC2)c2nc(Nc3ccc4c(c3)CS(=O)(=O)C4)ncc2N(C)C1=O] | *** | | 9-Cyclopentyl-2-(2,2-dioxo-2,3-dihydro-1H-2lambda*6*-benzo[c]thiophen-5-ylamino)-7-ethyl-5-methyl-5,7,8,9-tetrahydro-pyrimido[4,5-b][1,4]diazepin-6-one | 1H NMR (DMSO): 0.87 (3H, t, J 7.5 Hz, CH2CH3), 1.29-1.79 (9H, m, 4CH2, CH), 2.08 (1H, m, CH), 2.59 (1H, m, CHEt), 3.18 (3H, s, CH3), 3.38 (2H, d, J 6.5 Hz, NCH2), 4.4 (4H, m, 2CH2), 4.77 (1H, m, CH), 7.24 (1H, d, J 8.5 Hz, CH), 7.63 (1H, d, J 8.5 Hz, CH), 7.83 (1H, s, CH), 8.08 (1H, s, CH), 9.38 (1H, s, NH); MS(+ve): 456.3; tR = 3.31 min (XBridge 4). |
| 75 | 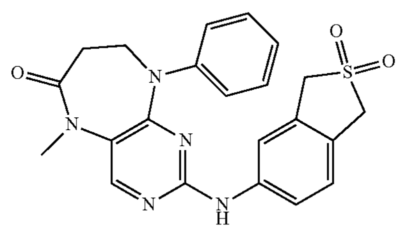 [SMILES: CN1C(=O)CCN(c2ccccc2)c2nc(Nc3ccc4c(c3)CS(=O)(=O)C4)ncc21] | *** | | 2-(2,2-Dioxo-2,3-dihydro-1H-2lambda*6*-benzo[c]thiophen-5-ylamino)-5-methyl-9-phenyl-5,7,8,9-tetrahydro-pyrimido[4,5-b][1,4]diazepin-6-one | 1H NMR (DMSO): 2.78 (2H, m, CH2), 3.27 (3H, s, CH3), 4.03 (2H, m, CH2), 4.09 (2H, s, CH2), 4.30 (2H, s, CH2), 6.93 (1H, d, J 8.5 Hz, CH), 7.19 (1 H, d, J 8.5 Hz, CH), 7.29 (4H, m, 4CH), 7.46 (2H, m, 2CH), 8.3 (1H, s, CH), 9.49 (1H, s, NH); MS(+ve): 436.3; tR = 2.66 min (XBridge 4). |
| 76 | 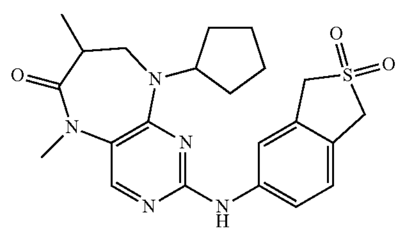 [SMILES: CC1CN(C2CCCC2)c2nc(Nc3ccc4c(c3)CS(=O)(=O)C4)ncc2N(C)C1=O] | *** | | 9-Cyclopentyl-2-(2,2-dioxo-2,3-dihydro-1H-2lambda*6*-benzo[c]thiophen-5-ylamino)-5,7-dimethyl-5,7,8,9-tetrahydro-pyrimido[4,5-b][1,4]diazepin-6-one | 1H NMR (DMSO): 1.01 (3H, d, J 6.5 Hz, CH3), 1.4-1.85 (6H, m, 3CH2), 2.07 (1H, m, CH), 2.83 (1H, m, CH), 3.18 (3H, s, CH3), 3.3 (2H, d, CH2), 3.4 (1H, t, J 11.5 Hz, CH), 4.3-4.5 (4H, m, 2CH2), 4.73 (1H, m, CH), 7.24 (1H, d, J 8.5 Hz, CH), 7.64 (1H, dd, J 9, 2Hz, CH), 7.84 (1H, s, CH), 8.06 (1H, s, CH), 9.37 (1H, s, NH); MS(+ve): 442.3; tR = 3.06 min (XBridge 4). |

TABLE 2-continued

| Cpd | Structure | AurA IC50 | PLK1 IC50 | Name | Data |
|---|---|---|---|---|---|
| 77 | 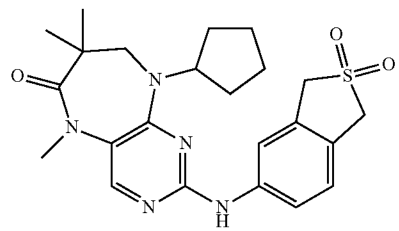 [SMILES: CN1C(=O)C(C)(C)CN(C2CCCC2)c2nc(Nc3ccc4c(c3)CS(=O)(=O)C4)ncc21] |  |  | 9-Cyclopentyl-2-(2,2-dioxo-2,3-dihydro-1H-2lambda*6*-benzo[c]thiophen-5-ylamino)-5,7,7-trimethyl-5,7,8,9-tetrahydro-pyrimido[4,5-b][1,4]diazepin-6-one | 1H NMR (DMSO): 1.09 (6H, s, 2CH3), 1.58 (4H, m, 2CH2), 1.72 (2H, m, CH2), 1.86 (2H, m, CH2), 3.18 (3H, s, CH3), 3.35 (2H, s, CH2), 4.39 (2H, s, CH2), 4.43 (2H, s, CH2), 5.21 (1H, m, CHN), 7.23 (1H, d, J 8.5 Hz, CH), 7.6 (1H, dd, J 8.5, 2 Hz, CH), 7.83 (1H, s, CH), 7.95 (1H, s, CH), 9.30 (1H, s, NH); MS(+ve): 456.3; tR = 3.25 min (XBridge 4). |
| 78 | 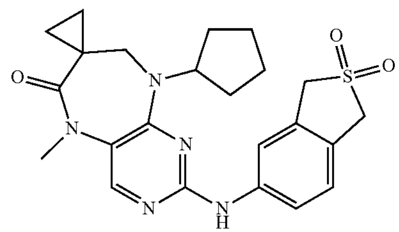 [SMILES: CN1C(=O)C2(CC2)CN(C2CCCC2)c2nc(Nc3ccc4c(c3)CS(=O)(=O)C4)ncc21] | * |  | (9-Cyclopentyl-2-(2,2-dioxo-2,3-dihydro-1H-2lambda*6*-benzo[c]thiophen-5-ylamino)5-methyl-6-oxo-6,7,8,9-tetrahydro-5H-spiro[pyrimido[4,5-b][1,4]diazepin-3,1'-cyclopropane] | 1H NMR (DMSO): 0.66 (2H, m, CH2) 0.89 (2H, m, CH2), 1.47 (2H, m, CH2), 1.56 (2H, m, CH2), 1.67 (2H, m, CH2), 1.88 (2H, m, CH2), 3.16 (3H, s, CH3), 3.45 (2H, s, CH2), 4.39 (2H, s, CH2), 4.42 (2H, s, CH2), 4.86 (1H, m, CHN), 7.23 (1H, d, J 8.5 Hz, CH), 7.63 (1H, dd, J 8.5, 2 Hz, CH), 7.84 (1H, s, CH), 7.95 (1H, s, CH), 9.31 (1H, s, NH); MS(+ve): 454.3; tR = 3.03 min (XBridge 4). |
| 79 | 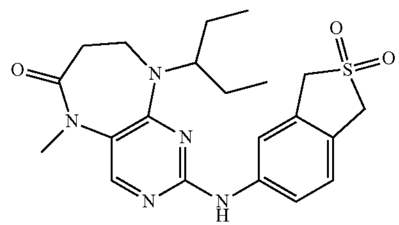 [SMILES: CCC(CC)N1CCC(=O)N(C)c2cnc(Nc3ccc4c(c3)CS(=O)(=O)C4)nc21] | *** | | 2-(2,2-Dioxo-2,3-dihydro-1H-2lambda*6*-benzo[c]thiophen-5-ylamino)-9-(1-ethyl-propyl)-5-methyl-5,7,8,9-tetrahydro-pyrimido[4,5-b][1,4]diazepin-6-one | 1H NMR (DMSO): 0.83 (6H, t, J 7.5 Hz, 2CH3), 1.58 (4H, m, 2CH2), 2.61 (2H, m, CH2), 3.17 (3H, s, CH3), 3.46 (2H, m, CH2), 4.39 (2H, s, CH2), 4.44 (2H, s, CH2), 4.66 (1H, m, CHN), 7.23 (1H, d, J 8.5 Hz, CH), 7.68 (1H, dd, J 8.5, 2 Hz, CH), 7.75 (1H, s, CH), 8.03 (1H, s, CH), 9.29 (1H, s, NH); MS(+ve): 430.3; tR = 2.88 min (XBridge 4). |
| 80 | 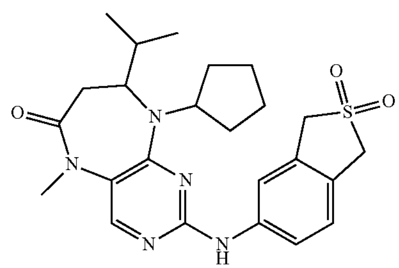 [SMILES: CC(C)C1CC(=O)N(C)c2cnc(Nc3ccc4c(c3)CS(=O)(=O)C4)nc2N1C1CCCC1] | ** | | 9-Cyclopentyl-2-(2,2-dioxo-2,3-dihydro-1H-2lambda*6*-benzo[c]thiophen-5-ylamino)-8-isopropyl-5-methyl-5,7,8,9-tetrahydro-pyrimido[4,5-b][1,4]diazepin-6-one | 1H NMR (DMSO): 0.72 (3H, d, J 7 Hz, CH3), 0.84 (3H, d, J 7 Hz, CH3), 1.26-2.4 (10 H, m, 5CH2), 2.54 (1H, m, CH), 3.14 (3H, s, CH3), 3.85 (1H, m, CH), 4.2 (1H, m, CH), 4.39-4.5 (4H, m, 2CH2), 7.25 (1H, d, J 8.5 Hz, CH), 7.68 (1H, dd, J 8.5, 2 Hz, CH), 7.84 (1H, s, CH), 8.24 (1H, s, CH), 9.49 (1H, s, NH); MS(+ve): 470.3; tR = 3.30 min (XBridge 4). |

TABLE 2-continued

| Cpd | Structure | AurA IC50 | PLK1 IC50 | Name | Data |
|---|---|---|---|---|---|
| 81 | 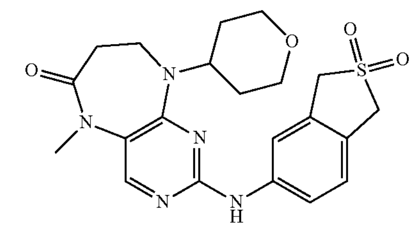 [SMILES: CN1C(=O)CCN(C2CCOCC2)c2nc(Nc3ccc4c(c3)CS(=O)(=O)C4)ncc21] | | ** | 2-(2,2-Dioxo-2,3-dihydro-1H-2lambda*6*-benzo[c]thiophen-5-ylamino)-9-(tetrahydro-pyran-4-yl)-5,7,8,9-tetrahydro-pyrimido[4,5-b][1,4]diazepin-6-one | 1H NMR (DMSO): 1.7 (2H, m, CH2), 1.85 (2H, m, CH2), 2.57 (2H, m, CH2), 3.16 (3H, s, CH3), 3.43 (2H, t, J 11 Hz, CH2), 3.62 (2H, m, CH2), 3.97 (2H, m, CH2), 4.39 (2H, s, CH2), 4.46 (2H, s, CH2), 4.58 (1H, m, CHN), 7.26 (1H, d, J 8.5 Hz, CH), 7.63 (1H, s, CH), 7.73 (1H, dd, J 8.5, 2Hz, CH), 8.06 (1H, s, CH), 9.36 (1H, s, NH); MS(+ve): 444.3; tR = 2.35 min (XBridge 4). |
| 82 | 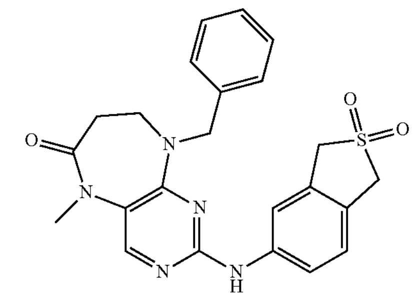 [SMILES: CN1C(=O)CCN(Cc2ccccc2)c2nc(Nc3ccc4c(c3)CS(=O)(=O)C4)ncc21] | | ** | 9-Benzyl-2-(2,2-dioxo-2,3-dihydro-1H-2lambda*6*-benzo[c]thiophen-5-ylamino)-5-methyl-5,7,8,9-tetrahydro-pyrimido[4,5-b][1,4]diazepin-6-one | 1H NMR (DMSO): 2.69 (2H, m, CH2), 3.22 (3H, s, CH3), 3.62 (2H, m, CH2), 4.01 (2H, s, CH2), 4.31 (2H, s, CH2), 4.86 (2H, s, CH2Ph), 7.04 (1H, d, J 8.5 Hz, CH), 7.42-7.27 (6H, m, 6CH), 7.69 (1H, s, CH), 8.13 (1H, s, CH), 9.40 (1H, s, NH); MS(+ve): 450.3; tR = 2.78 min (XBridge 4). |
| 83 | 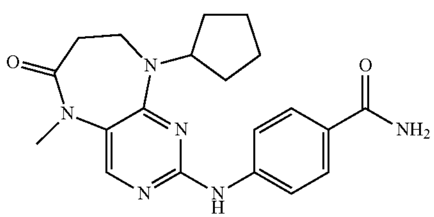 [SMILES: CN1C(=O)CCN(C2CCCC2)c2nc(Nc3ccc(C(N)=O)cc3)ncc21] | | *** | 4-(9-Cyclopentyl-5-methyl-6-oxo-6,7,8,9-tetrahydro-5H-pyrimido[4,5-b][1,4]diazepin-2-ylamino)-benzamide | 1H NMR (DMSO): 1.61 (4H, m, CH), 1.72 (2H, m, CH), 1.93 (2H, m, CH), 2.63 (2H, m, CH2), 3.17 (3H, s, N—CH3), 3.66 (2H, m, CH2), 4.85 (1H, m, CH), 7.18 (1H, bs, NH), 7.72 (2H, d, J 8.5 Hz, Ar—H), 7.83 (2H, d, J 8.5 Hz, Ar—H), 8.06 (1H, s, pyr—H), 9.77 (1H, bs, NH); MS(+ve): 381.3; tR = 2.45 min (xbridge 4). |
| 84 | 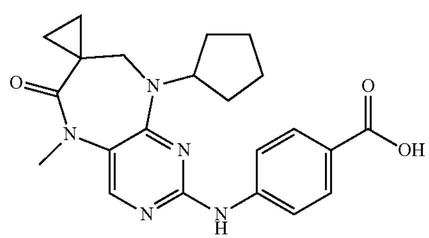 [SMILES: CN1C(=O)C2(CC2)CN(C2CCCC2)c2nc(Nc3ccc(C(=O)O)cc3)ncc21] | | * | 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-benzoic acid | 1H NMR (DMSO): 0.66 (2H, m, cyclopropyl-CH), 0.90 (2H, m, cyclopropyl-CH), 1.50 (2H, m, CH), 1.58 (2H, m, CH), 1.69 (2H, m, CH), 1.91 (2H, m, CH), 3.17 (3H, s, N—CH3), 3.47 (2H, s, CH2), 4.88 (1H, m, CH), 7.81 (4H, m, Ar—H), 7.99 (1H, s, NH), 9.56 (1H, s, pyr—H); MS(+ve); 408.3; tR = 1.81 min (xbridge 4). |

TABLE 2-continued

| Cpd | Structure | AurA IC50 | PLK1 IC50 | Name | Data |
|---|---|---|---|---|---|
| 85 | 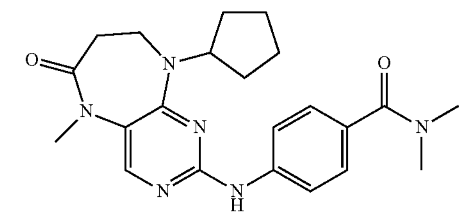 [SMILES: CN(C)C(=O)c1ccc(Nc2ncc3c(n2)N(C2CCCC2)CCC(=O)N3C)cc1] | *** | * | 4-(9-Cyclopentyl-5-methyl-6-oxo-6,7,8,9-tetrahydro-5H-pyrimido[4,5-b][1,4]diazepin-2-ylamino)-N,N-dimethyl-benzamide | 1H NMR (DMSO): 1.59 (4H, m, CH), 1.70 (2H, m, CH), 1.94 (2H, m, CH), 2.58 (2H, m, CH2), 2.96 (6H, s, CH3), 3.16 (3H, s, N—CH3), CH3), 3.62 (2H, m, CH2), 4.81 (1H, m, CH), 7.31 (2H, d, J 8.5 Hz, Ar—H), 7.78 (2H, d, J 8.5 Hz, Ar—H), 8.06 (1H, s, N—H), 9.41 (1H, s, pyr—H); MS(+ve): 409.3; tR = 2.71 min (xbridge 4). |
| 86 | 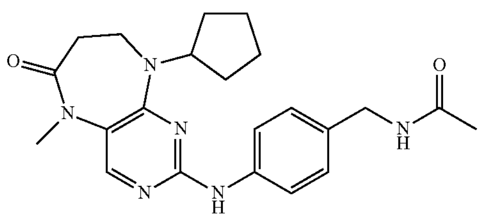 [SMILES: CC(=O)NCc1ccc(Nc2ncc3c(n2)N(C2CCCC2)CCC(=O)N3C)cc1] | *** | * | N-[4-(9-Cyclopentyl-5-methyl-6-oxo-6,7,8,9-tetrahydro-5H-pyrimido[4,5-b][1,4]diazepin-2-ylamino)-benzyl]-acetamide | 1H NMR (CD3OD): 1.62-1.98 (8H, m, alkyl-H), 2.00 (3H, s, CH3), 2.80 (2H, dd, J 5 Hz, CH2), 3.27 (3H, s, CH3), 3.80 (2H, dd, J 5 Hz, CH2), 4.37-4.38 (2H, m, CH2), 4.98-5.02 (1H, m, CH), 7.36 (2H, d, J 8.5 Hz, Ar—H), 7.47 (2H, d, J 8.5 Hz, Ar—H), 7.83 (1H, s, Ar—H), 8.50 (1H, bs, NH); MS(+ve): 409.3; tR = 2.53 (Xbridge 4). |
| 87 | 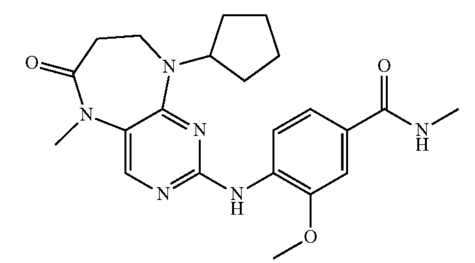 [SMILES: CNC(=O)c1ccc(Nc2ncc3c(n2)N(C2CCCC2)CCC(=O)N3C)c(OC)c1] | * | *** | 4-(9-Cyclopentyl-5-methyl-6-oxo-6,7,8,9-tetrahydro-5H-pyrimido[4,5-b][1,4]diazepin-2-ylamino)-3-methoxy-N-methyl-benzamide | |
| 88 | 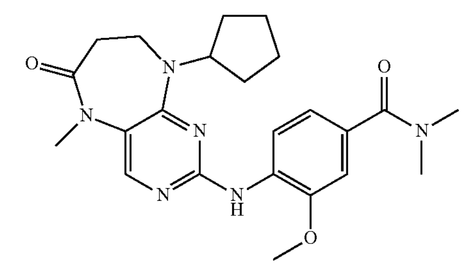 [SMILES: COc1cc(C(=O)N(C)C)ccc1Nc1ncc2c(n1)N(C1CCCC1)CCC(=O)N2C] | * | ** | 4-(9-Cyclopentyl-5-methyl-6-oxo-6,7,8,9-tetrahydro-5H-pyrimido[4,5-b][1,4]diazepin-2-ylamino)-3-methoxy-N,N-dimethyl-benzamide | |

TABLE 2-continued

| Cpd | Structure | AurA IC50 | PLK1 IC50 | Name |
|---|---|---|---|---|
| 89 | 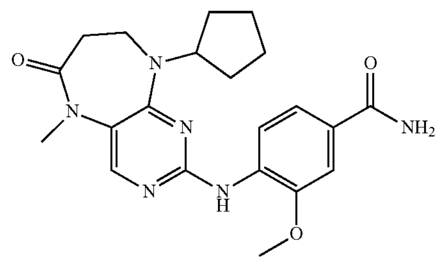 [SMILES: COc1cc(C(N)=O)ccc1Nc1ncc2c(n1)N(C1CCCC1)CCC(=O)N2C] | * | *** | 4-(9-Cyclopentyl-5-methyl-6-oxo-6,7,8,9-tetrahydro-5H-pyrimido[4,5-b][1,4]diazepin-2-ylamino)-3-methoxy-benzamide |
| 90 | 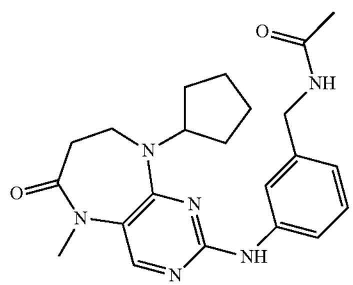 [SMILES: CC(=O)NCc1cccc(Nc2ncc3c(n2)N(C2CCCC2)CCC(=O)N3C)c1] | | ** | N-[3-(9-Cyclopentyl-5-methyl-6-oxo-6,7,8,9-tetrahydro-5H-pyrimido[4,5-b][1,4]diazepin-2-ylamino)-benzyl]-acetamide |
| 91 | 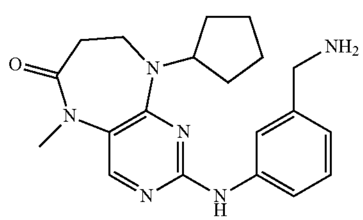 [SMILES: CN1C(=O)CCN(C2CCCC2)c2nc(Nc3cccc(CN)c3)ncc21] | | ** | 2-(3-Aminomethyl-phenylamino)-9-cyclopentyl-5-methyl-5,7,8,9-tetrahydro-pyrimido[4,5-b][1,4]diazepin-6-one |
| 92 | 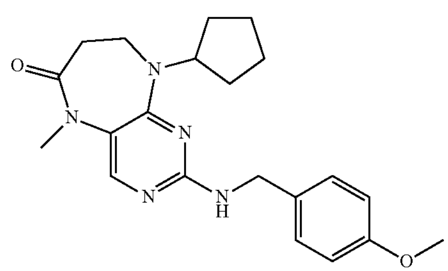 [SMILES: COc1ccc(CNc2ncc3c(n2)N(C2CCCC2)CCC(=O)N3C)cc1] | | * | 9-Cyclopentyl-2-(4-methoxy-benzylamino)-5-methyl-5,7,8,9-tetrahydro-pyrimido[4,5-b][1,4]diazepin-6-one |

TABLE 2-continued

| Cpd | Structure | AurA IC50 | PLK1 IC50 | Name | Data |
|---|---|---|---|---|---|
| 93 | 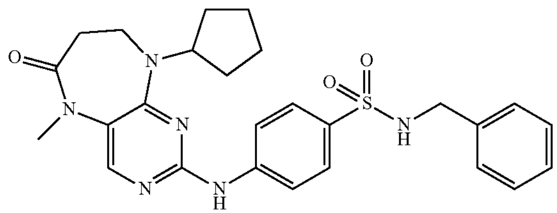 [SMILES: CN1C(=O)CCN(C2CCCC2)c2nc(Nc3ccc(S(=O)(=O)NCc4ccccc4)cc3)ncc21] | | *** | N-Benzyl-4-(9-cyclopentyl-5-methyl-6-oxo-6,7,8,9-tetrahydro-5H-pyrimido[4,5-b][1,4]diazepin-2-ylamino)-benzenesulfonamide | 1H NMR (CD3OD): 1.68-1.81 (8H, m, alkyl-H), 2.69-2.71 (2H, m, CH2), 3.29 (3H, s, CH3), 3.73-3.75 (2H, m, CH2), 4.06 (2H, s, CH2), 7.21-7.27 (5H, m, Ar—H), 7.73 (2H, d, J 9 Hz, Ar—H), 7.84 (2H, d, J 9 Hz, Ar—H), 8.04 (1H, bs, NH); MS(+ve): 507.28; tR = 3.39 (Xbridge 4). |
| 94 | 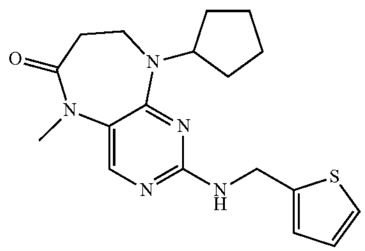 [SMILES: CN1C(=O)CCN(C2CCCC2)c2nc(NCc3cccs3)ncc21] | | * | 9-Cyclopentyl-5-methyl-2-[(thiophen-2-ylmethyl)-amino]-5,7,8,9-tetrahydro-pyrimido[4,5-b][1,4]diazepin-6-one | 1H NMR (CD3OD): 1.61 (4H, m, CH), 1.73 (2H, m, CH), 1.92 (2H, m, CH), 2.63 (2H, m, CH2), 3.23 (3H, s, N—CH3), 3.66 (2H, m, CH2), 4.71 (2H, s, CH2), 6.93 (1H, m, Ar—H), 6.97 (1H, m, Ar—H), 7.23 (1H, m, Ar—H), 7.84 (1H, s, pyr-H); MS(+ve): 358.3; tR = 3.32 min (xbridge 4). |
| 95 | 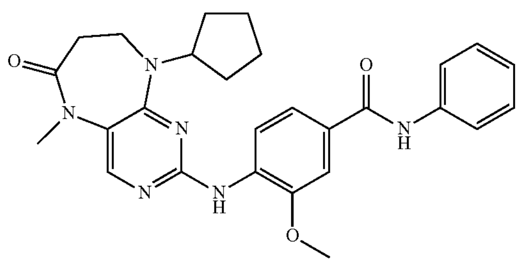 [SMILES: COc1cc(C(=O)Nc2ccccc2)ccc1Nc1ncc2c(n1)N(C1CCCC1)CCC(=O)N2C] | | * | 4-(9-Cyclopentyl-5-methyl-6-oxo-6,7,8,9-tetrahydro-5H-pyrimido[4,5-b][1,4]diazepin-2-ylamino)-3-methoxy-N-phenyl-benzamide | 1H NMR (CD3OD): 1.51-2.00 (8H, m, alkyl-H), 3.28 (3H, s, CH3), 2.69 (2H, dd, J 5.5 Hz, CH2), 3.72 (2H, dd, J 5.5 Hz, CH2), 4.03 (3H, s, CH3), 5.04-5.08 (1H, m, CH) 7.12-7.16 (2H, m, Ar—H), 7.34-7.37 (3H, m, Ar—H), 7.65 (1H, dd, J 2 and 8.5 Hz, Ar—H), 7.70-7.72 (2H, m, Ar—H), 7.80 (1H, s, Ar—H), 8.82 (1H, d, J 2 Hz, Ar—H); MS(+ve): 487.35; tR = 3.46 (Xbridge 4). |
| 96 | 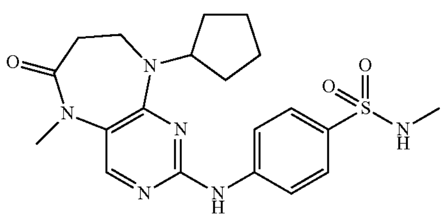 [SMILES: CNS(=O)(=O)c1ccc(Nc2ncc3c(n2)N(C2CCCC2)CCC(=O)N3C)cc1] | | *** | 4-(9-Cyclopentyl-5-methyl-6-oxo-6,7,8,9-tetrahydro-5H-pyrimido[4,5-b][1,4]diazepin-2-ylamino)-N-methyl-benzenesulfonamide | 1H NMR (CD3OD): 1.67-2.01 (8H, m, alkyl-H), 2.55 (3H, s, CH3), 2.80 (2H, dd, J 4.5 Hz, CH2), 3.29 (3H, s, CH3), 5.01-5.04 (1H, m, CH), 7.78-7.81 (2H, m, Ar—H), 7.84-7.86 (2H, m, Ar—H), 7.96-8.00 (2H, m, Ar—H and NH); MS(+ve): 431.32; tR = 2.81 (Xbridge 4) |

TABLE 2-continued

| Cpd | Structure | AurA IC50 | PLK1 IC50 | Name | Data |
|---|---|---|---|---|---|
| 97 | 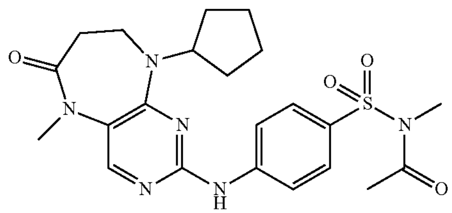 [SMILES: CC(=O)N(C)S(=O)(=O)c1ccc(Nc2ncc3c(n2)N(C2CCCC2)CCC(=O)N3C)cc1] | | *** | N-Acetyl-4-(9-cyclopentyl-5-methyl-6-oxo-6,7,8,9-tetrahydro-5H-pyrimido[4,5-b][1,4]diazepin-2-ylamino)-N-methyl-benzenesulfonamide | 1H NMR (CD3OD): 1.68-2.04 (8H, m, alkyl-H), 2.34 (3H, s, CH3), 2.76 (2H, dd, J 5 Hz, CH2), 3.29 (3H, s, CH3), 3.31 (3H, s, CH3), 3.79 (2H, dd, J 5 Hz, CH2), 4.94-5.00 (1H, m, CH), 7.86 (2H, d, J 9 Hz, Ar—H), 7.91 (2H, d, J 9 Hz, Ar—H), 8.01 (1H, s, Ar—H); MS(+ve): 473.35; tR = 3.15 (Xbridge 4). |
| 98 | 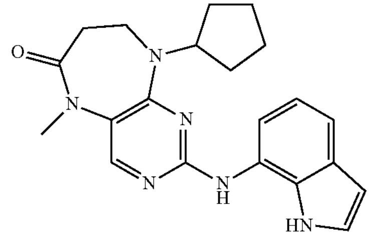 [SMILES: CN1C(=O)CCN(C2CCCC2)c2nc(Nc3cccc4cc[nH]c34)ncc21] | | ** | 9-Cyclopentyl-2-(1H-indol-7-ylamino)-5-methyl-5,7,8,9-tetrahydro-pyrimido[4,5-b][1,4]diazepin-6-one | 1H NMR (DMSO): 1.50-1.86 (8H, m, alkyl-H), 2.77 (2H, dd, J 4.5 Hz, CH2), 3.23 (3H, s, CH3), 3.74 (2H, dd, J 4.5 Hz, CH2), 4.87-4.91 (1H, m, CH), 6.63 (1H, s, Ar—H), 7.16 (1H, t, J 8 Hz, Ar—H), 7.33 (1H, d, J 8 Hz, Ar—H), 7.42-7.47 (3H, m, Ar—H), 8.03-8.04 (1H, m, Ar—H), 9.94 (1H, bs, NH), 11.31 (1H, bs, NH); MS(+ve): 377.28; tR = 3.13 (Xbridge 4) |
| 99 | 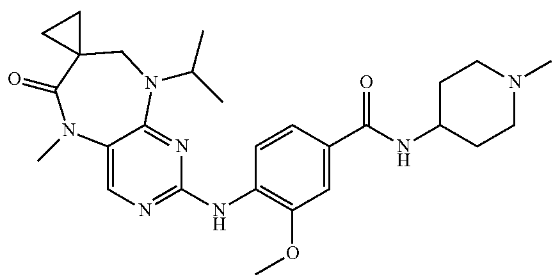 [SMILES: COc1cc(C(=O)NC2CCN(C)CC2)ccc1Nc1ncc2c(n1)N(C(C)C)CC1(CC1)C(=O)N2C] | | ** | 4-(9-Isopropyl-5-methyl-6-oxo-6,7,8,9-tetrahydro-5H-spiro[pyrimido[4,5-b][1,4]diazepin-3,1'-cyclopropane]-2-ylamino)-3-methoxy-N-(1-methyl-piperidin-4-yl)-benzamide | 1H NMR (DMSO): 0.68 (2H, m, cyclopropyl CH), 0.92 (2H, m, cyclopropyl CH), 1.17 (6H, d, J 6.5 Hz, CH3), 1.57 (2H, ddd, J 3.5 Hz, 12 Hz, 15 Hz, CH), 1.77 (2H, d, J 10 Hz, CH), 1.95 (2H, dd, J 10 Hz, 10 Hz, CH), 2.16 (3H, s, NCH3), 2.79 (2H, d, J 11.5 Hz, CH), 3.18 (3H, s, NCH3), 3.46 (2H, s, CH2), 3.77 (1H, m, CH), 3.46 (3H, s, OCH3), 4.84 (1H, m, CH), 7.48 (1H, s, Ar—H), 7.51 (1H, d, J 8.5 Hz, Ar—H), 7.97 (1H, s, Pyr-H), 8.08 (1H, d, J 8 Hz, Ar—H), 8.41 (1H, d, J 8.5 Hz, Ar—H); MS(+ve); 508.4; tR = 2.74 min (xbridge 4). |
| 100 | 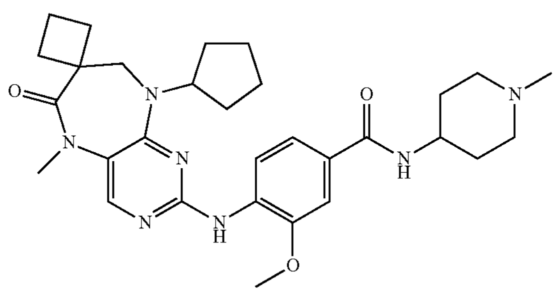 | | *** | 4-(9-Cyclopentyl-5-methyl-6-oxo-6,7,8,9-tetrahydro-5H-spiro[pyrimido[4,5-b][1,4]diazepin-3,1'-cyclobutane]-2-ylamino)-3-methoxy-N-(1-methyl-piperidin-4-yl)-benzamide | 1H NMR (DMSO): 1.60 (8H, m, CH + CH2), 1.75 (4H, m, 1.87-1.99 (6H, m, CH + CH2), 2.16 (3H, s, NCH3), 2.29 (2H, m, CH), 2.79 (2H,d, J 11 Hz, CH), 3.18 (3H, s, NCH3), 3.64 (2H, s, CH2), 3.73 (1H, m, CH), 3.94 (3H, s, OCH3), 4.82 (1H, m, CH), 7.48 (2H, m, Ar—H), 7.71 (1H, s, NH), 8.05 (1H, s, pyrH), 8.09 (1H, d, J 8 Hz, Ar—H), 8.36 (1H, d, J 8 Hz, Ar—H); MS(+ve); 548.4; tR = 3.20 min (xbridge 4). |

TABLE 2-continued

| Cpd | Structure | AurA IC50 | PLK1 IC50 | Name | Data |
|---|---|---|---|---|---|
| 101 | 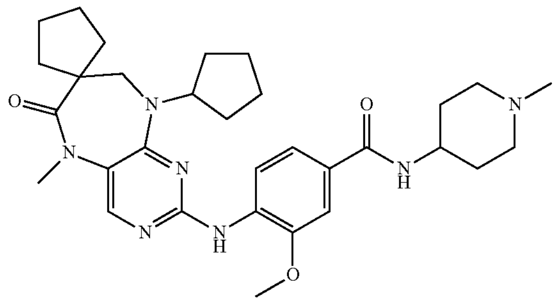 [SMILES: COc1cc(C(=O)NC2CCN(C)CC2)ccc1Nc1ncc2c(n1)N(C1CCCC1)CC1(CCCC1)C(=O)N2C] | ** | | 4-(9-Cyclopentyl-5-methyl-6-oxo-6,7,8,9-tetrahydro-5H-spiro[pyrimido[4,5-b][1,4]diazepine-3,1'-cyclopentane]-2-ylamino)-3-methoxy-N-(1-methyl-piperidin-4-yl)-benzamide | 1H NMR (DMSO): 1.30 (2H, m, CH2), 1.51-1.63 (10 H, m, 4 × CH2), 1.88 (4H, m, 2 × CH2), 1.91-2.17 (6H, m, 3 × Ch2), 2.17 (3H, s, NCH3), 2.89 (2H, d, J 8.5 Hz CH), 3.19 (3H, s, NCH3), 3.41 (2H, s, CH2), 3.71 (1H, m, CH), 3.94 (3H, s, OCH3), 5.02 (1H, m, CH), 7.48 (2H, m, Ar—H), 7.69 (1H, s, Ar—H), 8.01 (1H, s, Ar—H), 8.09 (1H, d, J 7.5 Hz Ar—H), 8.38 (1H, d, J 8.5 Hz, Ar—H); MS(+ve); 562.5; tR = 3.45 min (xbridge 4). |
| 102 | 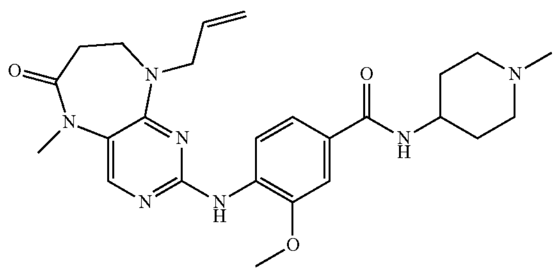 [SMILES: C=CCN1CCC(=O)N(C)c2cnc(Nc3ccc(C(=O)NC4CCN(C)CC4)cc3OC)nc21] | ** | | 4-(9-Allyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide | 1H NMR (CD3OD): 1.72 (2H, m, CH2), 1.96 (2H, m, CH2), 2.23 (2H, dd, J 10.5 Hz, 10.5 Hz, CH), 2.33 (3H, s, NCH3), 2.73 (2H, m, CH2), 2.94 (2H, d, J 12 Hz, CH2), 3.76 (2H, m, CH2), 3.91 (1H, m, CH), 4.01 (3H, s, OCH3), 4.30 (2H, d, J 5.5 Hz, CH2), 5.30 (2H, m, =CH2), 6.06 (1H, m, =CH), 7.46 (1H, dd, J 8.5 Hz, 2 Hz, ArH), 7.50 (1H, d, J 2 Hz, ArH), 8.06 (1H, s, pyrH), 8.49 (1H, d, J 8.5 Hz, ArH); MS(+ve); 480.3; tR = 2.49 min (xbridge 4). |
| 103 | 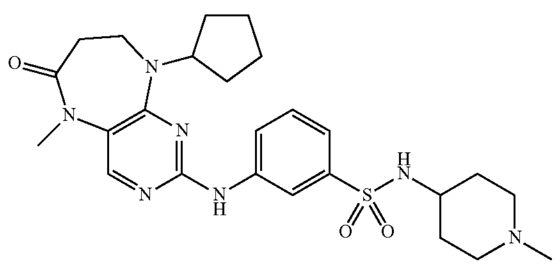 [SMILES: CN1CCC(NS(=O)(=O)c2cccc(Nc3ncc4c(n3)N(C3CCCC3)CCC(=O)N4C)c2)CC1] | ** | * | 3-(9-Cyclopentyl-5-methyl-6-oxo-6,7,8,9-tetrahydro-5H-pyrimido[4,5-b][1,4]diazepin-2-ylamino)-N-(1-methyl-piperidin-4-yl)-benzenesulfonamide | |

TABLE 2-continued

| Cpd | Structure | AurA IC50 | PLK1 IC50 | Name | Data |
|---|---|---|---|---|---|
| 104 | 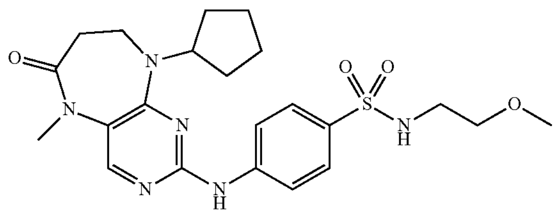 [SMILES: COCCNS(=O)(=O)c1ccc(Nc2ncc3c(n2)N(C2CCCC2)CCC(=O)N3C)cc1] | | *** | 4-(9-Cyclopentyl-5-methyl-6-oxo-6,7,8,9-tetrahydro-5H-pyrimido[4,5-b][1,4]diazepin-2-ylamino)-N-(2-methoxyethyl)-benzenesulfonamide | 1H NMR (CD$_3$OD): 1.67-1.99 (8H, m, alkyl-H), 2.80 (2H, dd, J 7.5 Hz, CH2), 3.04-3.06 (2H, m, CH2), 3.26 (3H, s, CH3), 3.38-3.41 (2H, m, CH2), 3.82 (2H, dd, J 4.5 Hz, CH2), 5.01-5.04 (1 H, m, CH), 7.76-7.79 (2H, m, Ar—H), 7.85-7.87 (2H, m, Ar—H), 7.96 (1H, s, Ar—H); MS(+ve): 475.33; tR = 2.87 (Xbridge 4). |
| 105 | 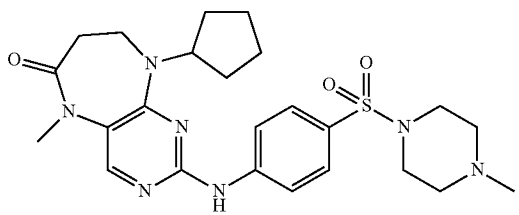 [SMILES: CN1CCN(S(=O)(=O)c2ccc(Nc3ncc4c(n3)N(C3CCCC3)CCC(=O)N4C)cc2)CC1] | | ** | 9-Cyclopentyl-5-methyl-2-[4-(4-methyl-piperazine-1-sulfonyl)-phenylamino]-5,7,8,9-tetrahydro-pyrimido[4,5-b][1,4]diazepin-6-one | MS(+ve): 500.33; tR = 2.97 (Xbridge 4). |
| 106 | 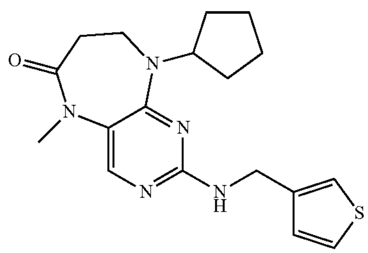 [SMILES: CN1C(=O)CCN(C2CCCC2)c2nc(NCc3ccsc3)ncc21] | | ** | 9-Cyclopentyl-5-methyl-2-[(thiophen-3-ylmethyl)-amino]-5,7,8,9-tetrahydro-pyrimido[4,5-b][1,4]diazepin-6-one | |
| 107 | 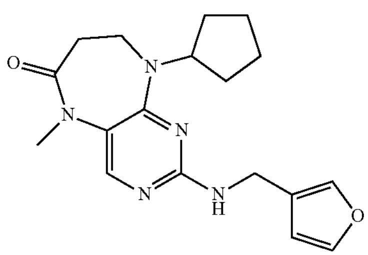 [SMILES: CN1C(=O)CCN(C2CCCC2)c2nc(NCc3ccoc3)ncc21] | | * | 9-Cyclopentyl-2-[(furan-3-ylmethyl)-amino]-5-methyl-5,7,8,9-tetrahydro-pyrimido[4,5-b][1,4]diazepin-6-one | |

TABLE 2-continued

| Cpd | Structure | AurA IC50 | PLK1 IC50 | Name | Data |
|---|---|---|---|---|---|
| 108 | 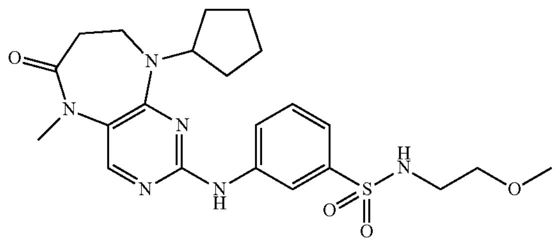 [SMILES: COCCNS(=O)(=O)c1cccc(Nc2ncc3c(n2)N(C2CCCC2)CCC(=O)N3C)c1] | ** | * | 3-(9-Cyclopentyl-5-methyl-6-oxo-6,7,8,9-tetrahydro-5H-pyrimido[4,5-b][1,4]diazepin-2-ylamino)-N-(2-methoxyethyl)-benzenesulfonamide | |
| 109 | 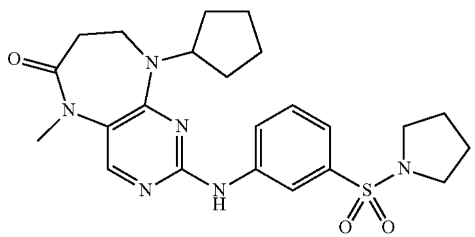 [SMILES: CN1C(=O)CCN(C2CCCC2)c2nc(Nc3cccc(S(=O)(=O)N4CCCC4)c3)ncc21] |  |  | 9-Cyclopentyl-5-methyl-2-[3-(pyrrolidine-1-sulfonyl)-phenylamino]-5,7,8,9-tetrahydro-pyrimido[4,5-b][1,4]diazepin-6-one | |
| 110 | 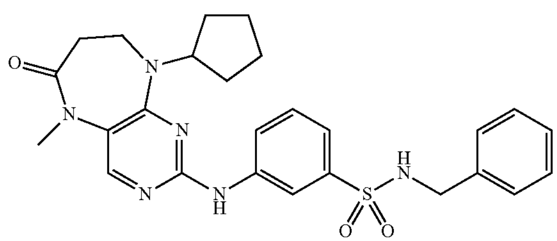 [SMILES: CN1C(=O)CCN(C2CCCC2)c2nc(Nc3cccc(S(=O)(=O)NCc4ccccc4)c3)ncc21] | ** | * | N-Benzyl-3-(9-cyclopentyl-5-methyl-6-oxo-6,7,8,9-tetrahydro-5H-pyrimido[4,5-b][1,4]diazepin-2-ylamino)-benzenesulfonamide | |
| 111 | 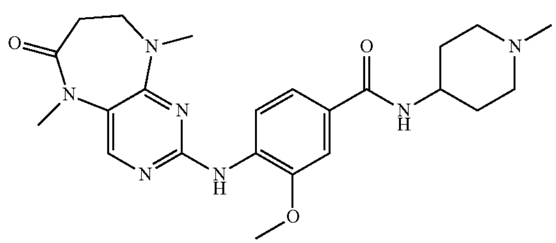 [SMILES: COc1cc(C(=O)NC2CCN(C)CC2)ccc1Nc1ncc2c(n1)N(C)CCC(=O)N2C] |  |  | 4-(5,9-Dimethyl-6-oxo-6,7,8,9-tetrahydro-5H-pyrimido[4,5-b][1,4]diazepin-2-ylamino)-3-methoxy-N-(1-methyl-piperidin-4-yl)-benzamide | 1H NMR (DMSO): 1.63 (2H, m, CH), 1.79 (2H, m, CH), 2.26 (2H, m, CH), 2.60 (2H, m, CH2), 2.89 (2H, m, CH), 3.06 (3H, s, NCH3), 3.17 (3H, s, NCH3), 3.29 (3H, s, NCH3), 3.68 (2H, m, CH2), 3.78 (1H, m, CH), 3.94 (3H, s, OCH3), 7.47 (1H, s, ArH), 7.53 (1H, d, J 9 Hz, ArH), 8.10 (2H, m, ArH), 8.46 (1H, d, J 8.5 Hz, ArH); MS(+ve); 454.4; tR = 2.33 min (xbridge 4). |

TABLE 2-continued

| Cpd | Structure | AurA IC50 | PLK1 IC50 | Name | Data |
|---|---|---|---|---|---|
| 112 | 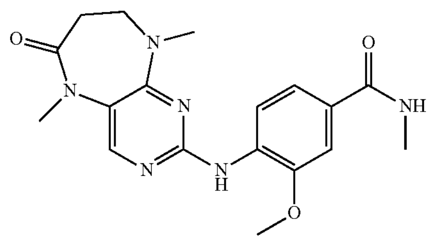 [SMILES: CNC(=O)c1ccc(Nc2ncc3c(n2)N(C)CCC(=O)N3C)c(OC)c1] | | * | 4-(5,9-Dimethyl-6-oxo-6,7,8,9-tetrahydro-5H-pyrimido[4,5-b][1,4]diazepin-2-ylamino)-3-methoxy-N-methyl-benzamide | 1H NMR (DMSO): 2.60 2H, m, CH2), 2.78 (3H, m, NCH3), 3.06 (3H, s, NCH3) 3.17 (3H, s, NCH3), 3.68 (2H, m, CH2), 3.93 (3H, s, OCH3), 7.49 (2H, m, ArH), 7.73 (1H, m, ArH), 8.10 (1H, d, J 2.5 Hz, ArH), 8.29 (1H, bs, NH), 8.45 (1H, dd, J 9 Hz, 2.5 Hz, ArH); MS(+ve); 371.3; tR = 2.29 min (xbridge 4). |
| 113 | 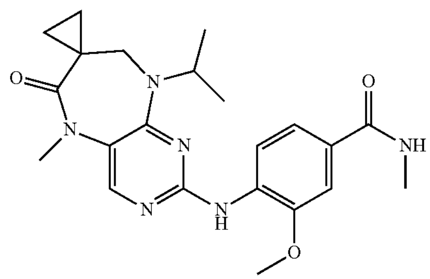 [SMILES: CNC(=O)c1ccc(Nc2ncc3c(n2)N(C(C)C)CC2(CC2)C(=O)N3C)c(OC)c1] | | ** | 4-(9-isopropyl-5-methyl-6-oxo-6,7,8,9-tetrahydro-5H-spiro[pyrimido[4,5-b][1,4]diazepin-3,1'-cyclopropane]-2-ylamino)-3-methoxy-N-methyl-benzamide | 1H NMR (DMSO): 0.67 (2H, m, cyclopropyl H), 0.92 (2H, m, cyclopropyl H), 1.17 (6H, d, J 6.5 Hz), 2.78 (3H, d, J 5 Hz, NCH3), 3.16 (3H, s, NCH3), 3.46 (2H, s, CH2), 3.93 (3H, s, OCH3), 4.83 (1H, m, CH), 7.47 (2H, m, ArH), 7.63 (1H, s, NH), 7.97 (1H, s, pyrH), 8.29 (1 H, d, J4.5 Hz, NH), 8.42 (1H, d, J 8.5 Hz, ArH); MS(+ve); 425.3; tR = 2.70 min (xbridge 4). |
| 114 | 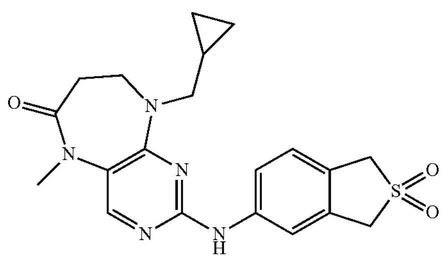 [SMILES: CN1C(=O)CCN(CC2CC2)c2nc(Nc3ccc4c(c3)CS(=O)(=O)C4)ncc21] | | *** | 9-Cyclopropylmethyl-2-(2,2-dioxo-2,3-dihydro-1H-2lambda*6*-benzo[c]thiophen-5-ylamino)-5-methyl-5,7,8,9-tetrahydro-pyrimido[4,5-b][1,4]diazepin-6-one | MS(+ve): 414.2; tR = 2.64 min (XBridge 4). |
| 115 | 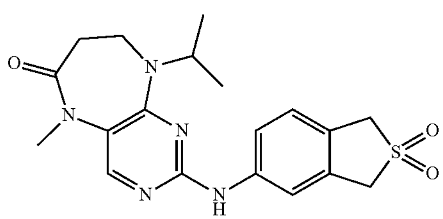 [SMILES: CC(C)N1CCC(=O)N(C)c2cnc(Nc3ccc4c(c3)CS(=O)(=O)C4)nc21] | | *** | 2-(2,2-Dioxo-2,3-dihydro-1H-2lambda*6*-benzo[c]thiophen-5-ylamino)-9-isopropyl-5-methyl-5,7,8,9-tetrahydro-pyrimido[4,5-b][1,4]diazepin-6-one | 1H NMR (DMSO): 1.21 (6H, d, J 7 Hz, 2CH3), 2.58 (2H, t, J 5 Hz, CH2), 3.16 (3H, s, CH3), 3.59 (2H, t, J 5 Hz, CH2), 4.39 (2H, s, CH2), 4.46 (2H, s, CH2), 4.8 (1H, m, CH(CH3)2), 7.24 (1H, d, J 8.5 Hz, CH), 7.59 (1H, dd, J 8.5, 2 Hz, CH), 7.87 (1H, s, CH), 8.03 (1H, s, CH), 9.39 (1H, s, NH); MS(+ve): 402.3; tR = 2.58 min (XBridge 4). |

TABLE 2-continued

| Cpd | Structure | AurA IC50 | PLK1 IC50 | Name | Data |
|---|---|---|---|---|---|
| 116 | (structure) | | ** | 2-(2,2-Dioxo-2,3-dihydro-1H-2lambda*6*-benzo[c]thiophen-5-ylamino)-5-methyl-9-(3-methyl-butyl)-5,7,8,9-tetrahydro-pyrimido[4,5-b][1,4]diazepin-6-one | 1H NMR (DMSO): 0.90 (3H, s, CH3), 0.91 (3H, s, CH3), 1.51 (2H, m, CH2), 1.60 (1H, m, CH(CH3)2), 2.60 (2H, t, J 5.0 Hz, C(O)CH2), 3.15 (3H, s, CH3N), 3.59 (2H, t, J 7.5 Hz, CH2N), 3.67 (2H, t, J 5.0 Hz, CH2N), 4.39 (2H, s, CH2), 4.43 (2H, s, CH2), 7.22 (1H, d, J 8 Hz, CH), 7.69 (1 H, s, CH), 7.74 (1H, d, J 8 Hz, CH), 8.04 (1 H, s, CH), 9.37 (1H, s, NH); MS(+ve): 430.3; tR = 3.01 min (XBridge 4). |
| 117 | (structure) | | ** | (9-Cyclopentyl-2-(2,2-dioxo-2,3-dihydro-1H-2lambda*6*-benzo[c]thiophen-5-ylamino)5-methyl-6-oxo-6,7,8,9-tetrahydro-5H-spiro[pyrimido[4,5-b][1,4]diazepin-3,1'-cyclobutane] | 1H NMR (DMSO): 1.5-2.0 (12H, m, 6CH2), 2.27 (2H, m, CH2), 3.18 (3H, s, CH3), 3.62 (2H, s, CH2N), 4.40 (2H, s, CH2), 4.43 (2H, s, CH2), 4.82 (1H, m, CHN), 7.24 (1H, d, J 8 Hz, CH), 7.62 (1 H, d, J 8 Hz, CH), 7.83 (1H, s, CH), 8.04 (1H, s, CH), 9.35 (1H, s, NH); MS(+ve): 468.3; tR = 3.32 min (XBridge 4). |
| 118 | (structure) | | ** | (9-Cyclopentyl-2-(2,2-dioxo-2,3-dihydro-1H-2lambda*6*-benzo[c]thiophen-5-ylamino)5-methyl-6-oxo-6,7,8,9-tetrahydro-5H-spiro[pyrimido[4,5-b][1,4]diazepin-3,1'-cyclopentane] | 1H NMR (DMSO): 1.33 (2H, m, CH2), 1.45-1.65 (8H, m, 4CH2), 1.71 (2H, m, CH2), 1.89 (2H, m, CH2), 2.01 (2H, m, CH2), 3.18 (3H, s, CH3), 3.40 (2H, m, CH2), 4.39 (2H, s, CH2), 4.43 (2H, s, CH2), 5.02 (1H, m, CHN), 7.24 (1 H, d, J 8.5 Hz, CH), 7.61 (1H, d, J 8.5 Hz, CH), 7.82 (1H, s, CH), 7.98 (1H, s, CH), 9.37 (1H, s, NH); MS(+ve): 482.3; tR = 3.57 min (XBridge 2). |
| 119 | (structure) | | *** | 9-Allyl-2-(2,2-dioxo-2,3-dihydro-1H-2lambda*6*-benzo[c]thiophen-5-ylamino)-5-methyl-5,7,8,9-tetrahydro-pyrimido[4,5-b][1,4]diazepin-6-one | 1H NMR (DMSO): 2.64 (2H, m, CH2), 3.18 (3H, s, CH3), 3.63 (2H, m, CH2), 4.17 (2H, m, CH2), 4.39 (2H, s, CH2), 4.42 (2H, s, CH2), 5.22 (2H, m, CH=CH2), 5.97 (1H, m, CH=CH2), 7.22 (1 H, d, J 8.5 Hz, CH), 7.59 (1H, dd, J 8.5, 2 Hz, CH), 7.85 (1H, s, CH), 8.08 (1H, s, CH), 9.43 (1H, s, NH); MS(+ve): 400.3; tR = 2.60 min (XBridge 4). |

TABLE 2-continued

| Cpd | Structure | AurA IC50 | PLK1 IC50 | Name | Data |
|---|---|---|---|---|---|
| 120 | 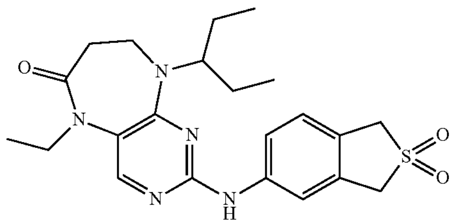 [SMILES: CCC(CC)N1CCC(=O)N(CC)c2cnc(Nc3ccc4c(c3)CS(=O)(=O)C4)nc21] | | *** | 2-(2,2-Dioxo-2,3-dihydro-1H-2lambda*6*-benzo[c]thiophen-5-ylamino)-5-ethyl-9-(1-ethyl-propyl)-5,7,8,9-tetrahydro-pyrimido[4,5-b][1,4]diazepin-6-one | 1H NMR (DMSO): 0.83 (6H, t, J 7.5 Hz, 2CH3), 0.93 (3H, t, J 7 Hz, CH2CH3), 1.59 (4H, m, 2CH2), 2.57 (2H, m, CH2), 3.45 (2H, m, CH2), 3.74 (2H, q, J 7.0 Hz, CH2CH3), 4.4 (2H, m, CH2), 4.45 (2H, s, CH2), 4.58 (1H, m, CHN), 7.25 (1H, d, J 8 Hz, CH), 7.69 (1H, d, J 8 Hz, CH), 7.73 (1 H, s, CH), 8.08 (1H, s, CH), 9.38 (1H, s, NH); MS(+ve): 442.3; tR = 3.08 min (XBridge 4). |
| 121 | 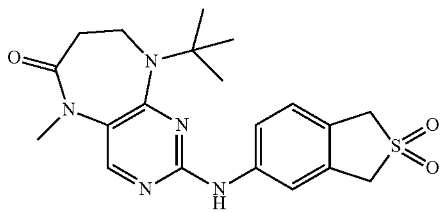 [SMILES: CN1C(=O)CCN(C(C)(C)C)c2nc(Nc3ccc4c(c3)CS(=O)(=O)C4)ncc21] | | ** | 9-tert-Butyl-2-(2,2-dioxo-2,3-dihydro-1H-2lambda*6*-benzo[c]thiophen-5-ylamino)-5-methyl-5,7,8,9-tetrahydro-pyrimido[4,5-b][1,4]diazepin-6-one | 1H NMR (DMSO): 2.60 (2H, m, CH2), 3.19 (3H, s, CH3), 3.54 (2H, m, CH2), 4.38 (2H, s, CH2), 4.43 (2H, s, CH2), 7.21 (1H, d, J 8.5 Hz, CH), 7.45 (1H, s, NH), 7.68 (1H, dd, J 8.5, 2 Hz, CH), 7.89 (1H, s, CH), 8.06 (1H, s, CH), 9.3 (1H, s, NH); MS(+ve): 360.2; tR = 2.18 min (XBridge 4). |
| 122 | 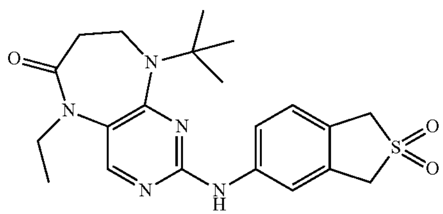 [SMILES: CCN1C(=O)CCN(C(C)(C)C)c2nc(Nc3ccc4c(c3)CS(=O)(=O)C4)ncc21] | | ** | 9-tert-Butyl-2-(2,2-dioxo-2,3-dihydro-1H-2lambda*6*-benzo[c]thiophen-5-ylamino)-5-ethyl-5,7,8,9-tetrahydro-pyrimido[4,5-b][1,4]diazepin-6-one | 1H NMR (DMSO): 0.91 (3H, t, J 7.0 Hz, CH2CH3), 1.41 (9H, s, C(CH3)3), 2.39 (2H, t, J 6 Hz, CH2), 3.60 (2H, t, J 6 Hz, CH2), 3.67 (2H, q, J 7.0 Hz, CH2), 4.4 (2H, s, CH2), 4.45 (2H, s, CH2), 7.26 (1 H, d, J 8 Hz, CH), 7.62 (1H, d, J 8 Hz, CH), 7.83 (1 H, s, CH), 8.22 (1H, s, CH), 9.41 (1H, s, NH); MS(+ve): 430.3; tR = 2.94 min (XBridge 4). |
| 123 | 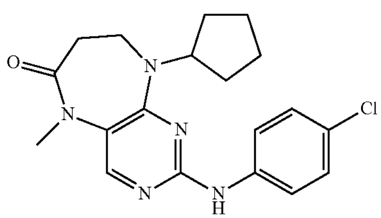 [SMILES: CN1C(=O)CCN(C2CCCC2)c2nc(Nc3ccc(Cl)cc3)ncc21] | | ** | 2-(4-Chloro-phenylamino)-9-cyclopentyl-5-methyl-5,7,8,9-tetrahydro-pyrimido[4,5-b][1,4]diazepin-6-one | 1H NMR (DMSO): 1.61 (4H, m, 2CH2), 1.68 (2H, m, CH2), 1.92 (2H, m, CH2), 2.57 (2H, t, J 5 Hz, CH2), 3.16 (3H, s, CH3), 3.60 (2H, t, J 5 Hz, CH2), 4.78 (1H, m, CHN), 7.28 (2H, d, J 9 Hz, 2CH), 7.74 (2H, d, J 9 Hz, 2CH), 8.04 (1H, s, CH), 9.35 (1 H, s, NH); MS(+ve): 372.3; tR = 3.93 min (XBridge 4). |

TABLE 2-continued

| Cpd | Structure | AurA IC50 | PLK1 IC50 | Name | Data |
|---|---|---|---|---|---|
| 124 | 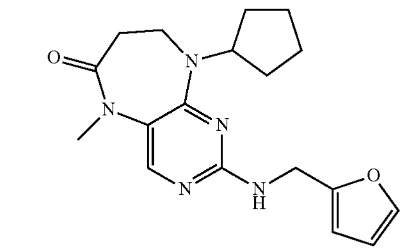 | | * | 9-Cyclopentyl-2-[(furan-2-ylmethyl)-amino]-5-methyl-5,7,8,9-tetrahydro-pyrimido[4,5-b][1,4]diazepin-6-one | |
| 125 | 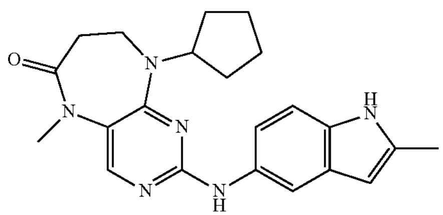 [SMILES: Cc1cc2cc(Nc3ncc4c(n3)N(C3CCCC3)CCC(=O)N4C)ccc2[nH]1] | ** | | 9-Cyclopentyl-5-methyl-2-(2-methyl-1H-indol-5-ylamino)-5,7,8,9-tetrahydro-pyrimido[4,5-b][1,4]diazepin-6-one | 1H NMR (CD3OD): 2.38-2.80 (8H, m, alkyl-H), 3.15 (3H, s, CH3), 3.36 (2H, dd, J 5 Hz, CH2), 3.96 (3H, s, CH3), 4.39 (2H, dd, J 5 Hz, CH2), 5.60-5.64 (1H, m, CH), 6.78 (1H, s, Ar—H), 7.91-7.98 (2H, m, Ar—H), 8.68 (1H, s, Ar—H), 8.80 (1H, s, Ar—H), 9.65 (1H, s, Ar—H), 11.47 (1H, bs, NH); 391.35; tR = 3.21 (Xbridge 4). |
| 126 | 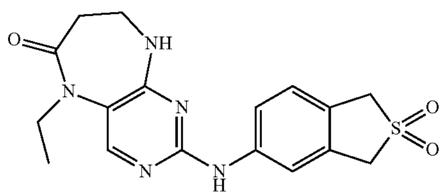 [SMILES: CCN1C(=O)CCNc2nc(Nc3ccc4c(c3)CS(=O)(=O)C4)ncc21] | * | | 2-(2,2-Dioxo-2,3-dihydro-1H-2lambda*6*-benzo[c]thiophen-5-ylamino)-5-ethyl-5,7,8,9-tetrahydro-pyrimido[4,5-b][1,4]diazepin-6-one | 1H NMR (DMSO): 1.02 (3H, t, J 7 Hz, CH2CH3), 2.55 (2H, m, CH2), 3.53 (2H, m, CH2), 3.74 (2H, q, J 7 Hz, CH2CH3), 4.4 (2H, s, CH2), 4.43 (2H, s, CH2), 7.22 (1 H, d, J 8.5 Hz, CH), 7.42 (1 H, s, NH), 7.68 (1H, dd, J 8.5, 1.5 Hz, CH), 7.89 (1H, s, CH), 8.10 (1H, s, CH), 9.35 (1H, s, NH); MS(+ve): 374.2; tR = 2.2min (XBridge4). |
| 127 | 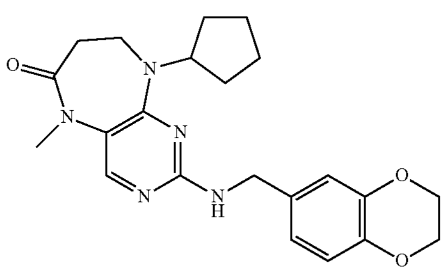 [SMILES: CN1C(=O)CCN(C2CCCC2)c2nc(NCc3ccc4c(c3)OCCO4)ncc21] | * | | 9-Cyclopentyl-2-[(2,3-dihydro-benzo[1,4]dioxin-6-ylmethyl)-amino]-5-methyl-5,7,8,9-tetrahydro-pyrimido[4,5-b][1,4]diazepin-6-one | 1H NMR (DMSO): 1.50-1.78 (8H, m, alkyl-H), 2.48 (2H, dd, J 5.5 Hz, CH2), 3.09 (3H, s, CH3), 3.50 (2H, dd, J 5.5 Hz, CH2), 4.17-4.19 (4H, m, 2 × CH2), 4.27 (2H, d, J 6 Hz, CH2NH), 4.57 (1H, bs, CH), 6.75-6.78 (3H, m, Ar—H), 7.22 (1H, bs, NH), 7.89 (1H, s, Ar-H); MS(+ve): 410.35; tR = 3.22 (Xbridge 4). |

TABLE 2-continued

| Cpd | AurA IC50 | PLK1 IC50 | Name | Data |
|---|---|---|---|---|
| 128 | * | ** | 9-Cyclopentyl-2-[(2,3-dihydro-benzo[1,4]dioxin-5-ylmethyl)-amino]-5-methyl-5,7,8,9-tetrahydro-pyrimido[4,5-b][1,4]diazepin-6-one | 1H NMR (DMSO): 1.46-1.99 (8H, m, alkyl-H), 2.61 (2H, dd, J 5.5 Hz, CH2), 3.23 (3H, s, CH3), 3.63 (2H, dd, J 5.5 Hz, CH2), 4.24-4.27 (2H, m, CH2), 4.29-4.32 (2H, m, CH2), 4.50 (2H, s, CH2), 4.66-4.69 (1H, m, CH), 6.71-6.72 (m, 2H, Ar—H), 6.77-6.79 (1H, m, Ar—H), 7.83 (1H, s, AR—H); MS(+ve): 410.35; tR = 3.34 (Xbridge 4). |
| 129 | * |  | 2-[(Benzo[b]thiophen-2-ylmethyl)-amino]-9-cyclopentyl-5-methyl-5,7,8,9-tetrahydro-pyrimido[4,5-b][1,4]diazepin-6-one | 1H NMR (DMSO): 1.17-1.60 (8H, m, alkyl-H), 2.48 (2H, dd, J 4.5 Hz, 2H, CH2), 3.10 (3H, s, CH3), 3.49 (2H, dd, J 4.5 Hz, CH2), 4.65 (2H, d, J 6 Hz, CH2NH), 7.35-7.42 (4H, m, Ar—H), 7.89 (1H, s, Ar—H), 7.95-7.97 (1H, m, Ar—H); MS(+ve): 408.30; tR = 3.78 (Xbridge 4). |
| 130 | ** | * | 9-Cyclopentyl-2-(1H-indol-6-ylamino)-5-methyl-5,7,8,9-tetrahydro-pyrimido[4,5-b][1,4]diazepin-6-one | 1H NMR (CD3OD): 1.60-1.80 (8H, m, alkyl-H), 2.02 (3H, s, CH3), 2.65 (2H, dd, J 5.5 Hz, CH2), 3.68 (2H, dd, J 5.5 Hz, CH2), 6.37 (1H, d, J 2.5 Hz, Ar—H), 6.88 (1H, s, Ar—H), 7.12-7.18 (1H, m, Ar—H), 7.21 (1H, d, J 3 Hz, Ar—H), 7.84 (1H, d, J 1.5 Hz, Ar—H), 7.90 (1H, s, Ar—H); MS(+ve): 377.32; tR = 3.02 (Xbridge 4). |

TABLE 2-continued

| Cpd | Structure | AurA IC50 | PLK1 IC50 | Name | Data |
|---|---|---|---|---|---|
| 131 | 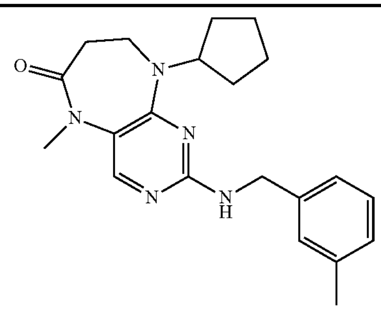 | | * | 9-Cyclopentyl-5-methyl-2-(3-methyl-benzylamino)-5,7,8,9-tetrahydro-pyrimido[4,5-b][1,4]diazepin-6-one | 1H NMR (DMSO): 1.48-1.77 (8H, m, alkyl-H), 2.27 (3H, s, CH3), 2.47 (2H, dd, J 4.5 Hz, CH2), 3.09 (3H, s, CH3), 3.50 (2H, dd, J 4.5 Hz, CH2), 4.36 (2H, d, J 6 Hz, CH2), 4.56 (1H, bs, CH), 7.00 (1H, d, J 7.5 Hz, Ar—H), 7.08-7.11 (2H, m, Ar—H), 7.16 (1H, t, J 7.5 Hz, Ar—H), 7.27 (1H, bs, NH), 7.86 (1H, s, Ar—H); MS(+ve): 366.29; tR = 3.65 (Xbridge 4). |
| 132 | 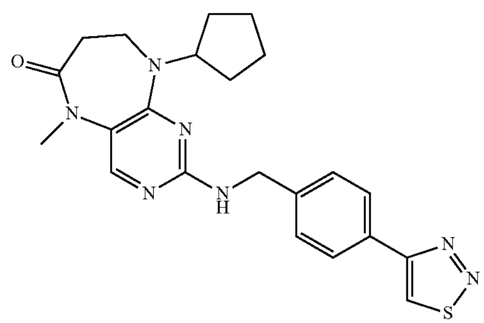 [SMILES: CN1C(=O)CCN(C2CCCC2)c2nc(NCc3ccc(-c4csnn4)cc3)ncc21] | | * | 9-Cyclopentyl-5-methyl-2-(4-[1,2,3]thiadiazol-4-yl-benzylamino)-5,7,8,9-tetrahydro-pyrimido[4,5-b][1,4]diazepin-6-one | 1H NMR (CD3OD): 1.59-1.79 (8H, m, alkyl-H), 2.75 (2H, dd, J 5 Hz, CH2), 3.24 (3H, s, CH3), 3.73 (2H, dd, J 5 Hz, CH2), 4.71 (2H, s, CH2), 7.53 (2H, d, J 8 Hz, Ar—H), 7.83 (1H, s, Ar—H), 8.12 (2H, d, J 8 Hz, Ar—H), 9.26 (1H, S, Ar—H); MS(+ve): 436.29; tR = 3.28 (Xbridge 4). |
| 133 | 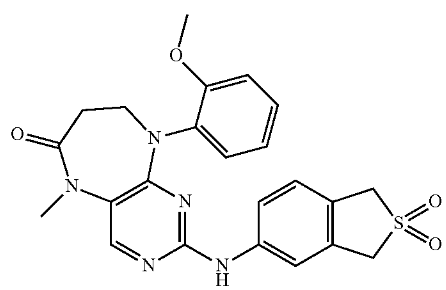 [SMILES: COc1ccccc1N1CCC(=O)N(C)c2cnc(Nc3ccc4c(c3)CS(=O)(=O)C4)nc21] | | ** | 2-(2,2-Dioxo-2,3-dihydro-1H-2lambda*6*-benzo[c]thiophen-5-ylamino)-9-(2-methoxy-phenyl)-5-methyl-5,7,8,9-tetrahydro-pyrimido[4,5-b][1,4]diazepin-6-one | 1H NMR (DMSO): 2.80 (2H, m, CH2), 3.26 (3H, s, CH3), 3.69 (3H, s, CH3), 3.87 (2H, m, CH2), 4.13 (2H, s, CH2), 4.29 (2H, s, CH2), 6.88 (1H, d, J 8 Hz, CH), 7.08 (1H, m, CH), 7.12 (2H, m, 2CH), 7.22 (1H, d, J 8 Hz, CH), 7.31 (1H, m, CH), 7.41 (1H, m, CH), 8.17 (1H, s, CH), 9.36 (1H, s, NH); MS(+ve): 466.3; tR = 2.68 min (XBridge 4). |

TABLE 2-continued

| Cpd | Structure | AurA IC50 | PLK1 IC50 | Name | Data |
|---|---|---|---|---|---|
| 134 | 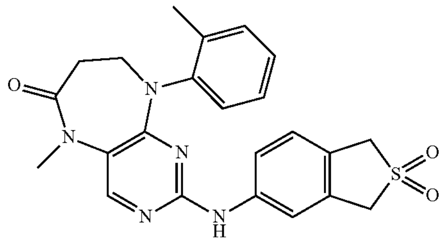 [SMILES: Cc1ccccc1N1CCC(=O)N(C)c2cnc(Nc3ccc4c(c3)CS(=O)(=O)C4)nc21] | ** | | 2-(2,2-Dioxo-2,3-dihydro-1H-2lambda*6*-benzo[c]thiophen-5-ylamino)-9-o-tolyl-5,7,8,9-tetrahydro-pyrimido[4,5-b][1,4]diazepin-6-one | 1H NMR (DMSO): 2.06 (3H, s, CH3), 2.8 (1H, s, CH), 2.93 (1H, s, CH), 3.28 (3H, s, CH3), 3.82 (1H, s, CH), 4.03 (1H, s, CH), 4.09 (2H, d, J 8.5 Hz, CH2), 4.28 (2H, s, CH2), 6.85 (1H, d, J 9 Hz, CH), 7.09 (2H, m, 2CH), 7.35 (4H, m, 4CH), 8.19 (1H, s, CH), 9.38 (1H, s, NH); MS(+ve): 450.25; tR = 2.76 min (XBridge 4). |
| 135 | 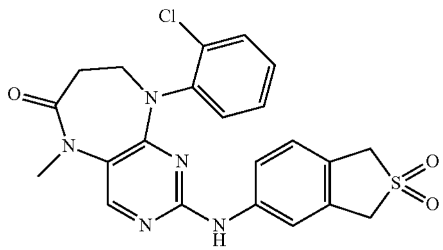 [SMILES: CN1C(=O)CCN(c2ccccc2Cl)c2nc(Nc3ccc4c(c3)CS(=O)(=O)C4)ncc21] | ** | | 9-(2-Chloro-phenyl)-2-(2,2-dioxo-2,3-dihydro-1H-2lambda*6*-benzo[c]thiophen-5-ylamino)-5-methyl-5,7,8,9-tetrahydro-pyrimido[4,5-b][1,4]diazepin-6-one | MS(+ve): 470.21; tR = 2.76 min (XBridge 4). |
| 136 | 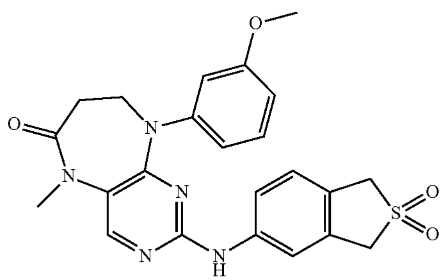 [SMILES: COc1cccc(N2CCC(=O)N(C)c3cnc(Nc4ccc5c(c4)CS(=O)(=O)C5)nc32)c1] | ** | | 2-(2,2-Dioxo-2,3-dihydro-1H-2lambda*6*-benzo[c]thiophen-5-ylamino)-9-(3-methoxy-phenyl)-5-methyl-5,7,8,9-tetrahydro-pyrimido[4,5-b][1,4]diazepin-6-one | 1H NMR (DMSO): 2.77 (2H, m, CH2), 3.27 (3H, s, CH3), 3.74 (3H, s, CH3), 4.02 (2H, m, CH2), 4.10 (2H, s, CH2), 4.32 (2H, s, CH2), 6.89 (3H, m, 3CH), 6.95 (1H, d, J 8.5 Hz, CH), 7.25 (1H, d, J 9 Hz, CH), 7.36 (2H, m, 2CH), 8.3 (1H, s, CH), 9.51 (1H, s, NH); MS(+ve): 466.3; tR = 2.68 min (XBridge 4). |
| 137 | 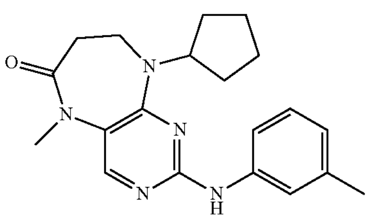 [SMILES: Cc1cccc(Nc2ncc3c(n2)N(C2CCCC2)CCC(=O)N3C)c1] | *** | * | 9-Cyclopentyl-5-methyl-2-m-tolylamino-5,7,8,9-tetrahydro-pyrimido[4,5-b][1,4]diazepin-6-one | 1H NMR (DMSO): 1.58 (4H, m, 2CH2), 1.7 (2H, m, CH2), 1.95 (2H, m, CH2), 2.26 (3H, s, CH3), 2.56 (2H, m, CH2), 3.16 (3H, s, CH3), 3.60 (2H, m, CH2), 4.84 (1H, m, CH), 6.71 (1H, d, J 7.5 Hz, CH), 7.10 (1H, m, CH), 7.40 (1H, d, J 8 Hz, CH), 7.67 (1H, s, CH), 8.03 (1H, s, CH), 9.11 (1H, s, NH); MS(+ve): 352.3; tR = 3.72 min (XBridge 4). |

TABLE 2-continued

| Cpd | Structure | AurA IC50 | PLK1 IC50 | Name | Data |
|---|---|---|---|---|---|
| 138 | 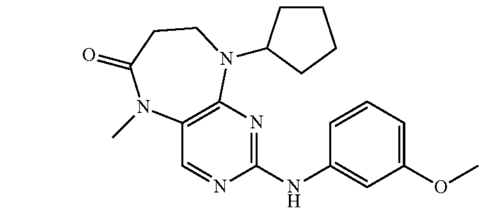 [SMILES: COc1cccc(Nc2ncc3c(n2)N(C2CCCC2)CCC(=O)N3C)c1] | ** | * | 9-Cyclopentyl-2-(3-methoxy-phenylamino)-5-methyl-5,7,8,9-tetrahydro-pyrimido[4,5-b][1,4]diazepin-6-one | 1H NMR (DMSO): 1.57 (4H, m, 2CH2), 1.69 (2H, m, CH2), 1.95 (2H, m, CH2), 2.56 (2H, m, CH2), 3.16 (3H, s, CH3), 3.60 (2H, m, CH2), 3.72 (3H, s, CH3), 4.82 (1 H, m, CHN), 6.48 (1H, dd, J 8, 2 Hz, CH), 7.12 (1H, t, J 8 Hz, CH), 7.25 (1 H, dd, J 8, 1 Hz, CH), 7.45 (1H, s, CH), 8.04 (1H, s, CH), 9.15 (1H, s, NH); MS(+ve): 368.3; tR = 3.47 min (XBridge 4). |
| 139 | 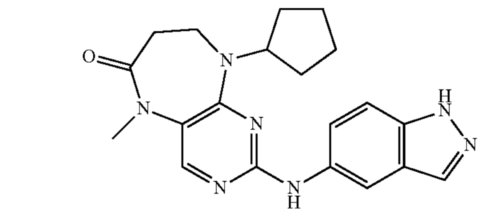 [SMILES: CN1C(=O)CCN(C2CCCC2)c2nc(Nc3ccc4[nH]ncc4c3)ncc21] | *** | | 9-Cyclopentyl-2-(1H-indazol-5-ylamino)-5-methyl-5,7,8,9-tetrahydro-pyrimido[4,5-b][1,4]diazepin-6-one | 1H NMR (DMSO): 1.58-1.95 (8H, m, alkyl-H), 2.54 (2H, dd, J 5 Hz, CH2), 3.16 (3H, s, CH3), 3.60 (2H, dd, J 5 Hz, CH2), 4.80-4.84 (1H, m, CH), 7.41 (1H, d, J 9 Hz, Ar—H), 7.52 (1H, d, J 9 Hz, Ar—H), 7.89 (1H, s, Ar—H), 8.04 (1H, s, Ar—H), 8.21 (1H, s, Ar—H), 9.14 (1H, bs, NH), 12.86 (1H, bs, NH); MS(+ve): 376.30; tR = 2.59 (Xbridge 4). |
| 140 | 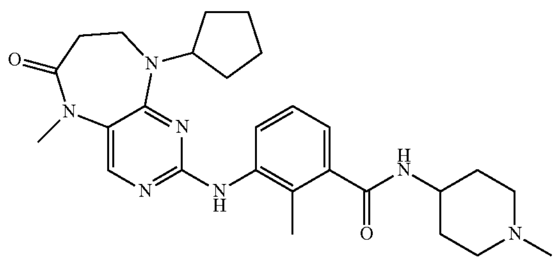 [SMILES: Cc1c(Nc2ncc3c(n2)N(C2CCCC2)CCC(=O)N3C)cccc1C(=O)NC1CCN(C)CC1] | * | | 3-(9-Cyclopentyl-5-methyl-6-oxo-6,7,8,9-tetrahydro-5H-pyrimido[4,5-b][1,4]diazepin-2-ylamino)-2-methyl-N-(1-methyl-piperidin-4-yl)-benzamide | 1H NMR (DMSO): 1.47 (6H, m, CH), 1.62 (2H, m, CH), 1.81 (4H, m, CH), 1.93 (2H, dd, J 10 Hz, 10 Hz, CH2), 2.14 (3H, s, CH3), 2.19 (3H, s, CH3), 2.54 (2H, m, CH2), 2.74 (2H, m, CH2), 3.14 (3H, s, CH3), 3.54 (2H, m, CH2), 3.69 (1H, m, CH), 4.65 (1H, m, CH), 6.96 (1H, d, J 7 Hz, Ar—H), 7.15 (1H, dd, J 7.5 Hz, 7.5 Hz, Ar—H), 7.63 (1H, d, J 7 Hz, Ar—H), 7.96 (1H, s, NH), 8.15 (1H, d, J 8 Hz, Ar—H), 8.35 (1H, s, Pyr—H); MS(+ve): 492.4; tR = 2.57 min (xbridge 4). |
| 141 | 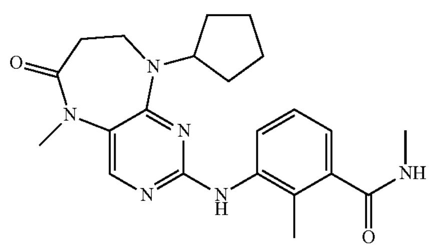 [SMILES: CNC(=O)c1cccc(Nc2ncc3c(n2)N(C2CCCC2)CCC(=O)N3C)c1C] | * | | 3-(9-Cyclopentyl-5-methyl-6-oxo-6,7,8,9-tetrahydro-5H-pyrimido[4,5-b][1,4]diazepin-2-ylamino)-2,N-dimethyl-benzamide | 1H NMR (DMSO): 1.45 (4H, m, CH), 1.62 (2H, m, CH), 1.80 (2H, m, CH2), 2.19 (3H, s, N—CH3), 2.55 (2H, m, CH2), 2.74 (3H, d, J 5 Hz, N—CH3), 3.29 (3H, s, CH3), 3.56 (2H, m, CH2), 4.61 (1H, s, CH), 6.99 (1H, d, J 8 Hz, Ar—H), 7.16 (1H, dd, J 7.5 Hz 8 Hz, Ar—H), 7.61 (1H, d, J 8 Hz, Ar—H), 7.96 (1H, s, NH), 8.13 (1H, m, Ar—H), 8.35 (1H, s, Pyr—H): MS(+ve): 409.3; tR = 2.58 min (xbridge 4). |

TABLE 2-continued

| Cpd | Structure | AurA IC50 | PLK1 IC50 | Name | Data |
|---|---|---|---|---|---|
| 142 | 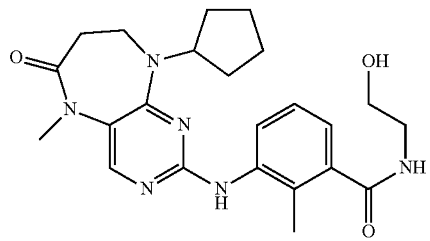 [SMILES: Cc1c(Nc2ncc3c(n2)N(C2CCCC2)CCC(=O)N3C)cccc1C(=O)NCCO] | | * | 3-(9-Cyclopentyl-5-methyl-6-oxo-6,7,8,9-tetrahydro-5H-pyrimido[4,5-b][1,4]diazepin-2-ylamino)-N-(2-hydroxyethyl)-2-methyl-benzamide | 1H NMR (DMSO): 1.47 (4H, m, CH), 1.62 (2H, m, CH), 1.79 (2H, m, CH), 2.14 (3H, s, CH3), 2.20 (3H, s, CH3), 2.55 (2H, m, CH2), 3.14 (3H, s, CH3), 3.27 (2H, m, CH2), 3.49 (2H, m, CH2), 3.56 (2H, m, CH2), 4.63 (1H, m, CH), 4.67 (1H, bs, OH), 7.01 (1H, d, J 7 Hz, Ar—H), 7.16 (1H, dd, J 7.5 Hz, J 7.5 Hz, Ar—H), 7.63 (1H, d, J 7 Hz, Ar—H), 7.96 (1H, s, NH), 8.13 (1H, m, Ar—H), 8.35 (1H, s, Pyr—H); MS(+ve); 439.3; tR = 2.39 min (xbridge 4). |
| 143 | 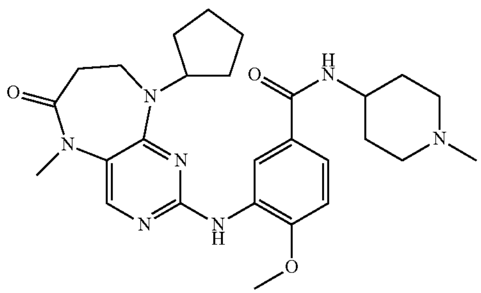 [SMILES: COc1ccc(C(=O)NC2CCN(C)CC2)cc1Nc1ncc2c(n1)N(C1CCCC1)CCC(=O)N2C] | | ** | 3-(9-Cyclopentyl-5-methyl-6-oxo-6,7,8,9-tetrahydro-5H-pyrimido[4,5-b][1,4]diazepin-2-ylamino)-4-methoxy-N-(1-methyl-piperidin-4-yl)-benzamide | 1H NMR (DMSO): 1.49-1.57 (8H, m, CH), 1.74 (2H, m, CH), 1.84 (2H, m, CH), 1.94 (2H, dd, J 10.5 Hz, 10.5 Hz, CH), 2.15 (3H, s, CH3), 2.53 (2H, m, CH2), 2.76 (2H, d, J 11.5 Hz, CH), 3.16 (3H, s, NCH3), 3.58 (2H, m, CH2), 3.68 (1H, m, CH), 3.89 (3H, s, OCH3), 4.81 (1H, m, CH), 7.04 (1H, d, J 8.5 Hz, Ar—H), 7.50 (1H, d, J 8.5 Hz, Ar—H), 7.70 (1H, s, NH), 8.00 (1H, d, J 7 Hz, Ar—H), 8.03 (1H, s, NH), 8.56 (1H, s, pyr—H): MS(+ve); 508.4; tR = 2.64 min (xbridge 4). |
| 144 | 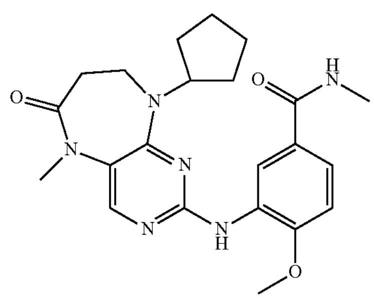 [SMILES: CNC(=O)c1ccc(OC)c(Nc2ncc3c(n2)N(C2CCCC2)CCC(=O)N3C)c1] | | ** | 3-(9-Cyclopentyl-5-methyl-6-oxo-6,7,8,9-tetrahydro-5H-pyrimido[4,5-b][1,4]diazepin-2-ylamino)-4-methoxy-N-methyl-benzamide | 1H NMR (DMSO): 1.60 (6H, m, CH), 1.86 (2H, m, CH), 2.56 (2H, m, CH2), 2.74 (3H, d, J 4.5 Hz, NCH3), 3.16 (3H, s, NCH3), 3.58 (2H, m, CH2), 3.90 (3H, s, CH3), 4.42 (1H, m, CH), 7.04 (1H, d, J 8.5 Hz, Ar—H), 7.43 (1H, d, J 8.5 Hz, Ar—H), 7.68 (1H, s, NH), 8.04 (1H, s, N—H), 8.20 (1H, m, Ar—H), 8.60 (1H, s, pyr—H): MS(+ve); 425.3; tR = 2.64 min (xbridge 4). |

TABLE 2-continued

| Cpd | Structure | AurA IC50 | PLK1 IC50 | Name | Data |
|---|---|---|---|---|---|
| 145 | 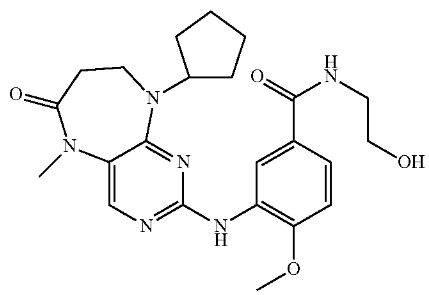 [SMILES: COc1ccc(C(=O)NCCO)cc1Nc1ncc2c(n1)N(C1CCCC1)CCC(=O)N2C] | | ** | 3-(9-Cyclopentyl-5-methyl-6-oxo-6,7,8,9-tetrahydro-5H-pyrimido[4,5-b][1,4]diazepin-2-ylamino)-N-(2-hydroxy-ethyl)-4-methoxy-benzamide | 1H NMR (DMSO): 1.55 (6H, m, CH), 1.86 (2H, m, CH), 2.56 (2H, m, CH2), 3.16 (3H, s, CH3), 3.30 (2H, m, CH2), 3.49 (2H, m, CH2), 3.59 (2H, m, CH2), 3.90 (3H, s, OCH3), 4.69 (1H, m, CH), 4.84 (1H, bs, OH), 7.04 (1H, d, J8.5 Hz, Ar—H), 7.48 (1H, d, J 8 Hz, Ar—H), 7.61 (1H, s, NH), 8.03 (1H, s, NH), 8.21 (1H, d, J5.5 Hz, Ar—H), 8.61 (1H, s, pyr—H); MS(+ve); 455.3; tR = 2.46 min (xbridge 4). |
| 146 | 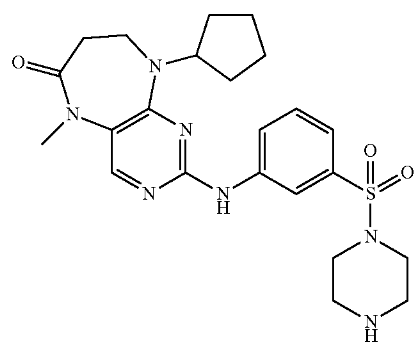 [SMILES: CN1C(=O)CCN(C2CCCC2)c2nc(Nc3cccc(S(=O)(=O)N4CCNCC4)c3)ncc21] | * | | 9-Cyclopentyl-5-methyl-2-[3-(piperazine-1-sulfonyl)-phenylamino]-5,7,8,9-tetrahydro-pyrimido[4,5-b][1,4]diazepin-6-one | |
| 147 | 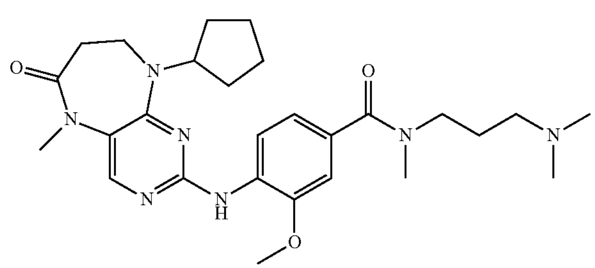 [SMILES: COc1cc(C(=O)N(C)CCCN(C)C)ccc1Nc1ncc2c(n1)N(C1CCCC1)CCC(=O)N2C] | | ** | 4-(9-Cyclopentyl-5-methyl-6-oxo-6,7,8,9-tetrahydro-5H-pyrimido[4,5-b][1,4]diazepin-2-ylamino)-N-(3-dimethylamino-propyl)-3-methoxy-N-methyl-benzamide | |

TABLE 2-continued

| Cpd | Structure | AurA IC50 | PLK1 IC50 | Name | Data |
|---|---|---|---|---|---|
| 148 | 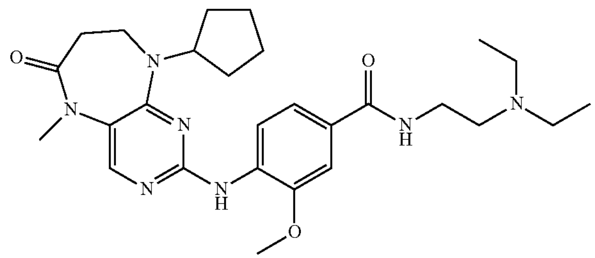 [SMILES: CCN(CC)CCNC(=O)c1ccc(Nc2ncc3c(n2)N(C2CCCC2)CCC(=O)N3C)c(OC)c1] | | | 4-(9-Cyclopentyl-5-methyl-6-oxo-6,7,8,9-tetrahydro-5H-pyrimido[4,5-b][1,4]diazepin-2-ylamino)-N-(2-diethylamino-ethyl)-3-methoxy-benzamide | *** |
| 149 | 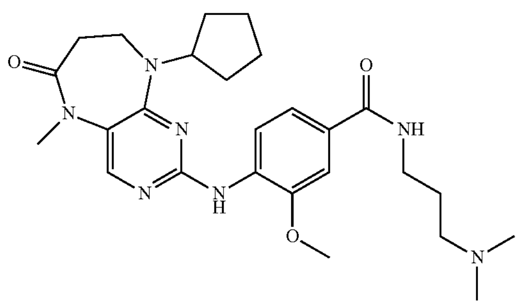 [SMILES: COc1cc(C(=O)NCCCN(C)C)ccc1Nc1ncc2c(n1)N(C1CCCC1)CCC(=O)N2C] | | | 4-(9-Cyclopentyl-5-methyl-6-oxo-6,7,8,9-tetrahydro-5H-pyrimido[4,5-b][1,4]diazepin-2-ylamino)-N-(3-dimethylamino-propyl)-3-methoxy-benzamide | ** |
| 150 | 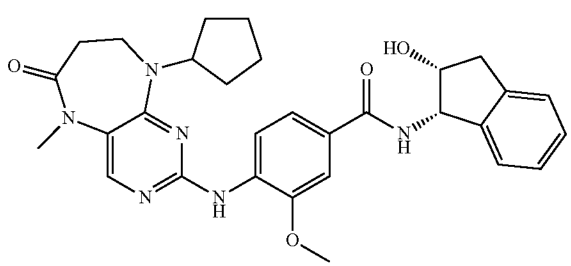 [SMILES: COc1cc(C(=O)N[C@H]2c3ccccc3C[C@H]2O)ccc1Nc1ncc2c(n1)N(C1CCCC1)CCC(=O)N2C] | | | 4-(9-Cyclopentyl-5-methyl-6-oxo-6,7,8,9-tetrahydro-5H-pyrimido[4,5-b][1,4]diazepin-2-ylamino)-N-((1S,2R)-2-hydroxy-indan-1-yl)-3-methoxy-benzamide | ** |

TABLE 2-continued

| Cpd | Structure | AurA IC50 | PLK1 IC50 | Name | Data |
|---|---|---|---|---|---|
| 151 | 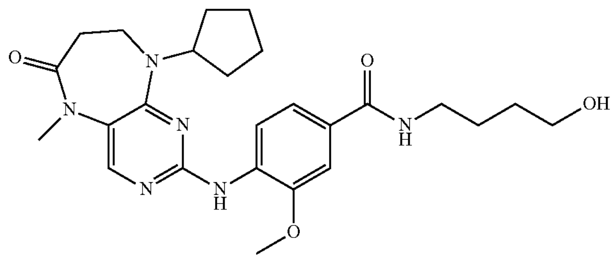 [SMILES: COc1cc(C(=O)NCCCCO)ccc1Nc1ncc2c(n1)N(C1CCCC1)CCC(=O)N2C] | * | ** | 4-(9-Cyclopentyl-5-methyl-6-oxo-6,7,8,9-tetrahydro-5H-pyrimido[4,5-b][1,4]diazepin-2-ylamino)-N-(4-hydroxy-butyl)-3-methoxy-benzamide | |
| 152 | 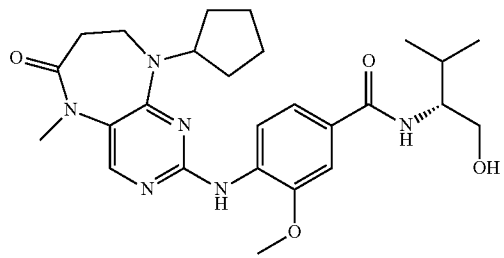 [SMILES: COc1cc(C(=O)N[C@@H](CO)C(C)C)ccc1Nc1ncc2c(n1)N(C1CCCC1)CCC(=O)N2C] | | ** | 4-(9-Cyclopentyl-5-methyl-6-oxo-6,7,8,9-tetrahydro-5H-pyrimido[4,5-b][1,4]diazepin-2-ylamino)-N-((R)-1-hydroxymethyl-2-methyl-propyl)-3-methoxy-benzamide | |
| 153 | 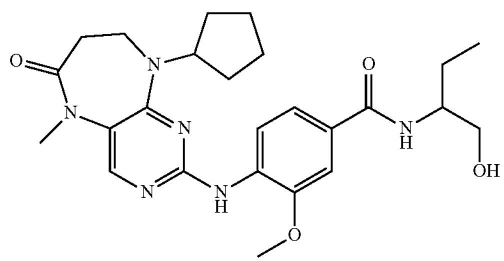 [SMILES: CCC(CO)NC(=O)c1ccc(Nc2ncc3c(n2)N(C2CCCC2)CCC(=O)N3C)c(OC)c1] | | ** | 4-(9-Cyclopentyl-5-methyl-6-oxo-6,7,8,9-tetrahydro-5H-pyrimido[4,5-b][1,4]diazepin-2-ylamino)-N-(1-hydroxymethyl-propyl)-3-methoxy-benzamide | |
| 154 | 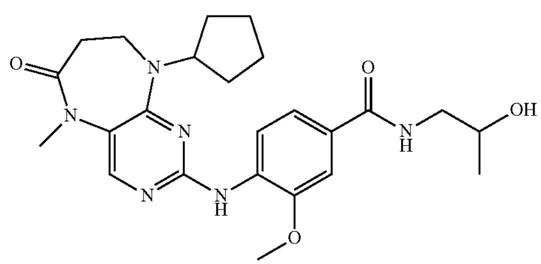 [SMILES: COc1cc(C(=O)NCC(C)O)ccc1Nc1ncc2c(n1)N(C1CCCC1)CCC(=O)N2C] | | ** | 4-(9-Cyclopentyl-5-methyl-6-oxo-6,7,8,9-tetrahydro-5H-pyrimido[4,5-b][1,4]diazepin-2-ylamino)-N-(2-hydroxy-propyl)-3-methoxy-benzamide | |

TABLE 2-continued

| Cpd | Structure | AurA IC50 | PLK1 IC50 | Name | Data |
|---|---|---|---|---|---|
| 155 | 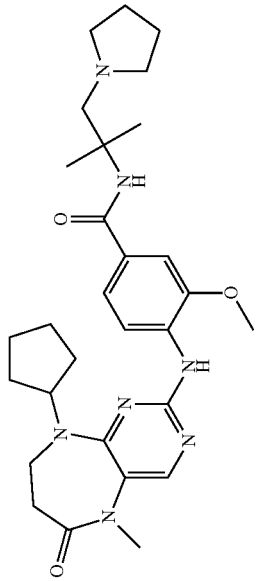 | | | 4-(9-Cyclopentyl-5-methyl-6-oxo-6,7,8,9-tetrahydro-5H-pyrimido[4,5-b][1,4]diazepin-2-ylamino)-N-(1,1-dimethyl-2-pyrrolidin-1-yl-ethyl)-3-methoxy-benzamide | ** |
| 156 | 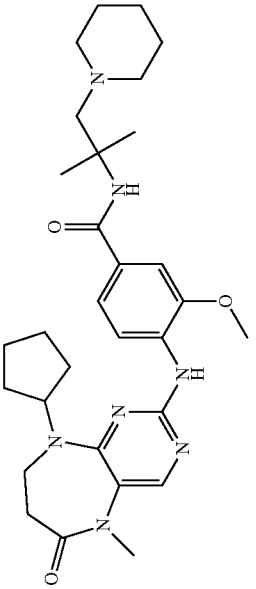 | | | 4-(9-Cyclopentyl-5-methyl-6-oxo-6,7,8,9-tetrahydro-5H-pyrimido[4,5-b][1,4]diazepin-2-ylamino)-N-(1,1-dimethyl-2-piperidin-1-yl-ethyl)-3-methoxy-benzamide | *** |
| 157 | 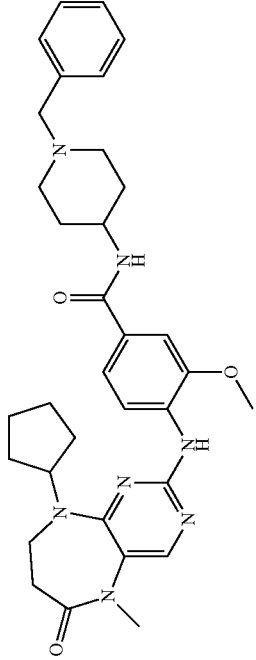 | | | N-(1-Benzyl-piperidin-4-yl)-4-(9-cyclopentyl-5-methyl-6-oxo-6,7,8,9-tetrahydro-5H-pyrimido[4,5-b][1,4]diazepin-2-ylamino)-3-methoxy-benzamide | *** |

TABLE 2-continued

| Cpd | Structure | AurA IC50 | PLK1 IC50 | Name | Data |
|---|---|---|---|---|---|
| 158 | 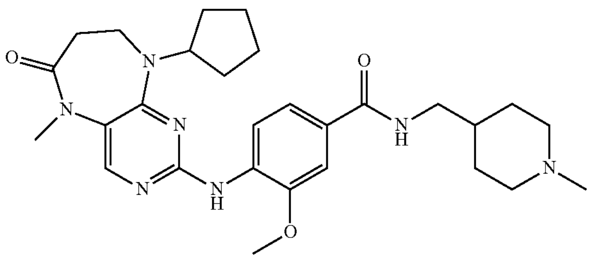 [SMILES: COc1cc(C(=O)NCC2CCN(C)CC2)ccc1Nc1ncc2c(n1)N(C1CCCC1)CCC(=O)N2C] | | *** | 4-(9-Cyclopentyl-5-methyl-6-oxo-6,7,8,9-tetrahydro-5H-pyrimido[4,5-b][1,4]diazepin-2-ylamino)-3-methoxy-N-(1-methyl-piperidin-4-ylmethyl)-benzamide | |
| 159 | 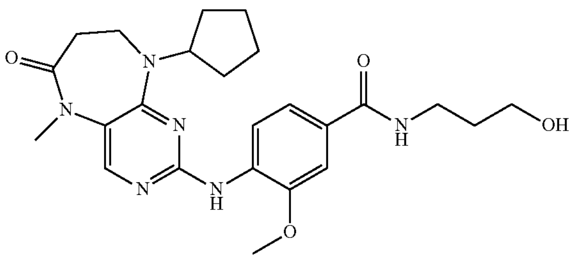 [SMILES: COc1cc(C(=O)NCCCO)ccc1Nc1ncc2c(n1)N(C1CCCC1)CCC(=O)N2C] | | ** | 4-(9-Cyclopentyl-5-methyl-6-oxo-6,7,8,9-tetrahydro-5H-pyrimido[4,5-b][1,4]diazepin-2-ylamino)-N-(3-hydroxy-propyl)-3-methoxy-benzamide | |
| 160 | 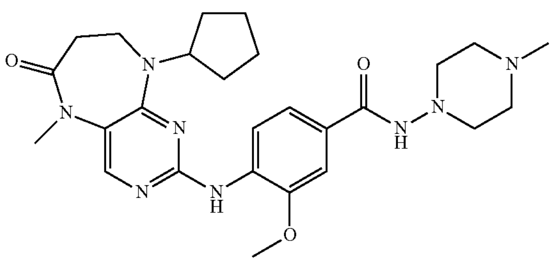 [SMILES: COc1cc(C(=O)NN2CCN(C)CC2)ccc1Nc1ncc2c(n1)N(C1CCCC1)CCC(=O)N2C] | | *** | 4-(9-Cyclopentyl-5-methyl-6-oxo-6,7,8,9-tetrahydro-5H-pyrimido[4,5-b][1,4]diazepin-2-ylamino)-3-methoxy-N-(4-methyl-piperazin-1-yl)-benzamide | |
| 161 | 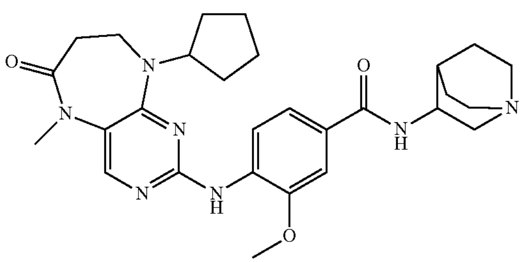 [SMILES: COc1cc(C(=O)NC2CN3CCC2CC3)ccc1Nc1ncc2c(n1)N(C1CCCC1)CCC(=O)N2C] | | *** | N-(1-Aza-bicyclo[2.2.2]oct-3-yl)-4-(9-cyclopentyl-5-methyl-6-oxo-6,7,8,9-tetrahydro-5H-pyrimido[4,5-b][1,4]diazepin-2-ylamino)-3-methoxy-benzamide | |

TABLE 2-continued

| Cpd | Structure | AurA IC50 | PLK1 IC50 | Name | Data |
|---|---|---|---|---|---|
| 162 | 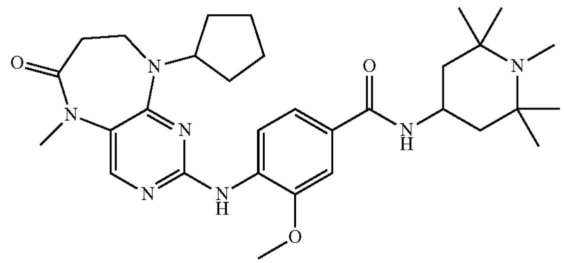 [SMILES: COc1cc(C(=O)NC2CC(C)(C)N(C)C(C)(C)C2)ccc1Nc1ncc2c(n1)N(C1CCCC1)CCC(=O)N2C] | | *** | 4-(9-Cyclopentyl-5-methyl-6-oxo-6,7,8,9-tetrahydro-5H-pyrimido[4,5-b][1,4]diazepin-2-ylamino)-3-methoxy-N-(1,2,2,6,6-pentamethyl-piperidin-4-yl)-benzamide | |
| 163 | 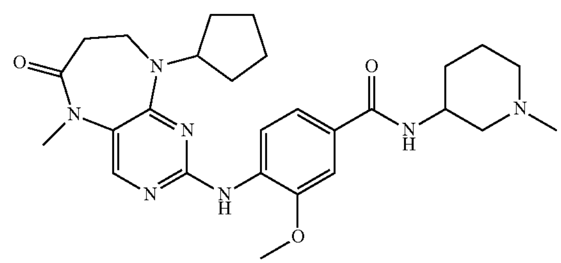 [SMILES: COc1cc(C(=O)NC2CCCN(C)C2)ccc1Nc1ncc2c(n1)N(C1CCCC1)CCC(=O)N2C] | | *** | 4-(9-Cyclopentyl-5-methyl-6-oxo-6,7,8,9-tetrahydro-5H-pyrimido[4,5-b][1,4]diazepin-2-ylamino)-3-methoxy-N-(1-methyl-piperidin-3-yl)-benzamide | |
| 164 | 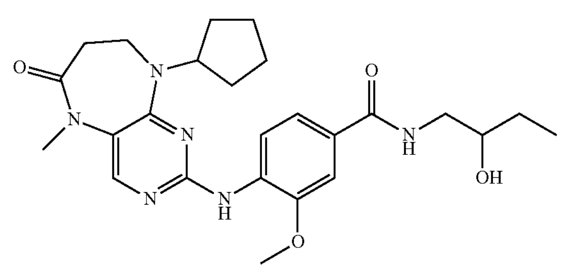 [SMILES: CCC(O)CNC(=O)c1ccc(Nc2ncc3c(n2)N(C2CCCC2)CCC(=O)N3C)c(OC)c1] | | ** | 4-(9-Cyclopentyl-5-methyl-6-oxo-6,7,8,9-tetrahydro-5H-pyrimido[4,5-b][1,4]diazepin-2-ylamino)-N-(2-hydroxy-butyl)-3-methoxy-benzamide | |

TABLE 2-continued

| Cpd | Structure | AurA IC50 | PLK1 IC50 | Name | Data |
|---|---|---|---|---|---|
| 165 | 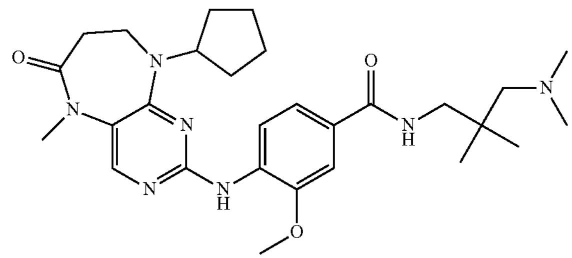 [SMILES: COc1cc(C(=O)NCC(C)(C)CN(C)C)ccc1Nc1ncc2c(n1)N(C1CCCC1)CCC(=O)N2C] | | | 4-(9-Cyclopentyl-5-methyl-6-oxo-6,7,8,9-tetrahydro-5H-pyrimido[4,5-b][1,4]diazepin-2-ylamino)-N-(3-dimethylamino-2,2-dimethyl-propyl)-3-methoxy-benzamide | *** |
| 166 | 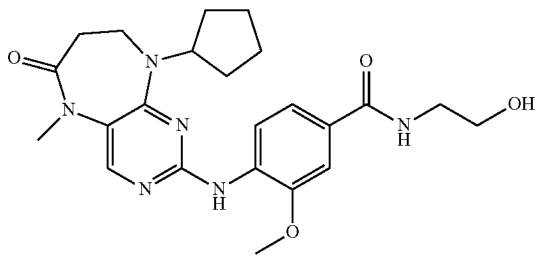 [SMILES: COc1cc(C(=O)NCCO)ccc1Nc1ncc2c(n1)N(C1CCCC1)CCC(=O)N2C] | | | 4-(9-Cyclopentyl-5-methyl-6-oxo-6,7,8,9-tetrahydro-5H-pyrimido[4,5-b][1,4]diazepin-2-ylamino)-N-(2-hydroxy-ethyl)-3-methoxy-benzamide | ** |
| 167 | 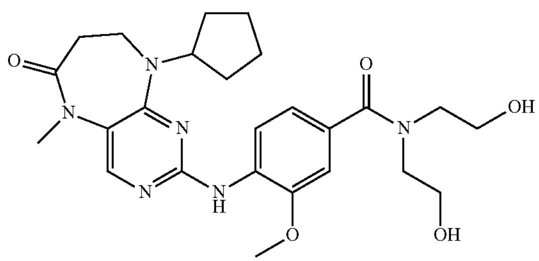 [SMILES: COc1cc(C(=O)N(CCO)CCO)ccc1Nc1ncc2c(n1)N(C1CCCC1)CCC(=O)N2C] | | | 4-(9-Cyclopentyl-5-methyl-6-oxo-6,7,8,9-tetrahydro-5H-pyrimido[4,5-b][1,4]diazepin-2-ylamino)-N,N-bis-(2-hydroxy-ethyl)-3-methoxy-benzamide | * |
| 168 | 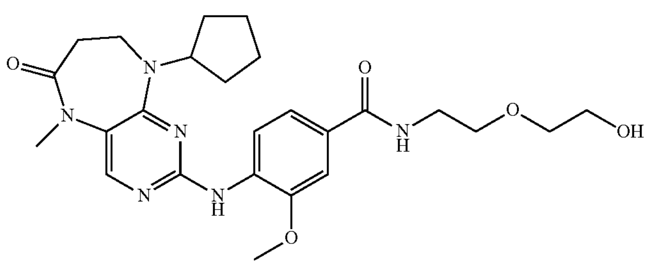 [SMILES: COc1cc(C(=O)NCCOCCO)ccc1Nc1ncc2c(n1)N(C1CCCC1)CCC(=O)N2C] | | | 4-(9-Cyclopentyl-5-methyl-6-oxo-6,7,8,9-tetrahydro-5H-pyrimido[4,5-b][1,4]diazepin-2-ylamino)-N-[2-(2-hydroxy-ethoxy)-ethyl]-3-methoxy-benzamide | ** |

TABLE 2-continued

| Cpd | Structure | AurA IC50 | PLK1 IC50 | Name | Data |
|---|---|---|---|---|---|
| 169 | 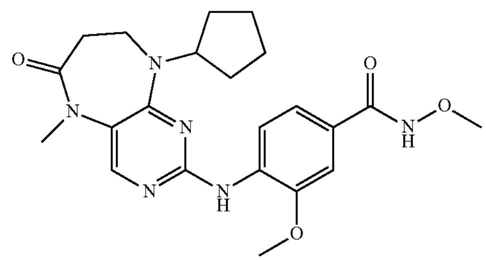 [SMILES: CONC(=O)c1ccc(Nc2ncc3c(n2)N(C2CCCC2)CCC(=O)N3C)c(OC)c1] | | ** | 4-(9-Cyclopentyl-5-methyl-6-oxo-6,7,8,9-tetrahydro-5H-pyrimido[4,5-b][1,4]diazepin-2-ylamino)-3,N-dimethoxy-benzamide | |
| 170 | 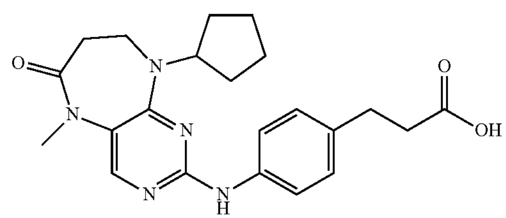 [SMILES: CN1C(=O)CCN(C2CCCC2)c2nc(Nc3ccc(CCC(=O)O)cc3)ncc21] | | * | 3-[4-(9-Cyclopentyl-5-methyl-6-oxo-6,7,8,9-tetrahydro-5H-pyrimido[4,5-b][1,4]diazepin-2-ylamino)-phenyl]-propionic acid | |
| 171 | 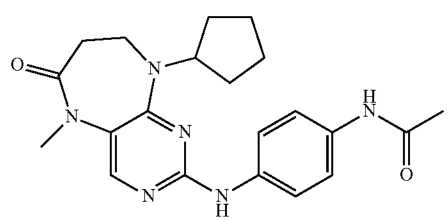 [SMILES: CC(=O)Nc1ccc(Nc2ncc3c(n2)N(C2CCCC2)CCC(=O)N3C)cc1] | | *** | N-[4-(9-Cyclopentyl-5-methyl-6-oxo-6,7,8,9-tetrahydro-5H-pyrimido[4,5-b][1,4]diazepin-2-ylamino)-phenyl]-acetamide | |
| 172 | 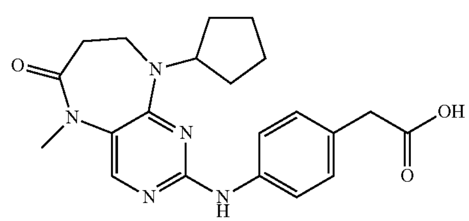 [SMILES: CN1C(=O)CCN(C2CCCC2)c2nc(Nc3ccc(CC(=O)O)cc3)ncc21] | | *** | [4-(9-Cyclopentyl-5-methyl-6-oxo-6,7,8,9-tetrahydro-5H-pyrimido[4,5-b][1,4]diazepin-2-ylamino)-phenyl]-acetic acid | |

TABLE 2-continued

| Cpd | Structure | AurA IC50 | PLK1 IC50 | Name | Data |
|---|---|---|---|---|---|
| 173 | 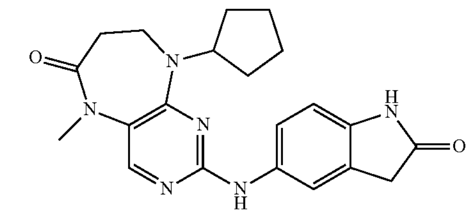 [SMILES: CN1C(=O)CCN(C2CCCC2)c2nc(Nc3ccc4c(c3)CC(=O)N4)ncc21] | *** | * | 9-Cyclopentyl-5-methyl-2-(2-oxo-2,3-dihydro-1H-indol-5-ylamino)-5,7,8,9-tetrahydro-pyrimido[4,5-b][1,4]diazepin-6-one | 1H NMR (DMSO): 1.51-1.69 (8H, m, alkyl-H), 1.85 (2H, bs, CH2), 2.66 (2H, dd, J 4.5 Hz, CH2), 3.15 (3H, s, CH3), 3.66 (2H, dd, J 4.5 Hz, Ch2), 4.78-4.83 (1H, m, CH), 6.79 (1H, d, J 8 Hz, Ar—H), 7.30 (1H, d, J 8 Hz, Ar—H), 7.47 (1H, s, Ar—H), 7.96 (1H, s, Ar—H), 9.86 (1H, bs, NH), 10.35 (1H, bs, NH); MS(+ve): 393.32; tR = 2.46 (Xbridge 4). |
| 174 | 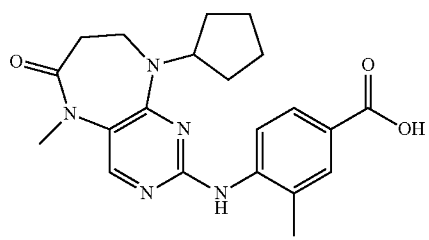 [SMILES: Cc1cc(C(=O)O)ccc1Nc1ncc2c(n1)N(C1CCCC1)CCC(=O)N2C] | ** | * | 4-(9-Cyclopentyl-5-methyl-6-oxo-6,7,8,9-tetrahydro-5H-pyrimido[4,5-b][1,4]diazepin-2-ylamino)-3-methyl-benzoic acid | 1H NMR (DMSO): 1.49-1.83 (8H, m, alkyl-H), 2.31 (3H, s, CH3), 2.57 (2H, dd, J 4.5 Hz, CH2), 3.14 (3H, s, CH3), 3.58 (2H, dd, J 4.5 Hz, CH2), 4.68-4.71 (1H, m, CH), 7.70 (1H, d, J 8.5 Hz, Ar—H), 7.75 (1H, s, Ar—H), 7.98 (1H, d, J 8.5 Hz, Ar—H), 9.04 (1H, s, Ar—H), 8.35 (s, 1H, Ar—H), 12.55 (1H, bs, NH); MS(+ve): 396.32; tR = 1.78 (Xbridge 4). |
| 175 | 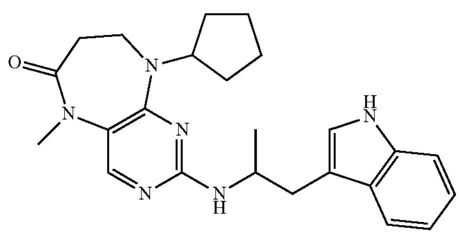 [SMILES: CC(Cc1c[nH]c2ccccc12)Nc1ncc2c(n1)N(C1CCCC1)CCC(=O)N2C] | * | | 9-Cyclopentyl-2-[2-(1H-indol-3-yl)-1-methyl-ethylamino]-5-methyl-5,7,8,9-tetrahydro-pyrimido[4,5-b][1,4]diazepin-6-one | 1H NMR (CD3OD): 1.22 (3H, d, J 5.5 Hz, CH3), 1.52-1.97 (8H, m, alkyl-H), 2.57 (2H, dd, J 6 Hz, CH2), 2.90-3.04 (2H, m, CH2), 3.19 (3H, s, CH3), 3.58 (2H, dd, J 6 Hz, CH2), 4.35-4.39 (1H, m, CH), 4.68-4.74 (1H, m, CH), 6.97 (1H, t, J 8 Hz, Ar—H), 7.04-7.08 (2H, m, Ar—H), 7.31 (1H, d, J 8 Hz, Ar—H), 7.54 (1H, d, J 8 Hz, Ar—H), 7.75 (1 H, s, Ar—H); MS(+ve): 419.36; tR = 3.60 (Xbridge 4). |
| 176 | 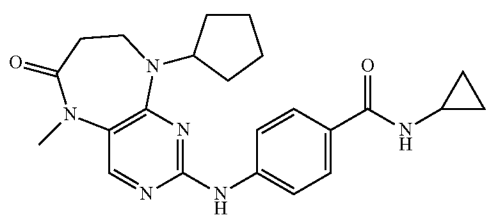 [SMILES: CN1C(=O)CCN(C2CCCC2)c2nc(Nc3ccc(C(=O)NC4CC4)cc3)ncc21] | * |  | 4-(9-Cyclopentyl-5-methyl-6-oxo-6,7,8,9-tetrahydro-5H-pyrimido[4,5-b][1,4]diazepin-2-ylamino)-N-cyclopropyl-benzamide | 1H NMR (DMSO): 0.55 (2H, m, CH2), 0.66 (2H, m, CH2), 1.61 (4H, m, 2CH2), 1.72 (2H, m, CH2), 1.95 (2H, m, CH2), 2.58 (2H, m, CH2), 2.81 (1H, m, CH), 3.17 (3H, s, CH3), 3.62 (2H, m, CH2), 4.82 (1H, m, CHN), 7.72 (2H, d, J 9 Hz, 2CH), 7.78 (2H, d, J 9 Hz, 2CH), 8.08 (1H, s, CH), 8.21 (1H, d, J 14 Hz, NH) 9.47 (1H, s, NH); MS(+ve): 421.4; tR = 2.75 min (XBridge 4). |

TABLE 2-continued

| Cpd | AurA IC50 | PLK1 IC50 | Name | Data |
|---|---|---|---|---|
| 177 | *** | ** | 9-Cyclopentyl-2-[3-(1,1-dioxo-thiomorpholin-4-ylmethyl)-phenylamino]-5-methyl-5,7,8,9-tetrahydro-pyrimido[4,5-b][1,4]diazepin-6-one | 1H NMR (DMSO): 1.6 (4H, m, 2CH2), 1.71 (2H, m, CH2), 1.97 (2H, m, CH2), 2.56 (2H, m, CH2), 2.86 (4H, m, 2CH2), 3.11 (4H, m, 2CH2), 3.16 (3H, s, CH3), 3.61 (4H, m, 2CH2), 4.84 (1H, m, CHN), 6.88 (1 H, d, J 7.5 Hz, CH), 7.2 (1H, t, J 8 Hz, CH), 7.61 (1H, d, J 8.5 Hz, CH), 7.71 (1H, s, CH), 8.04 (1H, s, CH), 9.17 (1H, s, NH); MS(+ve): 485.4; tR = 3.0 min (XBridge 4). |
| 178 | *** | ** | Cyclopropanecarboxylic acid [4-(9-cyclopentyl-5-methyl-6-oxo-6,7,8,9-tetrahydro-5H-pyrimido[4,5-b][1,4]diazepin-2-ylamino)-phenyl]-amide | 1H NMR (DMSO): 0.76 (4H, m, 2CH2), 1.57 (5H, m, 2CH2 + CH), 1.72 (2H, m, CH2), 1.91 (2H, m, CH2), 2.56 (2H, m, CH2), 3.15 (3H, s, CH3), 3.59 (2H, m, CH2), 4.77 (1H, m, CHN), 7.44 (2H, d, J 9 Hz, 2CH), 7.61 (2H, d, J 9 Hz, 2CH), 8.01 (1H, s, CH), 9.09 (1H, s, NH) 10.0 (1H, s, NH); MS(+ve): 421.4; tR = 2.9 min (XBridge4). |
| 179 | *** | * | Cyclopropanecarboxylic acid [4-(9-cyclopentyl-5-methyl-6-oxo-6,7,8,9-tetrahydro-5H-pyrimido[4,5-b][1,4]diazepin-2-ylamino)-2-methyl-phenyl]-amide | 1H NMR (DMSO): 0.75 (4H, m, 2CH2), 1.57 (4H, m, 2CH2), 1.7 (2H, m, CH2), 1.8 (1H, m, CH), 1.96 (2H, m, CH2), 2.51 (3H, s, CH3), 2.56 (2H, m, CH2), 3.15 (3H, s, CH3N), 3.60 (2H, m, CH2), 4.83 (1H, m, CHN), 7.17 (1H, d, J 8.5 Hz, CH), 7.38 (1H, d, J 8.5 Hz, CH), 7.64 (1H, s, CH), 8.03 (1H, s, CH), 9.01 (1H, s, NH) 9.38 (1H, s, NH); MS(+ve): 435.4; tR = 2.89 min (XBridge4). |
| 180 | *** | | 3-[4-(9-Cyclopentyl-5-methyl-6-oxo-6,7,8,9-tetrahydro-5H-pyrimido[4,5-b][1,4]diazepin-2-ylamino)-phenyl]-N-(1-methyl-piperidin-4-yl)-propionamide | |

TABLE 2-continued

| Cpd | Structure | AurA IC50 | PLK1 IC50 | Name | Data |
|---|---|---|---|---|---|
| 181 | 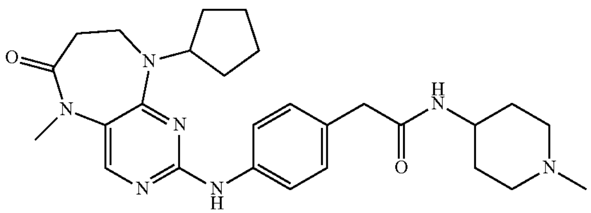 [SMILES: CN1CCC(NC(=O)Cc2ccc(Nc3ncc4c(n3)N(C3CCCC3)CCC(=O)N4C)cc2)CC1] | | * | 2-[4-(9-Cyclopentyl-5-methyl-6-oxo-6,7,8,9-tetrahydro-5H-pyrimido[4,5-b][1,4]diazepin-2-ylamino)-phenyl]-N-(1-methyl-piperidin-4-yl)-acetamide | |
| 182 | 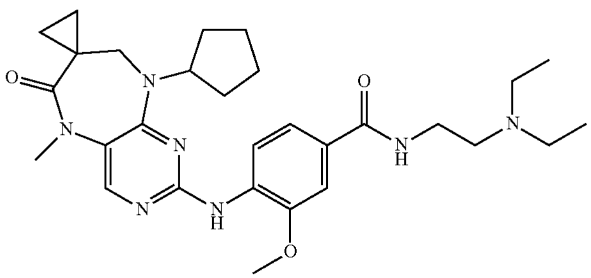 [SMILES: CCN(CC)CCNC(=O)c1ccc(Nc2ncc3c(n2)N(C2CCCC2)CC2(CC2)C(=O)N3C)c(OC)c1] | *** | | 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-N-(2-diethylamino-ethyl)-3-methoxy-benzamide | MS(+ve); 536.5; tR = 3.42 min (xbridge 4). |
| 183 | 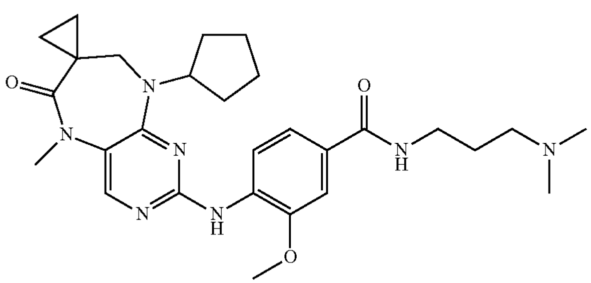 [SMILES: COc1cc(C(=O)NCCCN(C)C)ccc1Nc1ncc2c(n1)N(C1CCCC1)CC1(CC1)C(=O)N2C] | *** | | 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-N-(3-methylamino-propyl)-3-methoxy-benzamide | MS(+ve); 522.5; tR = 3.12 min (xbridge4). |

TABLE 2-continued

| Cpd | Structure | AurA IC50 | PLK1 IC50 | Name | Data |
|---|---|---|---|---|---|
| 184 | 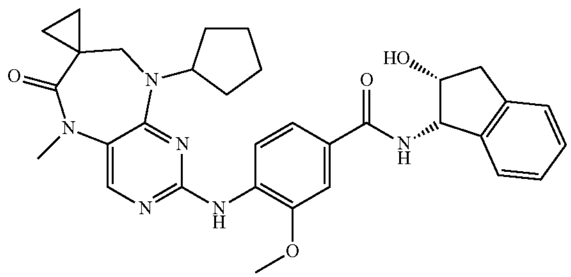 | ** | | 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-N-((1S,2R)-2-hydroxy-indan-1-yl)-3-methoxy-benzamide | MS(+ve); 569.5; tR = 3.50 min (xbridge 4). |
| 185 | 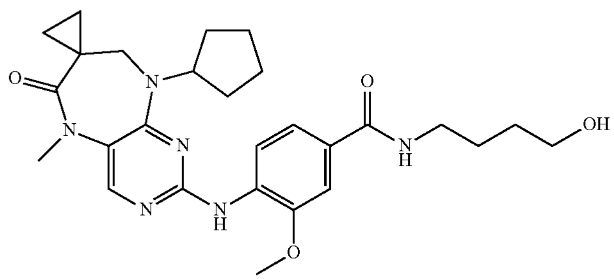 [SMILES: COc1cc(C(=O)NCCCCO)ccc1Nc1ncc2c(n1)N(C1CCCC1)CC1(CC1)C(=O)N2C] | *** | | 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-N-(4-hydroxy-butyl)-3-methoxy-benzamide | MS(+ve); 509.3; tR = 2.77 min (xbridge 4). |
| 186 | 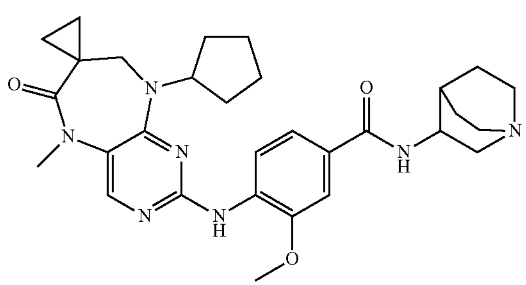 [SMILES: COc1cc(C(=O)NC2CN3CCC2CC3)ccc1Nc1ncc2c(n1)N(C1CCCC1)CC1(CC1)C(=O)N2C] | *** | | N-(1-Aza-bicyclo[2.2.2]oct-3-yl)-4-(9-cyclopentyl-5-methyl-6-oxo-6,7,8,9-tetrahydro-5H-spiro[pyrimido[4,5-b][1,4]diazepin-3,1'-cyclopropane]-2-ylamino)-3-methoxy-benzamide | MS(+ve); 546.4; tR = 3.02 min (xbridge 4). |

TABLE 2-continued

| Cpd | Structure | AurA IC50 | PLK1 IC50 | Name | Data |
|---|---|---|---|---|---|
| 187 | 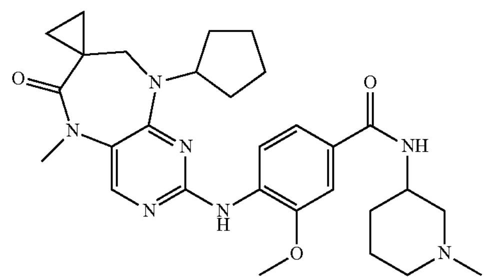 [SMILES: COc1cc(C(=O)NC2CCCN(C)C2)ccc1Nc1ncc2c(n1)N(C1CCCC1)CC1(CC1)C(=O)N2C] | | *** | 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-3-methoxy-N-(1-methyl-piperidin-3-yl)-benzamide | MS(+ve); 534.4; tR = 3.12 min (xbridge 4). |
| 188 | 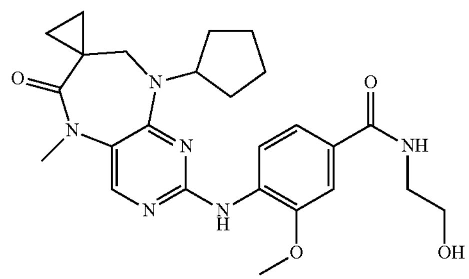 [SMILES: COc1cc(C(=O)NCCO)ccc1Nc1ncc2c(n1)N(C1CCCC1)CC1(CC1)C(=O)N2C] | | *** | 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-N-(2-hydroxy-ethyl)-3-methoxy-benzamide | MS(+ve); 481.3; tR = 2.67 min (xbridge 4). |
| 189 | 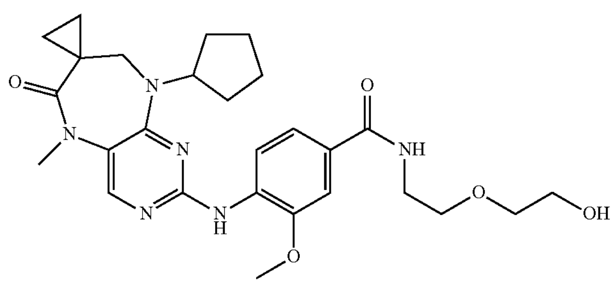 [SMILES: COc1cc(C(=O)NCCOCCO)ccc1Nc1ncc2c(n1)N(C1CCCC1)CC1(CC1)C(=O)N2C] | | *** | 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-N-[2-(2-hydroxy-ethoxy)-ethyl]-3-methoxy-benzamide | MS(+ve); 525.4; tR = 2.68 min (xbridge 4). |

TABLE 2-continued

| Cpd | Structure | AurA IC50 | PLK1 IC50 | Name | Data |
|---|---|---|---|---|---|
| 190 | 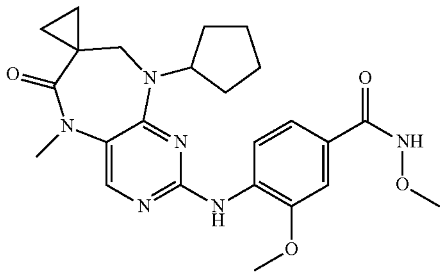 [SMILES: CONC(=O)c1ccc(Nc2ncc3c(n2)N(C2CCCC2)CC2(CC2)C(=O)N3C)c(OC)c1] | | *** | 4-(9-Cyclopentyl-5-methyl-6-oxo-6,7,8,9-tetrahydro-5H-spiro[pyrimido[4,5-b][1,4]diazepin-3,1-cyclopropane]-2-ylamino)-3,N-dimethoxy-benzamide | MS(+ve): 467.4; tR = 2.51 min (xbridge 4). |
| 191 | 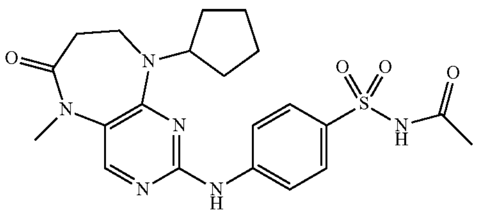 [SMILES: CC(=O)NS(=O)(=O)c1ccc(Nc2ncc3c(n2)N(C2CCCC2)CCC(=O)N3C)cc1] | | | N-Acetyl-4-(9-cyclopentyl-5-methyl-6-oxo-6,7,8,9-tetrahydro-5H-pyrimido[4,5-b][1,4]diazepin-2-ylamino)-benzenesulfonamide | 1H NMR (DMSO): 1.6 (4H, m, 2CH2), 1.72 (2H, m, CH2), 1.9 (3H, s, CH3), 1.95 (2H, m, CH2), 2.59 (2H, m, CH2), 3.17 (3H, s, CH3), 3.62 (2H, m, CH2), 4.83 (1H, m, CHN), 7.45 (2H, d, J 8.5 Hz, 2CH), 7.92 (2H, d, J 8.5 Hz, 2CH), 8.10 (1H, s, CH), 9.76 (1H, s, NH), 11.86 (1H, s, NH); MS(+ve): 459.3; tR = 1.63 min (XBridge 4). |
| 192 | 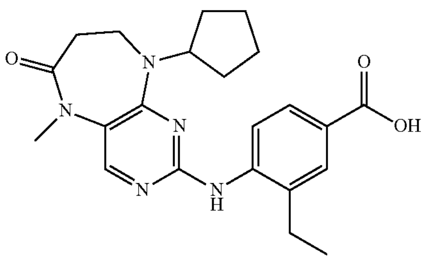 [SMILES: CCc1cc(C(=O)O)ccc1Nc1ncc2c(n1)N(C1CCCC1)CCC(=O)N2C] | | * | 4-(9-Cyclopentyl-5-methyl-6-oxo-6,7,8,9-tetrahydro-5H-pyrimido[4,5-b][1,4]diazepin-2-ylamino)-3-ethyl benzoic acid | 1H NMR (CD3OD): 1.28 (3H, t, J 7.5 Hz, CH2CH3), 1.51-1.54 (2H, m, alkyl-H), 1.63-1.65 (m, 2H, alkyl-H), 1.71-1.75 (2H, m, alkyl-H), 1.83 (2H, bs, alkyl-H), 2.76 (2H, q, J 7.5 Hz, CH2CH3), 2.79 (2H, dd, J 5 Hz, CH2), 3.27 (3H, s, CH3), 3.78 (2H, dd, J 5 Hz, CH2), 7.63 (1H, d, J 8 Hz, Ar—H), 7.84 (1H, s, Ar—H), 7.95 (1H, dd, J 1.5 and 8 Hz, Ar—H), 8.05 (1H, d, J 1.5 Hz, Ar—H); MS(+ve): 410.36; tR = 1.89 (Xbridge 4). |
| 193 | 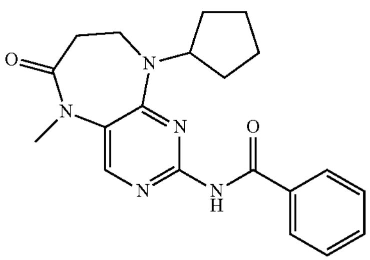 [SMILES: CN1C(=O)CCN(C2CCCC2)c2nc(NC(=O)c3ccccc3)ncc21] | | * | N-(9-Cyclopentyl-5-methyl-6-oxo-6,7,8,9-tetrahydro-5H-pyrimido[4,5-b][1,4]diazepin-2-yl)-benzamide | |

TABLE 2-continued

| Cpd | Structure | AurA IC50 | PLK1 IC50 | Name | Data |
|---|---|---|---|---|---|
| 194 | 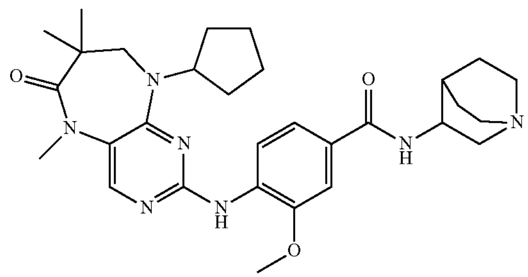 [SMILES: COc1cc(C(=O)NC2CN3CCC2CC3)ccc1Nc1ncc2c(n1)N(C1CCCC1)CC(C)(C)C(=O)N2C] | | *** | N-(1-Aza-bicyclo[2.2.2]oct-3-yl)-4-(9-cyclopentyl-5,7,7-trimethyl-6-oxo-6,7,8,9-tetrahydro-5H-pyrimido[4,5-b][1,4]diazepin-2-ylamino)-3-methoxy-benzamide | |
| 195 | 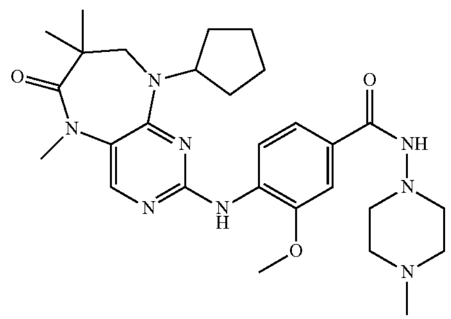 [SMILES: COc1cc(C(=O)NN2CCN(C)CC2)ccc1Nc1ncc2c(n1)N(C1CCCC1)CC(C)(C)C(=O)N2C] | | *** | 4-(9-Cyclopentyl-5,7,7-trimethyl-6-oxo-6,7,8,9-tetrahydro-5H-pyrimido[4,5-b][1,4]diazepin-2-ylamino)-3-methoxy-N-(4-methyl-piperazin-1-yl)-benzamide | |
| 196 | 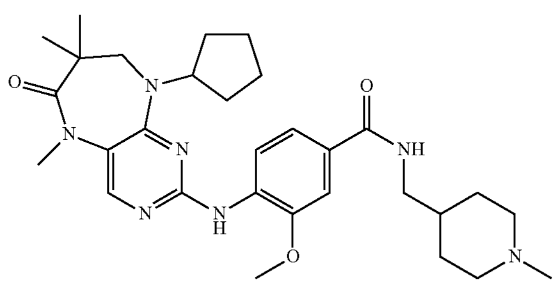 [SMILES: COc1cc(C(=O)NCC2CCN(C)CC2)ccc1Nc1ncc2c(n1)N(C1CCCC1)CC(C)(C)C(=O)N2C] | | *** | 4-(9-Cyclopentyl-5,7,7-trimethyl-6-oxo-6,7,8,9-tetrahydro-5H-pyrimido[4,5-b][1,4]diazepin-2-ylamino)-3-methoxy-N-(1-methyl-piperidin-4-ylmethyl)-benzamide | |

TABLE 2-continued

| Cpd | Structure | AurA IC50 | PLK1 IC50 | Name | Data |
|---|---|---|---|---|---|
| 197 | 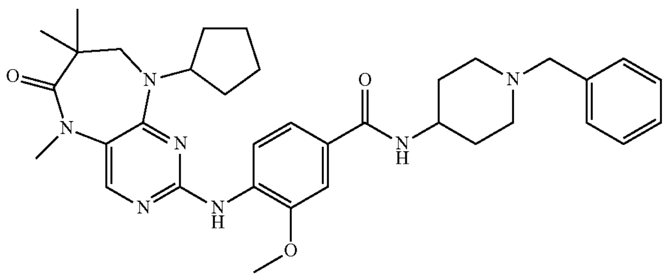 [SMILES: COc1cc(C(=O)NC2CCN(Cc3ccccc3)CC2)ccc1Nc1ncc2c(n1)N(C1CCCC1)CC(C)(C)C(=O)N2C] | | *** | N-(1-Benzyl-piperidin-4-yl)-4-(9-cyclopentyl-5,7,7-trimethyl-6-oxo-6,7,8,9-tetrahydro-5H-pyrimido[4,5-b][1,4]diazepin-2-ylamino)-3-methoxy-benzamide | |
| 198 | 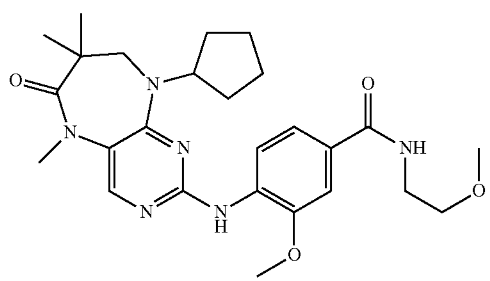 [SMILES: COCCNC(=O)c1ccc(Nc2ncc3c(n2)N(C2CCCC2)CC(C)(C)C(=O)N3C)c(OC)c1] | | ** | 4-(9-Cyclopentyl-5,7,7-trimethyl-6-oxo-6,7,8,9-tetrahydro-5H-pyrimido[4,5-b][1,4]diazepin-2-ylamino)-3-methoxy-N-(2-methoxy-ethyl)-benzamide | |
| 199 | 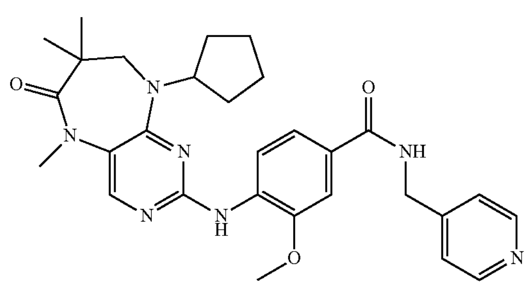 [SMILES: COc1cc(C(=O)NCc2ccncc2)ccc1Nc1ncc2c(n1)N(C1CCCC1)CC(C)(C)C(=O)N2C] | | *** | 4-(9-Cyclopentyl-5,7,7-trimethyl-6-oxo-6,7,8,9-tetrahydro-5H-pyrimido[4,5-b][1,4]diazepin-2-ylamino)-3-methoxy-N-pyridin-4-ylmethyl-benzamide | |

TABLE 2-continued

| Cpd | Structure | AurA IC50 | PLK1 IC50 | Name | Data |
|---|---|---|---|---|---|
| 200 | 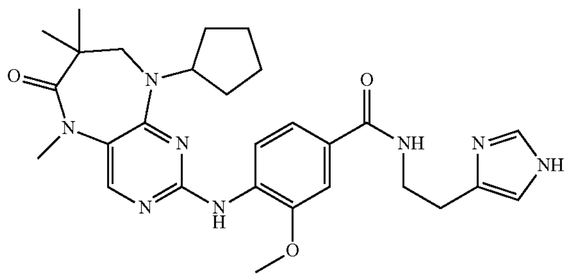 [SMILES: COc1cc(C(=O)NCCc2c[nH]cn2)ccc1Nc1ncc2c(n1)N(C1CCCC1)CC(C)(C)C(=O)N2C] | | *** | 4-(9-Cyclopentyl-5,7,7-trimethyl-6-oxo-6,7,8,9-tetrahydro-5H-pyrimido[4,5-b][1,4]diazepin-2-ylamino)-N-[2-(1H-imidazol-4-yl)-ethyl]-3-methoxy-benzamide | |
| 201 | 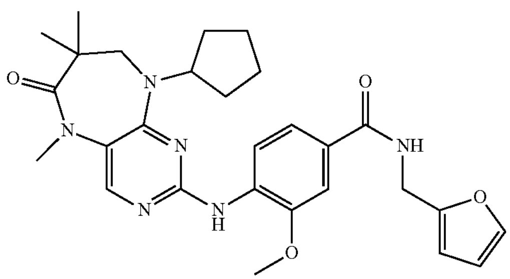 [SMILES: COc1cc(C(=O)NCc2ccco2)ccc1Nc1ncc2c(n1)N(C1CCCC1)CC(C)(C)C(=O)N2C] | | *** | 4-(9-Cyclopentyl-5,7,7-trimethyl-6-oxo-6,7,8,9-tetrahydro-5H-pyrimido[4,5-b][1,4]diazepin-2-ylamino)-N-furan-2-ylmethyl-3-methoxy-benzamide | |
| 202 | 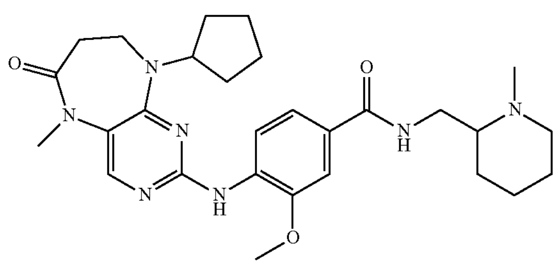 [SMILES: COc1cc(C(=O)NCC2CCCCN2C)ccc1Nc1ncc2c(n1)N(C1CCCC1)CCC(=O)N2C] | | ** | 4-(9-Cyclopentyl-5-methyl-6-oxo-6,7,8,9-tetrahydro-5H-pyrimido[4,5-b][1,4]diazepin-2-ylamino)-3-methoxy-N-(1-methyl-piperidin-2-ylmethyl)-benzamide | |

TABLE 2-continued

| Cpd | Structure | AurA IC50 | PLK1 IC50 | Name | Data |
|---|---|---|---|---|---|
| 203 | 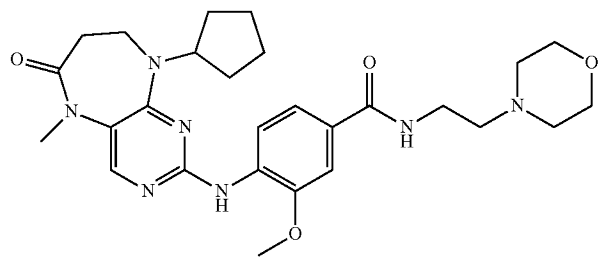 [SMILES: COc1cc(C(=O)NCCN2CCOCC2)ccc1Nc1ncc2c(n1)N(C1CCCC1)CCC(=O)N2C] | | ** | 4-(9-Cyclopentyl-5-methyl-6-oxo-6,7,8,9-tetrahydro-5H-pyrimido[4,5-b][1,4]diazepin-2-ylamino)-3-methoxy-N-(2-morpholin-4-yl-ethyl)-benzamide | |
| 204 | 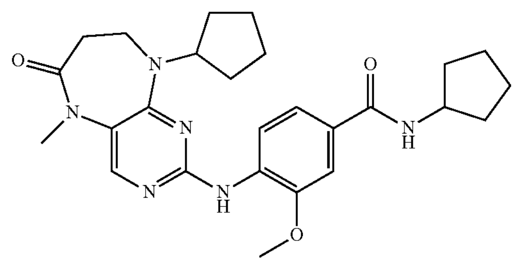 [SMILES: COc1cc(C(=O)NC2CCCC2)ccc1Nc1ncc2c(n1)N(C1CCCC1)CCC(=O)N2C] | | *** | N-Cyclopentyl-4-(9-cyclopentyl-5-methyl-6-oxo-6,7,8,9-tetrahydro-5H-pyrimido[4,5-b][1,4]diazepin-2-ylamino)-3-methoxy-benzamide | |
| 205 | 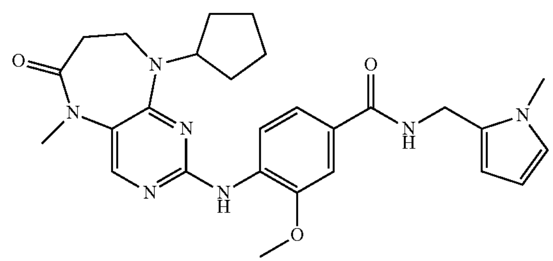 [SMILES: COc1cc(C(=O)NCc2cccn2C)ccc1Nc1ncc2c(n1)N(C1CCCC1)CCC(=O)N2C] | | *** | 4-(9-Cyclopentyl-5-methyl-6-oxo-6,7,8,9-tetrahydro-5H-pyrimido[4,5-b][1,4]diazepin-2-ylamino)-3-methoxy-N-(1-methyl-1H-pyrrol-2-ylmethyl)-benzamide | |
| 206 | 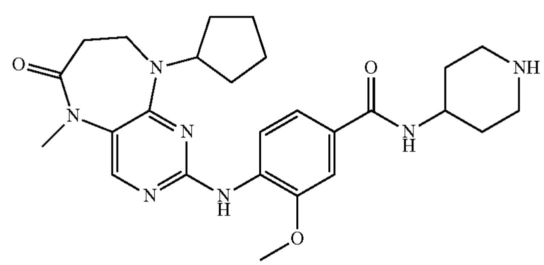 [SMILES: COc1cc(C(=O)NC2CCNCC2)ccc1Nc1ncc2c(n1)N(C1CCCC1)CCC(=O)N2C] | | *** | 4-(9-Cyclopentyl-5-methyl-6-oxo-6,7,8,9-tetrahydro-5H-pyrimido[4,5-b][1,4]diazepin-2-ylamino)-3-methoxy-N-piperidin-4-yl-benzamide | |

TABLE 2-continued

| Cpd | Structure | AurA IC50 | PLK1 IC50 | Name | Data |
|---|---|---|---|---|---|
| 207 | 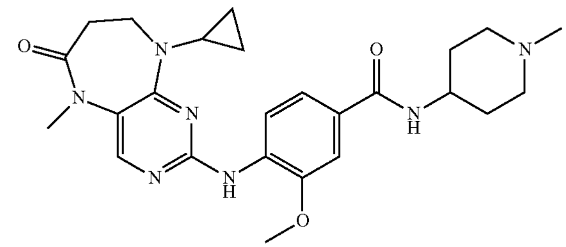 [SMILES: COc1cc(C(=O)NC2CCN(C)CC2)ccc1Nc1ncc2c(n1)N(C1CC1)CCC(=O)N2C] | | | 4-(9-Cyclopropyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide | * |
| 208 | 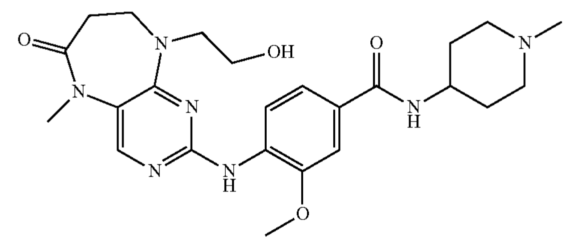 [SMILES: COc1cc(C(=O)NC2CCN(C)CC2)ccc1Nc1ncc2c(n1)N(CCO)CCC(=O)N2C] | | | 4-[9-(2-Hydroxy-ethyl)-5-methyl-6-oxo-6,7,8,9-tetrahydro-5H-pyrimido[4,5-b][1,4]diazepin-2-ylamino]-3-methoxy-N-(1-methyl-piperidin-4-yl)-benzamide | ** |
| 209 | 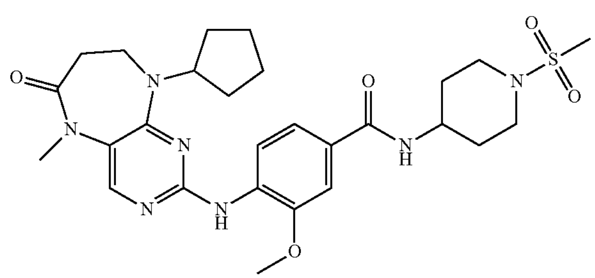 [SMILES: COc1cc(C(=O)NC2CCN(S(C)(=O)=O)CC2)ccc1Nc1ncc2c(n1)N(C1CCCC1)CCC(=O)N2C] | | | 4-(9-Cyclopentyl-5-methyl-6-oxo-6,7,8,9-tetrahydro-5H-pyrimido[4,5-b][1,4]diazepin-2-ylamino)-N-(1-methanesulfonyl-piperidin-4-yl)-3-methoxy-benzamide | ** |

TABLE 2-continued

| Cpd | Structure | AurA IC50 | PLK1 IC50 | Name | Data |
|---|---|---|---|---|---|
| 210 | 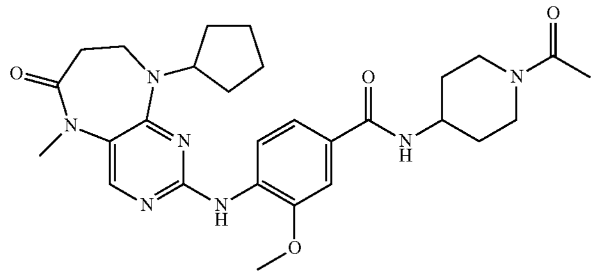 [SMILES: COc1cc(C(=O)NC2CCN(C(C)=O)CC2)ccc1Nc1ncc2c(n1)N(C1CCCC1)CCC(=O)N2C] | | ** | N-(1-Acetyl-piperidin-4-yl)-4-(9-cyclopentyl-5-methyl-6-oxo-6,7,8,9-tetrahydro-5H-pyrimido[4,5-b][1,4]diazepin-2-ylamino)-3-methoxy-benzamide | |
| 211 | 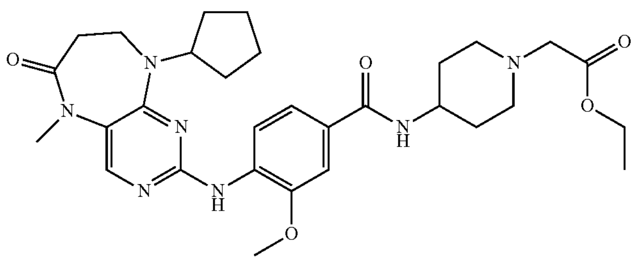 [SMILES: CCOC(=O)CN1CCC(NC(=O)c2ccc(Nc3ncc4c(n3)N(C3CCCC3)CCC(=O)N4C)c(OC)c2)CC1] | | ** | {4-[4-(9-Cyclopentyl-5-methyl-6-oxo-6,7,8,9-tetrahydro-5H-pyrimido[4,5-b][1,4]diazepin-2-ylamino)-3-methoxy-benzoylamino]-piperidin-1-yl}-acetic acid ethyl ester | |
| 212 | 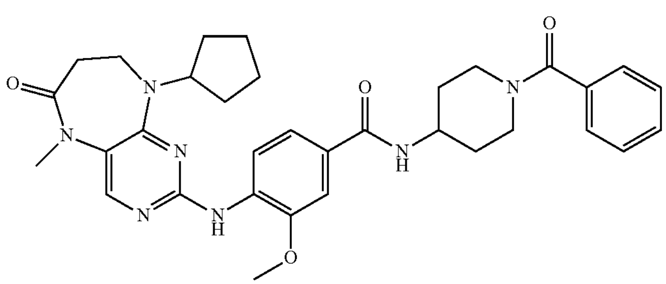 [SMILES: COc1cc(C(=O)NC2CCN(C(=O)c3ccccc3)CC2)ccc1Nc1ncc2c(n1)N(C1CCCC1)CCC(=O)N2C] | | ** | N-(1-Benzoyl-piperidin-4-yl)-4-(9-cyclopentyl-5-methyl-6-oxo-6,7,8,9-tetrahydro-5H-pyrimido[4,5-b][1,4]diazepin-2-ylamino)-3-methoxy-benzamide | |

TABLE 2-continued

| Cpd | Structure | AurA IC50 | PLK1 IC50 | Name | Data |
|---|---|---|---|---|---|
| 213 | 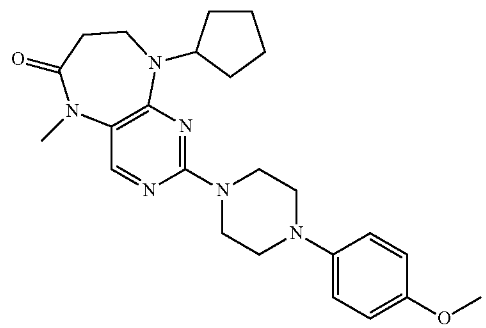 [SMILES: COc1ccc(N2CCN(c3ncc4c(n3)N(C3CCCC3)CCC(=O)N4C)CC2)cc1] | * | | 9-Cyclopentyl-2-[4-(4-methoxy-phenyl)-piperazin-1-yl]-5-methyl-5,7,8,9-tetrahydro-pyrimido[4,5-b][1,4]diazepin-6-one | |
| 214 | 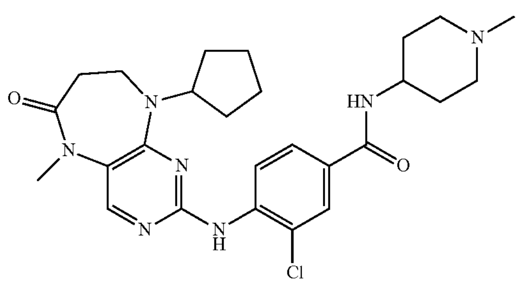 [SMILES: CN1CCC(NC(=O)c2ccc(Nc3ncc4c(n3)N(C3CCCC3)CCC(=O)N4C)c(Cl)c2)CC1] | *** | | 3-Chloro-4-(9-cyclopentyl-5-methyl-6-oxo-6,7,8,9-tetrahydro-5H-pyrimido[4,5-b][1,4]diazepin-2-ylamino)-N-(1-methyl-piperidin-4-yl)-benzamide | |
| 215 | 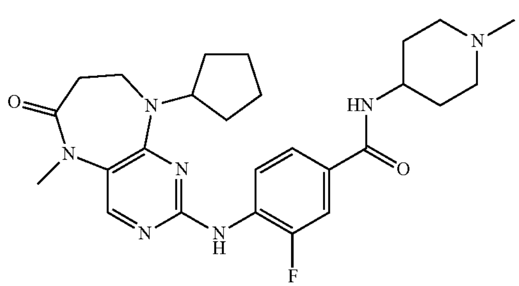 [SMILES: CN1CCC(NC(=O)c2ccc(Nc3ncc4c(n3)N(C3CCCC3)CCC(=O)N4C)c(F)c2)CC1] | * | | 4-(9-Cyclopentyl-5-methyl-6-oxo-6,7,8,9-tetrahydro-5H-pyrimido[4,5-b][1,4]diazepin-2-ylamino)-3-fluoro-N-(1-methyl-piperidin-4-yl)-benzamide | |

TABLE 2-continued

| Cpd | Structure | AurA IC50 | PLK1 IC50 | Name | Data |
|---|---|---|---|---|---|
| 216 | 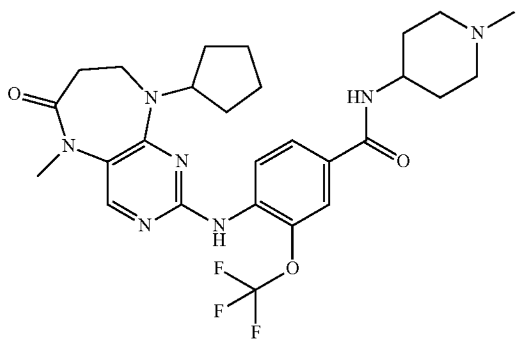 [SMILES: CN1CCC(NC(=O)c2ccc(Nc3ncc4c(n3)N(C3CCCC3)CCC(=O)N4C)c(OC(F)(F)F)c2)CC1] | | ** | 4-(9-Cyclopentyl-5-methyl-6-oxo-6,7,8,9-tetrahydro-5H-pyrimido[4,5-b][1,4]diazepin-2-ylamino)-N-(1-methyl-piperidin-4-yl)-3-trifluoromethoxy-benzamide | |
| 217 | 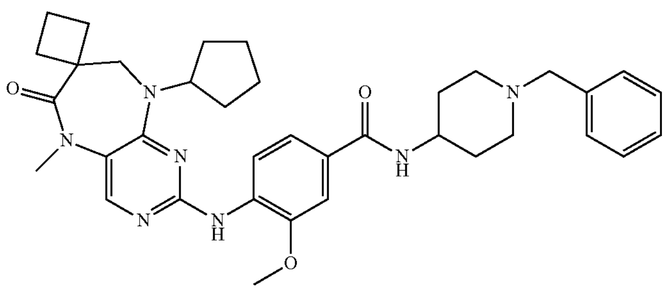 [SMILES: COc1cc(C(=O)NC2CCN(Cc3ccccc3)CC2)ccc1Nc1ncc2c(n1)N(C1CCCC1)CC1(CCC1)C(=O)N2C] | | ** | 4-(9-Cyclopentyl-5-methyl-6-oxo-6,7,8,9-tetrahydro-5H-spiro[pyrimido[4,5-b][1,4]diazepin-3,1'-cyclobutane]-2-ylamino)-3-methoxy-N-(1-benzylpiperidin-4-yl)-benzamide | |
| 218 | 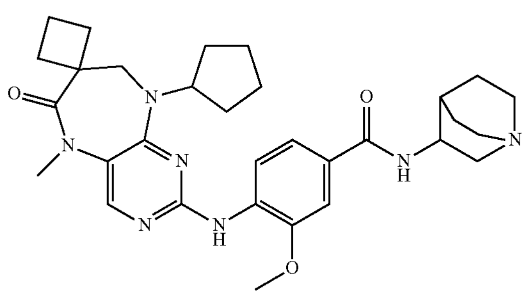 [SMILES: COc1cc(C(=O)NC2CN3CCC2CC3)ccc1Nc1ncc2c(n1)N(C1CCCC1)CC1(CCC1)C(=O)N2C] | | *** | N-(1-Aza-bicyclo[2.2.2]oct-3-yl)-4-(9-Cyclopentyl-5-methyl-6-oxo-6,7,8,9-tetrahydro-5H-spiro[pyrimido[4,5-b][1,4]diazepin-3,1'-cyclobutane]-2-ylamino)-3-methoxy-benzamide | |

TABLE 2-continued

| Cpd | Structure | AurA IC50 | PLK1 IC50 | Name | Data |
|---|---|---|---|---|---|
| 219 | 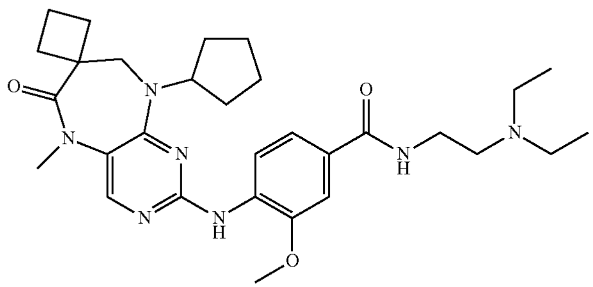 [SMILES: CCN(CC)CCNC(=O)c1ccc(Nc2ncc3c(n2)N(C2CCCC2)CC2(CCC2)C(=O)N3C)c(OC)c1] | | *** | 4-(9-Cyclopentyl-5-methyl-6-oxo-6,7,8,9-tetrahydro-5H-spiro[pyrimido[4,5-b][1,4]diazepin-3,1'-cyclobutane]-2-ylamino)-N-(2-diethylamino-ethyl)-3-methoxy-benzamide | |
| 220 | 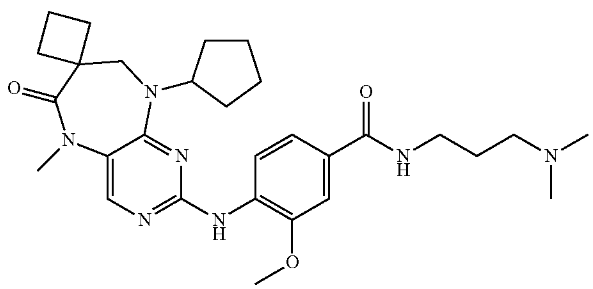 [SMILES: COc1cc(C(=O)NCCCN(C)C)ccc1Nc1ncc2c(n1)N(C1CCCC1)CC1(CCC1)C(=O)N2C] | | *** | 4-(9-Cyclopentyl-5-methyl-6-oxo-6,7,8,9-tetrahydro-5H-spiro[pyrimido[4,5-b][1,4]diazepin-3,1'-cyclobutane]-2-ylamino)-N-(2-dimethylamino-propyl)-3-methoxy-benzamide | |
| 221 | 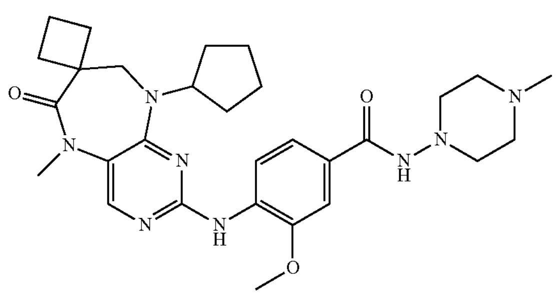 [SMILES: COc1cc(C(=O)NN2CCN(C)CC2)ccc1Nc1ncc2c(n1)N(C1CCCC1)CC1(CCC1)C(=O)N2C] | | *** | 4-(9-Cyclopentyl-5-methyl-6-oxo-6,7,8,9-tetrahydro-5H-spiro[pyrimido[4,5-b][1,4]diazepin-3,1'-cyclobutane]-2-ylamino)-N-(4-methyl-piperazin-1-yl)-3-methoxy-benzamide | |

TABLE 2-continued

| Cpd | Structure | AurA IC50 | PLK1 IC50 | Name | Data |
|---|---|---|---|---|---|
| 222 | 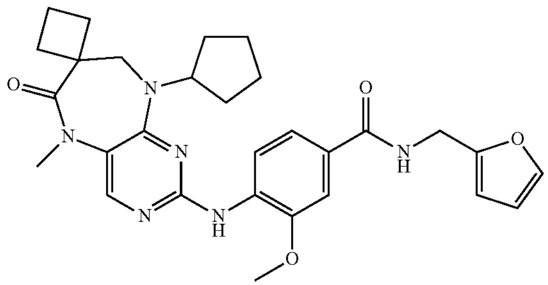 [SMILES: COc1cc(C(=O)NCc2ccco2)ccc1Nc1ncc2c(n1)N(C1CCCC1)CC1(CCC1)C(=O)N2C] | | ** | 4-(9-Cyclopentyl-5-methyl-6-oxo-6,7,8,9-tetrahydro-5H-spiro[pyrimido[4,5-b][1,4]diazepin-3,1'-cyclobutane]-2-ylamino)-N-furan-2-ylmethyl-3-methoxy-benzamide | |
| 223 | 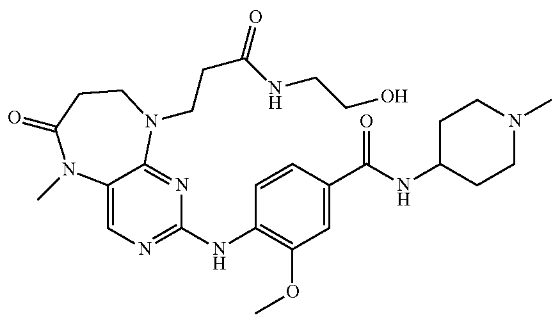 [SMILES: COc1cc(C(=O)NC2CCN(C)CC2)ccc1Nc1ncc2c(n1)N(CCC(=O)NCCO)CCC(=O)N2C] | | * | 4-{9-[2-(2-Hydroxy-ethylcarbamoyl)-ethyl]-5-methyl-6-oxo-6,7,8,9-tetrahydro-5H-pyrimido[4,5-b][1,4]diazepin-2-ylamino}-3-methoxy-N-(1-methyl-piperidin-4-yl)-benzamide | |
| 224 | 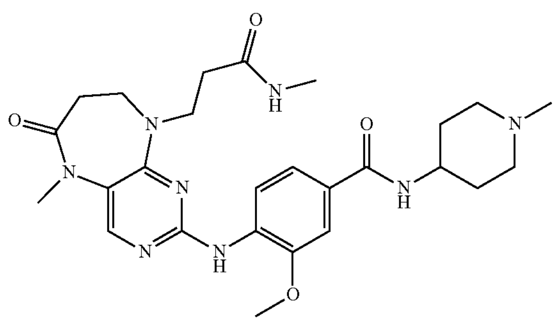 [SMILES: CNC(=O)CCN1CCC(=O)N(C)c2cnc(Nc3ccc(C(=O)NC4CCN(C)CC4)cc3OC)nc21] | | ** | 3-Methoxy-4-[5-methyl-9-(2-methylcarbamoyl-ethyl)-6-oxo-6,7,8,9-tetrahydro-5H-pyrimido[4,5-b][1,4]diazepin-2-ylamino]-N-(1-methyl-piperidin-4-yl)-benzamide | |

TABLE 2-continued

| Cpd | Structure | AurA IC50 | PLK1 IC50 | Name Data |
|---|---|---|---|---|
| 225 | 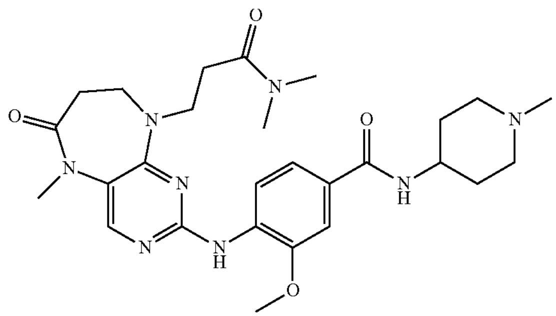 [SMILES: COc1cc(C(=O)NC2CCN(C)CC2)ccc1Nc1ncc2c(n1)N(CCC(=O)N(C)C)CCC(=O)N2C] | ** | | 4-[9-(2-Dimethylcarbamoyl-ethyl)-5-methyl-6-oxo-6,7,8,9-tetrahydro-5H-pyrimido[4,5-b][1,4]diazepin-2-ylamino]-3-methoxy-N-(1-methyl-piperidin-4-yl)-benzamide |
| 226 | 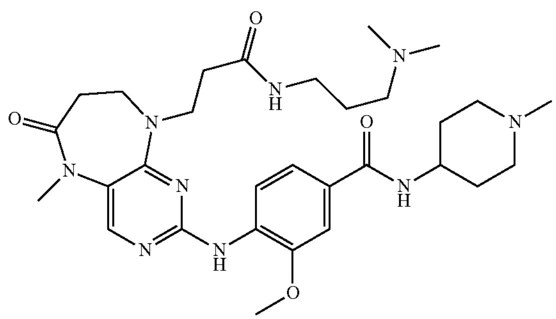 [SMILES: COc1cc(C(=O)NC2CCN(C)CC2)ccc1Nc1ncc2c(n1)N(CCC(=O)NCCCN(C)C)CCC(=O)N2C] | ** | | 4-{9-[2-(3-Dimethylamino-propylcarbamoyl)-ethyl]-5-methyl-6-oxo-6,7,8,9-tetrahydro-5H-pyrimido[4,5-b][1,4]diazepin-2-ylamino}-3-methoxy-N-(1-methyl-piperidin-4-yl)-benzamide |
| 227 | 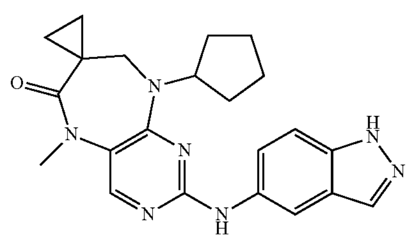 [SMILES: CN1C(=O)C2(CC2)CN(C2CCCC2)c2nc(Nc3ccc4[nH]ncc4c3)ncc21] |  | * | 9-Cyclopentyl-2-(1H-indazol-5-ylamino)-5-methyl-5,7,8,9-tetrahydro-pyrimido[4,5-b][1,4]diazepin-3,1'-cyclopropane-6-one |

TABLE 2-continued

| Cpd | Structure | AurA IC50 | PLK1 IC50 | Name | Data |
|---|---|---|---|---|---|
| 228 | 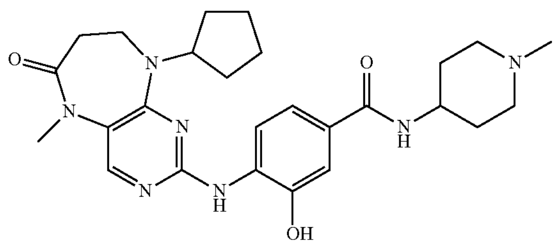 [SMILES: CN1CCC(NC(=O)c2ccc(Nc3ncc4c(n3)N(C3CCCC3)CCC(=O)N4C)c(O)c2)CC1] | | *** | 4-(9-Cyclopentyl-5-methyl-6-oxo-6,7,8,9-tetrahydro-5H-pyrimido[4,5-b][1,4]diazepin-2-ylamino)-3-hydroxy-N-(1-methyl-piperidin-4-yl)-benzamide | |
| 229 | 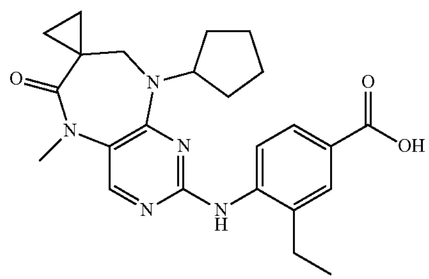 [SMILES: CCc1cc(C(=O)O)ccc1Nc1ncc2c(n1)N(C1CCCC1)CC1(CC1)C(=O)N2C] | | ** | 4-(9-Cyclopentyl-5-methyl-6-oxo-6,7,8,9-tetrahydro-5H-pyrimido[4,5-b][1,4]diazepin-3,1'-cyclopropane-2-ylamino)-3-ethyl-benzoic acid | |
| 230 | 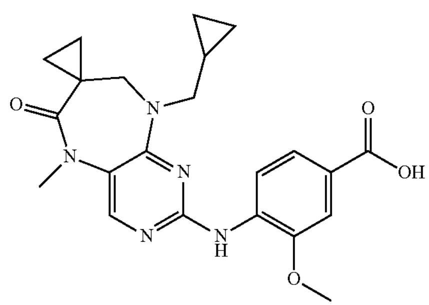 [SMILES: COc1cc(C(=O)O)ccc1Nc1ncc2c(n1)N(CC1CC1)CC1(CC1)C(=O)N2C] | | ** | 4-(9-Cyclopropylmethyl-5-methyl-6-oxo-6,7,8,9-tetrahydro-5H-pyrimido[4,5-b][1,4]diazepin-3,1'-cyclopropane-2-ylamino)-3-methoxy-benzoic acid | |

TABLE 2-continued

| Cpd | Structure | AurA IC50 | PLK1 IC50 | Name | Data |
|---|---|---|---|---|---|
| 231 | 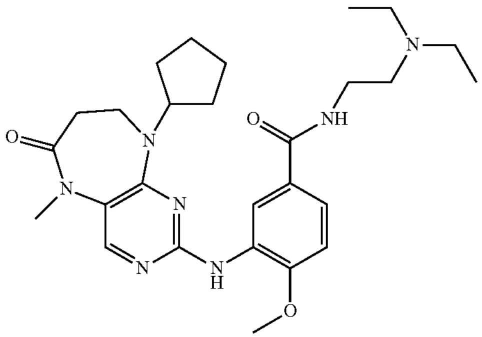 [SMILES: CCN(CC)CCNC(=O)c1ccc(OC)c(Nc2ncc3c(n2)N(C2CCCC2)CCC(=O)N3C)c1] | | ** | 3-(9-Cyclopentyl-5-methyl-6-oxo-6,7,8,9-tetrahydro-5H-pyrimido[4,5-b][1,4]diazepin-2-ylamino)-N-(2-diethylamino-ethyl)-4-methoxy-benzamide | |
| 232 | 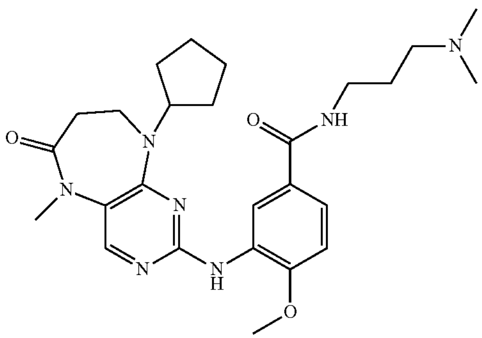 [SMILES: COc1ccc(C(=O)NCCCN(C)C)cc1Nc1ncc2c(n1)N(C1CCCC1)CCC(=O)N2C] | | ** | 3-(9-Cyclopentyl-5-methyl-6-oxo-6,7,8,9-tetrahydro-5H-pyrimido[4,5-b][1,4]diazepin-2-ylamino)-N-(3-dimethylamino-propyl)-4-methoxy-benzamide | |
| 233 | 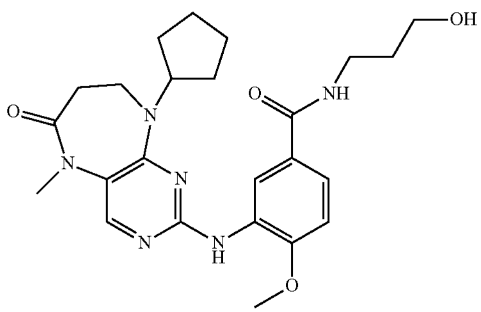 [SMILES: COc1ccc(C(=O)NCCCO)cc1Nc1ncc2c(n1)N(C1CCCC1)CCC(=O)N2C] | | ** | 3-(9-Cyclopentyl-5-methyl-6-oxo-6,7,8,9-tetrahydro-5H-pyrimido[4,5-b][1,4]diazepin-2-ylamino)-N-(3-hydroxy-propyl)-4-methoxy-benzamide | |

TABLE 2-continued

| Cpd | Structure | AurA IC50 | PLK1 IC50 | Name | Data |
|---|---|---|---|---|---|
| 234 | 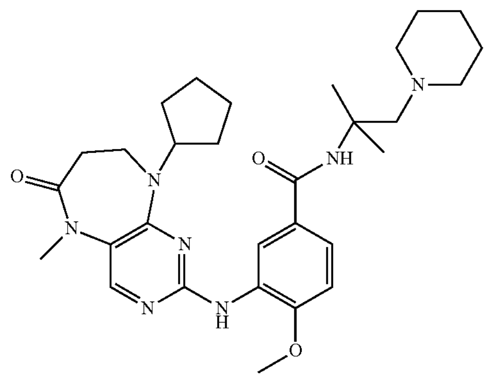 [SMILES: COc1ccc(C(=O)NC(C)(C)CN2CCCCC2)cc1Nc1ncc2c(n1)N(C1CCCC1)CCC(=O)N2C] | | | 3-(9-Cyclopentyl-5-methyl-6-oxo-6,7,8,9-tetrahydro-5H-pyrimido[4,5-b][1,4]diazepin-2-ylamino)-N-(1,1-dimethyl-2-piperidin-1-yl-ethyl)-4-methoxy-benzamide | * |
| 235 | 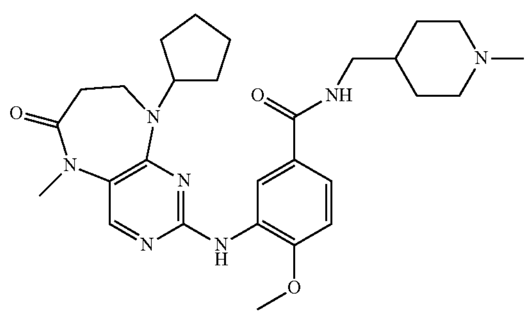 [SMILES: COc1ccc(C(=O)NCC2CCN(C)CC2)cc1Nc1ncc2c(n1)N(C1CCCC1)CCC(=O)N2C] | | | 3-(9-Cyclopentyl-5-methyl-6-oxo-6,7,8,9-tetrahydro-5H-pyrimido[4,5-b][1,4]diazepin-2-ylamino)-4-methoxy-N-(1-methyl-piperidin-4-ylmethyl)-benzamide | ** |
| 236 | 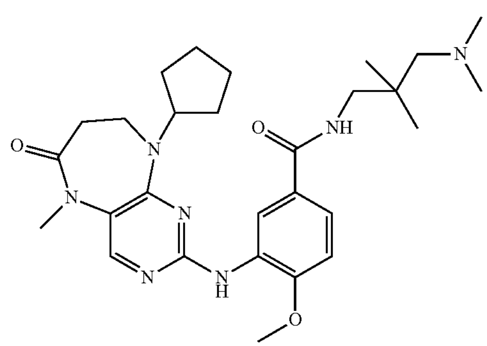 [SMILES: COc1ccc(C(=O)NCC(C)(C)CN(C)C)cc1Nc1ncc2c(n1)N(C1CCCC1)CCC(=O)N2C] | | | 3-(9-Cyclopentyl-5-methyl-6-oxo-6,7,8,9-tetrahydro-5H-pyrimido[4,5-b][1,4]diazepin-2-ylamino)-N-(3-dimethylamino-2,2-dimethyl-propyl)-4-methoxy-benzamide | |

TABLE 2-continued

| Cpd | Structure | AurA IC50 | PLK1 IC50 | Name | Data |
|---|---|---|---|---|---|
| 237 | 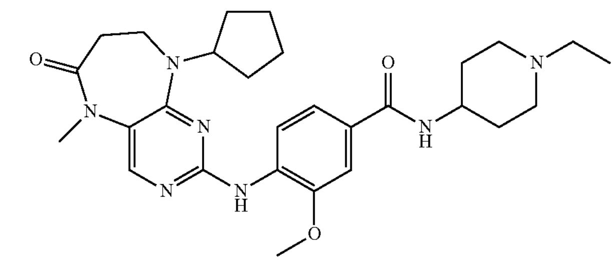 [SMILES: CCN1CCC(NC(=O)c2ccc(Nc3ncc4c(n3)N(C3CCCC3)CCC(=O)N4C)c(OC)c2)CC1] | | *** | 4-(9-Cyclopentyl-5-methyl-6-oxo-6,7,8,9-tetrahydro-5H-pyrimido[4,5-b][1,4]diazepin-2-ylamino)-N-(1-ethyl-piperidin-4-yl)-3-methoxy-benzamide | |
| 238 | 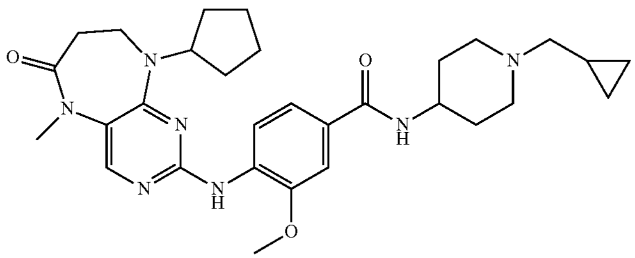 [SMILES: COc1cc(C(=O)NC2CCN(CC3CC3)CC2)ccc1Nc1ncc2c(n1)N(C1CCCC1)CCC(=O)N2C] | | *** | 4-(9-Cyclopentyl-5-methyl-6-oxo-6,7,8,9-tetrahydro-5H-pyrimido[4,5-b][1,4]diazepin-2-ylamino)-N-(1-cyclopropylmethyl-piperidin-4-yl)-3-methoxy-benzamide | |
| 239 | 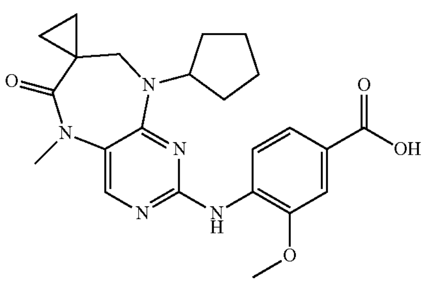 [SMILES: COc1cc(C(=O)O)ccc1Nc1ncc2c(n1)N(C1CCCC1)CC1(CC1)C(=O)N2C] | | ** | 4-(9-Cyclopentyl-5-methyl-6-oxo-6,7,8,9-tetrahydro-5H-pyrimido[4,5-b][1,4]diazepin-3,1'-cyclopropane-2-ylamino)-3-methoxy-benzoic acid | |

TABLE 2-continued

| Cpd | Structure | AurA IC50 | PLK1 IC50 | Name | Data |
|---|---|---|---|---|---|
| 240 | 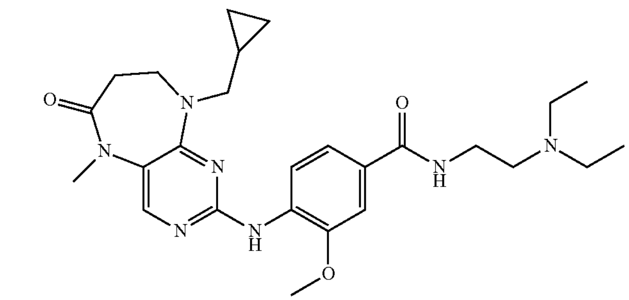 [SMILES: CCN(CC)CCNC(=O)c1ccc(Nc2ncc3c(n2)N(CC2CC2)CCC(=O)N3C)c(OC)c1] | | *** | 4-(9-Cyclopropylmethyl-5-methyl-6-oxo-6,7,8,9-tetrahydro-5H-pyrimido[4,5-b][1,4]diazepin-2-ylamino)-N-(2-diethylamino-ethyl)-3-methoxy-benzamide | |
| 241 | 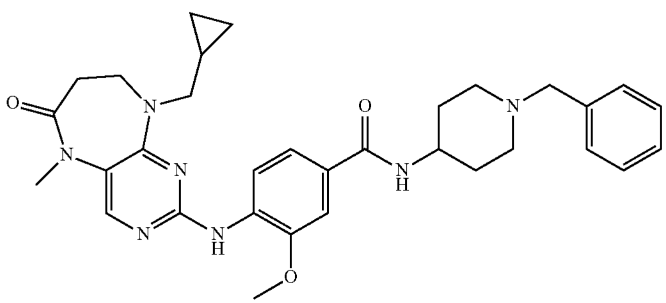 [SMILES: COc1cc(C(=O)NC2CCN(Cc3ccccc3)CC2)ccc1Nc1ncc2c(n1)N(CC1CC1)CCC(=O)N2C] | | ** | N-(1-Benzyl-piperidin-4-yl)-4-(9-cyclopropylmethyl-5-methyl-6-oxo-6,7,8,9-tetrahydro-5H-pyrimido[4,5-b][1,4]diazepin-2-ylamino)-3-methoxy-benzamide | |
| 242 | 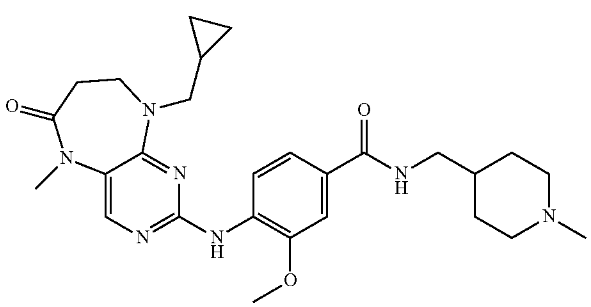 [SMILES: COc1cc(C(=O)NCC2CCN(C)CC2)ccc1Nc1ncc2c(n1)N(CC1CC1)CCC(=O)N2C] | | ** | 4-(9-Cyclopropylmethyl-5-methyl-6-oxo-6,7,8,9-tetrahydro-5H-pyrimido[4,5-b][1,4]diazepin-2-ylamino)-3-methoxy-N-(1-methyl-piperidin-4-ylmethyl)-benzamide | |

TABLE 2-continued

| Cpd | Structure | AurA IC50 | PLK1 IC50 | Name | Data |
|---|---|---|---|---|---|
| 243 | 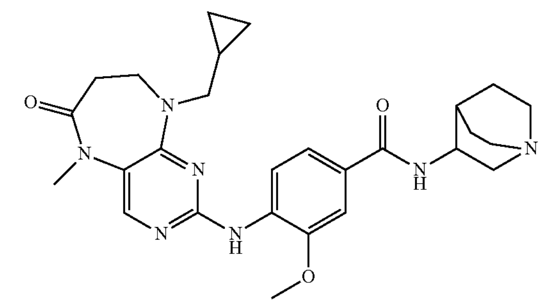 [SMILES: COc1cc(C(=O)NC2CN3CCC2CC3)ccc1Nc1ncc2c(n1)N(CC1CC1)CCC(=O)N2C] | | ** | N-(1-Aza-bicyclo[2.2.2]oct-3-yl)-4-(9-cyclopropylmethyl-5-methyl-6-oxo-6,7,8,9-tetrahydro-5H-pyrimido[4,5-b][1,4]diazepin-2-ylamino)-3-methoxy-benzamide | |
| 244 | 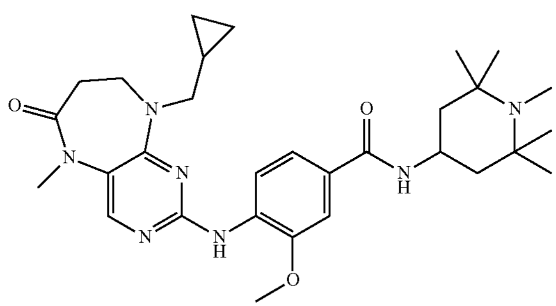 [SMILES: COc1cc(C(=O)NC2CC(C)(C)N(C)C(C)(C)C2)ccc1Nc1ncc2c(n1)N(CC1CC1)CCC(=O)N2C] | | ** | 4-(9-Cyclopropylmethyl-5-methyl-6-oxo-6,7,8,9-tetrahydro-5H-pyrimido[4,5-b][1,4]diazepin-2-ylamino)-3-methoxy-N-(1,2,2,6,6-pentamethyl-piperidin-4-yl)-benzamide | |
| 245 | 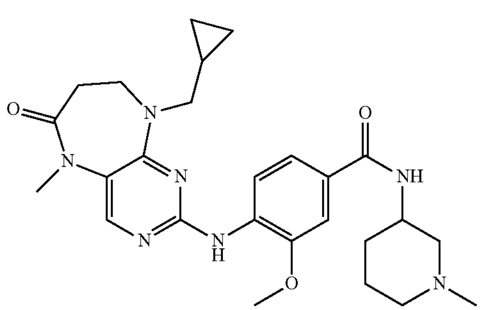 [SMILES: COc1cc(C(=O)NC2CCCN(C)C2)ccc1Nc1ncc2c(n1)N(CC1CC1)CCC(=O)N2C] | | ** | 4-(9-Cyclopropylmethyl-5-methyl-6-oxo-6,7,8,9-tetrahydro-5H-pyrimido[4,5-b][1,4]diazepin-2-ylamino)-3-methoxy-N-(1-methyl-piperidin-3-yl)-benzamide | |

TABLE 2-continued

| Cpd | Structure | AurA IC50 | PLK1 IC50 | Name | Data |
|-----|-----------|-----------|-----------|------|------|
| 246 | 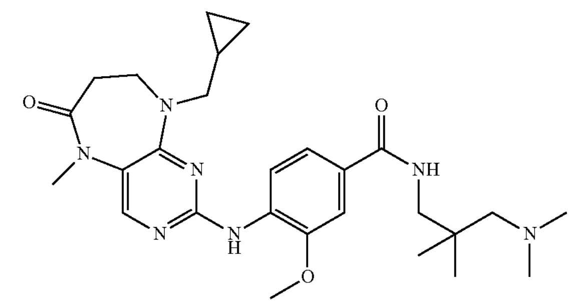 [SMILES: COc1cc(C(=O)NCC(C)(C)CN(C)C)ccc1Nc1ncc2c(n1)N(CC1CC1)CCC(=O)N2C] | | ** | 4-(9-Cyclopropylmethyl-5-methyl-6-oxo-6,7,8,9-tetrahydro-5H-pyrimido[4,5-b][1,4]diazepin-2-ylamino)-N-(3-dimethylamino-2,2-dimethyl-propyl)-3-methoxy-benzamide | |
| 247 | 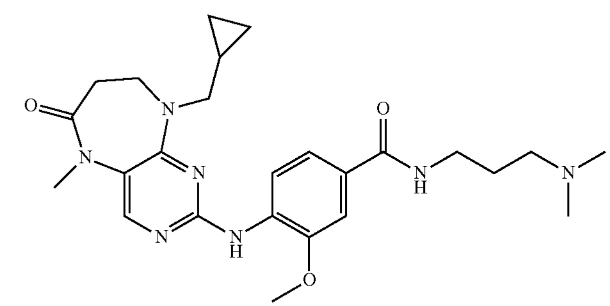 [SMILES: COc1cc(C(=O)NCCCN(C)C)ccc1Nc1ncc2c(n1)N(CC1CC1)CCC(=O)N2C] | | ** | 4-(9-Cyclopropylmethyl-5-methyl-6-oxo-6,7,8,9-tetrahydro-5H-pyrimido[4,5-b][1,4]diazepin-2-ylamino)-N-(3-dimethylamino-propyl)-3-methoxy-benzamide | |
| 248 | 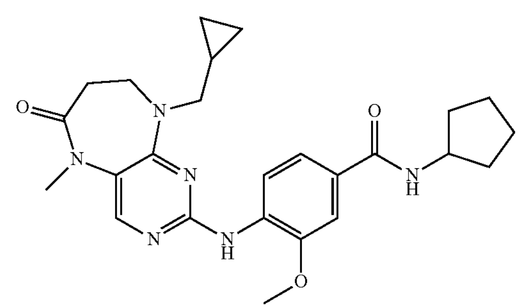 [SMILES: COc1cc(C(=O)NC2CCCC2)ccc1Nc1ncc2c(n1)N(CC1CC1)CCC(=O)N2C] | | ** | N-Cyclopentyl-4-(9-cyclopropylmethyl-5-methyl-6-oxo-6,7,8,9-tetrahydro-5H-pyrimido[4,5-b][1,4]diazepin-2-ylamino)-3-methoxy-benzamide | |

TABLE 2-continued

| Cpd | Structure | AurA IC50 | PLK1 IC50 | Name | Data |
|---|---|---|---|---|---|
| 249 | 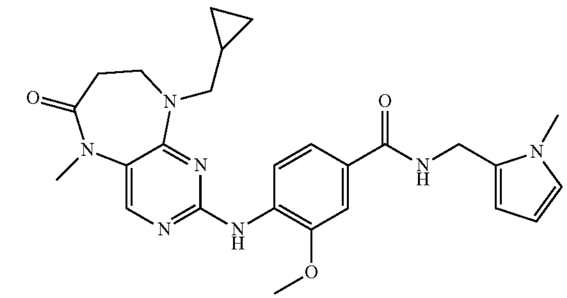 [SMILES: COc1cc(C(=O)NCc2cccn2C)ccc1Nc1ncc2c(n1)N(CC1CC1)CCC(=O)N2C] | | ** | 4-(9-Cyclopropylmethyl-5-methyl-6-oxo-6,7,8,9-tetrahydro-5H-pyrimido[4,5-b][1,4]diazepin-2-ylamino)-3-methoxy-N-(1-methyl-1H-pyrrol-2-ylmethyl)-benzamide | |
| 250 | 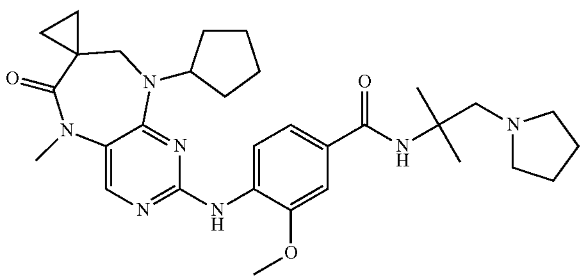 [SMILES: COc1cc(C(=O)NC(C)(C)CN2CCCC2)ccc1Nc1ncc2c(n1)N(C1CCCC1)CC1(CC1)C(=O)N2C] | | ** | 4-(9-Cyclopentyl-5-methyl-6-oxo-6,7,8,9-tetrahydro-5H-pyrimido[4,5-b][1,4]diazepin-3,1'-cyclopropane-2-ylamino)-N-(1,1-dimethyl-2-pyrrolidin-1-yl-ethyl)-3-methoxy-benzamide | |
| 251 | 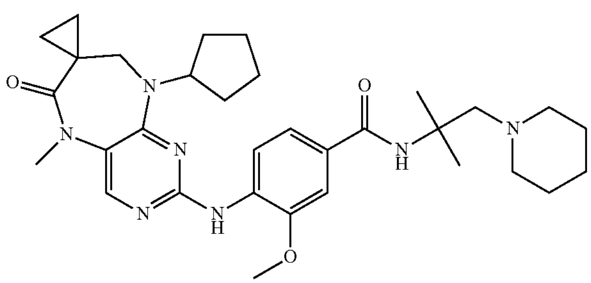 [SMILES: COc1cc(C(=O)NC(C)(C)CN2CCCCC2)ccc1Nc1ncc2c(n1)N(C1CCCC1)CC1(CC1)C(=O)N2C] | | ** | 4-(9-Cyclopentyl-5-methyl-6-oxo-6,7,8,9-tetrahydro-5H-pyrimido[4,5-b][1,4]diazepin-3,1'-cyclopropane-2-ylamino)-N-(1,1-dimethyl-2-piperidin-1-yl-ethyl)-3-methoxy-benzamide | |

TABLE 2-continued

| Cpd | Structure | AurA IC50 | PLK1 IC50 | Name | Data |
|---|---|---|---|---|---|
| 252 | 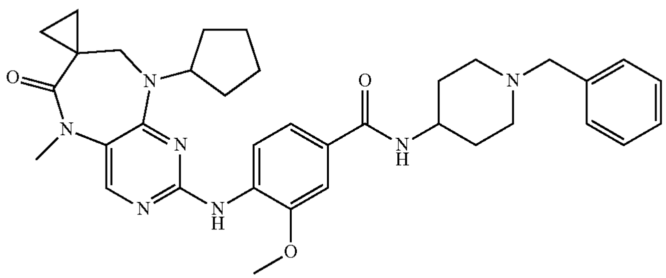 [SMILES: COc1cc(C(=O)NC2CCN(Cc3ccccc3)CC2)ccc1Nc1ncc2c(n1)N(C1CCCC1)CC1(CC1)C(=O)N2C] | | ** | 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-3-methoxy-N-(1-benzylpiperidin-4-yl)-benzamide | |
| 253 | 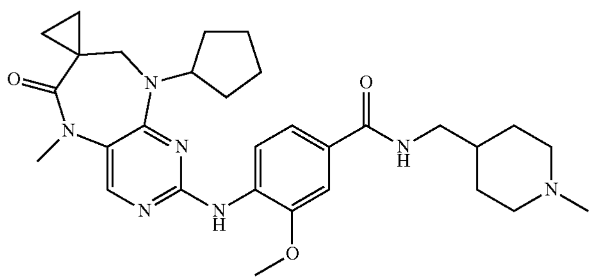 [SMILES: COc1cc(C(=O)NCC2CCN(C)CC2)ccc1Nc1ncc2c(n1)N(C1CCCC1)CC1(CC1)C(=O)N2C] | | *** | 4-(9-Cyclopentyl-5-methyl-6-oxo-6,7,8,9-tetrahydro-5H-pyrimido[4,5-b][1,4]diazepin-3,1'-cyclopropane-2-ylamino)-3-methoxy-N-(1-methyl-piperidin-4-ylmethyl)-benzamide | |
| 254 | 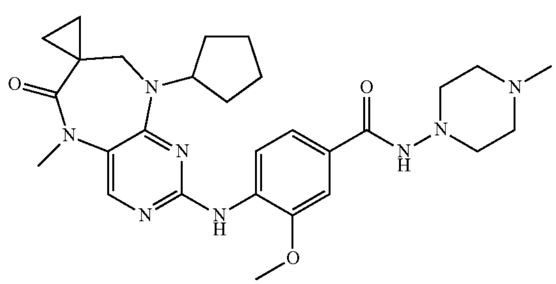 [SMILES: COc1cc(C(=O)NN2CCN(C)CC2)ccc1Nc1ncc2c(n1)N(C1CCCC1)CC1(CC1)C(=O)N2C] | | *** | 4-(9-Cyclopentyl-5-methyl-6-oxo-6,7,8,9-tetrahydro-5H-pyrimido[4,5-b][1,4]diazepin-3,1'-cyclopropane-2-ylamino)-3-methoxy-N-(4-methyl-piperazin-1-yl)-benzamide | |

TABLE 2-continued

| Cpd | Structure | AurA IC50 | PLK1 IC50 | Name | Data |
|---|---|---|---|---|---|
| 255 | 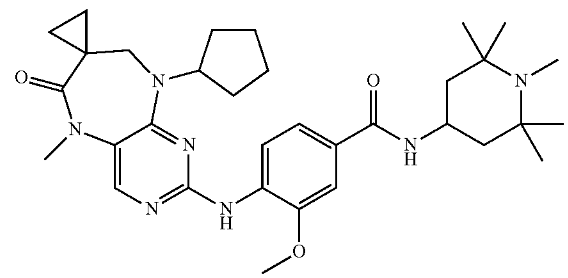 [SMILES: COc1cc(C(=O)NC2CC(C)(C)N(C)C(C)(C)C2)ccc1Nc1ncc2c(n1)N(C1CCCC1)CC1(CC1)C(=O)N2C] | | *** | 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-3-methoxy-N-(1,2,2,6,6-pentamethyl-piperidin-4-yl)-benzamide | |
| 256 | 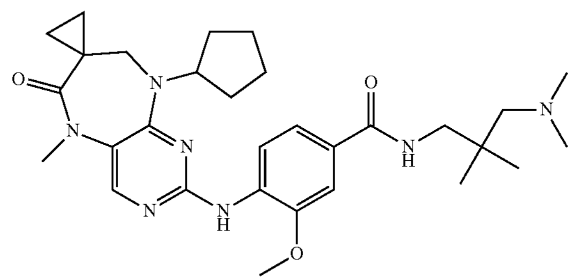 [SMILES: COc1cc(C(=O)NCC(C)(C)CN(C)C)ccc1Nc1ncc2c(n1)N(C1CCCC1)CC1(CC1)C(=O)N2C] | | *** | 4-(9-Cyclopentyl-5-methyl-6-oxo-6,7,8,9-tetrahydro-5H-pyrimido[4,5-b][1,4]diazepin-3,1'-cyclopropane-2-ylamino)-N-(3-dimethylamino-2,2-dimethyl-propyl)-3-methoxy-benzamide | |
| 257 | 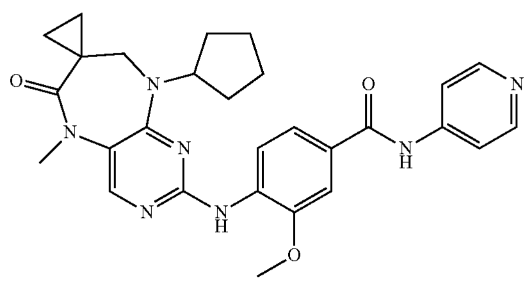 [SMILES: COc1cc(C(=O)Nc2ccncc2)ccc1Nc1ncc2c(n1)N(C1CCCC1)CC1(CC1)C(=O)N2C] | | | 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-3-methoxy-N-pyridin-4-yl-benzamide | |

TABLE 2-continued

| Cpd | Structure | AurA IC50 | PLK1 IC50 | Name | Data |
|---|---|---|---|---|---|
| 258 | 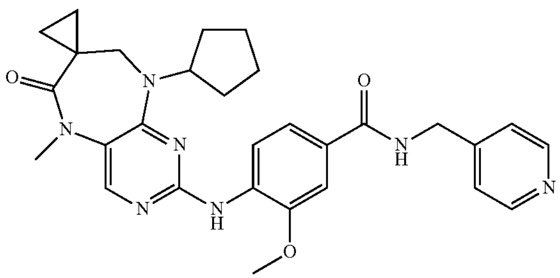 [SMILES: COc1cc(C(=O)NCc2ccncc2)ccc1Nc1ncc2c(n1)N(C1CCCC1)CC1(CC1)C(=O)N2C] | | *** | 4-(9-Cyclopentyl-5-methyl-6-oxo-6,7,8,9-tetrahydro-5H-pyrimido[4,5-b][1,4]diazepin-3,1'-cyclopropane-2-ylamino)-3-methoxy-N-pyridin-4-ylmethyl-benzamide | |
| 259 | 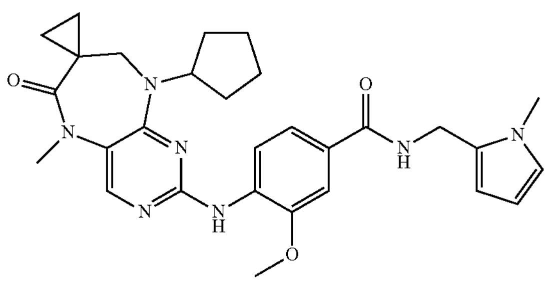 [SMILES: COc1cc(C(=O)NCc2cccn2C)ccc1Nc1ncc2c(n1)N(C1CCCC1)CC1(CC1)C(=O)N2C] | | *** | 4-(9-Cyclopentyl-5-methyl-6-oxo-6,7,8,9-tetrahydro-5H-pyrimido[4,5-b][1,4]diazepin-3,1'-cyclopropane-2-ylamino)-3-methoxy-N-(1-methyl-1H-pyrrol-2-ylmethyl)-benzamide | |
| 260 | 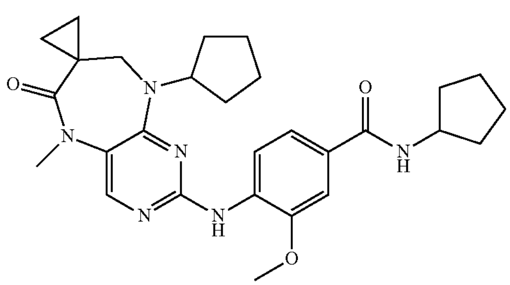 [SMILES: COc1cc(C(=O)NC2CCCC2)ccc1Nc1ncc2c(n1)N(C1CCCC1)CC1(CC1)C(=O)N2C] | | *** | N-Cyclopentyl-4-(9-Cyclopentyl-5-methyl-6-oxo-6,7,8,9-tetrahydro-5H-spiro[pyrimido[4,5-][1,4]diazepin-3,1'-cyclopropane]-2-ylamino)-3-methoxy-benzamide | |

TABLE 2-continued

| Cpd | Structure | AurA IC50 | PLK1 IC50 | Name | Data |
|---|---|---|---|---|---|
| 261 | 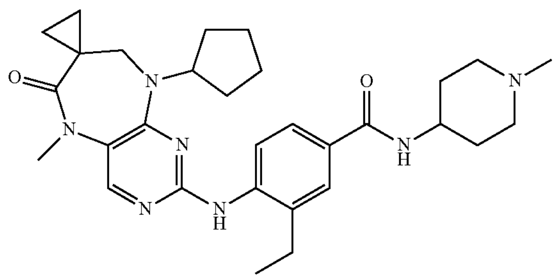 [SMILES: CCc1cc(C(=O)NC2CCN(C)CC2)ccc1Nc1ncc2c(n1)N(C1CCCC1)CC1(CC1)C(=O)N2C] | | *** | 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-3-ethyl-N-(1-methyl-piperidin-4-yl)-benzamide | |
| 262 | 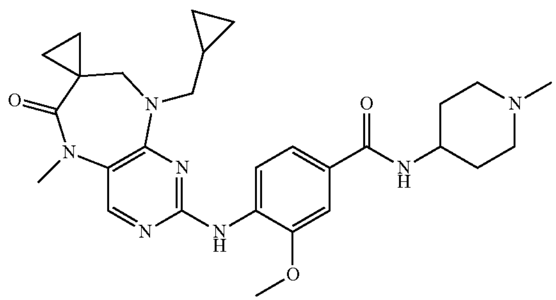 [SMILES: COc1cc(C(=O)NC2CCN(C)CC2)ccc1Nc1ncc2c(n1)N(CC1CC1)CC1(CC1)C(=O)N2C] | | *** | 4-(9-Cyclopropylmethyl-5-methyl-6-oxo-6,7,8,9-tetrahydro-5H-pyrimido[4,5-b][1,4]diazepin-3,1'-cyclopropane-2-ylamino)-3-methoxy-N-(1-methyl-piperidin-4-yl)-benzamide | |
| 263 | 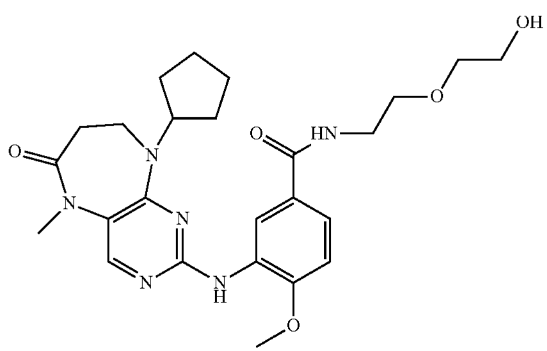 [SMILES: COc1ccc(C(=O)NCCOCCO)cc1Nc1ncc2c(n1)N(C1CCCC1)CCC(=O)N2C] | | ** | 3-(9-Cyclopentyl-5-methyl-6-oxo-6,7,8,9-tetrahydro-5H-pyrimido[4,5-b][1,4]diazepin-2-ylamino)-N-[2-(2-hydroxy-ethoxy)-ethyl]-4-methoxy-benzamide | |

TABLE 2-continued
| Cpd | Structure | AurA IC50 | PLK1 IC50 | Name | Data |
|---|---|---|---|---|---|
| 264 | 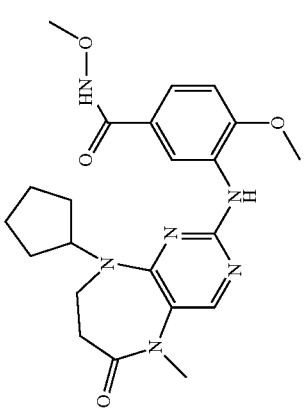 | | ** | 3-(9-Cyclopentyl-5-methyl-6-oxo-6,7,8,9-tetrahydro-5H-pyrimido[4,5-b][1,4]diazepin-2-ylamino)-4,N-dimethoxy-benzamide | |
| 265 | 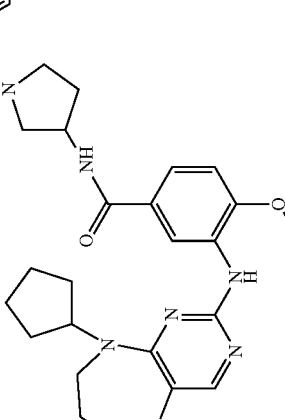 | | ** | N-(1-Benzyl-pyrrolidin-3-yl)-3-(9-cyclopentyl-5-methyl-6-oxo-6,7,8,9-tetrahydro-5H-pyrimido[4,5-b][1,4]diazepin-2-ylamino)-4-methoxy-benzamide | |
| 266 | 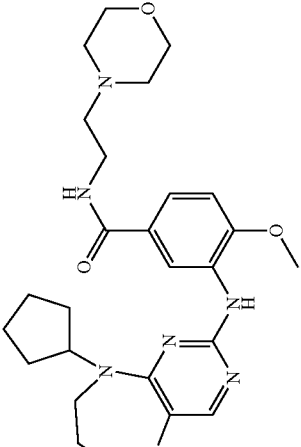 | | ** | 3-(9-Cyclopentyl-5-methyl-6-oxo-6,7,8,9-tetrahydro-5H-pyrimido[4,5-b][1,4]diazepin-2-ylamino)-4-methoxy-N-(2-morpholin-4-yl-ethyl)-benzamide | |

TABLE 2-continued

| Cpd | Structure | AurA IC50 | PLK1 IC50 | Name | Data |
|---|---|---|---|---|---|
| 267 | 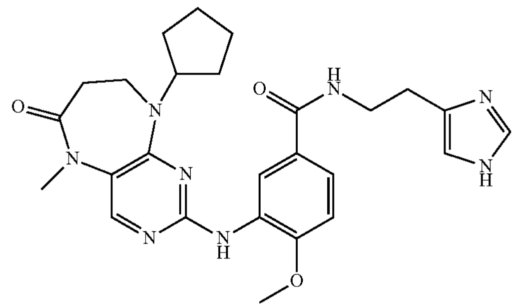 [SMILES: COc1ccc(C(=O)NCCc2c[nH]cn2)cc1Nc1ncc2c(n1)N(C1CCCC1)CCC(=O)N2C] | | ** | 3-(9-Cyclopentyl-5-methyl-6-oxo-6,7,8,9-tetrahydro-5H-pyrimido[4,5-b][1,4]diazepin-2-ylamino)-N-[2-(1H-imidazol-4-yl)-ethyl]-4-methoxy-benzamide | |
| 268 | 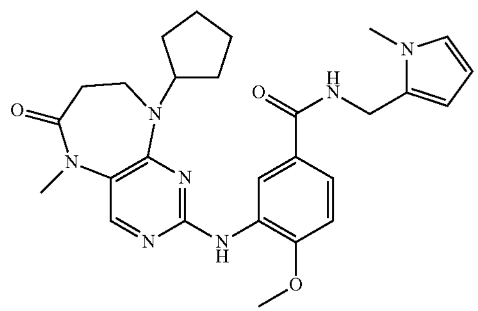 [SMILES: COc1ccc(C(=O)NCc2cccn2C)cc1Nc1ncc2c(n1)N(C1CCCC1)CCC(=O)N2C] | | ** | 3-(9-Cyclopentyl-5-methyl-6-oxo-6,7,8,9-tetrahydro-5H-pyrimido[4,5-b][1,4]diazepin-2-ylamino)-4-methoxy-N-(1-methyl-1H-pyrrol-2-ylmethyl)-benzamide | |
| 269 | 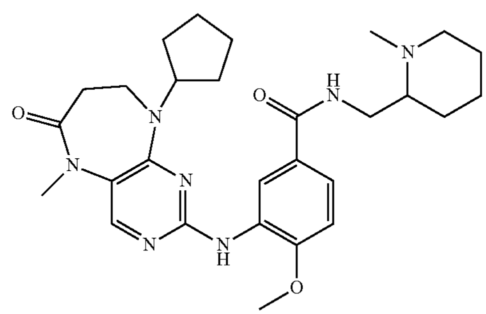 [SMILES: COc1ccc(C(=O)NCC2CCCCN2C)cc1Nc1ncc2c(n1)N(C1CCCC1)CCC(=O)N2C] | | ** | 3-(9-Cyclopentyl-5-methyl-6-oxo-6,7,8,9-tetrahydro-5H-pyrimido[4,5-b][1,4]diazepin-2-ylamino)-4-methoxy-N-(1-methyl-piperidin-2-ylmethyl)-benzamide | |

TABLE 2-continued

| Cpd | Structure | AurA IC50 | PLK1 IC50 | Name | Data |
|---|---|---|---|---|---|
| 270 | 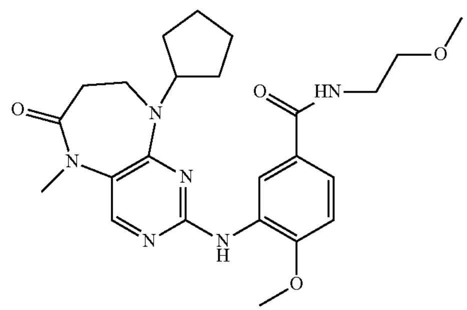 [SMILES: COCCNC(=O)c1ccc(OC)c(Nc2ncc3c(n2)N(C2CCCC2)CCC(=O)N3C)c1] | | ** | 3-(9-Cyclopentyl-5-methyl-6-oxo-6,7,8,9-tetrahydro-5H-pyrimido[4,5-b][1,4]diazepin-2-ylamino)-4-methoxy-N-(2-methoxy-ethyl)-benzamide | |
| 271 | 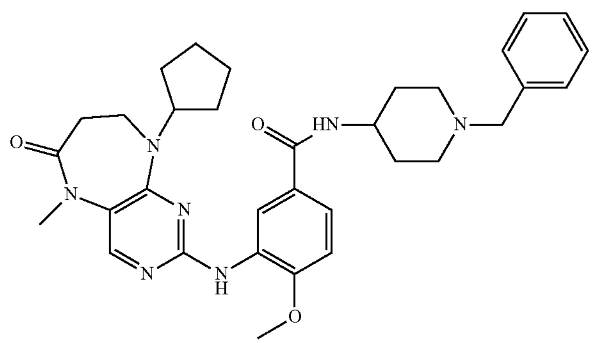 [SMILES: COc1ccc(C(=O)NC2CCN(Cc3ccccc3)CC2)cc1Nc1ncc2c(n1)N(C1CCCC1)CCC(=O)N2C] | | ** | N-(1-Benzyl-piperidin-4-yl)-3-(9-cyclopentyl-5-methyl-6-oxo-6,7,8,9-tetrahydro-5H-pyrimido[4,5-b][1,4]diazepin-2-ylamino)-4-methoxy-benzamide | |
| 272 | 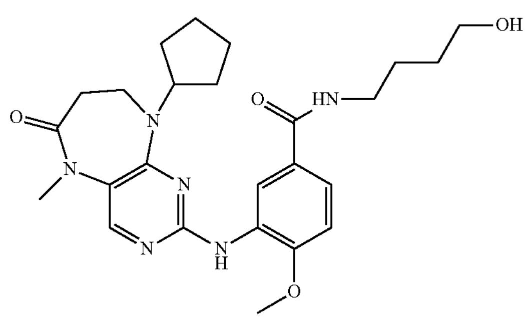 [SMILES: COc1ccc(C(=O)NCCCCO)cc1Nc1ncc2c(n1)N(C1CCCC1)CCC(=O)N2C] | | ** | 3-(9-Cyclopentyl-5-methyl-6-oxo-6,7,8,9-tetrahydro-5H-pyrimido[4,5-b][1,4]diazepin-2-ylamino)-N-(4-hydroxy-butyl)-4-methoxy-benzamide | |

TABLE 2-continued

| Cpd | Structure | AurA IC50 | PLK1 IC50 | Name | Data |
|---|---|---|---|---|---|
| 273 | 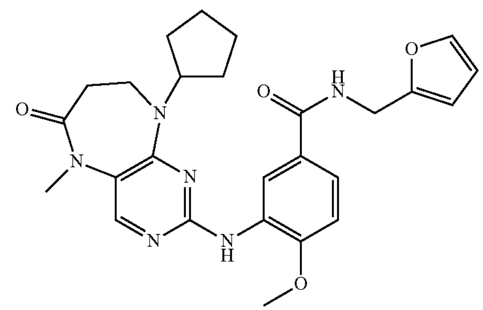 [SMILES: COc1ccc(C(=O)NCc2ccco2)cc1Nc1ncc2c(n1)N(C1CCCC1)CCC(=O)N2C] | | ** | 3-(9-Cyclopentyl-5-methyl-6-oxo-6,7,8,9-tetrahydro-5H-pyrimido[4,5-b][1,4]diazepin-2-ylamino)-N-furan-2-ylmethyl-4-methoxy-benzamide | |
| 274 | 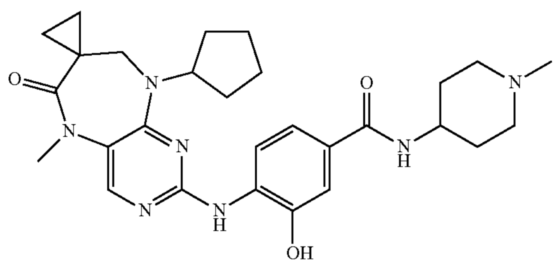 [SMILES: CN1CCC(NC(=O)c2ccc(Nc3ncc4c(n3)N(C3CCCC3)CC3(CC3)C(=O)N4C)c(O)c2)CC1] | | ** | 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-3-hydroxy-N-(1-methyl-piperidin-4-yl)-benzamide | |
| 275 | 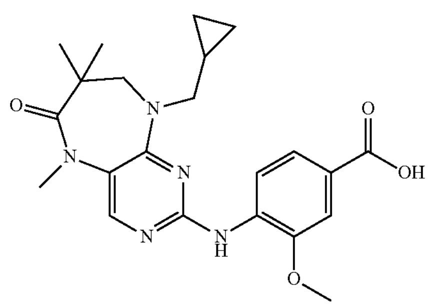 [SMILES: COc1cc(C(=O)O)ccc1Nc1ncc2c(n1)N(CC1CC1)CC(C)(C)C(=O)N2C] | | ** | 4-(9-Cyclopropylmethyl-5,7,7-trimethyl-6-oxo-6,7,8,9-tetrahydro-5H-pyrimido[4,5-b][1,4]diazepin-2-ylamino)-3-methoxy-benzoic acid | |

TABLE 2-continued

| Cpd | Structure | AurA IC50 | PLK1 IC50 | Name | Data |
|---|---|---|---|---|---|
| 276 | 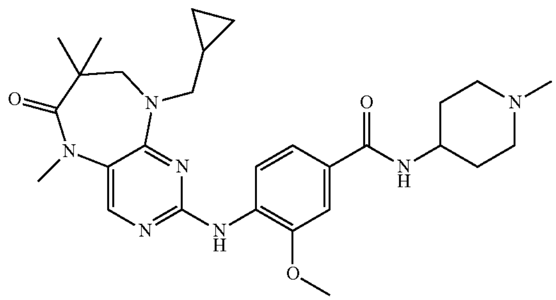 [SMILES: COc1cc(C(=O)NC2CCN(C)CC2)ccc1Nc1ncc2c(n1)N(CC1CC1)CC(C)(C)C(=O)N2C] | ** | | 4-(9-Cyclopropylmethyl-5,7,7-trimethyl-6-oxo-6,7,8,9-tetrahydro-5H-pyrimido[4,5-b][1,4]diazepin-2-ylamino)-3-methoxy-N-(1-methyl-piperidin-4-yl)-benzamide | |
| 277 | 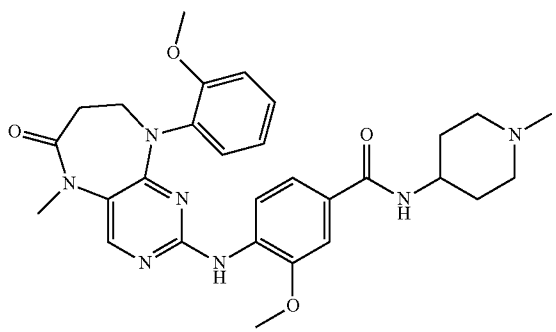 [SMILES: COc1cc(C(=O)NC2CCN(C)CC2)ccc1Nc1ncc2c(n1)N(c1ccccc1OC)CCC(=O)N2C] | * | | 3-Methoxy-4-[9-(2-methoxy-phenyl)-5-methyl-6-oxo-6,7,8,9-tetrahydro-5H-pyrimido[4,5-b][1,4]diazepin-2-ylamino]-N-(1-methyl-piperidin-4-yl)-benzamide | |
| 278 | 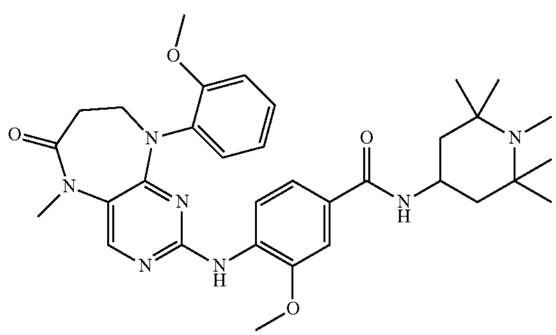 [SMILES: COc1cc(C(=O)NC2CC(C)(C)N(C)C(C)(C)C2)ccc1Nc1ncc2c(n1)N(c1ccccc1OC)CCC(=O)N2C] | * | | 3-Methoxy-4-[9-(2-methoxy-phenyl)-5-methyl-6-oxo-6,7,8,9-tetrahydro-5H-pyrimido[4,5-b][1,4]diazepin-2-ylamino]-N-(1,2,2,6,6-pentamethyl-piperidin-4-yl)-benzamide | |

TABLE 2-continued

| Cpd | Structure | AurA IC50 | PLK1 IC50 | Name |
|---|---|---|---|---|
| 279 | 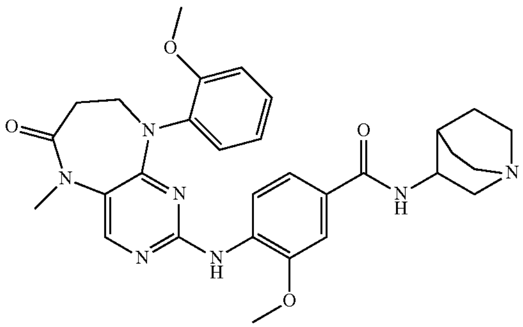 [SMILES: COc1cc(C(=O)NC2CN3CCC2CC3)ccc1Nc1ncc2c(n1)N(c1ccccc1OC)CCC(=O)N2C] | | * | N-(1-Aza-bicyclo[2.2.2]oct-3-yl)-3-methoxy-4-[9-(2-methoxy-phenyl)-5-methyl-6-oxo-6,7,8,9-tetrahydro-5H-pyrimido[4,5-b][1,4]diazepin-2-ylamino]-benzamide |
| 280 | 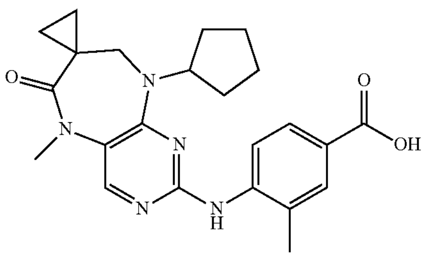 [SMILES: Cc1cc(C(=O)O)ccc1Nc1ncc2c(n1)N(C1CCCC1)CC1(CC1)C(=O)N2C] | | * | 4-(9-Cyclopentyl-5-methyl-6-oxo-6,7,8,9-tetrahydro-5H-pyrimido[4,5-b][1,4]diazepin-3,1'-cyclopropane-2-ylamino)-3-methyl-benzoic acid |
| 281 | 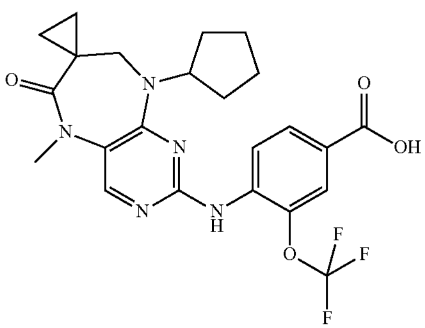 [SMILES: CN1C(=O)C2(CC2)CN(C2CCCC2)c2nc(Nc3ccc(C(=O)O)cc3OC(F)(F)F)ncc21] | | | 4-(9-Cyclopentyl-5-methyl-6-oxo-6,7,8,9-tetrahydro-5H-pyrimido[4,5-b][1,4]diazepin-3,1'-cyclopropane-2-ylamino)-3-trifluoromethoxy-benzoic acid |

TABLE 2-continued

| Cpd | Structure | AurA IC50 | PLK1 IC50 | Name | Data |
|-----|-----------|-----------|-----------|------|------|
| 282 | 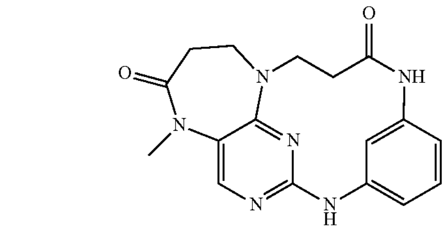 [SMILES: CN1C(=O)CCN2CCC(=O)Nc3cccc(c3)Nc3ncc1c2n3] | * | | | |
| 283 | 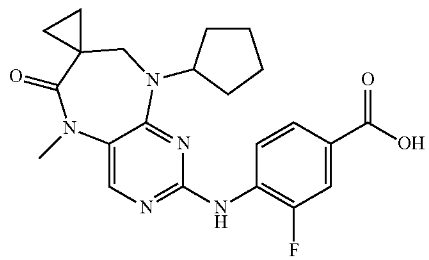 [SMILES: CN1C(=O)C2(CC2)CN(C2CCCC2)c2nc(Nc3ccc(C(=O)O)cc3F)ncc21] | | *** | 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-3-fluorobenzoic acid | |
| 284 | 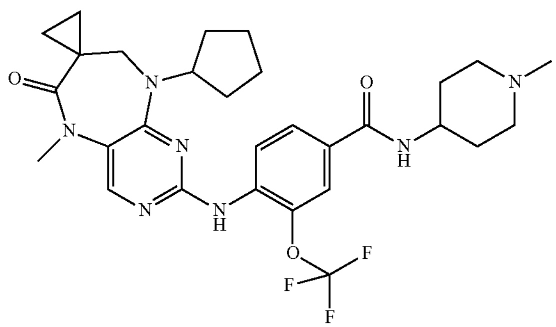 [SMILES: CN1CCC(NC(=O)c2ccc(Nc3ncc4c(n3)N(C3CCCC3)CC3(CC3)C(=O)N4C)c(OC(F)(F)F)c2)CC1] | | *** | 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-3-trifluoromethoxy-N-(1-methyl-piperidin-4-yl)-benzamide | |
| 285 | 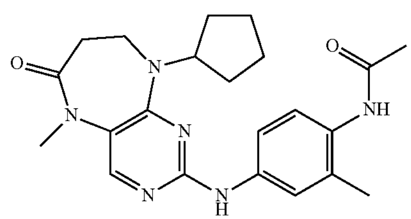 [SMILES: CC(=O)Nc1ccc(Nc2ncc3c(n2)N(C2CCCC2)CCC(=O)N3C)cc1C] | * | *** | N-[4-(9-Cyclopentyl-5-methyl-6-oxo-6,7,8,9-tetrahydro-5H-pyrimido[4,5-b][1,4]diazepin-2-ylamino)-2-methyl-phenyl]-acetamide | 1H NMR (DMSO): 1.57 (4H, m, 2CH2), 1.7 (2H, m, CH2), 1.93 (2H, m, CH2), 2.01 (3H, s, CH3), 2.14 (3H, s, CH3), 2.56 (2H, m, CH2), 3.16 (3H, s, CH3), 3.6 (2H, m, CH2), 4.83 (1H, m, CHN), 7.15 (1H, d, J 8.5 Hz, CH), 7.39 (1H, d, J 8.5 Hz, CH), 7.64 (1H, s, CH), 8.02 (1H, s, CH), 9.10 (1H, s, NH), 9.16 (1H, s, NH); MS(+ve): 409.4; tR = 2.58 min (XBridge 4). |

TABLE 2-continued

| Cpd | Structure | AurA IC50 | PLK1 IC50 | Name | Data |
|---|---|---|---|---|---|
| 286 | 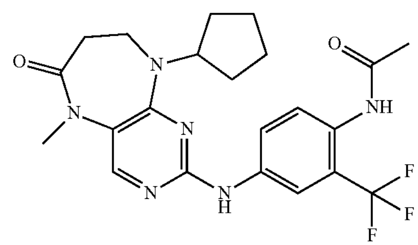 [SMILES: CC(=O)Nc1ccc(Nc2ncc3c(n2)N(C2CCCC2)CCC(=O)N3C)cc1C(F)(F)F] | | ** | N-[4-(9-Cyclopentyl-5-methyl-6-oxo-6,7,8,9-tetrahydro-5H-pyrimido[4,5-b][1,4]diazepin-2-ylamino)-2-trifluoromethyl-phenyl]-acetamide | 1H NMR (DMSO): 1.56 (4H, m, 2CH2), 1.69 (2H, m, CH2), 1.92 (2H, m, CH2), 2.01 (3H, s, CH3), 2.58 (2H, m, CH2), 3.16 (3H, s, CH3), 3.61 (2H, m, CH2), 4.84 (1H, m, CHN), 7.27 (1H, d, J 8.5 Hz, CH), 7.8 (1H, d, J 8.5 Hz, CH), 8.08 (1H, s, CH), 8.24 (1H, s, CH), 9.39 (1H, s, NH), 9.54 (1H, s, NH); MS(+ve): 463.34; tR = 2.85 min (XBridge 4). |
| 287 | 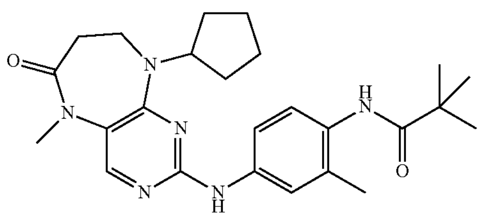 [SMILES: Cc1cc(Nc2ncc3c(n2)N(C2CCCC2)CCC(=O)N3C)ccc1NC(=O)C(C)(C)C] | | * | N-[4-(9-Cyclopentyl-5-methyl-6-oxo-6,7,8,9-tetrahydro-5H-pyrimido[4,5-b][1,4]diazepin-2-ylamino)-2-methyl-phenyl]-2,2-dimethyl-propionamide | 1H NMR (DMSO): 1.22 (9H, s, C(CH3)3), 1.58 (4H, m, 2CH2), 1.70 (2H, m, CH2), 1.94 (2H, m, CH2), 2.10 (3H, s, CH3), 2.57 (2H, m, CH2), 3.16 (3H, s, CH3), 3.60 (2H, m, CH2), 4.84 (1H, m, CHN), 6.98 (1H, d, J 8.5 Hz, CH), 7.41 (1H, d, J 8.5 Hz, CH), 7.67 (1H, s, CH), 8.03 (1H, s, CH), 8.76 (1H, s, NH), 9.14 (1H, s, NH); MS(+ve): 451.42; tR = 3.29 min (XBridge 4). |
| 288 | 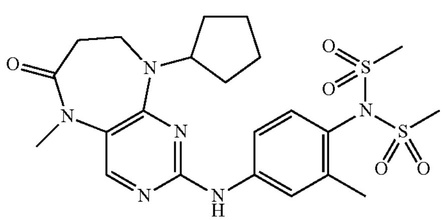 [SMILES: Cc1cc(Nc2ncc3c(n2)N(C2CCCC2)CCC(=O)N3C)ccc1N(S(C)(=O)=O)S(C)(=O)=O] | | *** | N-[4-(9-Cyclopentyl-5-methyl-6-oxo-6,7,8,9-tetrahydro-5H-pyrimido[4,5-b][1,4]diazepin-2-ylamino)-2-methyl-phenyl]-methanesulfonimide | 1H NMR (DMSO): 1.6 (4H, m, 2CH2), 1.71 (2H, m, CH2), 1.95 (2H, m, CH2), 2.3 (3H, s, CH3), 2.58 (2H, m, CH2), 3.17 (3H, s, CH3), 3.5 (6H, s, 2CH3), 3.62 (2H, m, CH2), 4.86 (1H, m, CHN), 7.27 (1H, d, J 8.5 Hz, CH), 7.51 (1H, d, J 8.5 Hz, CH), 7.86 (1H, s, CH), 8.07 (1H, s, CH), 9.42 (1H, s, NH); MS(+ve): 523.28; tR = 3.12 min (XBridge 4). |
| 289 | 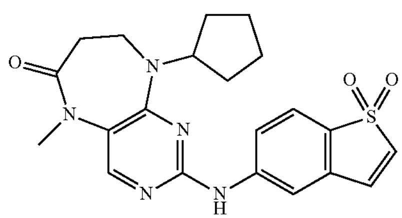 [SMILES: CN1C(=O)CCN(C2CCCC2)c2nc(Nc3ccc4c(c3)C=CS4(=O)=O)ncc21] | | ** | 9-Cyclopentyl-2-(1,1-dioxo-1H-1lambda*6*-benzo[b]thiophen-5-ylamino)-5-methyl-5,7,8,9-tetrahydro-pyrimido[4,5-b][1,4]diazepin-6-one | 1H NMR (DMSO): 1.59 (4H, m, 2CH2), 1.7 (2H, m, CH2), 1.94 (2H, m, CH2), 2.59 (2H, m, CH2), 3.18 (3H, s, CH3), 3.62 (2H, m, CH2), 4.83 (1H, m, CHN), 7.3 (1H, d, J 6.5 Hz, CH), 7.49 (1H, d, J 6.5 Hz, CH), 7.69 (1H, d, J 8.5 Hz, CH), 7.84 (1H, d, J 8.5 Hz, CH), 7.98 (1H, s, CH), 8.11 (1H, s, CH), 9.82 (1H, s, NH); MS(+ve): 426.31; tR = 2.95 min (XBridge 4). |

TABLE 2-continued

| Cpd | Structure | AurA IC50 | PLK1 IC50 | Name | Data |
|---|---|---|---|---|---|
| 290 | 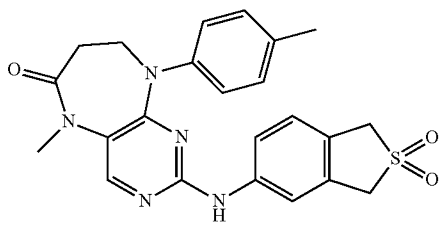 [SMILES: Cc1ccc(N2CCC(=O)N(C)c3cnc(Nc4ccc5c(c4)CS(=O)(=O)C5)nc32)cc1] | *** | * | 2-(2,2-Dioxo-2,3-dihydro-1H-2lambda*6*-benzo[c]thiophen-5-ylamino)-5-methyl-9-p-tolyl-5,7,8,9-tetrahydro-pyrimido[4,5-b][1,4]diazepin-6-one | 1H NMR (DMSO): 2.38 (3H, s, CH3), 2.78 (2H, m, CH2), 3.26 (3H, s, CH3), 4.0 (2H, m, CH2), 4.03 (2H, s, CH2), 4.31 (2H, s, CH2), 6.93 (1H, d, J 8.0 Hz, CH), 7.16 (1H, d, J 8.0 Hz, CH), 7.2 (2H, d, J 8.0 Hz, 2CH), 7.27 (2H, d, J 8.0 Hz, 2CH), 7.32 (1H, s, CH), 8.25 (1H, s, CH), 9.45 (1H, s, NH); MS(+ve): 450.33; tR = 2.82 min (XBridge 4). |
| 291 | 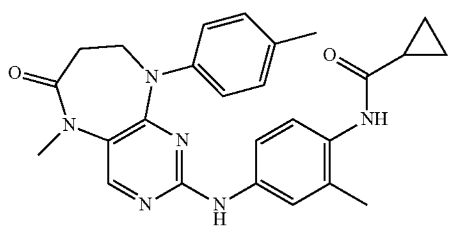 [SMILES: Cc1ccc(N2CCC(=O)N(C)c3cnc(Nc4ccc(NC(=O)C5CC5)c(C)c4)nc32)cc1] | *** | * | Cyclopropanecarboxylic acid [2-methyl-4-(5-methyl-6-oxo-9-p-tolyl-6,7,8,9-tetrahydro-5H-pyrimido[4,5-b][1,4]diazepin-2-ylamino)-phenyl]-amide | 1H NMR (DMSO): 0.72 (4H, m, 2CH2), 1.78 (1H, m, CH), 1.87 (3H, s, CH3), 2.33 (3H, s, CH3), 2.78 (2H, m, CH2), 3.25 (3H, s, CH3), 3.99 (2H, m, CH2), 6.87 (1H, m, CH), 6.96 (1H, m, CH), 7.16 (3H, m, 3CH), 7.21 (2H, d, J 8.0 Hz, 2CH), 8.25 (1H, s, CH), 9.17 (1H, s, NH), 9.24 (1H, s, NH); MS(+ve): 457.41; tR = 2.89 min (XBridge 4). |
| 292 | 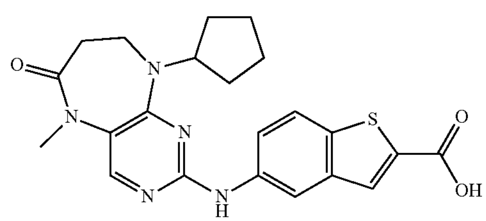 [SMILES: CN1C(=O)CCN(C2CCCC2)c2nc(Nc3ccc4sc(C(=O)O)cc4c3)ncc21] | * |  | 5-(9-Cyclopentyl-5-methyl-6-oxo-6,7,8,9-tetrahydro-5H-pyrimido[4,5-b][1,4]diazepin-2-ylamino)-benzo[b]thiophene-2-carboxylic acid | 1H NMR (DMSO): 1.60 (4H, m, 2CH2), 1.72 (2H, m, CH2), 1.97 (2H, m, CH2), 2.58 (2H, m, CH2), 3.17 (3H, s, CH3), 3.61 (2H, m, CH2), 4.87 (1H, m, CHN), 7.53 (1H, s, CH), 7.55 (1H, d, J 8.5 Hz, CH), 7.73 (1H, d, J 8.5 Hz, CH), 8.06 (1H, s, CH), 8.40 (1H, s, CH), 9.29 (1H, s, NH); MS(+ve): 438.28; tR = 1.90 min (XBridge 4). |
| 293 | 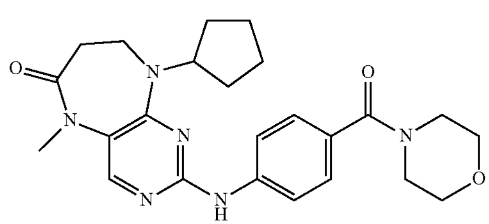 [SMILES: CN1C(=O)CCN(C2CCCC2)c2nc(Nc3ccc(C(=O)N4CCOCC4)cc3)ncc21] | *** | * | 9-Cyclopentyl-5-methyl-2-[4-(morpholine-4-carbonyl)-phenylamino]-5,7,8,9-tetrahydro-pyrimido[4,5-b][1,4]diazepin-6-one | 1H NMR (DMSO): 1.59 (4H, m, 2CH2), 1.70 (2H, m, CH2), 1.94 (2H, m, CH2), 2.57 (2H, m, CH2), 3.17 (3H, s, CH3), 3.5 (4H, m, 2CH2), 3.60 (6H, m, 3CH2), 4.81 (1H, m, CHN), 7.32 (2H, d, J 8.5 Hz, 2CH), 7.79 (2H, d, J 8.5 Hz, 2CH), 8.06 (1H, s, CH), 9.43 (1H, s, NH); MS(+ve): 451.40; tR = 2.63 min (XBridge 4). |

TABLE 2-continued

| Cpd | Structure | AurA IC50 | PLK1 IC50 | Name | Data |
|---|---|---|---|---|---|
| 294 | 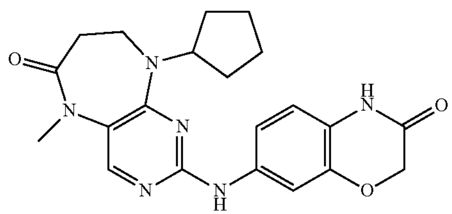 [SMILES: CN1C(=O)CCN(C2CCCC2)c2nc(Nc3ccc4c(c3)OCC(=O)N4)ncc21] | ** | | 9-Cyclopentyl-5-methyl-2-(3-oxo-3,4-dihydro-2H-benzo[1,4]oxazin-7-ylamino)-5,7,8,9-tetrahydro-pyrimido[4,5-b][1,4]diazepin-6-one | 1H NMR (DMSO): 1.58 (4H, m, 2CH2), 1.69 (2H, m, CH2), 1.93 (2H, m, CH2), 2.54 (2H, m, CH2), 3.15 (3H, s, CH3), 3.58 (2H, m, CH2), 4.51 (2H, s, CH2), 4.77 (1H, m, CHN), 6.75 (1H, d, J 8.5 Hz, CH), 7.2 (1H, d, J 8.5 Hz, CH), 7.50 (1H, s, CH), 8.02 (1H, s, CH), 9.13 (1H, s, NH), 10.5 (1H, s, NH); MS(+ve): 409.33; tR = 2.60 min (XBridge 4). |
| 295 | 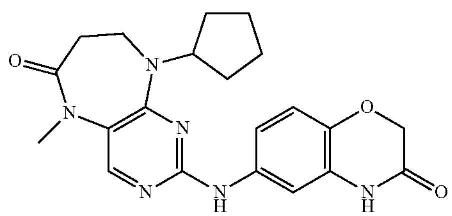 [SMILES: CN1C(=O)CCN(C2CCCC2)c2nc(Nc3ccc4c(c3)NC(=O)CO4)ncc21] | *** | * | 9-Cyclopentyl-5-methyl-2-(3-oxo-3,4-dihydro-2H-benzo[1,4]oxazin-6-ylamino)-5,7,8,9-tetrahydro-pyrimido[4,5-b][1,4]diazepin-6-one | 1H NMR (DMSO): 1.54 (4H, m, 2CH2), 1.66 (2H, m, CH2), 1.91 (2H, m, CH2), 2.55 (2H, m, CH2), 3.15 (3H, s, CH3), 3.58 (2H, m, CH2), 4.48 (2H, s, CH2), 4.74 (1H, m, CHN), 6.82 (1H, d, J 8.5 Hz, CH), 7.22 (2H, m, 2CH), 7.99 (1H, s, CH), 9.05 (1H, s, NH), 10.65 (1H, s, NH); MS(+ve): 409.33; tR = 2.75 min (XBridge 4). |
| 296 | 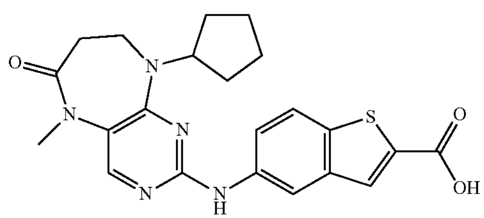 [SMILES: CN1C(=O)CCN(C2CCCC2)c2nc(Nc3ccc4sc(C(=O)O)cc4c3)ncc21] | * |  | 5-(9-Cyclopentyl-5-methyl-6-oxo-6,7,8,9-tetrahydro-5H-pyrimido[4,5-b][1,4]diazepin-2-ylamino)-benzo[b]thiophene-2-carboxylic acid | |
| 297 | 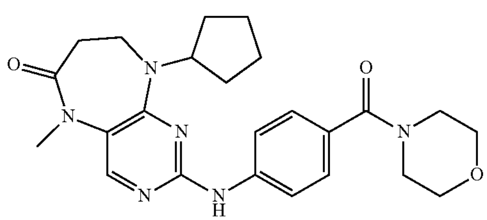 [SMILES: CN1C(=O)CCN(C2CCCC2)c2nc(Nc3ccc(C(=O)N4CCOCC4)cc3)ncc21] | *** | * | 9-Cyclopentyl-5-methyl-2-[4-(morpholine-4-carbonyl)-phenylamino]-5,7,8,9-tetrahydro-pyrimido[4,5-b][1,4]diazepin-6-one | |

TABLE 2-continued

| Cpd | AurA IC50 | PLK1 IC50 | Name | Data |
|---|---|---|---|---|
| 298 | ** |  | 9-Cyclopentyl-5-methyl-2-(3-oxo-3,4-dihydro-2H-benzo[1,4]oxazin-7-ylamino)-5,7,8,9-tetrahydro-pyrimido[4,5-b][1,4]diazepin-6-one |  |
| 299 | *** |  | 9-Cyclopentyl-5-methyl-2-(3-oxo-3,4-dihydro-2H-benzo[1,4]oxazin-6-ylamino)-5,7,8,9-tetrahydro-pyrimido[4,5-b][1,4]diazepin-6-one |  |
| 300 | *** |  | 4-(9-Cyclopentyl-5-methyl-6-oxo-6,7,8,9-tetrahydro-5H-pyrimido[4,5-b][1,4]diazepin-2-ylamino)-N,N-dimethyl-benzenesulfonamide | 1H NMR (DMSO): 1.59 (4H, m, 2CH2), 1.70 (2H, m, CH2), 1.95 (2H, m, CH2), 2.57 (8H, m, 2CH3, CH2), 3.17 (3H, s, CH3), 3.62 (2H, m, CH2), 4.82 (1H, m, CHN), 7.6 (2H, d, J 8 Hz, 2CH), 7.96 (2H, d, J 8 Hz, 2CH), 8.10 (1H, s, CH), 9.73 (1H, s, NH); MS(+ve): 445.36; tR = 3.16 min (XBridge 4). |
| 301 | ** |  | 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-3-methyl-N-(1-methyl-piperidin-4-yl)-benzamide |  |

TABLE 2-continued

| Cpd | Structure | AurA IC50 | PLK1 IC50 | Name | Data |
|---|---|---|---|---|---|
| 302 | 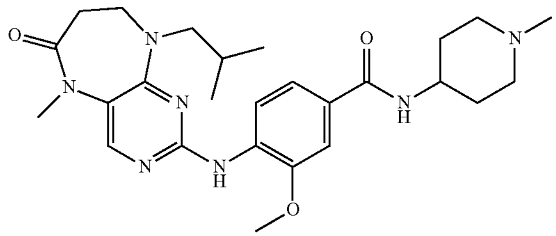 [SMILES: COc1cc(C(=O)NC2CCN(C)CC2)ccc1Nc1ncc2c(n1)N(CC(C)C)CCC(=O)N2C] | | ** | 4-(9-Isobutyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide | |
| 303 | 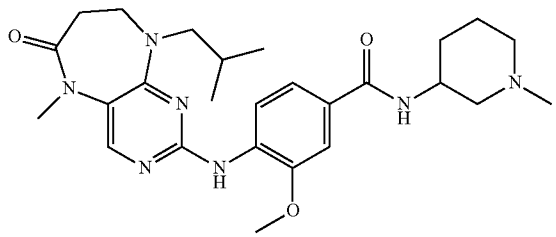 [SMILES: COc1cc(C(=O)NC2CCCN(C)C2)ccc1Nc1ncc2c(n1)N(CC(C)C)CCC(=O)N2C] | | ** | 4-(9-Isobutyl-5-methyl-6-oxo-6,7,8,9-tetrahydro-5H-pyrimido[4,5-b][1,4]diazepin-2-ylamino)-3-methoxy-N-(1-methyl-piperidin-3-yl)-benzamide | |
| 304 | 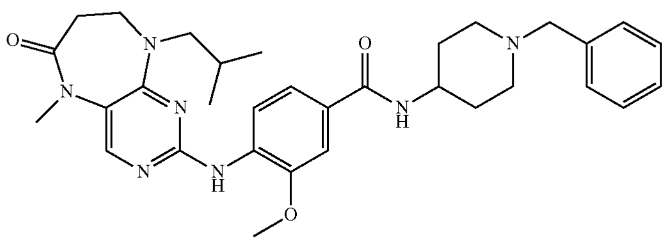 [SMILES: COc1cc(C(=O)NC2CCN(Cc3ccccc3)CC2)ccc1Nc1ncc2c(n1)N(CC(C)C)CCC(=O)N2C] | | ** | N-(1-Benzyl-piperidin-4-yl)-4-(9-isobutyl-5-methyl-6-oxo-6,7,8,9-tetrahydro-5H-pyrimido[4,5-b][1,4]diazepin-2-ylamino)-3-methoxy-benzamide | |
| 305 | 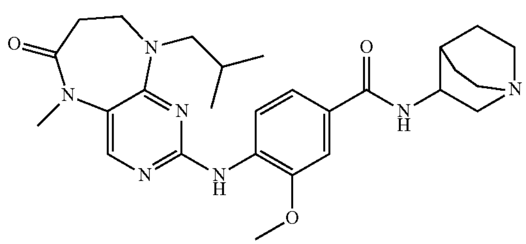 [SMILES: COc1cc(C(=O)NC2CN3CCC2CC3)ccc1Nc1ncc2c(n1)N(CC(C)C)CCC(=O)N2C] | | ** | N-(1-Aza-bicyclo[2.2.2]oct-3-yl)-4-(9-isobutyl-5-methyl-6-oxo-6,7,8,9-tetrahydro-5H-pyrimido[4,5-b][1,4]diazepin-2-ylamino)-3-methoxy-benzamide | |

TABLE 2-continued

| Cpd | Structure | AurA IC50 | PLK1 IC50 | Name | Data |
|---|---|---|---|---|---|
| 306 | 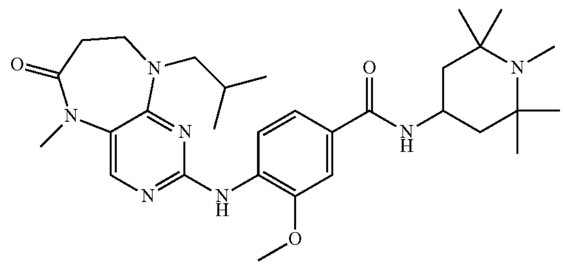 [SMILES: COc1cc(C(=O)NC2CC(C)(C)N(C)C(C)(C)C2)ccc1Nc1ncc2c(n1)N(CC(C)C)CCC(=O)N2C] | | ** | 4-(9-Isobutyl-5-methyl-6-oxo-6,7,8,9-tetrahydro-5H-pyrimido[4,5-b][1,4]diazepin-2-ylamino)-3-methoxy-N-(1,2,2,6,6-pentamethyl-piperidin-4-yl)-benzamide | |
| 307 | 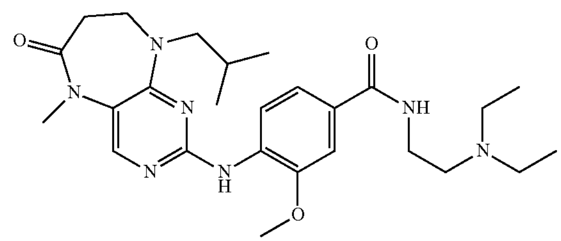 [SMILES: CCN(CC)CCNC(=O)c1ccc(Nc2ncc3c(n2)N(CC(C)C)CCC(=O)N3C)c(OC)c1] | | ** | N-(2-Diethylamino-ethyl)-4-(9-isobutyl-5-methyl-6-oxo-6,7,8,9-tetrahydro-5H-pyrimido[4,5-b][1,4]diazepin-2-ylamino)-3-methoxy-benzamide | |
| 308 | 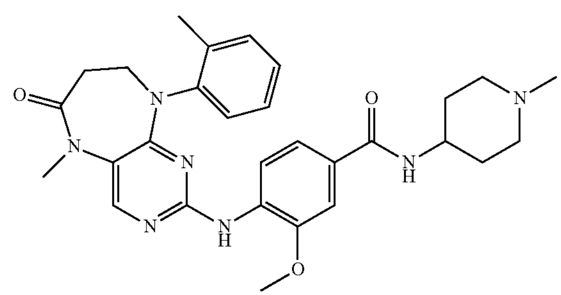 [SMILES: COc1cc(C(=O)NC2CCN(C)CC2)ccc1Nc1ncc2c(n1)N(c1ccccc1C)CCC(=O)N2C] | | * | 3-Methoxy-4-(5-methyl-6-oxo-9-o-tolyl-6,7,8,9-tetrahydro-5H-pyrimido[4,5-b][1,4]diazepin-2-ylamino)-N-(1-methyl-piperidin-4-yl)-benzamide | |

TABLE 2-continued

| Cpd | Structure | AurA IC50 | PLK1 IC50 | Name | Data |
|---|---|---|---|---|---|
| 309 | 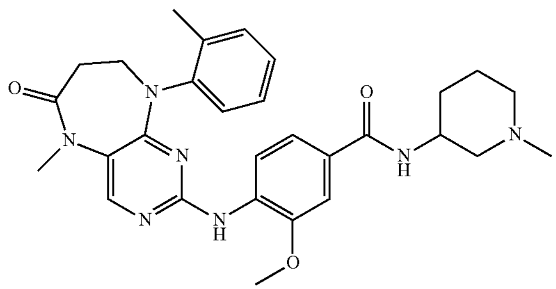 [SMILES: COc1cc(C(=O)NC2CCCN(C)C2)ccc1Nc1ncc2c(n1)N(c1ccccc1C)CCC(=O)N2C] | | * | 3-Methoxy-4-(5-methyl-6-oxo-9-o-tolyl-6,7,8,9-tetrahydro-5H-pyrimido[4,5-b][1,4]diazepin-2-ylamino)-N-(1-methyl-piperidin-3-yl)-benzamide | |
| 310 | 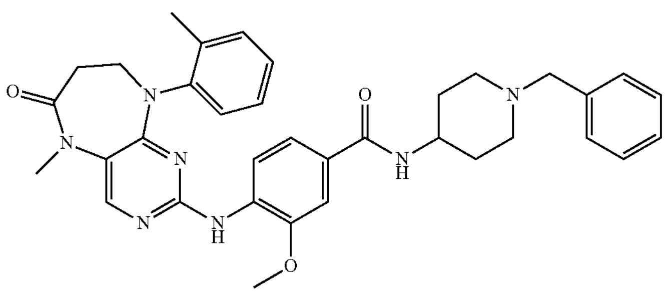 [SMILES: COc1cc(C(=O)NC2CCN(Cc3ccccc3)CC2)ccc1Nc1ncc2c(n1)N(c1ccccc1C)CCC(=O)N2C] | | * | N-(1-Benzyl-piperidin-4-yl)-3-methoxy-4-(5-methyl-6-oxo-9-o-tolyl-6,7,8,9-tetrahydro-5H-pyrimido[4,5-b][1,4]diazepin-2-ylamino)-benzamide | |
| 311 | 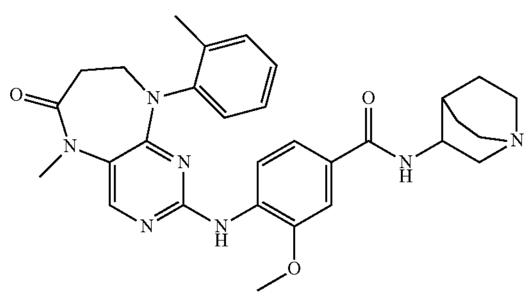 [SMILES: COc1cc(C(=O)NC2CN3CCC2CC3)ccc1Nc1ncc2c(n1)N(c1ccccc1C)CCC(=O)N2C] | | ** | N-(1-Aza-bicyclo[2.2.2]oct-3-yl)-3-methoxy-4-(5-methyl-6-oxo-9-o-tolyl-6,7,8,9-tetrahydro-5H-pyrimido[4,5-b][1,4]diazepin-2-ylamino)-benzamide | |

TABLE 2-continued

| Cpd | Structure | AurA IC50 | PLK1 IC50 | Name | Data |
|---|---|---|---|---|---|
| 312 | 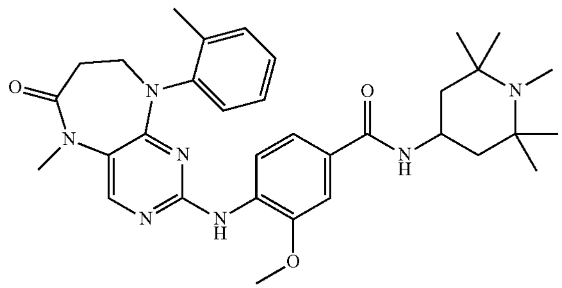 [SMILES: COc1cc(C(=O)NC2CC(C)(C)N(C)C(C)(C)C2)ccc1Nc1ncc2c(n1)N(c1ccccc1C)CCC(=O)N2C] | | * | 3-Methoxy-4-(5-methyl-6-oxo-9-o-tolyl-6,7,8,9-tetrahydro-5H-pyrimido[4,5-b][1,4]diazepin-2-ylamino)-N-(1,2,2,6,6-pentamethyl-piperidin-4-yl)-benzamide | |
| 313 | 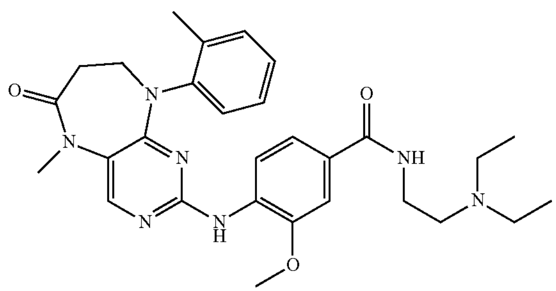 [SMILES: CCN(CC)CCNC(=O)c1ccc(Nc2ncc3c(n2)N(c2ccccc2C)CCC(=O)N3C)c(OC)c1] | | * | N-(2-Diethylamino-ethyl)-3-methoxy-4-(5-methyl-6-oxo-9-o-tolyl-6,7,8,9-tetrahydro-5H-pyrimido[4,5-b][1,4]diazepin-2-ylamino)-benzamide | |
| 314 | 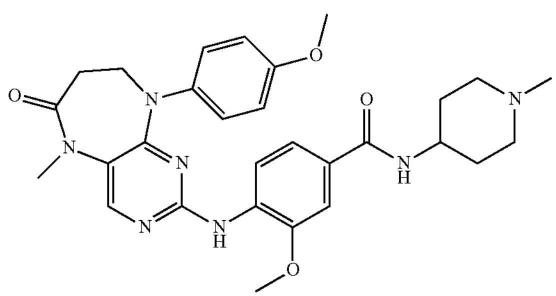 [SMILES: COc1ccc(N2CCC(=O)N(C)c3cnc(Nc4ccc(C(=O)NC5CCN(C)CC5)cc4OC)nc32)cc1] | | ** | 3-Methoxy-4-[9-(4-methoxy-phenyl)-5-methyl-6-oxo-6,7,8,9-tetrahydro-5H-pyrimido[4,5-b][1,4]diazepin-2-ylamino]-N-(1-methyl-piperidin-4-yl)-benzamide | |

TABLE 2-continued

| Cpd | Structure | AurA IC50 | PLK1 IC50 | Name | Data |
|---|---|---|---|---|---|
| 315 | 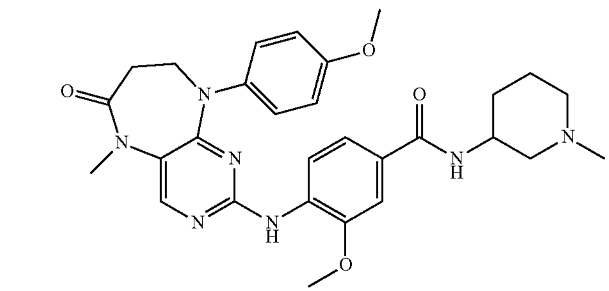 [SMILES: COc1ccc(N2CCC(=O)N(C)c3cnc(Nc4ccc(C(=O)NC5CCCN(C)C5)cc4OC)nc32)cc1] | | ** | 3-Methoxy-4-[9-(4-methoxy-phenyl)-5-methyl-6-oxo-6,7,8,9-tetrahydro-5H-pyrimido[4,5-b][1,4]diazepin-2-ylamino]-N-(1-methyl-piperidin-3-yl)-benzamide | |
| 316 | 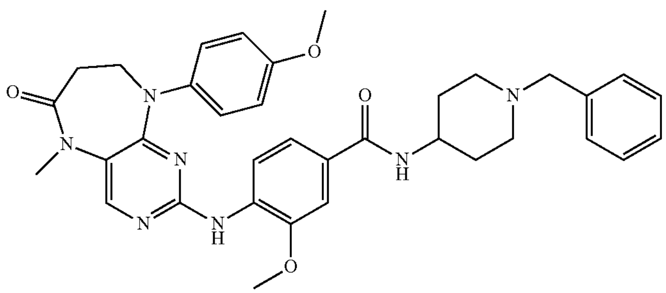 [SMILES: COc1ccc(N2CCC(=O)N(C)c3cnc(Nc4ccc(C(=O)NC5CCN(Cc6ccccc6)CC5)cc4OC)nc32)cc1] | | ** | N-(1-Benzyl-piperidin-4-yl)-3-methoxy-4-[9-(4-methoxy-phenyl)-5-methyl-6-oxo-6,7,8,9-tetrahydro-5H-pyrimido[4,5-b][1,4]diazepin-2-ylamino]-benzamide | |
| 317 | 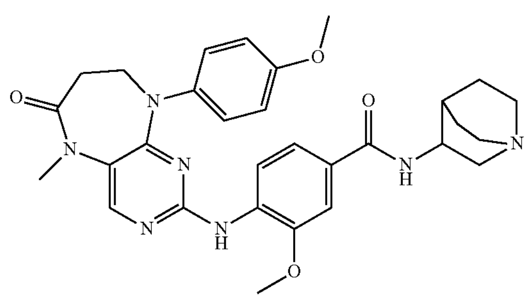 [SMILES: COc1ccc(N2CCC(=O)N(C)c3cnc(Nc4ccc(C(=O)NC5CN6CCC5CC6)cc4OC)nc32)cc1] | | ** | N-(1-Aza-bicyclo[2.2.2]oct-3-yl)-3-methoxy-4-[9-(4-methoxy-phenyl)-5-methyl-6-oxo-6,7,8,9-tetrahydro-5H-pyrimido[4,5-b][1,4]diazepin-2-ylamino]-benzamide | |

TABLE 2-continued

| Cpd | Structure | AurA IC50 | PLK1 IC50 | Name | Data |
|---|---|---|---|---|---|
| 318 | 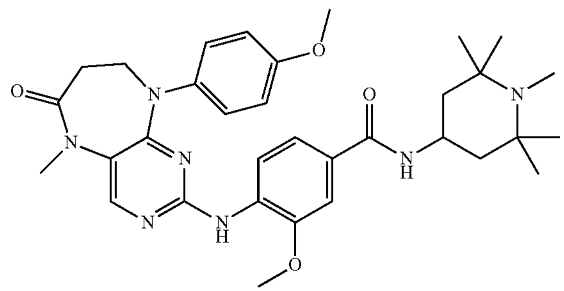 [SMILES: COc1ccc(N2CCC(=O)N(C)c3cnc(Nc4ccc(C(=O)NC5CC(C)(C)N(C)C(C)(C)C5)cc4OC)nc32)cc1] | | | 3-Methoxy-4-[9-(4-methoxy-phenyl)-5-methyl-6-oxo-6,7,8,9-tetrahydro-5H-pyrimido[4,5-b][1,4]diazepin-2-ylamino]-N-(1,2,2,6,6-pentamethyl-piperidin-4-yl)-benzamide | ** |
| 319 | 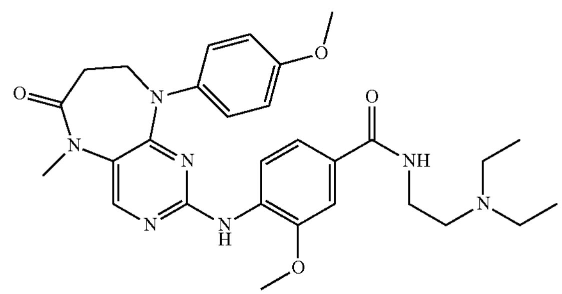 [SMILES: CCN(CC)CCNC(=O)c1ccc(Nc2ncc3c(n2)N(c2ccc(OC)cc2)CCC(=O)N3C)c(OC)c1] | | | N-(2-Diethylamino-ethyl)-3-methoxy-4-[9-(4-methoxy-phenyl)-5-methyl-6-oxo-6,7,8,9-tetrahydro-5H-pyrimido[4,5-b][1,4]diazepin-2-ylamino]-benzamide | * |
| 320 | 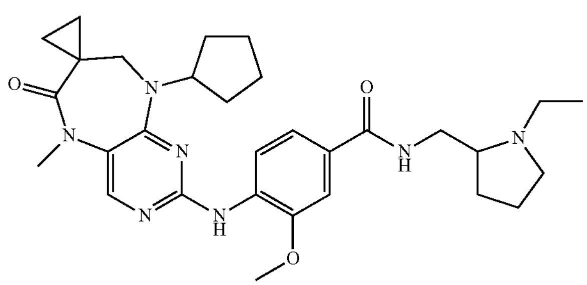 [SMILES: CCN1CCCC1CNC(=O)c1ccc(Nc2ncc3c(n2)N(C2CCCC2)CC2(CC2)C(=O)N3C)c(OC)c1] | | | 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-N-(1-ethyl-pyrrolidin-3-yl)-3-methoxy-N-benzamide | *** |

TABLE 2-continued

| Cpd | Structure | AurA IC50 | PLK1 IC50 | Name | Data |
|---|---|---|---|---|---|
| 321 | 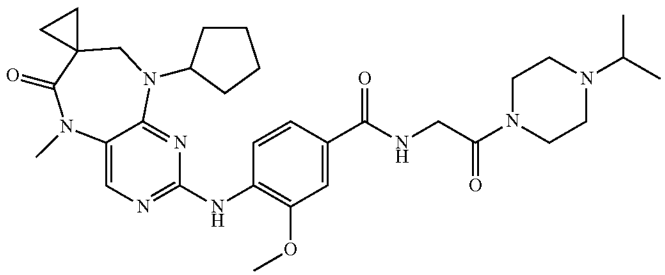 [SMILES: COc1cc(C(=O)NCC(=O)N2CCN(C(C)C)CC2)ccc1Nc1ncc2c(n1)N(C1CCCC1)CC1(CC1)C(=O)N2C] | | | 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-N-[2-(4-iso | ** |
| 322 | 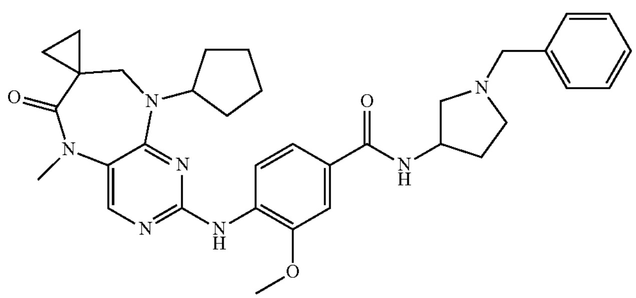 [SMILES: COc1cc(C(=O)NC2CCN(Cc3ccccc3)C2)ccc1Nc1ncc2c(n1)N(C1CCCC1)CC1(CC1)C(=O)N2C] | | | N-(1-Benzyl-pyrrolidin-3-yl)-4-(9-cyclopentyl-5-methyl-6-oxo-6,7,8,9-tetrahydro-5H-spiro[pyrimido[4,5-b][1,4]diazepin-3,1'-cyclopropane]-2-ylamino)-3-methoxy-N-benzamide | *** |
| 323 | 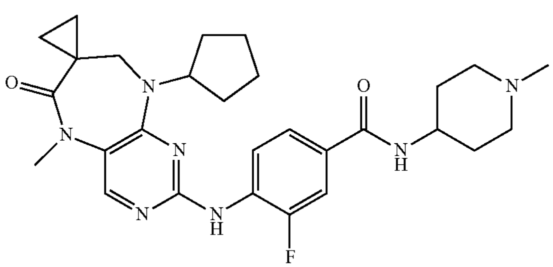 [SMILES: CN1CCC(NC(=O)c2ccc(Nc3ncc4c(n3)N(C3CCCC3)CC3(CC3)C(=O)N4C)c(F)c2)CC1] | | | 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-3-fluoro-N-(1-methyl-piperidin-4-yl)-benzamide | *** |

TABLE 2-continued

| Cpd | Structure | AurA IC50 | PLK1 IC50 | Name | Data |
|---|---|---|---|---|---|
| 324 | 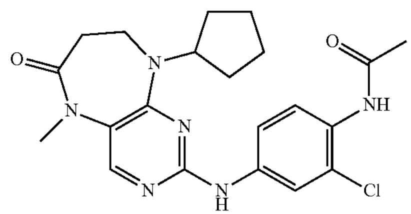 [SMILES: CC(=O)Nc1ccc(Nc2ncc3c(n2)N(C2CCCC2)CCC(=O)N3C)cc1Cl] | ** | * | N-[2-Chloro-4-(9-cyclopentyl-5-methyl-6-oxo-6,7,8,9-tetrahydro-5H-pyrimido[4,5-b][1,4]diazepin-2-ylamino)-phenyl]-acetamide | 1H NMR (DMSO): 1.60 (4H, m, 2CH2), 1.70 (2H, m, CH2), 1.96 (2H, m, CH2), 2.04 (3H, s, CH3), 2.58 (2H, m, CH2), 3.16 (3H, s, CH3), 3.61 (2H, m, CH2), 4.83 (1H, m, CHN), 7.42 (2H, s, 2CH), 8.06 (1H, s, CH), 8.15 (1H, s, CH), 9.38 (1H, s, NH), 9.40 (1H, s, NH); MS(+ve): 429.28; tR = 2.76 min (XBridge 4). |
| 325 | 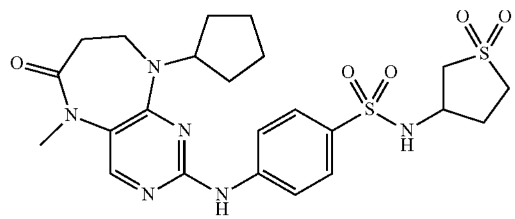 [SMILES: CN1C(=O)CCN(C2CCCC2)c2nc(Nc3ccc(S(=O)(=O)NC4CCS(=O)(=O)C4)cc3)ncc21] | ** | | 4-(9-Cyclopentyl-5-methyl-6-oxo-6,7,8,9-tetrahydro-5H-pyrimido[4,5-b][1,4]diazepin-2-ylamino)-N-(1,1-dioxo-tetrahydro-1lambda*6*-thiophen-3-yl)-benzenesulfonamide | MS(+ve): 535.27; tR = 2.54 min (XBridge 4). |
| 326 | 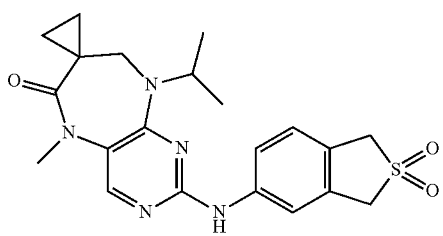 | *** | * | | MS(+ve): 431.25; tR = 2.80 min (XBridge 4). |
| 327 | 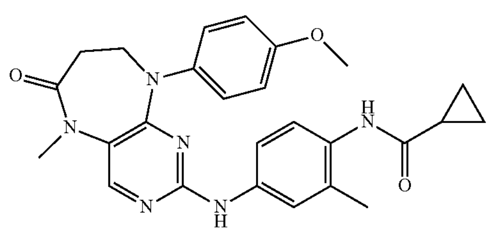 [SMILES: COc1ccc(N2CCC(=O)N(C)c3cnc(Nc4ccc(NC(=O)C5CC5)c(C)c4)nc32)cc1] | *** | | Cyclopropanecarboxylic acid {4-[9-(4-methoxy-phenyl)-5-methyl-6-oxo-6,7,8,9-tetrahydro-5H-pyrimido[4,5-b][1,4]diazepin-2-ylamino]-2-methyl-phenyl}-amide | 1H NMR (DMSO): 0.73 (4H, m, 2CH2), 1.78 (1H, m, CH), 1.89 (3H, s, CH3), 2.77 (2H, m, CH2), 3.25 (3H, s, CH3), 3.79 (3H, s, CH3), 3.98 (2H, m, CH2), 6.85 (1H, d, J 8.5 Hz, CH), 6.96 (1H, m, CH), 6.98 (2H, d, J 8.5 Hz, 2CH), 7.11 (1H, s, CH), 7.23 (2H, d, J 8.5 Hz, 2CH), 8.19 (1H, s, CH), 9.11 (1H, s, NH), 9.25 (1H, s, NH); MS(+ve): 473.35; tR = 2.73 min (XBridge 4). |

TABLE 2-continued

| Cpd | Structure | AurA IC50 | PLK1 IC50 | Name | Data |
|---|---|---|---|---|---|
| 328 | 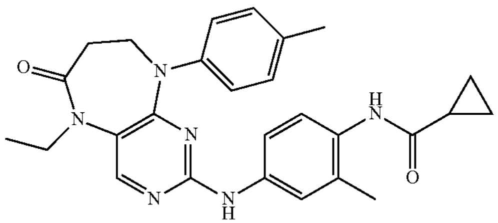 [SMILES: CCN1C(=O)CCN(c2ccc(C)cc2)c2nc(Nc3ccc(NC(=O)C4CC4)c(C)c3)ncc21] | | * | Cyclopropanecarboxylic acid [4-(5-ethyl-6-Oxo-9-p-tolyl-6,7,8,9-tetrahydro-5H-pyrimido[4,5-b][1,4]diazepin-2-ylamino)-2-methyl-phenyl]-amide | 1H NMR (DMSO): 0.73 (4H, m, 2CH2), 1.05 (3H, t, J 7 Hz, CH3), 1.78 (1H, m, CH), 1.87 (3H, s, CH3), 2.32 (3H, q, J 7 Hz, CH3), 2.68 (2H, m, CH2), 3.78 (2H, q, J 7 Hz, CH2), 3.98 (2H, m, CH2), 6.93 (1H, m, CH), 7.0 (1H, m, CH), 7.09 (2H, d, J 8 Hz, 2CH), 7.19 (2H, d, J 8.0 Hz, 2CH), 7.23 (1H, s, CH), 8.32 (1H, s, CH), 9.28 (2H, m, 2NH); MS(+ve): 471.34; tR = 3.05 min (XBridge 4). |
| 329 | 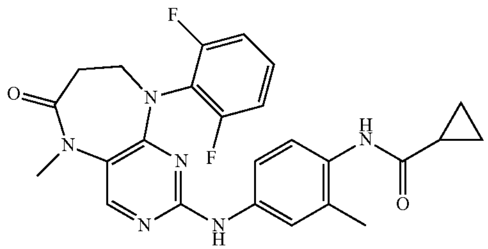 [SMILES: Cc1cc(Nc2ncc3c(n2)N(c2c(F)cccc2F)CCC(=O)N3C)ccc1NC(=O)C1CC1] | | ** | Cyclopropanecarboxylic acid {4-[9-(2,6-difluoro-phenyl)-5-methyl-6-oxo-6,7,8,9-tetrahydro-5H-pyrimido[4,5-b][1,4]diazepin-2-ylamino]-2-methyl-phenyl}-amide | 1H NMR (DMSO): 0.73 (4H, m, 2CH2), 1.77 (1H, m, CH), 1.96 (3H, s, CH3), 2.86 (2H, m, CH2), 3.27 (3H, s, CH3), 3.89 (2H, m, CH2), 6.77 (1H, d, J 9 Hz, CH), 6.90 (1H, d, J 9 Hz, CH), 6.99 (1H, s, CH), 7.29 (2H, m, 2CH), 7.52 (1H, m, CH), 8.24 (1H, s, CH), 9.22 (1H, s, NH), 9.3 (1H, s, NH); MS(+ve): 479.27; tR = 2.78 min (XBridge 4). |
| 330 | 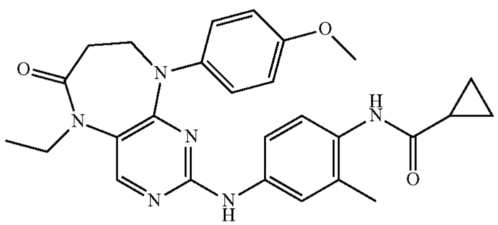 [SMILES: CCN1C(=O)CCN(c2ccc(OC)cc2)c2nc(Nc3ccc(NC(=O)C4CC4)c(C)c3)ncc21] | | * | Cyclopropanecarboxylic acid {4-[5-ethyl-9-(4-methoxy-phenyl)-6-oxo-6,7,8,9-tetrahydro-5H-pyrimido[4,5-b][1,4]diazepin-2-ylamino]-2-methyl-phenyl}-amide | 1H NMR (DMSO): 1.06 (3H, t, J 7 Hz, CH3), 1.78 (1H, m, CH), 1.89 (3H, s, CH3), 2.70 (2H, m, CH2), 3.78 (5H, m, CH2, CH3), 3.98 (2H, m, CH2), 6.90 (1H, d, J 8.5 Hz, CH), 6.97 (3H, m, 3CH), 7.17 (3H, m, 3CH), 8.25 (1H, s, CH), 9.20 (1H, s, NH), 9.26 (1H, s, NH); MS(+ve): 487.31; tR = 2.86 min (XBridge 4). |
| 331 | 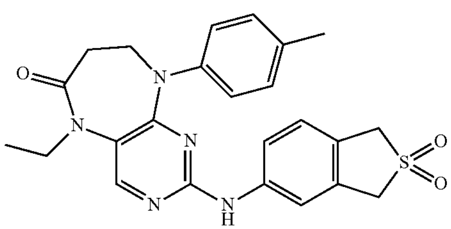 [SMILES: CCN1C(=O)CCN(c2ccc(C)cc2)c2nc(Nc3ccc4c(c3)CS(=O)(=O)C4)ncc21] | | *** | 2-(2,2-Dioxo-2,3-dihydro-1H-2lambda*6*-benzo[c]thiophen-5-ylamino)-5-ethyl-9-p-tolyl-5,7,8,9-tetrahydro-pyrimido[4,5-b][1,4]diazepin-6-one | 1H NMR (DMSO): 1.06 (3H, t, J 7 Hz, CH3), 2.36 (3H, s, CH3), 2.70 (2H, m, CH2), 3.78 (2H, q, J 7 Hz, CH2), 3.99 (2H, m, CH2), 4.04 (2H, s, CH2), 4.32 (2H, s, CH2), 6.97 (1H, d, J 8.0 Hz, CH), 7.13 (2H, d, J 8.0 Hz, 2CH), 7.2 (1H, d, J 8.0 Hz, CH), 7.25 (2H, d, J 8.0 Hz, 2CH), 7.38 (1H, s, CH), 8.33 (1H, s, CH), 9.53 (1H, s, NH); MS(+ve): 464.29; tR = 2.96 min (XBridge 4). |

TABLE 2-continued

| Cpd | Structure | AurA IC50 | PLK1 IC50 | Name | Data |
|---|---|---|---|---|---|
| 332 | 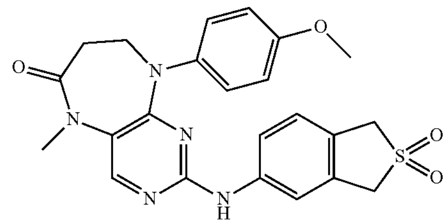 [SMILES: COc1ccc(N2CCC(=O)N(C)c3cnc(Nc4ccc5c(c4)CS(=O)(=O)C5)nc32)cc1] | | *** | 2-(2,2-Dioxo-2,3-dihydro-1H-2lambda*6*-benzo[c]thiophen-5-ylamino)-9-(4-methoxy-phenyl)-5-methyl-5,7,8,9-tetrahydro-pyrimido[4,5-b][1,4]diazepin-6-one | 1H NMR (DMSO): 2.8 (2H, m, CH2), 3.26 (3H, s, CH3), 3.82 (3H, s, CH3), 3.99 (2H, m, CH2), 4.02 (2H, s, CH2), 4.31 (2H, s, CH2), 6.94 (1H, d, J 8.5 Hz, CH), 7.05 (2H, d, J 8 Hz, 2CH), 7.15 (1H, d, J 8.5 Hz, CH), 7.27 (3H, m, 3CH), 8.20 (1H, d, J 8.5 Hz, CH), 9.41 (1H, s, NH); MS(+ve): 466.23; tR = 2.67 min (XBridge 4). |
| 333 | 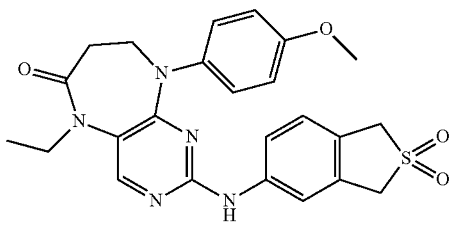 [SMILES: CCN1C(=O)CCN(c2ccc(OC)cc2)c2nc(Nc3ccc4c(c3)CS(=O)(=O)C4)ncc21] | | *** | 2-(2,2-Dioxo-2,3-dihydro-1H-2lambda*6*-benzo[c]thiophen-5-ylamino)-5-ethyl-9-(4-methoxy-phenyl)-5,7,8,9-tetrahydro-pyrimido[4,5-b][1,4]diazepin-6-one | 1H NMR (DMSO): 1.07 (3H, t, J 7 Hz, CH3), 2.72 (2H, m, CH2), 3.78 (2H, q, J 7 Hz, CH2), 3.81 (3H, s, CH3), 3.99 (2H, m, CH2), 4.03 (2H, s, CH2), 4.32 (2H, s, CH2), 6.97 (1H, d, J 8.5 Hz, CH), 7.04 (2H, d, J 8.5 Hz, 2CH), 7.18 (1H, m, CH), 7.21 (2H, d, J 8.5 Hz, 2CH), 7.32 (1H, s, CH), 8.26 (1H, s, CH), 9.48 (1H, s, NH); MS(+ve): 480.22; tR = 2.82 min (XBridge 4). |
| 334 | 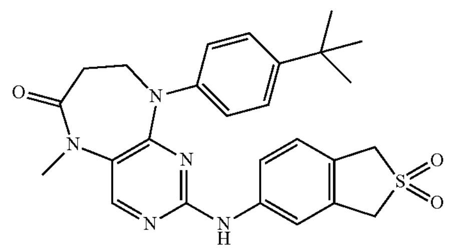 [SMILES: CN1C(=O)CCN(c2ccc(C(C)(C)C)cc2)c2nc(Nc3ccc4c(c3)CS(=O)(=O)C4)ncc21] | | * | 9-(4-tert-Butyl-phenyl)-2-(2,2-dioxo-2,3-dihydro-1H-2lambda*6*-benzo[c]thiophen-5-ylamino)-5-methyl-5,7,8,9-tetrahydro-pyrimido[4,5-b][1,4]diazepin-6-one | 1H NMR (DMSO): 1.33 (9H, s, C(CH3)3), 2.76 (2H, m, CH2), 3.26 (3H, s, CH3), 3.99 (2H, m, CH2), 4.12 (2H, s, CH2), 4.29 (2H, s, CH2), 6.92 (1H, d, J 8 Hz, CH), 7.20 (2H, d, J 8.5 Hz, 2CH), 7.28 (1H, d, J 8 Hz, CH), 7.44 (3H, m, 3CH), 8.31 (1H, d, J 8.5 Hz, CH), 9.5 (1H, s, NH); MS(+ve): 492.36; tR = 3.32 min (XBridge 4). |
| 335 | 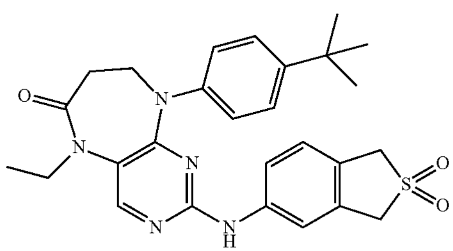 [SMILES: CCN1C(=O)CCN(c2ccc(C(C)(C)C)cc2)c2nc(Nc3ccc4c(c3)CS(=O)(=O)C4)ncc21] | | * | 9-(4-tert-Butyl-phenyl)-2-(2,2-dioxo-2,3-dihydro-1H-2lambda*6*-benzo[c]thiophen-5-ylamino)-5-ethyl-5,7,8,9-tetrahydro-pyrimido[4,5-b][1,4]diazepin-6-one | 1H NMR (DMSO): 1.04 (3H, t, J 7 Hz, CH3), 1.32 (9H, s, C(CH3)3), 2.68 (2H, m, CH2), 3.78 (2H, q, J 7 Hz, CH2), 3.98 (2H, m, CH2), 4.12 (2H, s, CH2), 4.31 (2H, s, CH2), 6.98 (1H, d, J 8.5 Hz, CH), 7.12 (2H, d, J 8.5 Hz, 2CH), 7.31 (1H, d, J 8.5 Hz, CH), 7.41 (2H, d, J 8.5 Hz, 2CH), 7.52 (1H, s, CH), 8.4 (1H, s, CH), 9.6 (1H, s, NH); MS(+ve): 506.32; tR = 3.45 min (XBridge 4). |

TABLE 2-continued

| Cpd | Structure | AurA IC50 | PLK1 IC50 | Name | Data |
|---|---|---|---|---|---|
| 336 | 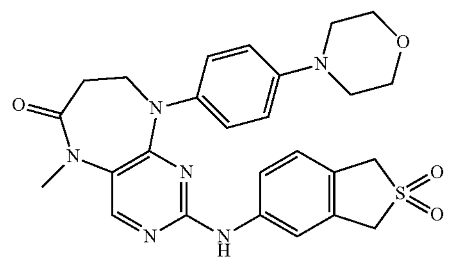 [SMILES: CN1C(=O)CCN(c2ccc(N3CCOCC3)cc2)c2nc(Nc3ccc4c(c3)CS(=O)(=O)C4)ncc21] | | *** | 2-(2,2-Dioxo-2,3-dihydro-1H-2lambda*6*-benzo[c]thiophen-5-ylamino)-5-methyl-9-(4-morpholin-4-yl-phenyl)-5,7,8,9-tetrahydro-pyrimido[4,5-b][1,4]diazepin-6-one | 1H NMR (DMSO): 2.79 (2H, m, CH2), 3.19 (4H, m, 2CH2), 3.26 (3H, s, CH3), 3.79 (4H, m, 2CH2), 3.98 (2H, m, CH2), 4.04 (2H, s, CH2), 4.30 (2H, s, CH2), 7.01 (1H, d, J 8.5 Hz, CH), 7.05 (2H, d, J 8.5 Hz, 2CH), 7.10 (1H, d, J 8.5 Hz, CH), 7.20 (2H, d, J 8.5 Hz, 2CH), 7.31 (1H, s, CH), 8.18 (1H, s, CH), 9.39 (1H, s, NH); MS(+ve): 521.30; tR = 2.60 min (XBridge 4). |
| 337 | 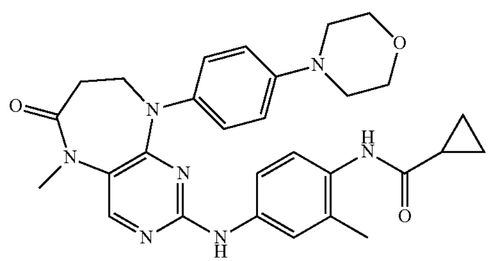 [SMILES: Cc1cc(Nc2ncc3c(n2)N(c2ccc(N4CCOCC4)cc2)CCC(=O)N3C)ccc1NC(=O)C1CC1] | | *** | Cyclopropanecarboxylic acid {2-methyl-4-[5-methyl-9-(4-morpholin-4-yl-phenyl)-6-oxo-6,7,8,9-tetrahydro-5H-pyrimido[4,5-b][1,4]diazepin-2-ylamino]-phenyl}-amide | 1H NMR (DMSO): 0.73 (4H, m, 2CH2), 1.79 (1H, m, CH), 1.92 (3H, s, CH3), 2.77 (2H, m, CH2), 3.13 (4H, m, 2CH2), 3.25 (3H, s, CH3), 3.75 (4H, m, 2CH2), 3.97 (2H, m, CH2), 6.89 (1H, d, J 8 Hz, CH), 6.98 (3H, m, 3CH), 7.10 (1H, s, CH), 7.16 (2H, d, J 8.5 Hz, 2CH), 8.17 (1H, s, CH), 9.09 (1H, s, NH), 9.21 (1H, s, NH); MS(+ve): 528.33; tR = 2.60 min (XBridge 4). |
| 338 | 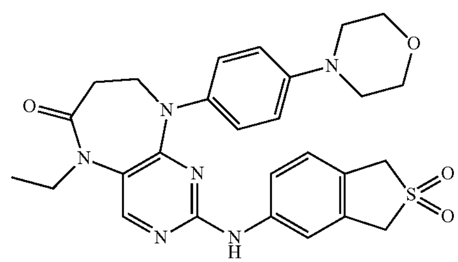 [SMILES: CCN1C(=O)CCN(c2ccc(N3CCOCC3)cc2)c2nc(Nc3ccc4c(c3)CS(=O)(=O)C4)ncc21] | | ** | 2-(2,2-Dioxo-2,3-dihydro-1H-2lambda*6*-benzo[c]thiophen-5-ylamino)-5-ethyl-9-(4-morpholin-4-yl-phenyl)-5,7,8,9-tetrahydro-pyrimido[4,5-b][1,4]diazepin-6-one | 1H NMR (DMSO): 1.07 (3H, t, J 7 Hz, CH3), 2.71 (2H, m, CH2), 3.18 (4H, m, 2CH2), 3.79 (6H, m, 3CH2), 3.97 (2H, m, CH2), 4.05 (2H, s, CH2), 4.30 (2H, s, CH2), 7.03 (3H, m, 3CH), 7.14 (3H, m, 3CH), 7.35 (1H, s, CH), 8.24 (1H, s, CH), 9.46 (1H, s, NH); MS(+ve): 535.27; tR = 2.72 min (XBridge 4). |
| 339 | 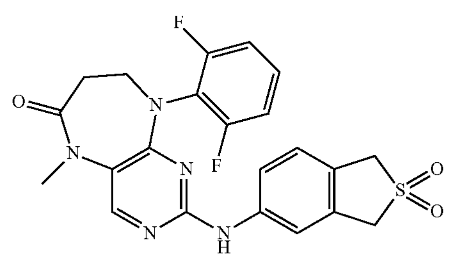 [SMILES: CN1C(=O)CCN(c2c(F)cccc2F)c2nc(Nc3ccc4c(c3)CS(=O)(=O)C4)ncc21] | | *** | 9-(2,6-Difluoro-phenyl)-2-(2,2-dioxo-2,3-dihydro-1H-2lambda*6*-benzo[c]thiophen-5-ylamino)-5-methyl-5,7,8,9-tetrahydro-pyrimido[4,5-b][1,4]diazepin-6-one | 1H NMR (DMSO): 2.87 (2H, m, CH2), 3.28 (3H, s, CH3), 3.91 (2H, m, CH2), 4.18 (2H, s, CH2), 4.30 (2H, s, CH2), 6.91 (1H, d, J 8 Hz, CH), 7.13 (2H, m, 2CH), 7.35 (2H, m, 2CH), 7.57 (1H, m, CH), 8.27 (1H, s, CH), 9.53 (1H, s, NH); MS(+ve): 472.18; tR = 2.72 min (XBridge 4). |

TABLE 2-continued

| Cpd | AurA IC50 | PLK1 IC50 | Name | Data |
|---|---|---|---|---|
| 340 | ** | | 9-(2,6-Difluoro-phenyl)-2-(2,2-dioxo-2,3-dihydro-1H-2lambda*6*-benzo[c]thiophen-5-ylamino)-5-ethyl-5,7,8,9-tetrahydro-pyrimido[4,5-b][1,4]diazepin-6-one | 1H NMR (DMSO): 1.03 (3H, t, J 7 Hz, CH3), 2.80 (2H, m, CH2), 3.83 (2H, q, J 7 Hz, CH2), 3.9 (2H, m, CH2), 4.18 (2H, s, CH2), 4.31 (2H, s, CH2), 6.93 (1H, d, J 9 Hz, CH), 7.16 (2H, m, 2CH), 7.34 (2H, m, 2CH), 7.57 (1H, m, CH), 8.32 (1H, s, CH), 9.57 (1H, s, NH); MS(+ve): 486.22; tR = 2.87 min (XBridge 4). |
| 341 | *** | | 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-3-methoxy-N-(1-methyl-piperidin-4-yl)-benzamide mesylate | |
| 342 | * | | Cyclopropanecarboxylic acid {4-[9-(4-tert-butyl-phenyl)-5-methyl-6-oxo-6,7,8,9-tetrahydro-5H-pyrimido[4,5-b][1,4]diazepin-2-ylamino]-2-methyl-phenyl}-amide | 1H NMR (DMSO): 0.71 (4H, m, 2CH2), 1.30 (9H, s, C(CH3)3), 1.77 (1H, m, CH), 1.91 (3H, s, CH3), 2.75 (2H, m, CH2), 3.25 (3H, s, CH3), 3.99 (2H, m, CH2), 6.88 (1H, d, J 8.5 Hz, CH), 7.05 (1H, d, J 8.5 Hz, CH), 7.17 (2H, d, J 8.5 Hz, 2CH), 7.19 (1H, s, CH), 7.41 (2H, d, J 8.5 Hz, 2CH), 8.28 (1H, s, CH), 9.22 (2H, s, 2NH); MS(+ve): 499.45; tR = 3.37 min (XBridge 4). |

TABLE 2-continued

| Cpd | Structure | AurA IC50 | PLK1 IC50 | Name | Data |
|---|---|---|---|---|---|
| 343 | 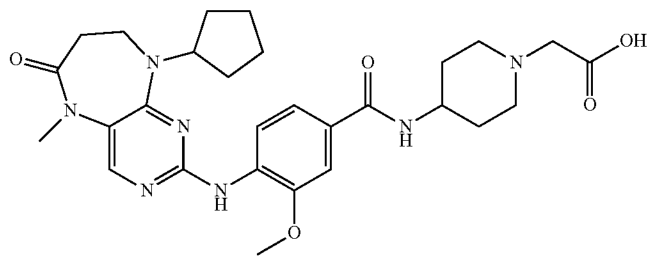 [SMILES: COc1cc(C(=O)NC2CCN(CC(=O)O)CC2)ccc1Nc1ncc2c(n1)N(C1CCCC1)CCC(=O)N2C] | | ** | {4-[4-(9-Cyclopentyl-5-methyl-6-oxo-6,7,8,9-tetrahydro-5H-pyrimido[4,5-b][1,4]diazepin-2-ylamino)-3-methoxy-benzoylamino]-piperidin-1-yl}-acetic acid | |
| 344 | 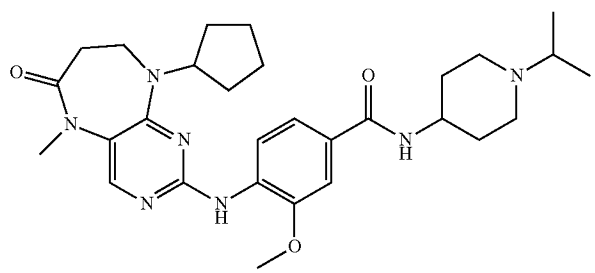 [SMILES: COc1cc(C(=O)NC2CCN(C(C)C)CC2)ccc1Nc1ncc2c(n1)N(C1CCCC1)CCC(=O)N2C] | | *** | 4-(9-Cyclopentyl-5-methyl-6-oxo-6,7,8,9-tetrahydro-5H-pyrimido[4,5-b][1,4]diazepin-2-ylamino)-N-(1-isopropyl-piperidin-4-yl)-3-methoxy-benzamide | |
| 345 | 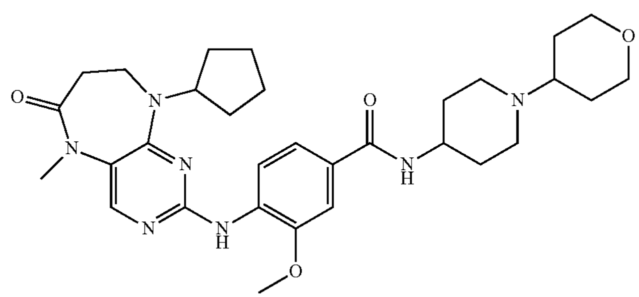 [SMILES: COc1cc(C(=O)NC2CCN(C3CCOCC3)CC2)ccc1Nc1ncc2c(n1)N(C1CCCC1)CCC(=O)N2C] | | *** | 4-(9-Cyclopentyl-5-methyl-6-oxo-6,7,8,9-tetrahydro-5H-pyrimido[4,5-b][1,4]diazepin-2-ylamino)-3-methoxy-N-[1-(tetrahydro-pyran-4-yl)-piperidin-4-yl]-benzamide | |

TABLE 2-continued

| Cpd | Structure | AurA IC50 | PLK1 IC50 | Name | Data |
|---|---|---|---|---|---|
| 346 | 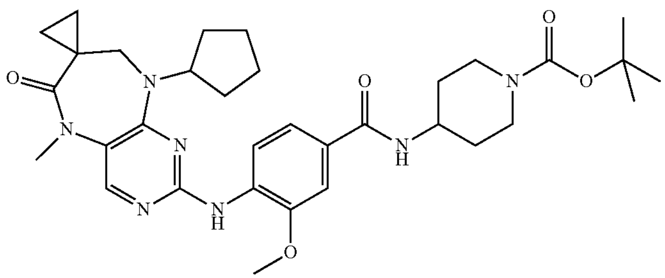 [SMILES: COc1cc(C(=O)NC2CCN(C(=O)OC(C)(C)C)CC2)ccc1Nc1ncc2c(n1)N(C1CCCC1)CC1(CC1)C(=O)N2C] | | | 4-(9-Cyclopentyl-5-methyl-6-oxo-6,7,8,9-tetrahydro-5H-spiro[pyrimido[4,5-b][1,4]diazepine-3,1'-cyclopropane]-2-ylamino)-3-methoxy-benzoylamino}-piperidine-1-carboxylic acid tert-butyl ester | |
| 347 | 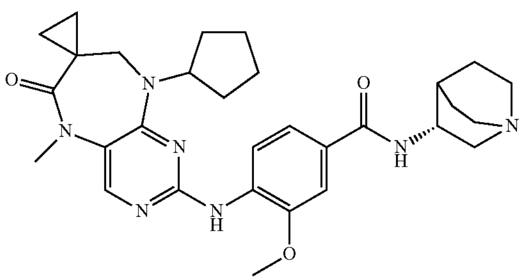 | | | N-(R)-(1-Aza-bicyclo[2.2.2]oct-3-yl)-4-(9-cyclopentyl-5-methyl-6-oxo-6,7,8,9-tetrahydro-5H-spiro[pyrimido[4,5-b][1,4]diazepine-3,1'-cyclopropane]-2-ylamino)-3-methoxy-benzamide | *** |
| 348 | 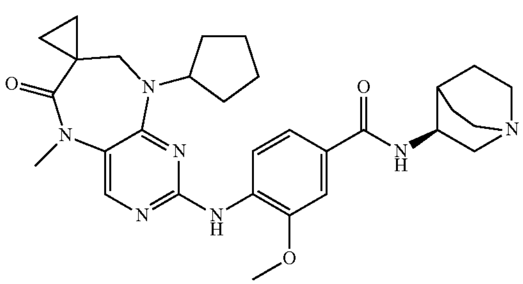 [SMILES: COc1cc(C(=O)N[C@@H]2CN3CCC2CC3)ccc1Nc1ncc2c(n1)N(C1CCCC1)CC1(CC1)C(=O)N2C] | | | N-(S)-(1-Aza-bicyclo[2.2.2]oct-3-yl)-4-(9-cyclopentyl-5-methyl-6-oxo-6,7,8,9-tetrahydro-5H-spiro[pyrimido[4,5-b][1,4]diazepine-3,1'-cyclopropane]-2-ylamino)-3-methoxy-benzamide | *** |

TABLE 2-continued

| Cpd | Structure | AurA IC50 | PLK1 IC50 | Name | Data |
|---|---|---|---|---|---|
| 349 | 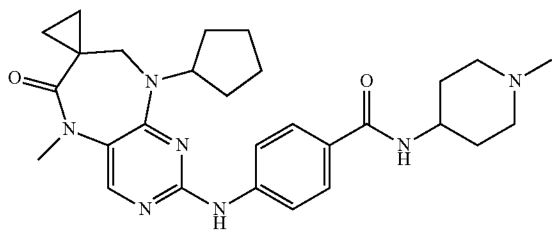 [SMILES: CN1CCC(NC(=O)c2ccc(Nc3ncc4c(n3)N(C3CCCC3)CC3(CC3)C(=O)N4C)cc2)CC1] | | * | 4-(9-Cyclopentyl-5-methyl-6-oxo-6,7,8,9-tetrahydro-5H-spiro[pyrimido[4,5-b][1,4]diazepin-3,1'-cyclopropane]-2-ylamino)-N-(1-methyl-piperidin-4-yl)-benzamide | |
| 350 | 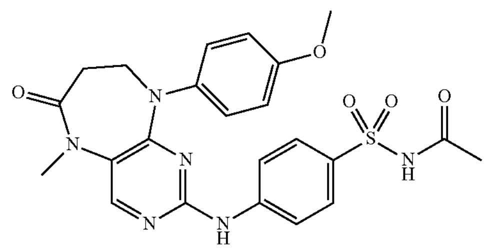 [SMILES: COc1ccc(N2CCC(=O)N(C)c3cnc(Nc4ccc(S(=O)(=O)NC(C)=O)cc4)nc32)cc1] | | ** | N-Acetyl-4-[9-(4-methoxy-phenyl)-5-methyl-6-oxo-6,7,8,9-tetrahydro-5H-pyrimido[4,5-b][1,4]diazepin-2-ylamino]-benzenesulfonamide | |
| 351 | 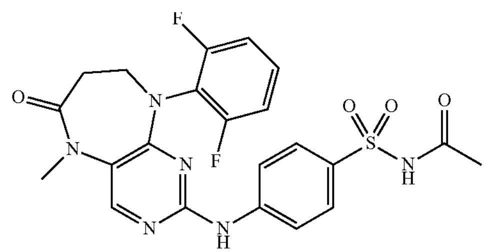 [SMILES: CC(=O)NS(=O)(=O)c1ccc(Nc2ncc3c(n2)N(c2c(F)cccc2F)CCC(=O)N3C)cc1] | | *** | N-Acetyl-4-[9-(2,6-difluoro-phenyl)-5-methyl-6-oxo-6,7,8,9-tetrahydro-5H-pyrimido[4,5-b][1,4]diazepin-2-ylamino]-benzenesulfonamide | |
| 352 | 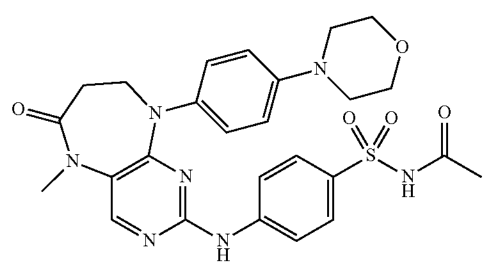 [SMILES: CC(=O)NS(=O)(=O)c1ccc(Nc2ncc3c(n2)N(c2ccc(N4CCOCC4)cc2)CCC(=O)N3C)cc1] | | ** | N-Acetyl-4-[5-methyl-9-(4-morpholin-4-yl-phenyl)-6-oxo-6,7,8,9-tetrahydro-5H-pyrimido[4,5-b][1,4]diazepin-2-ylamino]-benzenesulfonamide | |

TABLE 3

PLK IC$_{50}$ values and characterization data for selected compounds of the invention; * denotes <0.1 µM IC$_{50}$;  denotes between 0.1 µM and 1 µM IC$_{50}$; * denotes between 1 µM and 10 µM IC$_{50}$

| No. | Structure | | PLK1 Name | Data |
|---|---|---|---|---|
| 254 | 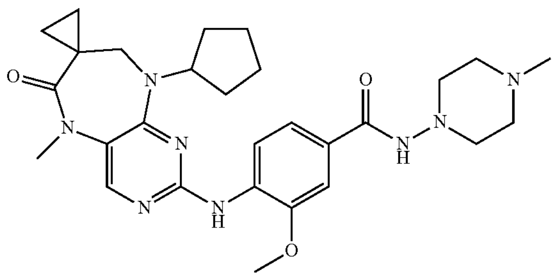 [SMILES: COc1cc(C(=O)NN2CCN(C)CC2)ccc1Nc1ncc2c(n1)N(C1CCCC1)CC1(CC1)C(=O)N2C] | *** | 4-(9'-cyclopentyl-1'-5'-methyl-6'-oxo-5',6,8,9'-tetrahydrospiro[cyclopropane-1,7'-pyrimido[4,5-b][1,4]diazepine]-2'-ylamino)-3-methoxy-N-(4-methylpiperazin-1-yl)benzamide | Rt = 2.63 min (Analytical_1); MS(+ve): 535.5; MS(-ve): 533.6; 1H NMR (DMSO-d6) δ ppm: 0.63-0.70 (2 H, m), 0.87-0.94 (2 H, m), 1.43-1.54 (2 H, m), 1.55-1.63 (2 H, m), 1.64-1.73 (2 H, m), 1.83-1.94 (2 H, m), 2.18 (3 H, s), 2.31-2.48 (4 H, m), 2.92 (4 H, m), 3.16 (3 H, s), 3.47 (2 H, s), 3.94 (3 H, s), 4.78-4.91 (1 H, m), 7.35-7.48 (2 H, m), 7.68 (1 H, s), 7.98 (1 H, s), 8.39 (1 H, d, J = 8.3 Hz), 9.31 (1 H, s). |
| 218 | 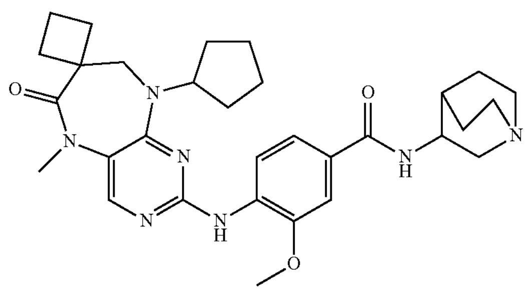 [SMILES: COc1cc(C(=O)NC2CN3CCC2CC3)ccc1Nc1ncc2c(n1)N(C1CCCC1)CC1(CCC1)C(=O)N2C] | *** | (±)-4-(9'-cyclopentyl-5'-methyl-6'-oxo-5',6',8',9'-tetrahydrospiro[cyclobutane-1,7'-pyrimido[4,5-b][1,4]diazepine]-2'-ylamino)-N-methoxy-N-(quinuclidin-3-yl)benzamide | Rt = 3.26 min (Analytical_1); MS(+ve): 560.4; 1H NMR (DMSO-d6) δ ppm: 8.37 (d, J = 8.3 Hz, 1H), 8.08 (d, J = 6.8 Hz, 1H), 8.05 (s, 1H), 7.73 (s, 1H), 7.45-7.53 (m, 2H), 4.82 (quin, J = 8.3 Hz, 1H), 3.84-4.01 (m, 4H), 3.64 (s, 2H), 3.18 (s, 3H), 3.04-3.14 (m, 1H), 2.88 (t, J = 9.8 Hz, 1H), 2.58-2.75 (m, 4H), 2.21-2.33 (m, 2H), 2.07 (s, 2H), 1.97 (br. s., 2H), 1.87 (br. s., 2H), 1.76 (d, J = 4.9 Hz, 2H), 1.56-1.70 (m, 8H), 1.30 (br. s., 1H) |
| 195 | 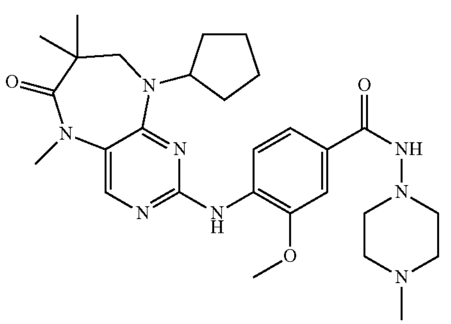 [SMILES: COc1cc(C(=O)NN2CCN(C)CC2)ccc1Nc1ncc2c(n1)N(C1CCCC1)CC(C)(C)C(=O)N2C] | *** | 4-(9-Cyclopentyl-5,7,7-trimethyl-6-oxo-6,7,8,9-tetrahydro-5H-pyrimido[4,5-b][1,4]diazepin-2-ylamino)-3-methoxy-N-(4-methyl-piperazin-1-yl)-benzamide | Rt = 2.81 min (Analytical_1); MS(+ve): 537.5; 1H NMR (DMSO-d6) δ ppm: 1.09 (6H, s), 1.61 (4H, m), 1.73 (2H, m), 1.87 (2H, m), 2.19 (3H, s), 2.42 (2H, m), 2.92 (4H, m), 3.29 (3H, s), 3.37 (3H, m), 3.93 (3H, s), 3.17 (1H, m), 7.40 (2H, m), 7.68 (1H, s), 7.98 (1H, s), 8.37 (1H, d, J 7 Hz), 9.30 (1H, s). |

TABLE 3-continued

PLK IC$_{50}$ values and characterization data for selected compounds of the invention; * denotes <0.1 μM IC$_{50}$;  denotes between 0.1 μM and 1 μM IC$_{50}$; * denotes between 1 μM and 10 μM IC$_{50}$.

| No. | | PLK1 | Name | Data |
|---|---|---|---|---|
| 221 | *** | | 4-(9'-cyclopentyl-5'methyl-6'-oxo-5,6,8,9-tetrahydrospiro[cyclobutane-1,7'-pyrimido[4,5-b][1,4]diazepine]-2'-ylamino)-3-methoxy-N-(4-methyl piperazin-1-yl)benzamide | Rt = 2.79 min (Analytical_1); MS(+ve): 549.5; 1H NMR (DMSO-d6) δ ppm: 9.31 (s, 1H), 8.37 (d, J = 8.3 Hz, 1 H), 8.05 (s, 1H), 7.72 (s, 1H), 7.37-7.47 (m, 2H), 4.73-4.86 (m, 1H), 3.93 (s, 3H), 3.64 (s, 2H), 3.18 (s, 3H), 2.92 (br. s., 4H), 2.36 (br. s., 4H), 2.27 (d, J = 9.3 Hz, 2H), 2.18 (s, 3H), 1.97 (br. s., 2H), 1.79-1.91 (m, 1H), 1.76 (br. s., 2H), 1.54-1.72 (m, 7H). |
| 371 | *** | | 4-(9'-cyclopentyl-5'-methyl-6'-oxo-5,6,8,9-tetrahydrospiro[cyclopropane-1,7'-pyrimido[4,5-b][1,4]diazepine]-2'-ylamino)-N-((trans)-4-(4-(cyclopropylmethyl)piperazin-1-yl)cyclohexyl)-3-methoxybenzamide | Rt = 3.18 min (Analytical_1); ES(+ve): 655.7; 1H NMR (DMSO-d6) δ ppm: 0.05 (d, J = 4.20 Hz, 3H), 0.44 (d, J = 7.74 Hz, 2H), 0.67 (d, J = 1.61 Hz, 2H), 0.74-0.85 (m, 1H), 0.90 (s, 2H), 1.23-1.44 (m, 3H), 1.44-1.55 (m, 2H), 1.54-1.64 (m, 2H), 1.64-1.74 (m, 2H), 1.88 (br. s., 5H), 2.08 (s, 3H), 2.13 (d, J = 6.45 Hz, 2H), 2.17-2.28 (m, 1H), 2.29-2.47 (m, 3H), 2.60-2.67 (m, 1H), 3.06-3.23 (m, 5H), 3.47 (s, 2H), 3.65-3.79 (m, 1H), 3.94 (s, 2H), 4.05-4.13 (m, 1H), 4.78-4.91 (m, 1H), 7.48 (s, 2H), 7.67 (s, 1H), 7.98 (s, 1H), 8.00-8.07 (m, 1H), 8.31-8.45 (m, 1H). |
| 372 | *** | | 4-(9'-cyclopentyl-5,7,7-trimethyl-6-oxo-6,7,8,9-tetrahydro-5H-pyrimido[4,5-b][1,4]diazepin-2-ylamino)-N-((trans)-4-(4-(cyclopropylmethyl)piperazin-1-yl)cyclohexyl)-3-methoxybenzamide | Rt = 3.38 min (Analytical_1); ES(+ve): 657.7; 1H NMR (DMSO-d6) δ ppm: 0.05 (d, J = 3.86 Hz, 3H), 0.40-0.48 (m, 3H), 0.73-0.84 (m, 2H), 1.03-1.13 (m, 10H), 1.18 (s, 1H), 1.24-1.43 (m, 6H), 1.61 (br. s., 3H), 1.74 (d, J = 9.65 Hz, 2H), 1.88 (br. s., 5H), 2.08 (s, 5H), 2.13 (d, J = 6.75 Hz, 2H), 2.17-2.25 (m, 1H), 2.36 (br. s., 3H), 2.60-2.67 (m, 1H), 3.14-3.22 (m, 2H), 3.37 (s, 1H), 3.51 (s, 1H), 3.94 (s, 2H), 5.18 (t, J = 8.52 Hz, 1H), 7.43-7.50 (m, 1H), 7.67 (s, 1H), 7.98 (s, 1H), 8.03 (d, J = 7.72 Hz, 1H), 8.35 (d, J = 8.36 Hz, 1H). |

TABLE 3-continued

PLK IC$_{50}$ values and characterization data for selected compounds of the invention; * denotes <0.1 µM IC$_{50}$;  denotes between 1 µM and 0.1 µM IC$_{50}$; * denotes between 10 µM and 1 µM IC$_{50}$.

| No. | | Structure | PLK1 Name | Data |
|---|---|---|---|---|
| 345 | *** | 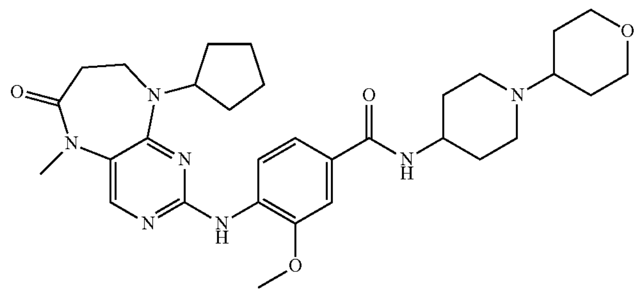 [SMILES: COc1cc(C(=O)NC2CCN(C3CCOCC3)CC2)ccc1Nc1ncc2c(n1)N(C1CCCC1)CCC(=O)N2C] | 4-(9-Cyclopentyl-5-methyl-6-oxo-6,7,8,9-tetrahydro-5H-pyrimido[4,5-b][1,4]diazepin-2-ylamino)-3-methoxy-N-[1-(tetrahydro-pyran-4-yl)-piperidin-4-yl]-benzamide | Rt = 2.74 min (Analytical_1); ES(+ve): 578.5; ES(−ve): 576.7. |
| 373 | *** | 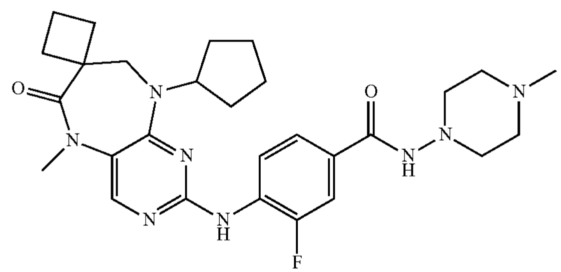 [SMILES: CN1CCN(NC(=O)c2ccc(Nc3ncc4c(n3)N(C3CCCC3)CC3(CCC3)C(=O)N4C)c(F)c2)CC1] | 4-(9'-cyclopentyl-5'-methyl-6'-oxo-5',6,8',9'-tetrahydrospiro[cyclobutane-1,7'-pyrimido[4,5-b][1,4]diazepine]-2'-ylamino)-N-(4-methylpiperazin-1-yl)benzamide | Rt = 2.74 min (Analytica_1); MS(+ve): 537.5; 1H NMR (DMSO-d6) δ ppm: 1.55-1.65 (8H, m), 1.71 (2H, m), 1.88 (2H, m), 2.18 (3H, s), 2.28 (2H, q, J 10.5 Hz), 2.41-2.52 (4H, m), 2.89 (4H, m), 3.18 (3H, s), 3.61 (2H, s), 4.76 (1H, quintet, 8.5 Hz), 7.61 (2H, m), 8.03 (1H, s), 8.12 (1H, dd, J 8 Hz, 8.5 Hz), 8.76 (1H, s), 9.36 (1H, s). |
| 374 | *** | 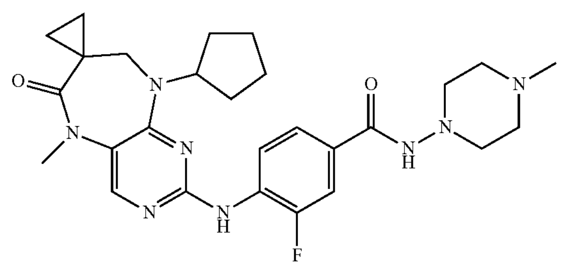 [SMILES: CN1CCN(NC(=O)c2ccc(Nc3ncc4c(n3)N(C3CCCC3)CC3(CC3)C(=O)N4C)c(F)c2)CC1] | 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-fluoro-N-(4-methylpiperazin-1-yl)benzamide | Rt = 2.58 min (Analytical_1); MS(+ve): 523.4; 1H NMR (DMSO-d6) δ ppm: 0.65-0.67 (2H, s, CH2), 0.85-0.95 (2H, m, CH2), 1.23-1.82 (8H, m, alkyl-H), 2.18 (3H, s, CH3), 2.36-2.41 (4H, m, alkyl-H), 2.88 (4H, s, alkyl-H), 3.16 (3H, s, CH3), 3.44 (2H, s, alkyl-H), 4.77-4.80 (1H, m, CH), 7.6 (2H, m, aryl-H), 7.96 (1H, s, aryl-H), 8.16 (1H, t, J = 8 Hz, aryl-H), 8.70 (1H, s, NH), 9.35(1H, s, NH). |

TABLE 3-continued

PLK IC$_{50}$ values and characterization data for selected compounds of the invention; * denotes <0.1 µM IC$_{50}$;  denotes between 0.1 µM and 1 µM IC$_{50}$; * denotes between 1 µM and 10 µM IC$_{50}$.

| No. | | Structure | PLK1 Name | Data |
|---|---|---|---|---|
| 194 | *** | 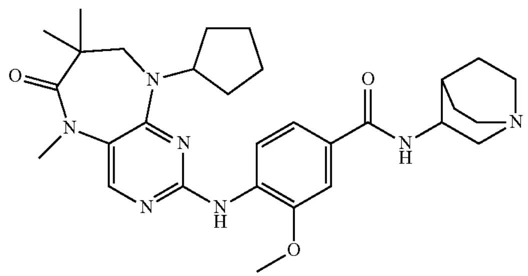 [SMILES: COc1cc(C(=O)NC2CN3CCC2CC3)ccc1Nc1ncc2c(n1)N(C1CCCC1)CC(C)(C)C(=O)N2C] | (±)-4-(9-cyclopentyl-5,7,7-trimethyl-6-oxo-6,7,8,9-tetrahydro-5H-pyrimido[4,5-b][1,4]diazepin-2-ylamino)-3-methoxy-N-(quinuclidin-3-yl)benzamide | Rt = 3.28 min (Analytical_1); MS(+ve): 548.5; 1H NMR (DMSO-d6) δ ppm: 8.37 (1H, d, J 8 Hz), 8.07 (1H, d, J 6.5 Hz), 7.98 (1H, S), 7.69 (1H, s), 7.47-7.50 (2H, m), 5.19 (1H, quint, J 8 Hz), 3.95 (4H, m), 3.37 (2H, s), 3.18 (3H, s), 3.11 (1H, m), 2.89 (1H, m), 2.65-2.72 (4H, m), 1.88 (2H, m), 1.73-1.87 (4H, m), 1.57-1.61 (6H, m), 1.31 (1H, m), 1.09 (6H, s). |
| 186 | *** | 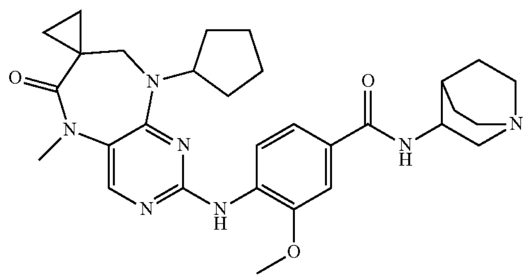 [SMILES: COc1cc(C(=O)NC2CN3CCC2CC3)ccc1Nc1ncc2c(n1)N(C1CCCC1)CC1(CC1)C(=O)N2C] | (±)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(quinuclidin-3-yl)benzamide | Rt = 3.02 min (Analytical_1); MS(+ve): 546.4; 1H NMR (DMSO-d6) δ ppm: 8.40 (1H, d, J 8 Hz), 8.08 (1H, d, J 7 Hz), 7.98 (1H, s), 7.69 (1H, s), 7.47-7.50 (2H, m), 4.87 (1H, quint, J 9 Hz), 4.10 (1H, q, J 5.5 Hz), 3.95 (4H, m), 3.47 (2H, s), 3.27 (3H, s), 3.07 (1H, m), 2.08 (1H, m), 2.63-2.86 (4H, m), 1.88 (3H, m), 1.78 (1H, m), 1.68 (2H, m), 1.50-1.62 (5H, m), 1.32 (1H, m), 0.90 (2H, m), 0.66 (2H, m). |
| 375 | *** | 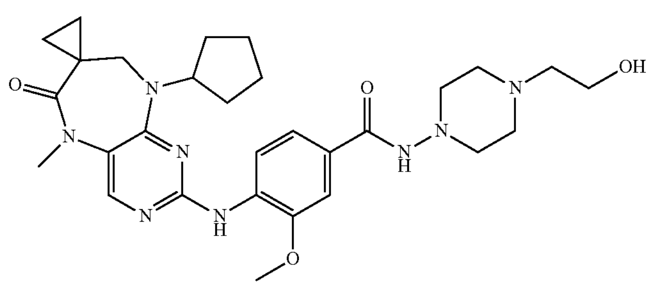 [SMILES: COc1cc(C(=O)NN2CCN(CCO)CC2)ccc1Nc1ncc2c(n1)N(C1CCCC1)CC1(CC1)C(=O)N2C] | 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-N-(4-(2-hydroxyethyl)piperazin-1-yl)-3-methoxybenzamide | Rt = 2.48 min (Analytical_1); MS(+ve): 565.4; 1H NMR (DMSO) δ ppm: 0.66-0.67 (2H, m, CH2), 0.88-0.90 (2H, m, CH2), 1.23-1.90 (8H, m, alkyl-H), 2.34-2.41 (4H, m, alkyl-H), 2.91 (4H, t, J = 4 Hz, alkyl-H), 3.16 (3H, s, CH3), 3.46-3.51 (4H, m,), 3.93 (3H, s, CH3), 4.38-4.45 (1H, m,), 4.81-4.87 (1H, m, CH), 7.40 (2H, d, J = 10.5 Hz, aryl-H ), 7.67 (1H, s), 7.98 (1H, s ), 8.39 (1H, d, J = 8 Hz, aryl-H ), 9.30 (1H, s, NH). |

TABLE 3-continued

PLK IC$_{50}$ values and characterization data for selected compounds of the invention; * denotes <0.1 μM IC$_{50}$;  denotes between 0.1 μM and 1 μM IC$_{50}$; * denotes between 1 μM and 10 μM IC$_{50}$.

| No. | | Structure | PLK1 Name | Data |
|---|---|---|---|---|
| 376 | *** | 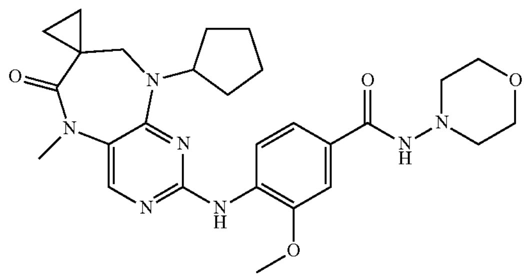 [SMILES: COc1cc(C(=O)NN2CCOCC2)ccc1Nc1ncc2c(n1)N(C1CCCC1)CC1(CC1)C(=O)N2C] | 4-(9'-Cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-morpholinobenzamide | Rt = 2.72 min (Analytical_1); MS(+ve): 522.4; 1H NMR (DMSO) δ ppm: 0.65-0.71 (2H, m, CH2), 0.85-0.91 (2H, m, CH2), 1.23-1.88 (8H, m, alkyl-H), 2.92 (4H, t, J = 4 Hz, alkyl-H), 3.16 (3H, s, CH3), 3.47 (2H, s, alkyl-H), 3.66 (4H, t, J = 4.5 Hz), 3.94 (3H, s, CH3), 4.81-4.87 (1H, m, CH), 7.41 (2H, d, J = 9.5 Hz ), 7.69 (1H, s), 7.98 (1H, s), 8.40 (1H, d, J = 8 Hz), 9.41 (1H, s, NH). |
| 347 | *** | 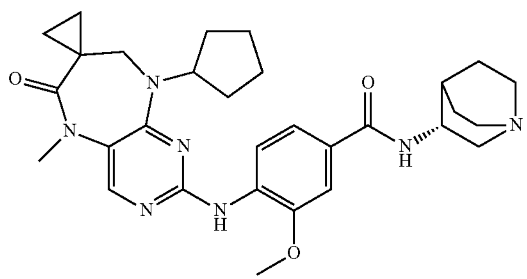 [SMILES: COc1cc(C(=O)N[C@H]2CN3CCC2CC3)ccc1Nc1ncc2c(n1)N(C1CCCC1)CC1(CC1)C(=O)N2C] | (R)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(quinuclidin-3-yl)benzamide | Rt = 3.07 min (Analytical_1); MS(+ve): 546.5; MS(-ve): 544.6; 1H NMR (DMSO-d6) δ ppm: 0.62-0.72 (2 H, m), 0.87-0.94 (2 H, m), 1.20-1.38 (1 H, m), 1.44-1.54 (2 H, m), 1.54-1.64 (4 H, m), 1.64-1.74 (2 H, m), 1.75-1.85 (1 H, m), 1.85-1.95 (3 H, m), 2.65-2.79 (4 H, m), 2.83-3.01 (1 H, m), 3.11-3.21 (4 H, m), 3.47 (2 H, s), 3.95 (4 H, s), 4.77-4.93 (1 H, m), 7.42-7.54 (2 H, m), 7.69 (1 H, s), 7.98 (1 H, s), 8.10 (1 H, d, J = 6.3 Hz), 8.39 (1 H, d, J = 8.3 Hz). |
| 348 | *** | 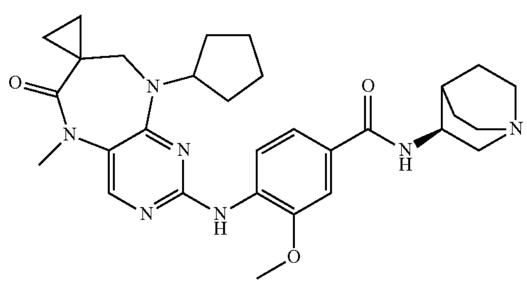 [SMILES: COc1cc(C(=O)N[C@@H]2CN3CCC2CC3)ccc1Nc1ncc2c(n1)N(C1CCCC1)CC1(CC1)C(=O)N2C] | (S)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxy-N-(quinuclidin-3-yl)benzamide | Rt = 3.04 min (Analytical_1); MS(+ve): 546.5; MS(-ve): 544.6; 1H NMR (DMSO-d6) δ ppm: 0.59-0.74 (2 H, m), 0.86-0.97 (2 H, m), 1.20-1.43 (1 H, m), 1.45-1.75 (7 H, m) 1.76-1.98 (4 H, m), 2.66-2.86 (3 H, m), 2.89-3.07 (1 H, m), 3.17 (3 H, s), 3.47 (3 H, s), 3.89-4.02 (4 H, m), 4.76-4.96 (1 H, m), 7.42-7.59 (2 H, m), 7.70 (1 H, s), 7.98 (1 H, s), 8.14 (1 H, d, J = 6.3 Hz), 8.40 (1 H, d, J = 7.8 Hz). |

TABLE 3-continued

PLK IC$_{50}$ values and characterization data for selected compounds of the invention; * denotes <0.1 μM IC$_{50}$;  denotes between 0.1 μM and 1 μM IC$_{50}$; * denotes between 1 μM and 10 μM IC$_{50}$.

| No. | | Structure | PLK1 Name | Data |
|---|---|---|---|---|
| 377 | *** | 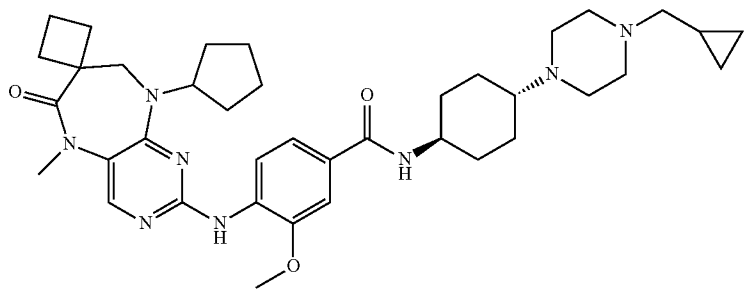 [SMILES: COc1cc(C(=O)N[C@H]2CC[C@H](N3CCN(CC4CC4)CC3)CC2)ccc1Nc1ncc2c(n1)N(C1CCCC1)CC1(CCC1)C(=O)N2C] | 4-(9'-cyclopentyl-5'-methyl-6'-oxo-5,6,8,9-tetrahydrospiro[4,5-b][1,4]diazepine]-2'-ylamino)-N-((trans)-4-(4-(cyclopropylmethyl)piperazin-1-yl)cyclohexyl)-3-methoxybenzamide | Rt = 3.41 min (Analytical_1); ES(+ve): 671.6; ES(-ve): 669.7; 1H NMR (DMSO-d$_6$) δ ppm: 0.03 (2H, dd, J 9.5 Hz, 5 Hz), 0.41 (2H, dd, J 10 Hz, 5 Hz), 0.79 (1H, m), 1.20-1.37 (4H, m), 1.55-1.94 (18H, m), 2.04 (2H, d, J 6.5 Hz), 2.16-2.46 (8H, m), 3.15 (3H, s), 3.32 (2H, s), 3.69 (1H, m), 3.90 (3H, s), 4.79 (1H, m), 7.44 (2H, m), 7.68 (1H, s), 8.01 (2H, m), 8.34 (1 H, d, J 8.5 Hz) |
| 378 | *** | 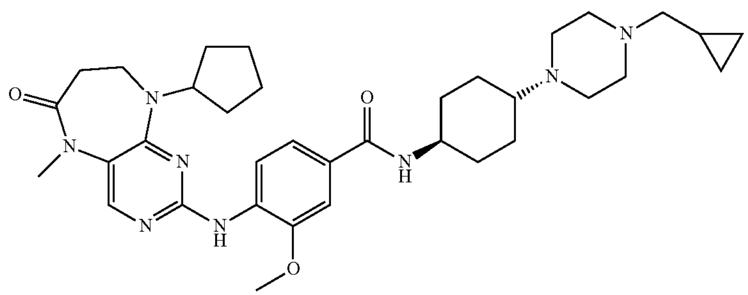 | 4-(9-cyclopentyl-5-methyl-6-oxo-6,7,8,9-tetrahydro-5H-pyrimido[4,5-b][1,4]diazepin-2-ylamino)-N-((trans)-4-(4-(cyclopropylmethyl)piperazin-1-yl)cyclohexyl)-3-methoxybenzamide | Rt = 2.88 min (Analytical_1); ES(+ve): 629.6; 1H NMR (DMSO-d6) δ ppm: -0.15-0.11 (m, 2 H), 0.40 (d, J = 8.06 Hz, 2 H), 0.63-0.85 (m, 1 H), 1.11-1.41 (m, 3 H), 1.57 (br. s., 2 H), 1.69 (d, J = 17.73 Hz, 2 H), 1.74-1.95 (m, 6 H), 2.04 (s, 2 H), 2.09 (d, J = 6.45 Hz, 2 H), 2.16 (d, J = 9.67 Hz, 1 H), 2.32 (br. s., 2 H), 2.49 (br. s., 1 H), 2.51-2.59 (m, 2 H), 2.59 (br. s., 1 H), 3.07-3.17 (m, 3 H), 3.27 (s, 5 H), 3.53-3.62 (m, 2 H), 3.67 (dd, J = 5.37 Hz, 1 H), 3.55 Hz, 1 H), 3.89 (s, 2 H), 4.04 (q, J = 5.37 Hz, 1 H), 4.76 (quin, J = 8.22 Hz, 1 H), 7.38-7.48 (m, 2 H), 7.68 (s, 1 H), 7.99 (d, J = 7.74 Hz, 1 H), 8.03 (s, 1 H), 8.33 (d, J = 8.06 Hz, 1 H) |
| 379 | *** | 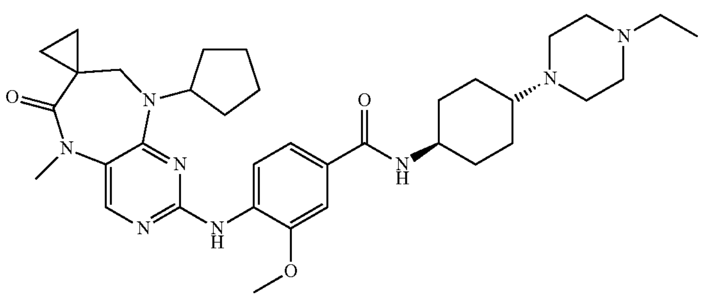 | 4-(9'-cyclopentyl-5'-methyl-6'-oxo-5,6,8,9-tetrahydrospiro[cyclopropane-1,7'-pyrimido[4,5-b][1,4]diazepine]-2'-ylamino)-N-((trans)-4-(4-ethylpiperazin-1-yl)cyclohexyl)-3-methoxybenzamide | Rt = 3.00 min (Analytical_1) MS(+ve) 631.6; MS(-ve) 629.7; 1H NMR (DMSO-d6) δ ppm: 0.59-0.72 (2 H, m), 0.81-0.92 (2 H, m), 0.97 (3 H, t, J = 7.1 Hz), 1.20-1.42 (4 H, m), 1.42-1.55 (2 H, m), 1.54-1.64 (2 H, m), 1.64-1.73 (2 H, m), 1.83 (2 H, d, J = 11.7 Hz), 1.89 (4 H, d, J = 7.8 Hz), 2.14-2.42 (7 H, m), 3.16 (3 H, s), 3.47 (2 H, s), 3.64-3.79 (1 H, m), 3.94 (3 H, s), 4.84 (1 H, quin, J = 8.7 Hz), 7.40-7.54 (2 H, m), 7.67 (1 H, s), 7.98 (1 H, s), 8.03 (1 H, d, J = 7.8 Hz), 8.38 (1 H, d, J = 8.3 Hz) |

TABLE 3-continued

PLK IC$_{50}$ values and characterization data for selected compounds of the invention; * denotes <0.1 µM IC$_{50}$;  denotes between 0.1 µM and 1 µM IC$_{50}$; * denotes between 1 µM and 10 µM IC$_{50}$.

| No. | | Structure | PLK1 Name | Data |
|---|---|---|---|---|
| 380 | *** | (structure) | 4-(9'-cyclopentyl-5'-methyl-6'-oxo-5,6,8',9'-tetrahydrospiro[cyclopropane-1,7'-pyrimido[4,5-b][1,4]diazepine]-2'-ylamino)-N-((cis)-4-(4-ethylpiperazin-1-yl)cyclohexyl)-3-methoxybenzamide | Rt = 3.13 min (Analytical_1) MS(+ve) 631.6; MS(−ve) 629.7; 1H NMR (DMSO-d6) δ ppm: 0.60-0.72 (2 H, m), 0.83-0.93 (2 H, m), 0.98 (3 H, t, J = 7.1 Hz), 1.38-1.55 (6 H, m), 1.55-1.63 (2 H, m), 1.63-1.80 (4 H, m), 1.80-1.96 (4 H, m), 2.02-2.17 (1 H, m), 2.16-2.44 (7 H, m), 3.16 (3 H, s), 3.47 (2 H, s), 3.79-3.92 (1 H, m), 3.94 (3 H, s), 4.84 (1 H, quin, J = 8.5 Hz), 7.44-7.58 (2 H, m), 7.67 (1 H, s), 7.98 (1 H, s), 8.03 (1 H, d, J = 7.3 Hz), 8.37 (2 H, d, J = 8.8 Hz) |
| 381 | *** | (structure) | 4-(9'-cyclopentyl-5'-methyl-6'-oxo-5,6,8',9'-tetrahydrospiro[cyclopropane-1,7'-pyrimido[4,5-b][1,4]diazepine]-2'-ylamino)-N-(4-(4-(cyclopropylmethyl)-1,4-diazepan-1-yl)cyclohexyl)-3-methoxybenzamide | Rt = 4.12 min (Analytical_1) MS(+ve) 671.6; MS(−ve) 669.7; 1H NMR (DMSO-d6) δ ppm: 0.01 (2 H, d, J = 4.4 Hz), 0.40 (2 H, d, J = 7.3 Hz), 0.63 (2 H, br. s.), 0.71-0.83 (1 H, m), 0.87 (2 H, br. s.), 1.02 (1 H, t, J = 7.1 Hz), 1.25-1.38 (2.5 H, m), 1.39-1.52 (3.5 H, m), 1.52-1.61 (2 H, m), 1.65 (4 H, d, J = 5.9 Hz), 1.70-1.80 (3 H, m), 1.85 (3 H, d, J = 4.4 Hz), 2.21-2.31 (1 H, m), 2.55-2.83 (8 H, m), 3.13 (3.5 H, s), 3.35-3.55 (3 H, m), 3.69 (0.5 H, br. s.), 3.91 (3.5 H, s), 4.31 (0.5 H, t, J = 5.1 Hz), 4.81 (1 H, t, J = 8.5 Hz), 7.25-7.54 (2 H, m), 7.64 (1 H, s), 7.84-8.16 (2 H, m), 8.35 (1 H, d, J = 8.3 Hz) |
| 382 | *** | (structure) | 4-(9'-cyclopentyl-5'-methyl-6'-oxo-5,6,8',9'-tetrahydrospiro[cyclopropane-1,7'-pyrimido[4,5-b][1,4]diazepine]-2'-ylamino)-N-(4-(4-ethyl-1,4-diazepan-1-yl)cyclohexyl)-3-methoxybenzamide | Rt = 3.98 min, 4.18 min (Analytical_1) MS(+ve) 645.6; MS(−ve) 643.7; 1H NMR (DMSO-d6) δ ppm: 0.57-0.74 (2 H, m), 0.82-0.93 (2 H, m), 0.95-1.09 (3 H, m), 1.30-1.42 (2 H, m), 1.42-1.54 (3.5 H, m), 1.58 (2 H, d, J = 4.4 Hz), 1.63-1.75 (3.5 H, m), 1.75-1.83 (1.5 H, m), 1.88 (3.5 H, br. s.), 1.98-2.16 (1.5 H, m), 2.59-2.86 (4 H, m), 3.17 (4 H, s), 3.41-3.53 (3.5 H, m), 3.78 (2.5 H, m), 3.88-4.02 (3.5 H, m), 4.06-4.38 (1 H, m), 4.76-4.91 (1 H, m), 7.39-7.57 (2 H, m), 7.59-7.78 (1 H, m), 7.98 (2 H, s), 8.31-8.45 (1 H, m) |

TABLE 3-continued

PLK IC$_{50}$ values and characterization data for selected compounds of the invention; * denotes <0.1 μM IC$_{50}$;  denotes between 0.1 μM and 1 μM IC$_{50}$; * denotes between 1 μM and 10 μM IC$_{50}$

| No. | PLK1 | Name | Data |
|---|---|---|---|
| 383 | ** | N-(4-(4-benzyl-1,4-diazepan-1-yl)cyclohexyl)-4-(9'-cyclopentyl-5'-methyl-6'-oxo-5',6,8',9'-tetrahydrospiro[cyclopropane-1,7'-pyrimido[4,5-b][1,4]diazepine]-2'-ylamino)-3-methoxybenzamide | Rt = 4.40 min (Analytical_1) MS(+ve) 707.6; MS(−ve) 705.7; 1H NMR (DMSO-d6) δ ppm: 0.73 (2 H, br. s.), 0.96 (2 H, br. s.), 1.22-2.22 (19 H, m), 2.64-2.91 (4 H, m), 3.23 (5 H, s), 3.53 (8 H, s), 3.89-4.24 (4 H, m), 4.91 (1 H, t, J = 8.5 Hz), 5.82 (0 H, s), 7.23-8.54 (10 H, m) |
| 384 | *** | 4-(9'-cyclopentyl-5'-methyl-6'-oxo-5',6,8',9'-tetrahydrospiro[cyclopropane-1,7'-pyrimido[4,5-b][1,4]diazepine]-2'-ylamino)-N-((trans)-4-(4-methylpiperazin-1-yl)cyclohexyl)-3-methoxybenzamide | Rt = 2.85 min (Analytical_1) MS(+ve) 617.5; MS(−ve) 615.6; 1H NMR (DMSO-d6) δ ppm: 0.61-0.76 (2 H, m), 0.89 (1 H, t, J = 6.8 Hz), 0.92-0.98 (2 H, m), 1.22-1.47 (5 H, m), 1.47-1.79 (6 H, m), 1.81-2.02 (5 H, m), 2.07-2.20 (3 H, m), 2.20-2.42 (4 H, m), 3.20 (4 H, s), 3.34 (3 H, s), 3.51 (2 H, s), 3.67-3.82 (1 H, m), 3.98 (3 H, s), 4.88 (1 H, quin, J = 8.5 Hz), 7.42-7.59 (2 H, m), 7.71 (1 H, s), 8.02 (1 H, s), 8.08 (1 H, d, J = 7.8 Hz), 8.42 (1 H, d, J = 8.3 Hz) |
| 385 | *** | 4-(9'-cyclopentyl-5'-methyl-6'-oxo-5',6,8',9'-tetrahydrospiro[cyclopropane-1,7'-pyrimido[4,5-b][1,4]diazepine]-2'-ylamino)-N-((cis)-4-(4-methylpiperazin-1-yl)cyclohexyl)-3-methoxybenzamide | Rt = 2.93 min (Analytical_1) MS(+ve) 617.5; MS(−ve) 615.6; 1H NMR (DMSO-d6) δ ppm: 0.62-0.80 (2 H, m), 0.84-1.02 (4 H, m), 1.18-1.36 (4 H, m), 1.43-1.84 (12 H, m), 1.84-2.03 (4 H, m), 2.09-2.22 (4 H, m), 2.41 (4 H, br. s.), 3.21 (3 H, s), 3.52 (3 H, s), 3.89-3.97 (1 H, m), 3.99 (3 H, s), 4.89 (1 H, quin, J = 8.5 Hz), 7.47-7.61 (2 H, m), 7.72 (1 H, s), 8.03 (1 H, s), 8.08 (1 H, d, J = 7.3 Hz), 8.43 (1 H, d, J = 9.3 Hz) |

TABLE 3-continued

PLK IC$_{50}$ values and characterization data for selected compounds of the invention; * denotes <0.1 μM IC$_{50}$;  denotes between 0.1 μM and 1 μM IC$_{50}$; * denotes between 1 μM and 10 μM IC$_{50}$.

| No. | | Structure | PLK1 Name | Data |
|---|---|---|---|---|
| 386 | *** | (structure) | N-((trans)-4-(4-benzylpiperazin-1-yl)cyclohexyl)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzamide | Rt = 3.64 min (Analytical_1) MS(+ve) 693.6; MS(−ve) 691.7; 1H NMR (DMSO-d6) δ ppm: 0.62-0.79 (2 H, m), 0.85-1.02 (2 H, m), 1.20-1.46 (4 H, m), 1.46-1.58 (2 H, m), 1.59-1.67 (2 H, m), 1.67-1.78 (2 H, m), 1.80-2.02 (6 H, m), 2.12 (1 H, s), 2.18-2.46 (6 H, m), 3.20 (3 H, s), 3.43-3.56 (5 H, m), 3.67-3.84 (1 H, m), 3.97 (3 H, s), 4.88 (1 H, quin, J = 8.4 Hz), 7.22-7.42 (6 H, m), 7.44-7.59 (2 H, m), 7.71 (1 H, s), 8.02 (1 H, s), 8.08 (1 H, d, J = 7.8 Hz), 8.42 (1 H, d, J = 7.8 Hz) |
| 387 | ** | (structure) | N-((cis)-4-(4-benzylpiperazin-1-yl)cyclohexyl)-4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-3-methoxybenzamide | Rt = 3.85 min (Analytical_1) MS(+ve) 693.6; MS(−ve) 691.7; 1H NMR (DMSO-d6) δ ppm: 0.62-0.79 (2 H, m), 0.87-1.01 (2 H, m), 1.43-1.59 (5 H, m), 1.59-1.67 (2 H, m), 1.66-1.74 (2 H, m), 1.75-1.84 (2 H, m), 1.92 (4 H, br. s.), 2.07-2.29 (2 H, m), 2.41 (4 H, br. s.), 3.20 (3 H, s), 3.51 (4 H, s), 3.87-4.05 (4 H, m), 4.74-4.99 (1 H, m), 7.24-7.39 (5 H, m), 7.50-7.56 (2 H, m), 7.71 (1 H, s), 8.02 (1 H, s), 8.07 (1 H, d, J = 6.8 Hz), 8.42 (1 H, d, J = 8.8 Hz) |
| 388 | *** | (structure) | 4-(9-cyclopentyl-5,7,7-trimethyl-6-oxo-6,7,8,9-tetrahydro-5H-pyrimido[4,5-b][1,4]diazepin-2-ylamino)-3-methoxy-N-((trans)-4-morpholinocyclohexyl)benzamide | Rt = 3.16 min (Analytical_1) MS(+ve) 606.4; MS(−ve) 604.5; 1H NMR (DMSO-d6) δ ppm: 1.07-1.18 (7 H, m), 1.24-1.49 (4 H, m), 1.58-1.71 (4 H, m), 1.71-1.84 (2 H, m), 1.83-2.03 (6 H, m), 2.23 (1 H, t, J = 10.5 Hz), 2.43-2.51 (3 H, m), 3.17-3.28 (4 H, m), 3.42 (3 H, br. s.), 3.60 (4 H, br. s.), 3.64 (1 H, br. s.), 3.71-3.83 (1 H, m), 3.98 (3 H, s), 5.23 (1 H, t, J = 8.3 Hz), 7.44-7.60 (2 H, m), 7.72 (1 H, s), 8.02 (1 H, s), 8.09 (1 H, d, J = 7.8 Hz), 8.40 (1 H, d, J = 8.3 Hz) |

TABLE 3-continued

PLK IC$_{50}$ values and characterization data for selected compounds of the invention; * denotes <0.1 μM IC$_{50}$;  denotes between 0.1 μM and 1 μM IC$_{50}$; * denotes between 1 μM and 10 μM IC$_{50}$.

| No. | | Structure | PLK1 Name | Data |
|---|---|---|---|---|
| 389 | ** | (structure) | 4-(9-cyclopentyl-5,7,7-trimethyl-6-oxo-6,7,8,9-tetrahydro-5H-pyrimido[4,5-b][1,4]diazepin-2-ylamino)-3-methoxy-N-((cis)-4-morpholinocyclohexyl)benzamide | Rt = 3.31 min (Analytical_1) MS(+ve) 606.4; MS(−ve) 604.5; 1H NMR (DMSO-d6) δ ppm: 1.13 (6 H, s), 1.39-1.60 (4 H, m), 1.60-1.71 (4 H, m), 1.71-1.85 (4 H, m), 1.85-2.01 (4 H, m), 2.07-2.22 (2 H, m), 2.42-2.48 (4 H, m), 3.22 (4 H, s), 3.64 (4 H, br. s.), 3.87-4.05 (4 H, m), 5.14-5.31 (1 H, m), 7.45-7.62 (2 H, m), 7.71 (1 H, s), 8.02 (1 H, s), 8.09 (1 H, d, J = 7.3 Hz), 8.39 (1 H, d, J = 8.3 Hz) |
| 390 | *** | (structure) | 4-(9′-cyclopentyl-5′-methyl-6′-oxotetrahydrospiro[cyclopropane-1,7′-pyrimido[4,5-b][1,4]diazepine]-2′-ylamino)-3-methoxy-N-((trans)-4-morpholinocyclohexyl)benzamide | Rt = 2.96 min (Analytical_1) MS(+ve) 604.4; MS(−ve) 602.5; 1H NMR (DMSO-d6) δ ppm: 0.72 (2 H, s), 0.95 (2 H, s), 1.24-1.49 (4 H, m), 1.49-1.60 (2 H, m), 1.60-1.69 (2 H, m), 1.69-1.82 (2 H, m), 1.82-2.03 (6 H, m), 2.14 (1 H, s), 2.17-2.32 (1 H, m), 3.22 (4 H, s), 3.53 (2 H, s), 3.61 (4 H, br. s.), 3.71-3.84 (1 H, m), 4.00 (3 H, s), 4.90 (1 H, quin, J = 8.5 Hz), 7.43-7.61 (2 H, m), 7.73 (1 H, s), 8.04 (1 H, s), 8.10 (1 H, d, J = 7.8 Hz), 8.44 (1 H, d, J = 8.3 Hz) |
| 391 | ** | (structure) | 4-(9′-cyclopentyl-5′-methyl-6′-oxo-5′,6′,8′,9′-tetrahydrospiro[cyclopropane-1,7′-pyrimido[4,5-b][1,4]diazepine]-2′-ylamino)-3-methoxy-N-((cis)-4-morpholinocyclohexyl)benzamide | Rt = 3.10 min (Analytical_1) MS(+ve) 604.4; MS(−ve) 602.5; 1H NMR (DMSO-d6) δ ppm: 0.66-0.81 (2 H, m), 0.88-1.03 (2 H, m), 1.45-1.86 (12 H, m), 1.87-2.02 (4 H, m), 2.10-2.21 (1 H, m), 2.47 (4 H, br. s.), 3.22 (3 H, s), 3.52 (2 H, s), 3.65 (4 H, br. s.), 3.89-4.05 (4 H, m), 4.90 (1 H, quin, J = 8.5 Hz), 7.50-7.63 (2 H, m), 7.73 (1 H, s), 8.03 (1 H, s), 8.10 (1 H, d, J = 7.3 Hz), 8.43 (1 H, d, J = 8.3 Hz) |

TABLE 4

PLK activity data for compound [218] versus selected prior art compounds

| Compound | Structure | PLK1 | PLK2 IC50/ PLK1 IC50 | PLK3 IC50/ PLK1 IC51 |
|---|---|---|---|---|
| [218] | 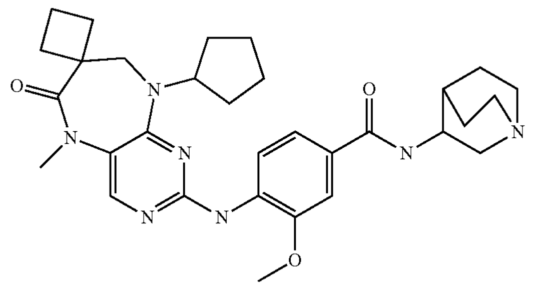 [SMILES: COc1cc(C(=O)NC2CN3CCC2CC3)ccc1Nc1ncc2c(n1)N(C1CCCC1)CC1(CCC1)C(=O)N2C] | *** | 35 | 330 |
| WO 2007/095188 [I-64] | 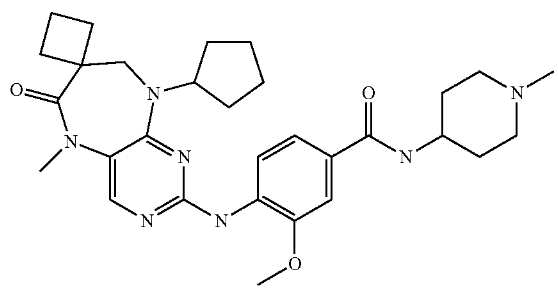 [SMILES: COc1cc(C(=O)NC2CCN(C)CC2)ccc1Nc1ncc2c(n1)N(C1CCCC1)CC1(CCC1)C(=O)N2C] | *** | 17 | 67 |
| WO 2007/095188 [I-76] | 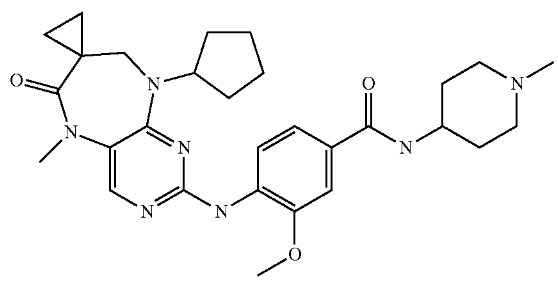 [SMILES: COc1cc(C(=O)NC2CCN(C)CC2)ccc1Nc1ncc2c(n1)N(C1CCCC1)CC1(CC1)C(=O)N2C] | *** | 6 | 26 |
| WO 2007/095188 [I-4] | 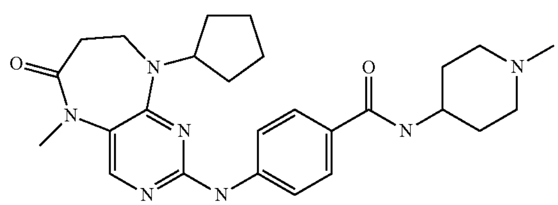 [SMILES: CN1CCC(NC(=O)c2ccc(Nc3ncc4c(n3)N(C3CCCC3)CCC(=O)N4C)cc2)CC1] | *** | 5 | 64 |

*** denotes <0.1 μM IC50

TABLE 5

Solubility data for compound [254] and its HCl salt versus Example [I-76] of WO 07/095188 and its HCl salt

| Compound | Description | Liquid phase | Concentration based on free base (mg/mL) | Forms stable solution | Forms gel? |
|---|---|---|---|---|---|
| [254] | free base | DMA/ PEG400/ 10 mM pH4 Tartrate buffer (1:3:6) | 8 | y | |
| Example [I-76] of WO 07/095188 | free base | DMA/ PEG400/ 10 mM pH4 Tartrate buffer (1:3:6) | 8 | n | y |
| [254] · HCl | HCl salt of [254] | 40% Captisol/ water | 20 | y | |

TABLE 5-continued

Solubility data for compound [254] and its HCl salt versus Example [I-76] of WO 07/095188 and its HCl salt

| Compound | Description | Liquid phase | Concentration based on free base (mg/mL) | Forms stable solution | Forms gel? |
|---|---|---|---|---|---|
| [254] · HCl | HCl salt of [254] | 30% Captisol/ water | 20 | y | |
| [254] · HCl | HCl salt of [254] | 20% HPβCD/ water | 20 | y | |
| [I-76] · HCl | HCl salt of [I-76] | 40% Captisol/ water | 20 | n | y |
| [I-76] · HCl | HCl salt of [I-76] | 30% Captisol/ water | 15 | n | y |
| [I-76] · HCl | HCl salt of [I-76] | 20% HPβCD/ water | 10 | n | y |

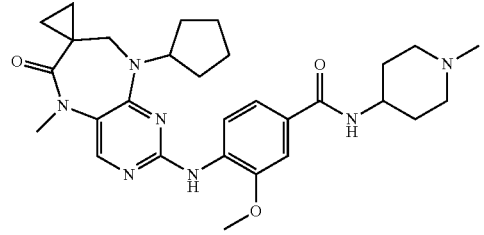

Compound [I-76] of WO 07/095188
(= Example 246 of WO 08/003958)

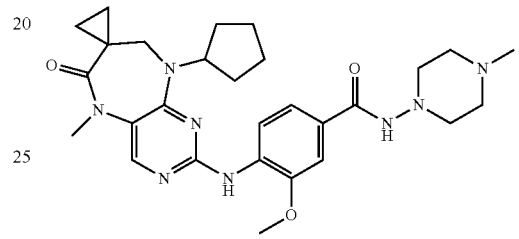

Compound [254]

TABLE 6

Nephelometry maximum soluble concentration for compound [254] of the invention versus compound [I-253] of WO 07/095188

| Compound | PLK1 Ki (nM) | Nephelometry maximum soluble concentration (µM) |
|---|---|---|
| Compound [254] | <10 | >200 |
| Example [I-253] of WO 07/095188 | <10 | 75 |
| [254] · HCl | <10 | >200 |

TABLE 7

Compounds tested in pharmacokinetic studies; compound H = compound [371]; compound I = compound [378]; compounds A-G are for comparative purposes

| Structure | Compound |
|---|---|
| 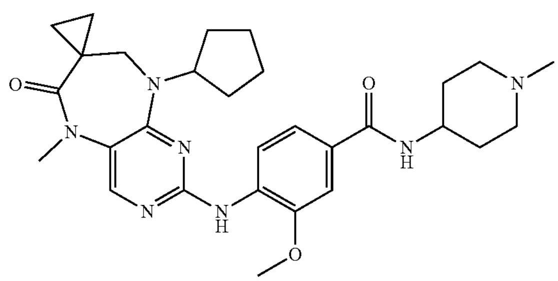 [SMILES: COc1cc(C(=O)NC2CCN(C)CC2)ccc1Nc1ncc2c(n1)N(C1CCCC1)CC1(CC1)C(=O)N2C] | A |
| 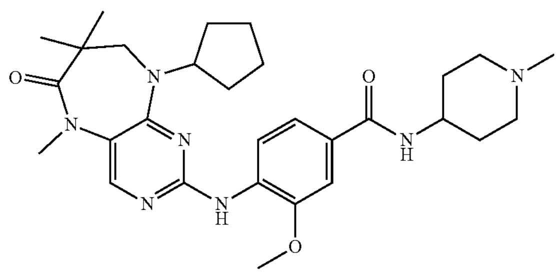 [SMILES: COc1cc(C(=O)NC2CCN(C)CC2)ccc1Nc1ncc2c(n1)N(C1CCCC1)CC(C)(C)C(=O)N2C] | B |
| 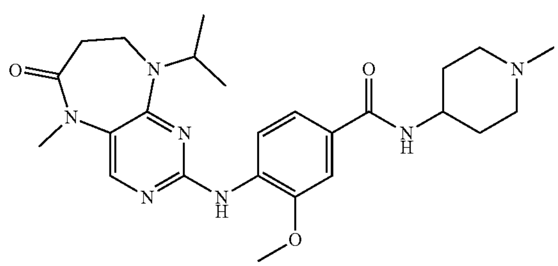 [SMILES: COc1cc(C(=O)NC2CCN(C)CC2)ccc1Nc1ncc2c(n1)N(C(C)C)CCC(=O)N2C] | C |
| 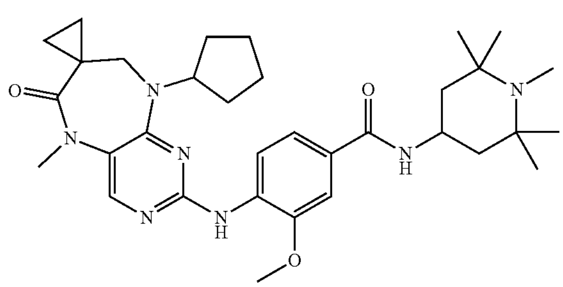 [SMILES: COc1cc(C(=O)NC2CC(C)(C)N(C)C(C)(C)C2)ccc1Nc1ncc2c(n1)N(C1CCCC1)CC1(CC1)C(=O)N2C] | D |
| 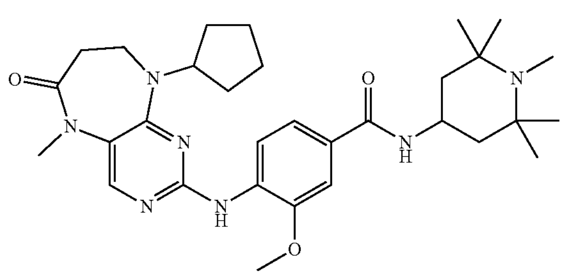 [SMILES: COc1cc(C(=O)NC2CC(C)(C)N(C)C(C)(C)C2)ccc1Nc1ncc2c(n1)N(C1CCCC1)CCC(=O)N2C] | E |

TABLE 7-continued

Compounds tested in pharmacokinetic studies; compound H = compound [371]; compound I = compound [378]; compounds A-G are for comparative purposes

| Structure | Compound |
|---|---|
| 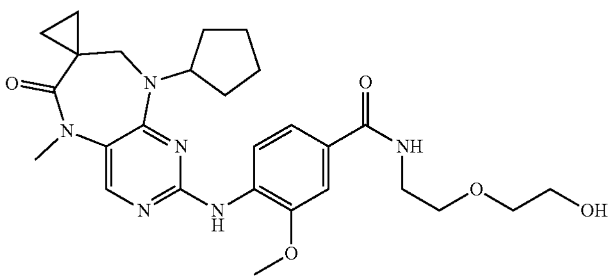 [SMILES: COc1cc(C(=O)NCCOCCO)ccc1Nc1ncc2c(n1)N(C1CCCC1)CC1(CC1)C(=O)N2C] | F |
| 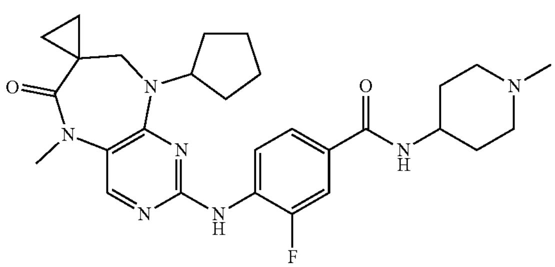 [SMILES: CN1CCC(NC(=O)c2ccc(Nc3ncc4c(n3)N(C3CCCC3)CC3(CC3)C(=O)N4C)c(F)c2)CC1] | G |
| 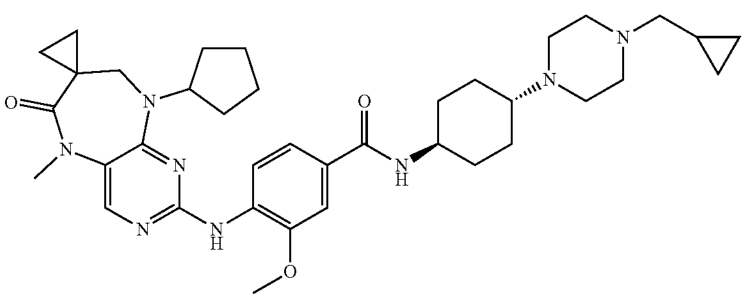 [SMILES: COc1cc(C(=O)N[C@H]2CC[C@H](N3CCN(CC4CC4)CC3)CC2)ccc1Nc1ncc2c(n1)N(C1CCCC1)CC1(CC1)C(=O)N2C] | H |
| 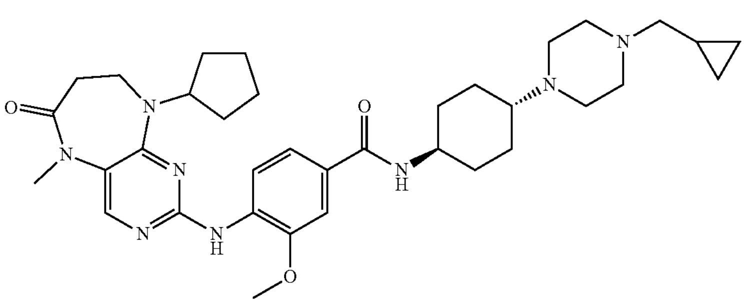 [SMILES: COc1cc(C(=O)N[C@H]2CC[C@H](N3CCN(CC4CC4)CC3)CC2)ccc1Nc1ncc2c(n1)N(C1CCCC1)CCC(=O)N2C] | I |

TABLE 8
Comparator compounds tested in cell assays; letters correspond to labels in FIG. 3.
| Structure | Figure label |
|---|---|
| 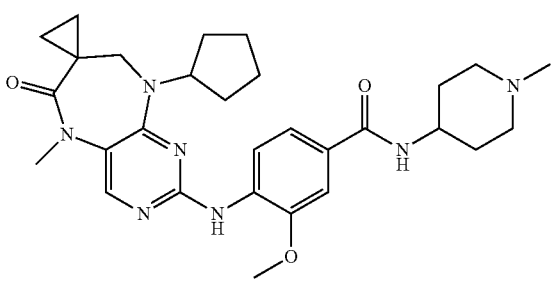<br>Example 76 in WO 07/095188 | A' |
| 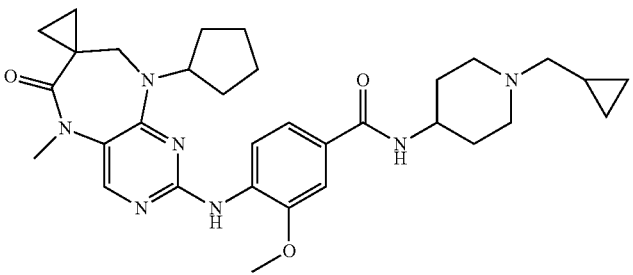<br>B (cf. Example 59 in WO 07/095188) | B' |
| 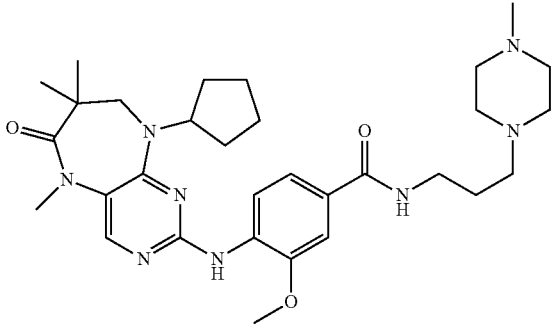<br>Example 28 in WO 07/095188 | C' |
| 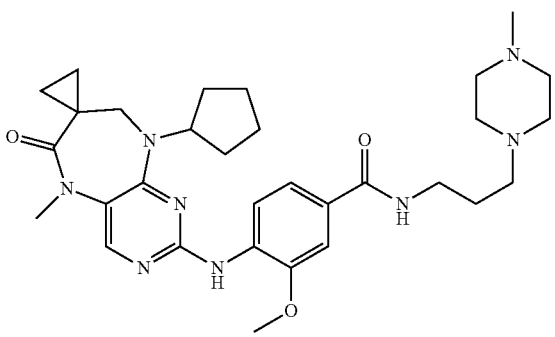<br>D (cf. Example 28 in WO 07/095188 | D' |

TABLE 8-continued
Comparator compounds tested in cell assays; letters correspond to labels in FIG. 3.
| Structure | Figure label |
| --- | --- |
| 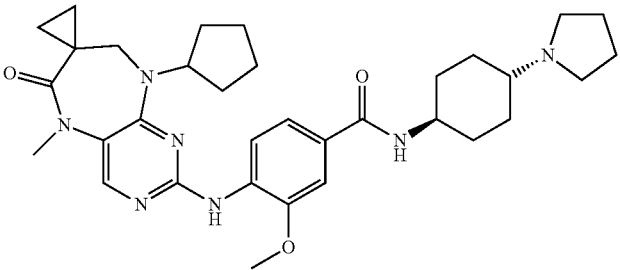<br>E (cf. Example 360 in WO 08/003958) | E' |
| 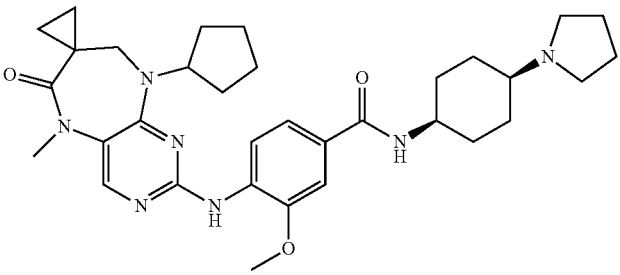<br>F (cf. Example 360 in WO 08/003958 | F' |
| 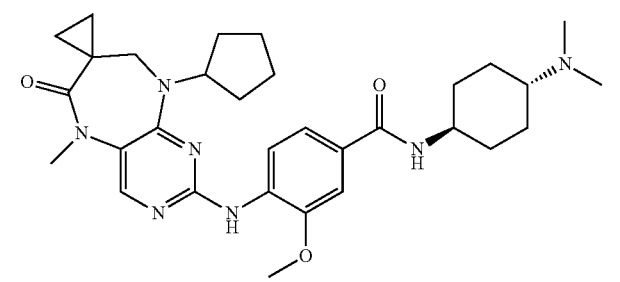<br>G (cf. Example 394 in WO 08/003958 | G' |
| 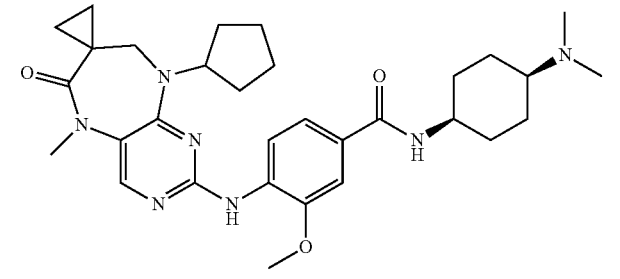<br>H (cf. Example 394 in WO 08/003958 | H' |

TABLE 8-continued

Comparator compounds tested in cell assays; letters correspond to labels in FIG. 3.

| Structure | Figure label |
|---|---|
| Example 360 in WO 08/003958 (trans) | I' |
| Example 360 in WO 08/003958 | J' |

The invention claimed is:

1. A compound selected from the following:

| Cpd | Structure |
|---|---|
| 73 | 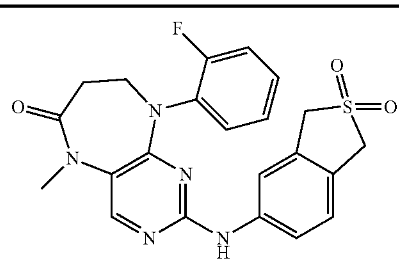 |
| 72 | 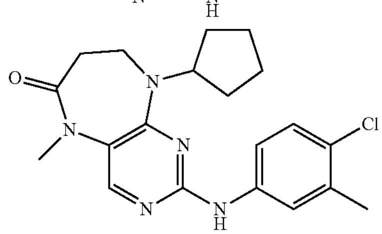 |
| 74 | 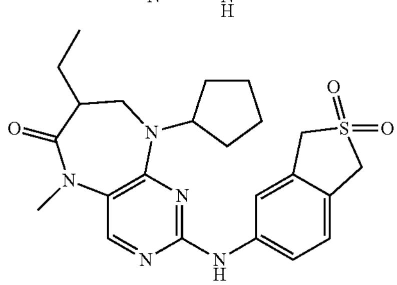 |
| 75 | |
| 76 | |
| 85 | |

329
-continued

| Cpd | Structure |
|---|---|
| 97 | 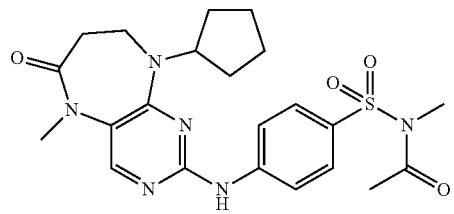 [SMILES: CC(=O)N(C)S(=O)(=O)c1ccc(Nc2ncc3c(n2)N(C2CCCC2)CCC(=O)N3C)cc1] |
| 46 | 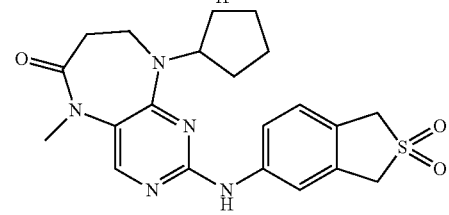 |
| 115 | 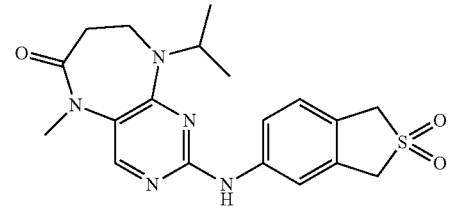 [SMILES: CC(C)N1CCC(=O)N(C)c2cnc(Nc3ccc4c(c3)CS(=O)(=O)C4)nc21] |

| Cpd | Name |
|---|---|
| 73 | 2-(2,2-Dioxo-2,3-dihydro-1H-2lambda*6*-benzo[c]thiophen-5-ylamino)-9-(2-fluoro-phenyl)-5-methyl-5,7,8,9-tetrahydro-pyrimido[4,5-b][1,4]diazepin-6-one |

330
-continued

| Cpd | Name |
|---|---|
| 72 | 2-(4-Chloro-3-methyl-phenylamino)-9-cyclopentyl-5-methyl-5,7,8,9-tetrahydro-pyrimido[4,5-b][1,4]diazepin-6-one |
| 74 | 9-Cyclopentyl-2-(2,2-dioxo-2,3-dihydro-1H-2lambda*6*-benzo[c]thiophen-5-ylamino)-7-ethyl-5-methyl-5,7,8,9-tetrahydro-pyrimido[4,5-b][1,4]diazepin-6-one |
| 75 | 2-(2,2-Dioxo-2,3-dihydro-1H-2lambda*6*-benzo[c]thiophen-5-ylamino)-5-methyl-9-phenyl-5,7,8,9-tetrahydro-pyrimido[4,5-b][1,4]diazepin-6-one |
| 76 | 9-Cyclopentyl-2-(2,2-dioxo-2,3-dihydro-1H-2lambda*6*-benzo[c]thiophen-5-ylamino)-5,7-dimethyl-5,7,8,9-tetrahydro-pyrimido[4,5-b][1,4]diazepin-6-one |
| 85 | 4-(9-Cyclopentyl-5-methyl-6-oxo-6,7,8,9-tetrahydro-5H-pyrimido[4,5-b][1,4]diazepin-2-ylamino)-N,N-dimethyl-benzamide |
| 97 | N-Acetyl-4-(9-cyclopentyl-5-methyl-6-oxo-6,7,8,9-tetrahydro-5H-pyrimido[4,5-b][1,4]diazepin-2-ylamino)-N-methyl-benzenesulfonamide |
| 46 | 9-Cyclopentyl-2-(2,2-dioxo-2,3-dihydro-1H-2lambda*6*-benzo[c]thiophen-5-ylamino)-5-methyl-5,7,8,9-tetrahydro-pyrimido[4,5-b][1,4]diazepin-6-one |
| 115 | 2-(2,2-Dioxo-2,3-dihydro-1H-2lambda*6*-benzo[c]thiophen-5-ylamino)-9-isopropyl-5-methyl-5,7,8,9-tetrahydro-pyrimido[4,5-b][1,4]diazepin-6-one | and pharmaceutically acceptable salts thereof.

2. A compound according to claim 1 which is selected from the following:

| Cpd | Structure | Name |
|---|---|---|
| 73 | 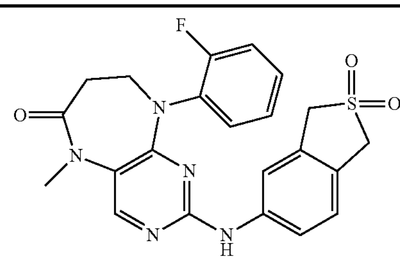 | 2-(2,2-Dioxo-2,3-dihydro-1H-2lambda*6*-benzo[c]thiophen-5-ylamino)-9-(2-fluoro-phenyl)-5-methyl-5,7,8,9-tetrahydro-pyrimido[4,5-b][1,4]diazepin-6-one |
| 74 | 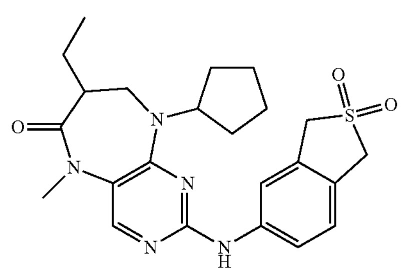 [SMILES: CCC1CN(C2CCCC2)c2nc(Nc3ccc4c(c3)CS(=O)(=O)C4)ncc2N(C)C1=O] | 9-Cyclopentyl-2-(2,2-dioxo-2,3-dihydro-1H-2lambda*6*-benzo[c]thiophen-5-ylamino)-7-ethyl-5-methyl-5,7,8,9-tetrahydro-pyrimido[4,5-b][1,4]diazepin-6-one |
| 75 | 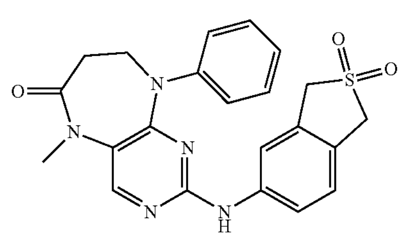 [SMILES: CN1C(=O)CCN(c2ccccc2)c2nc(Nc3ccc4c(c3)CS(=O)(=O)C4)ncc21] | 2-(2,2-Dioxo-2,3-dihydro-1H-2lambda*6*-benzo[c]thiophen-5-ylamino)-5-methyl-9-phenyl-5,7,8,9-tetrahydro-pyrimido[4,5-b][1,4]diazepin-6-one |

-continued

| Cpd | Structure | Name |
|---|---|---|
| 76 | | 9-Cyclopentyl-2-(2,2-dioxo-2,3-dihydro-1H-2lambda*6*-benzo[c]thiophen-5-ylamino)-5,7-dimethyl-5,7,8,9-tetrahydro-pyrimido[4,5-b][1,4]diazepin-6-one | and pharmaceutically acceptable salts thereof.

3. A compound according to claim 1 which is:

| Cpd | Structure | Name |
|---|---|---|
| 73 | | 2-(2,2-Dioxo-2,3-dihydro-1H-2lambda*6*-benzo[c]thiophen-5-ylamino)-9-(2-fluoro-phenyl)-5-methyl-5,7,8,9-tetrahydro-pyrimido[4,5-b][1,4]diazepin-6-one | or a pharmaceutically acceptable salt thereof.

4. A pharmaceutical composition comprising an effective amount of compound according to claim 1 admixed with a pharmaceutically acceptable diluent, excipient or carrier.

5. A pharmaceutical composition according to claim 4 which comprises one or more anticancer agents.

6. A method of treating cancer or leukemia, said method comprising administering to a subject an effective amount of a compound as defined in claim 1, and wherein said cancer or leukemia is selected from the group consisting of ovarian carcinoma, uterine sarcoma, non small cell lung carcinoma, osteosarcoma, acute myelogenous leukemia (AML) and acute lymphocytic leukemia (ALL).

7. A combination comprising a compound according to claim 1 and one or more anticancer agents.

8. The pharmaceutical composition of claim 4, formulated in unit dosage form.

* * * * *